US007341871B2

(12) United States Patent
Kurachi et al.

(10) Patent No.: US 7,341,871 B2
(45) Date of Patent: Mar. 11, 2008

(54) NUCLEOTIDE SEQUENCES FOR GENE REGULATION AND METHODS OF USE THEREOF

(75) Inventors: Kotoku Kurachi, Ibaraki (JP); Sumiko Kurachi, Ibaraki (JP)

(73) Assignee: The Regents of the University of Michigan, Ann Arbor, MI (US)

( * ) Notice: Subject to any disclaimer, the term of this patent is extended or adjusted under 35 U.S.C. 154(b) by 102 days.

(21) Appl. No.: 11/129,861

(22) Filed: May 16, 2005

(65) Prior Publication Data

US 2006/0031956 A1 Feb. 9, 2006

Related U.S. Application Data

(63) Continuation of application No. 10/032,084, filed on Dec. 19, 2001, now abandoned, which is a continuation of application No. 09/328,925, filed on Jun. 9, 1999, now Pat. No. 6,610,906.

(51) Int. Cl.
*C12N 15/85* (2006.01)
*A61K 48/00* (2006.01)
*C12N 5/16* (2006.01)
*C12N 5/18* (2006.01)
*C07H 21/00* (2006.01)

(52) U.S. Cl. .................. 435/455; 435/69.1; 435/320.1; 435/354; 514/44; 536/24.1; 800/25

(58) Field of Classification Search ..................... None
See application file for complete search history.

(56) References Cited

U.S. PATENT DOCUMENTS 4,683,195 A 7/1987 Mullis et al. .................. 435/6
4,683,202 A 7/1987 Mullis ......................... 435/91
4,965,188 A 10/1990 Mullis et al. .................. 435/6
5,545,806 A 8/1996 Lonberg et al. ................ 800/2
5,569,825 A 10/1996 Lonberg et al. ................ 800/2
5,591,601 A 1/1997 Wagner et al. ............. 435/69.1
5,625,126 A 4/1997 Lonberg et al. ................ 800/2
5,814,716 A * 9/1998 Jallat et al. ................... 800/10

FOREIGN PATENT DOCUMENTS

WO WO 9102056 A1 * 2/1991

OTHER PUBLICATIONS

Anson et al., "The gene structure of human anti-haemophilic factor IX," EMBO J 3(5): 1053-1060, 1984.*

Saito (1991) "Normal Hemostatic Mechanisms," in *Disorders of Hemostasis*, O.D. Ratnoff and C.D. Forbes, Eds., Sauders, Philadelphia, ed. 2, pp. 18-47.

Kurachi et al. (1993) "Biology of faxtor IX," Blood Coagul. Fibrinol. 4:953-974.

Yao et al. (1991) "Characterization of a Mouse Factor IX cDNA and Developmental Regulation of the Factor IX Gene Expression in Liver," *Thromb. Haemost*. 65:52-58.

Andrew et al. (1992) "Maturation of the Hemostatic System During Childhood," *Blood* 80:1998-2005.

Andrew et al. (1987) "Development of the Human Coagulation System in the Full-Term Infant," *Blood* 70:165-172.

Andrew et al. (1988) "Development of the Human Coagulation System in the Healthy Premature Infant," *Blood* 72:1651-1657.

Sweeney and Hoernig (1993) "Age-Dependent Effect on the Level of Factor IX," *Am. J. Clin. Pathol*. 99:687-688.

Kurachi et al. (1996) "Age and Sex Dependent Regulation of the Factor IX Gene in Mice," *Thromb. Haemost*. 76:965-969.

Mari et al. (1995) "Hypercoagulability in Centenarians: The Paradox of Successful Aging," *Blood* 85:3144-3149.

Conlan et al. (1993) "Associations of Factor VIII and von Willebrand Factor with Age, Race, Sex, and Risk Factors for Atherosclerosis, The Atherosclerosis Risk in Communities (ARIC) Study," *Thromb. Haemost*. 70:380-385.

Balleisen et al. (1985) "Epidemiological Study on Factor VII, Factor VIII and Fibrinogen in an Industrial Population: I. Baseline Data on the Relation to Age, Gender, Body-Weight, Smoking, Alcohol, Pill-Using, and Menopause," *Thromb. Haemost*. 54:475-479.

Rade et al. (1996) "Local adenoviral-mediated expression of recombinant hirudin reduces neointima formation after arterial injury," *Nat. Med*. 2:293-298.

Woodward et al. (1997) "Epidemiology of coagulation factors, inhibitors and activation markers: The Third Glasgow MONICA Survey II. Relationships to cardiovascular risk factors and prevalent cardiovascular disease," *Brit. J. Haemat*. 97:785-797.

Conlan et al. (1994) "Antithrombin III: Associations with Age, Race, Sex and Cardiovascular Disease Risk Factors," *Thromb. Haemost*. 72:551-556.

Lowe et al. (1997) "Epidemiology of coagulation factors, inhibitors and activation markers: The Third Glasgow MONICA Survey I. Illustrative reference ranges by age, sex and hormone use," *Brit. J. Haemat*. 97:775-784.

Kurachi et al. (1995) "Role of Intron I in Expression of the Human Factor IX Gene," *J. Biol. Chem*. 270:5276-5281.

Ross (1995) "mRNA Stability in Mammalian Cells," *Microbiol. Rev*. 59:423-450.

(Continued)

*Primary Examiner*—Scott D. Priebe
(74) *Attorney, Agent, or Firm*—Medlen & Caroll, LLP

(57) ABSTRACT

The invention provides nucleic acid sequences which regulate expression of a nucleotide sequence of interest. In particular, the invention provides nucleic acid sequences which regulate expression of a nucleotide sequence of interest in an age-related manner and/or in a liver-specific manner. The invention further provides methods of using the regulatory nucleic acid sequences provided herein for age-related and/or liver-specific expression of nucleotides seuqences of interest. The invention also provides host cells and transgenic non-human animals which harbor the regulatory nucleic acid sequences of the invention. The compositions and methods of the invention are useful in regulating expression of a nucleotide sequence of interest in an age-related and/or liver-specific manner.

6 Claims, 45 Drawing Sheets

OTHER PUBLICATIONS

Martin et al. (1988) "Activation of the polyomavirus enhancer by a murine activator protein 1 (AP1) homolog and two contiguous proteins," *Proc. Natl. Acad. Sci*. 85:5839-5843.
Xin et al. (1992) "Molecular cloning and characterization of PEA3, a new member of the *Ets* oncogene family that is differentially expressed in mouse embryonic cells," *Genes & Develop*. 6:481-496.
Chotteau-Lelièvre et al.(1997) "Differential expression patterns of the PEA3 group transcription factors through murine embryonic development," *Oncogene* 15:937-952.
Gutman and Wasylyk (1990) "The collagenase gene promoter contains a TPA and oncogene-responsive unit encompassing the PEA3 and AP-1 binding sites," *EMBO J*. 9:2241-2246.
Yang et al. (1998) "Apolipoprotein(a) Gene Enhancer Resides within a LINE Element," *J. Biol. Chem*. 273:891-897.
Caruthers et al. (1980) "New chemical methods for synthesizing polynucleotides," *Nuc. Acids Res. Symp. Ser*. 215-223.
Horn et al. (1980) "Synthesis of oligonucleotides on cellulose. Part II: design and synthetic strategy to the synthesis of 22 oligodeoxynucleotides coding for Gastric Inhibitory Polypeptide (GIP)[1]," *Nuc. Acids Res. Symp. Ser*. 225-232.
Kistner et al. (1996) "Doxycycline-mediated quantitative and tissue-specific control of gene expression in transgenic mice," *Proc. Natl. Acad. Sci. USA* 93:10933-10938.
Bartlett et al. (1996) "Efficient expression of protein coding genes from the murine U1 small nuclear RNA promoters," *Proc. Natl. Acad. Sci. USA* 93:8852-8857.
Wigler et al. (1977) "Transfer of Purified Herpes Virus Thymidine Kinase Gene to Cultured Mouse Cells," *Cell* 11:223-232.
Lowy et al. (1980) "Isolation of Transforming DNA: Cloning the Hamster aprt Gene," *Cell* 22:817-823.
Wigler et al. (1980) "Transformation of mammalian cells with an amplifiable dominant-acting gene," *Proc. Natl. Acad. Sci*. 77:3567-3570.
Colbere-Garapin et al. (1981) "A New Dominant Hybrid Selective Marker for High Eukaryotic Cells," *J. Mol. Biol*. 150:1-14.
Hartman and Mulligan (1988) "Two dominant-acting selectable markers for gene transfer studies in mammalian cells," *Proc. Natl. Acad. Sci*. 85:8047-8051.
Rhodes et al. (1995) "Transformation of Maize by Electroporation of Embryos," *Methods in Mol. Biol*. 55:121-131.
Gall and Pardue (1981) "Nucleic Acid Hybridization in Cytological Preparations," *Meth. Enzymol*. 21:470-480.
Angerer et al. (1985) "*In Situ* Hybridization to Cellular RNAs," in *Genetic Engineering: Principles and Methods*, vol. 7 pp. 43-65, Setlow & Hollaender (Eds.) Plenum Press, NY.
Maddox et al. (1983) "Elevated Serum Levels in Human Pregnancy of a Molecule Immunochemically Similar to Eosinophil Granule Major Basic Protein," *J. Exp. Med*. 158:1211-1226.
Hammer et al. (1986) "Genetic Engineering of Mammalian Embryos," *J. Animal Sci*. 63:269-278.
Hammer et al. (1985) "Production of transgenic rabbits, sheep and pigs by microinjection," *Nature* 315:680-683.
Jaenisch (1976) "Germ line integration and Mendelian transmission of the exogenous Moloney leukemia virus," *Proc. Natl. Acad. Sci USA* 73:1260-1264.
Jahner et al. (1985) "Insertion of the bacterial *gpt* gene into the germ line of mice by retroviral infection," *Proc. Natl. Acad. Sci. USA* 82:6927-6931.
Van der Putten et al. (1985) "Efficient insertion of genes into the mouse germ line via retroviral vectors," *Proc. Natl. Acad. Sci USA* 82:6148-6152.
Eistetter (1989) "Pluipotent Embryonal Stem Cell Lines Can Be Established from Disaggregated Mouse Morulae," *Dev. Gro. Differ*. 31:275-282.
Stewart et al. (1987) "Expression of retroviral vectors in transgenic mice obtained by embryo infection," *EMBO* 6:383-388.
Jahner et al. (1982) "*De novo* methylation and expression of retroviral genomes during mouse embryogenesis," *Nature* 298:623-628.
Doetschman et al. (1988) "Establishment of Hamster Blastocyst-Derived Embryonic Stem (ES) Cells," *Dev. Biol*. 127:224-227.
Tokunaga et al. (1989) "Establishment of the Mouse Embryonic Stem Cell Lines from Whole Blastocysts and Isolated Inner Cell Masses," *Jpn. J. Anim. Reprod*. 35:119-124.
Matsui et al. (1992) "Derivation of Pluripotential Embryonic Stem Cells from Murine Primordial Germ Cells in Culture," *Cell* 70:841-847.
Johnson et al. (1989) "Genetic Correction of Hereditary Disease," *Fetal Ther*. 4 (Suppl. 1):28-39
Bradley et al. (1984) "Formation of germ-line chimaeras from embryo-derived teratocarcinoma cell lines," *Nature* 309:255-256.
Bradley (1987) "Production and analysis of chimaeric mice," in *Teratocarcinomas and Embryonic Stem Cells: A Practical Approach*, E. J. Robertson, ed., IRL Press, Oxford, UK, pp. 113-151.
Nagy et al. (1990) "Embryonic stem cells alone are able to support fetal development in the mouse," *Development* 110:815-821.
Davidson et al. (1993) "A model system for in vivo gene transfer into the central nervous system using an adenoviral vector," *Nature Genet*. 3:219-223.
Shaked et al. (1994) "Adenovirus-Mediated Gene Transfer in the Transplant Setting," *Transplantation* 57:1508-1511.
Graham and Prevec (1991) "Manipulation of Adenovirus Vectors," in *Methods in Molecular Biology, vol. 7: Gene Transfer and Expression Protocols*, pp. 109-128, Murray (ed.), Humana Press, Clifton, NJ.
Engelhardt et al. (1994) "Ablation of *E2A* in recombinant adenoviruses improves transgene persistence and decreases inflammatory response in mouse liver," *Proc. Natl. Acad. Sci. USA* 91:6196-6200.
Ledley (1995) "Nonviral Gene Therapy: The Promise of Genes as Pharmaceutical Products," *Human Gene Ther*. 6:1129-1139.
Caplen et al. (1994) "Gene therapy for cystic fibrosis in humans by liposome-mediated DNA transfer: the production of resources and the regulatory process," *Gene Ther*. 1:139-147.
Alton et al. (1993) "Non-invasive liposome-mediated gene delivery can correct the ion transport defect in cystic fibrosis mutant mice," *Nature Genet*. 5:135-142.
Nabel et al. (1993) "Direct gene transfer with DNA-liposome complexes in melanoma: Expression, biologic activity, and lack of toxicity in humans," *Proc. Natl. Acad. Sci. USA* 90:11307-11311.
Sanford et al. (1993) "Optimizing the Biolistic Process for Different Biological Applications," *Methods Enzymol*. 217:483-509.
Yoshitake et al. (1985) "Nucleotide Sequence of the Gene for Human Factor IX (Antihemophilic Factor B)," *Biochem*. 24:3736-3750.
Kurachi et al. (1998) "Improved Transfection of HepG2 Cells Using FuGENE™ 6 Transfection Reagent," *Biochemica* 3:43-44.
Salier et al. (1990) "Functional Characterization of the 5'-Regulatory Region of Human Factor IX Gene," *J. Biol. Chem*. 265:7062-7068.
Yao et al. (1994) "Primary myoblast-mediated gene transfer: persistent expression of human factor IX in mice," *Gene Therapy* 1:99-107.
Kurachi et al. (1986) "Regulatory Mechanism of Human Factor IX Gene: Protein Binding at the Leyden-Specific Region," *Biochemistry* 33:1580-1591.
Karim et al. (1990) "The ETS-domain: a new DNA-binding motif that recognizes a purine-rich core DNA sequence," *Genes & Develop*. 4:1451-1453.
Nelsen et al. (1993) "Regulation of Lymphoid-Specific Immunoglobulin μ Heavy Chain Gene Enhancer by ETS-Domain Proteins," *Science* 261:82-86.
Fisher et al. (1991) "High-affinity DNA-protein interactions of the cellular ETS1 protein: the determination of the ETS binding motif," *Oncogene* 6:2249-2254.
Kazazian et al. (1988) "Haemophilia A resulting from *de novo* insertion of L/ sequences represents a novel mechanism for mutation in man," *Nature* 332:164-166.
Dombroski et al. (1993) "Two additional potential retrotransposons isolated from a human L1 subfamily that contains an active retrotransposable element," *Proc. Natl. Acad. Sci. USA* 90:6513-6517.

Minakami et al. (1992) "Identification of an internal *cis*-element essential for the human L1 transcription and a nuclear factor(s) binding to the element," *Nucl. Acids Res*. 20:3139-3145.
Dombroski et al. (1994) "An In Vivo Assay for the Reverse Transcriptase of Human Retrotransposon L1 in *Saccharomyces cerevisiae*," *Mol. Cell. Biol*. 14:4485-4492.
Türkay et al. (1999) "Production of Recombinant Human Protein C In Vitro and In Vivo by Muscle Cells," *Throm. Haemost*. 81:727-732.
Costa et al. (1997) "Male Infertility Caused by Epididymal Dysfunction in Transgenic Mice Expressing a Dominant Negative Mutation of Retinoic Acid Receptor α," *Biol. Repro*. 56:985-990.
Galdolfi (1998) "Spermatozoa, DNA binding and transgenic animals," *Transgenic Res*. 7:147-155 (Abstract Only).
Kurachi et al. (1998) "Mechanisms for the puberty-onset amelioration of hemophilia B Leyden: Animal model," *Blood* 92 (No. 10, Supplement 1):Abstract# 751.
Kurachi et al. (1998) "Molecular mechanisms of homeostasis in blood coagulation: age-associated regulation of the human Factor IX gene," *Blood* 92 (No. 10, Supplement 1):Abstract #2913.
Kurachi & Kurachi (1995) "Regulatory mechanisms of the Factor IX gene," *Thrombosis and Haemostasis* 73(3):333-339.
Markkula et al. (1995) "The Follicle-Stimulating Hormone (FSH) β- and Common α-Subunits are Expressed in Mouse Testis, as Determined in Wild-Type Mice and those Transgenic for the FSH β-Subunit/Herpes Simplex Virus Thymidine Kinase Fusion Gene," *Endocrinology* 136:4769-4775.
Nayernia et al. (1992) "Germ Cell-Specific Expression of a Proacrosin-CAT Fusion Gene in Transgenic Mouse Testis," *Molec. Repro. Devel*. 31:241-248.
O'Brien et al. (1995) "Boar Proacrosin Expressed in Spermatids of Transgenic Mice Does Not Reach the Acrosomes and Disrupts Spermatogenesis," *Mol. Repro. Devel*. 43:236-247.
Perry et al. (1999) "Mammalian Transgenesis by Intracytoplasmic Sperm Injection," *Science* 284:1180-1183.
Robl (1999) "New life for sperm-mediated transgenesis?," *Nature Biotech*. 17:636-637.
Smith (1999) "Sperm cell mediated transgenesis: a review," *Anim. Biotechnol*. 10:1-13 (Abstract Only).
Yamazaki et al. (1998) "In Vivo Gene Transfer to Mouse Spermatogenic Cells by Deoxyribonucleic Acid Injection into Seminiferous Tubules and Subsequent Electroporation," *Biol. Repro*. 59:1439-1444.
Youakim et al., (1994) "Overexpressing Sperm Surface β1,4-Galactosyltransferase in Transgenic Mice Affects Multiple Aspects of Sperm-Egg Interactions," *J. Cell Biol*. 126:1573-1583.
Mullins et al., (1993) "Transgenesis in Nonmurine Species," *Hypertension* 22:630-633.
Clay et al. (1999) "Potential Use of T Cell Receptor Genes to Modify Hematopoietic Stem Cells for the Gene Therapy of Cancer," *Path. Oncology Res*. 5(1):3-15.
Anderson (1998) "Human gene therapy," *Nature* 392(supp):25-30.
Hammer et al. (1990) "Spontaneous Inflammatory Disease in Transgenic Rats Expressing HLA-B27 and Human $\beta_2$m: An Animal Model of HLA-B27-Associated Human Disorders," *Cell* 63:1099-1112.
Cameron (1997) Review, "Recent Advances in Transgenic Technology," *Molecular Biotechnology* 7:253-265.
Kurachi et al. (1999) "Genetic Mechanisms of Age Regulation of Human Blood Coagulation Factor IX," *Science* 285:739-743.
Accession No. M27249, Database Embl158/Genbank 111, Apr. 7, 1993.
Accession No. L77890, Database Embl158/Genbank 111, Feb. 18, 1997.

* cited by examiner

```
GTATATCTAG AAAACCCCAT TGTCTCATTC CAAAATCACC TTAAGATGGA TAGGCAACTT CAGCAAAGTC TCAGGATAAC AAAATCAATG TGCAAAAATC  -2866
ACAGGCATTC TTATACACCA ATAGCAGACA AACAGACAGC CAAATCATGA GTGAACTCCC ATTCACAATT GCTTCAAAGA GAATAAAATA CCTAGGAATC  -2766
CTACTTACAA GGGATGTGAA GGACCTCTTC AAGGAGAACT ACAAACCACT GCTCAATGAA ATAAAAGAGG ATACAAACAA ATGGAAGAAC ATTACATGCT  -2666
CATGGGTAGG AAGAATCAAT ATCATGAAAA TGGCCATAAT GCCCAAGGTA ATTTATAGAT TCAATGCCAT CCCCATCAAG CTACCAATGA CTTTCTTCAC  -2566
AGAATTGGAA AAAACTACTT TAAAGTTCAT ATGGAACCAA AAAAGAGCCC GCATCGCCAA GTCAATCCTA AGCCAAAAGA ACAAAGCTGG AGGCATCATG  -2466
CTACCTGACT TCAAACTATA CTACAAGGCT ACAGTAACCA AAACAGCATG GTACTGGTAC CAAAACAGAG ATACAGACCA ATGGAACAGA ACAGAGCCCT  -2366
CAGAAATAAT GCCACATATC TACAACTATC TGATCTTTGA AAAACCTGAC AAAAACAAGA AATGGGGAAA GGAATCCCTA ATTAATAAAT GGTGCTGGGA  -2266
AAACTGGCTA GCCATATGTA GAAAGCTGAA ACTGGATCCC TTCCTTATAC CTTATACAAA AATTAATTCA AGATGGATTA AAGACTTCAT TGTTAGACCT  -2166
AAAACCATAA AAACCCTAGA AGAAAACCTA GGCAATACCA TTCAGGACAT AGGCATGGGC TTGGACTTCA TGTCTAAAAC ACCAAAAGCA ATGGCAACAA  -2066
AAGCCAAAAT TGACAAATGG GATCAAATGA AACTAAAGAG CTTCTGCACA GCAAAAGAAA CTACCATCAG AGTGAACAGG CAACCTAAAG AATGGGAGAA  -1966
AATTTTTGCA ATCTACTCAT CTGTCCAAGG GCTAATATCT AGAATCTAAA ATGAACTCAA ACAAATTTAC AGAAAAAAAC AAACAACCCC ATCAACAAGT  -1866
GGGTGAAGGA TATGAACAGA CACTTCTCAA AAGAAGACAT TTATGCAGCC AACAGACACA TGAAAAAATG CTCAGCATCA CCGGCCATCA GAGAAATGCA  -1766
AATCAAAACC ACAATGAGAT ACCATCTCAC ACAAGTTAGA ATGGCGATCA TCAAAAACTC AGGAAGCAAC AGGTGCTGGA GAGGATGTGG AGAAATAGGA  -1666
ACACTTTGAC ACTGTTGGTG GGACTGTAAA CTAGTTCAAC CATTGTGGAA GTCAGTGTGG CGATTCCTCA GGGATCTAGA CCTAGAAATA CCATCTGACC  -1566
CAGCCATCCC ATTATTGGGT ATATACCAAA GTATTATAAA TCATGCTGCT ATAAAGACAC ATGCACACGT ATGTTTATTG CGGCACTTTT CACAATAGCA  -1466
ATGACTTGGA ACCAACCCAA ATGTCCAACA ATGATAGACT GGATTAAGAA AATGTGGCAC ATATACACCT AGGAATACTA GGCAGCCATA AAAAGAAAAT  -1366
GAGTTCATGT CCTTTGTAGG GCATGGATGA AGCTAGAAAC CATCATTCTC AGCAAACTAT CGCAAGGACA AAAAACCAAA CACCGCATGT TCTCACTCAT  -1266
AGGTGGGAAC TGAACAATGA GAACACTTGG ACACAGGAAG GGGAACATCA CACACCGGGG CCTGTTGTGG GGTGGGGGGC GAGGGGAGGG ATAGCATTAG  -1166
GGGATATACC TAATGCTAAA TGACGAGTTA ATGGGTACAG CACACCAACA TGGCACATGT ATACATATGT AACAAACCTG CTCGTTGTGC ACATGTACCC  -1066
TAAAACTTAA AGTATAATAA TAAAAAAAAG ATCATTCTAA AATTTATACA AGCCCTTAGA ACAGTTAAAA ATATCTTACC AAAAGAAGAA TAAAGTTGGA   -966
GGAATCACTC TACCTAATAT AAAGTCTTAC TACATAGCTA CAGTAATTAT GACAGTGTTA TATTGGCAGA GGGATAAATA CATCAATGGC ACAAAGAATA   -866
GATAGAGAAA CTGGAAGTAG ACCCAAAACA ATATGGTTAA CTGACTTACG AAAAAATTTC AGAAGCCATT CAGTCGAGGA AGGATAGGGT GGTATTGTTG   -766
TTTTTTGTTT TAACAAATTG TGCTGGATAA ATTGGACATA CCTATGGAAA AAAAAATGAA GTTTGACCTA AACATCATAC TTTACACAAA TATTAACTCA   -666
AAATGGAGCA TGGGCATAAA TCTAAAACTT CAAACTGTAA AACATTTAGA AAAAAATAGG AAAAAAACTA TCAGGATCTA GTGTTAGTGG AAGAGTTCTA   -566
AATGTGATCC ATAAAACAAA AACAAATAAA CTGGACTACA TCAAAACTAA AAAATTCTAC TCTGTGAAAG ACCTAATTAA GAGGACAAAA GACAAGCTAC   -466
AGGCTGGAGA CAATATATTT AATCCACGTA TCTATGAAAG GATTCATATC TAGAATATAT AAACAACCTT AAGAATCTGA CAGTAAAAAA AAAAAATCAG   -366
ACTAACTGGA CCACTCATAC ATTGCTGATG GAAATGTAAA GTGGTACAGC CATTTTGGTA AACATCATTG CTCTCTGACA AAGATACGGT GGGTCCCACT   -266
GATGAACTGT GCTGCCACAG TAAATGTAGC CACTATGCCT ATCTCCATTC TGAAGATGTG TCACTTCCTG TTTCAGACTC AAATCAGCCA CAGTGGCAGA   -166
AGCCCACGAA ATCAGAGGTG AAATTTAATA ATGACCACTG CCCATTCTCT TCACTTGTCC CAAGAGGCCA TTGGAAATAG TCCAAAGACC CATTGAGGGA    -66
                                                                                                         -46
```

FIG. 8A

```
                                                                                                                                       Met
GATGGACATT ATTTCCCAGA AGTAAATACA GCTCAGCTTG TACTTTGGTA CAACTAATCG ACCTTACCAC TTTCACAATC TGCTAGCAAA GGTT ATG      32

Gln Arg Val Asn Met Ile Met Ala Glu Ser Pro Gly Leu Ile Thr Ile Cys Leu Leu Gly Tyr Leu Leu Ser Ala Glu Cys
CAG CGC GTG AAC ATG ATC ATG GCA GAA TCA CCA GGC CTC ATC ACC ATC TGC CTT TTA GGA TAT CTA CTC AGT GCT GAA TGT     113
-18
Thr
ACA G GTTT GTTTCCTTTT TTAAAATACA TTGAGTATGC TTGCCTTTTA GATATAGAAA TATCTGATGC TGTCTTCTTC ACTAAATTTT GATTACATGA  211
     ↑

TTTGACAGCA ATATTGAAGA GTCTAACAGC CAGCACGCAG GTTGGTAAGT ACTGGTTCTT TGTTAGCTAG GTTTTCTTCT TCTTCATTTT TAAAACTAAA   311
TAGATCGACA ATGCTTATGA TGCATTTATG TTTAATAAAC ACTGTTCAGT TCATGATTTG GTCATGTAAT TCCTGTTAGA AAACATTCAT CTCCTTGGTT   411
TAAAAAAATT AAAAGTGGGA AAACAAAGAA ATAGCAGAAT ATAGTGAAAA AAAATAACCA CATTATTTTT GTTTGGACTT ACCACTTTGA AATCAAAATG   511
GGAAACAAAA GCACAAACAA TGGCCTTATT TACACAAAAA GTCTGATTTT AAGATATATG ACATTTCAAG GTTTCAGAAG TATGTAATGA GGTGTGTCTC   611
TAATTTTTTA AATTATATAT CTTCAATTTA AAGTTTTAGT TAAAACATAA AGATTAACCT TTCATTAGCA AGCTGTTAGT TATCACCAAA GCTTTTCATG   711
GATTAGGAAA AAATCATTTT GTCTCTATGT CAAACATCTT GGAGTTTGAT TATTTGGGGA AACACAATAC TCAGTTGAGT TCCCTAGGGG AGAAAAGCAA   811
GCTTAAGAAT TGACATAAAG AGTAGGAAGT TAGCTAATGC AACATATATC ACTTTGTTTT TTCACAACTA CAGTGACTTT ATGTATTTCC CAGAGGAAGG   911
CATACAGGGA AGAAATTATC CCATTTGGAC AAACAGCATG TTCTCACAGG AAGCATTTAT CACACTTACT TGTCAACTTT CTAGAATCAA ATCTAGTAGC  1011
TGACAGTACC AGGATCAGGG GTGCCAACCC TAAGCACCCC CAGAAAGCTG ACTGGCCCTG TGGTTCCCAC TCCAGACATG ATGTCAGCTG TGAAATCAGA  1111
CTGAAATGCT GAAATAACGA TAAAAAAAAA TACAGAGGTT AAACTAGCAA AGTGAGTAAA GTCAAGGGAT AAAGAAAATT TGTTGGAAAA CTCACAAAGC  1211
AGGACATAAA GCAAGGCCAT TAGATATATC TCATTAGTGT GACATCTGGG AGGACAAAGC ATCCAAACCC TTTCTTCTAT ATAAGTGGTG AGATGATGAA  1311
GGTTGTAAGA GGCTTCTGCC CCCTTGAAGA CTTCAGATGC TGGGGAAAGG ATAGATAAGA ATAAGGATGA ACCTGGCTTT TGGAGCCTGG GAAATAATGA  1411
CTAGCGATAA ACCTGAAGGG AAGTTAAGTA TACGATCCCC AGATAATACT AAGGAGAAAG GCAATGTGAT TCTGCAGCCA TTGTAGCCAG AGATAATAAG  1511
CCCTTGAGGA AGGGGCCAGG GGAATTTTTC TAAGGATAGA CAGTATTAAT GCAGCACTCT CTTCTGCTAT TAAACTCTCA TTGGCTTCTA AAAGGAGTTT  1611
CGGTGAGTGA TTTGCTGAGA TGTTTGCATT TTCATGCTGC TGCCTTTAGG TTATTATTGC AACAGTTTGG AATTTTGAAA TTAAAACAGT TCTGTAAAAC  1711
CAGTTTAGTT TTGTAAAGTG TATGCATCAA AGATGTCCTT CATTCAGACA TTACTGAGTT ACAACTACGG TGGCAGGTAC TGTGTCAGGG TACTAGGGGT  1811
ATGGGGATAA ACCAGACTCC CTCTTTGATC TAAAGCAGCA TGAGGCCAGG TGAGAGGTTT CAATATATGT GATAAAATGT GCACTAGGTA CTAAGGGATC  1911
ATAGAGAAAG GAACACATTA AATGGGGAAA CAATTGATAG AGAGAGAATA TTTTCATCTG GGTCTTAAAA GATGAGTAGG CGTTCTCTCT CTTTAAATGT  2011
CTGATATAAG GGCATTTTAT GCAAAGAAGG ATCACTCGTG CAAAGACTCA GCTTTGCAAG AACGTGAGGT ATTTCAGGAG TTTTGTATGG TTCCATATGG  2111
ACTATGACAA GTGAGACAGG TAAACTAGGC AGAGCTGGTC ATCAGATAAT GAAGTCATTA ACCTAAGGAG ATTGGACAAT AAAATGCAAT ATGGAGGTAT  2211
CGAAGTATAA ACATAAGGAG TACCACTGAT GGCTGATTTA GGATGCCCAG TCTGGCAACA CGCTAATGAA ATGATAGTGG GGGAGGGGGC CGTACCAAGA  2311
CTAGGAGAGA GCAGTCCTGA GACTATTGCA ATTATCTGCG GGAGACATAA AGGCTAGAAC CTGAACAGTA GCAGTACAAA AAAAGAGGGG AGTTCAAATG  2411
ATATTAAGGA AGTAGAAGTG GTATGACTTA ACCATCTGGG TATGGAAGGG GAAATGGCTA GAGTCTTGGG GACTTTGTGT TTGATGTGAT TATGGACCAC  2511
```

FIG. 8B

```
AGAATAATGT CTAAGAGAAC TGGCTCTTTA GTCTGACTGC CAGAGTCTGA ATCCTGAATG TTTTAGTATG TTACCTTGCA AAGCCCTTAG CCTCTATGAA 2611
TCTATCTTCC TCATTTATAA AAATAAGATG ACAGTGCCTA TCTCGTGGGA CTTTTGTGAG GATGAAGTGA GATAATGGAT GCAAAGTTAC TGAGCACAGT 2711
GTCCAACACA GCAGAAGCAT TACATATACA TTAGCTATTA CTGGCTACAT TATGATATAC AGTTAGGGAG TTGGAAAGAT AATCTGAAAT TCAGGAGACG 2811
TATCTGACTA TAGGTGAGTA TTTGGAACTC ATTGTTCTGT AAACAGTAGT TACAGCACGT GTGTGGGCAT CTGGAGAGTG AGCATGGATA TTGTGATACC 2911
TAGTACAGTG CCTGGCAGTA GTGGTTGTAT GCTCAGTAAA TTTTGTTGAC AGGGTCAGGG CCGGACTAGA CTGTGGTAAG CAAGGCCTGT AGGGCATAAA 3011
TATACTTGTA TGCCCCGAGA AGTGAGGACC TCTTAAATAT TGTGCCCTAC ATGCCTTGTT TGGTTCACTC TTGTCCCAGC CCTAGCAAGT ATATATAAGG 3111
TGAAAAAGGA AAAAGCTGAG GCTGGAGCCT GGGAGAACCC TGGACATTTA AGGGCCATGG AGAGGAACAG GAGTTAATCA ATTCAAGTGC TGGATGGATA 3211
ACAGGAGTTA GAGCAAAGCG GGGAACCAGA ATAGAGTGAT TATTATAAAA AGAGTTTCCT AAAAAGGGAG AGATCAACAA TTAGAAATTA TTTAGAGCAG 3311
CCAGTAAATA CATAAACTCA AAATTATTCT TTAGGTCATT CCTGATTGTG ACAATAGTCA TTTCATTATA TAAATGTGAT TAAGGAAGGA AAAGAGCTAC 3411
ACAGAAGTTA TTAAAGAGCT AAAGAGAATT GAGAAATTTA AAACAGAAGA AAGTAGGGCC AACATGAAAG GAGTAGGGAG AAAAAGAGAT AACCAGCATA 3511
TTGTCTCACT GATCCTGCCA ACACCTGTGA GATAGATATT CTTATTATAC TACTGTTAAA CCTAATTTAC ATTTGACAAA GTTAAGGTTC AGAGCTTGTG 3611
TGACTTGTCC AAGGTCACAG GTCTAGAGGA GGCAGATACT TGATTCAAAC CTATTTCTGT CTGATCTGAT TCTAAAGTCT GTTTTTTCAC TCAACCACAC 3711
TGTACAGTCA GCTCTCCTTG TGAGTTCCAC AGCCACAGAT TCAATTAACT GCAGATCAAA AATATTCAAG AAAAAAATGG ATGGTTCGAT CTCTACTGAA 3811
CATGTACAGA CTCTTTTATC TTTCATTATT CCCTAAACAA TACAGCATAA CAACTATTTA CATAGCATTT ACATTGTATT AGCTATTAAG AGAAACCTAG 3911
AGATGATTTA AAGTACAAAG GAGGATGTGT TTAGGTTATA TGCAAATAGT AAGCCATTTT TATATCGGAG ACTTGAGCAT CCACAGATCT TGATATTTGC 4011
AGGGGGTCTT GCCACCAATT TTCCATGGAT ACTGAGGAAC GACTGTAAAT GGATGCAGGC ATGGATGCTA TTTAGGAGTG TCCAGGGCCA AGTAAATGAG 4111
TTGCTGAGCA GAGAGGTGGG TGGAGGCTGT GAGGCATCAA TATGTGGTGG CATCCATCTG CATTTTGGTG ATTTTTTTCC TTCACAGTCC TCGGCTGTCT 4211
GGGAAGAGAA GGATGAAGGC AGATGGCTGC TCCAATTTAG GGGCTAGGAT TGCAGGGTGG GCACAGCATT GCAAACGAGT GAAGGAAATT GAGAAATATG 4311
GCCAATGAAG AGTTGAAGAG AGGCCTGGCA TGGTGGCTCA CACCTATAAT CCCAGCACTT TCAGAGGCCC AGGCAGGCAG ATCACTTGAG GTCAGGAGTT 4411
CGACACCAGC CTGGCCAACA AGGTGAAATG GTGAAACCCC GGCTTTACTA AAAATACAAA AATTAGCTGG GCATGGTGGC GGGTGCCTGT AATCCCAGCT 4511
ACTTGGGAGG CTGAGGCAGG AGAATAGCTT GAACCTGGGA GATGGAGGTT GCAGTGAGCT GAGATCGCAC CACTGCACTC CAGCCTGGGC GACAGAGCAA 4611
GACTCTGTCA AAAAAAAAAG AGTTGAAGAG AAAAAGTCTA GGCTAAATTC AAAGAAAAAA AGTGAGCCCA AAAGGAACTT GCAGAGCAAG GGAAAAGCAG 4711
GGATGTCAAG GGACTAGAAC ACTCCATAAA GTGAACAGCT GCAATGAAAA TAAGGGAAGA AAGTTTAGTT CATCTCCGTT TCTTTCCTTT CCTTTTTACT 4811
TTCCTTTCTC TTCCTTTTTG GAGTTAGTCA GGAAGTAGTC CCAAATACCC CAGAAAGTTC ATCTTATAAG CCCTTGGTCC TCTTGAGATG GTATCAGATA 4911
TATTGCTAGA CCCTTGAAGA AAGGAACAAC TCCAGGCAAC TTCTTGAGTC CCTGTTATTA ATTTTATACA TACACACACA TATATGTATA TACATGAAAA 5011
CACACAAACA CATGTGTGTG TATACAGCCA TGCATTCCTT AACAATGGGG ATATATTCTG AGAAATGTGT CATTAAGCAA TTTCATCATT GTGCGAACAT 5111
AATAGAGTGT ACTTACCTAA ACCTAAATGG TATAGCTTAC TACATACCTA GGTTGTATTG ATGTGGCCTA TTGCTCCTAG GCTCCTGGGC TGCAAACCTG 5211
TACAGCATGT GACTGTACTG AACACTGTAG GCAATGGTAA CAGTGGTATT TGTGTATCTA AACATAGAAA AGGTACAGTG AAAATACAGT ATTATAACCT 5311
TATGGGACCA CTGTCGTATA ATGTGGTCCA TCATTGACCA AAATGTCATT GTGCAGCAAA TGATTATCTC ATATATATAT ATATATGATA TGATATATAT 5411
GATATATATG TGTGTGTATA TATGTATACA TATATATGTG TACATATATG TATACATATA TACACACACA TATATATGTA CACACATATA TGTATATATA 5511
TGTACACACA TATATGTATA TATATGTACA CACATATATG TATATATATA TGTACACACA TATATGTATA TATATATGTA CACACACACA CATAGAGAGA 5611
GAGAGAGAGG AGAGGAGAGG AAGGAGGGAG GGAAGGAGAA ATATGATTCA GATAGAGACA TCTATCCTCC AGAGTTCAGG AGTGTCTCTT CAGACTAGGT 5711
```

FIG. 8C

```
AGATGTAGCT TAAAAAAAAC ATATCCTGGA ATTCTAGAGA GATGCTTAAA TCACTGCAAT TCCTATAACA CTTGCCAACC AAAGGTGCTG TTGATCTGAA   5811
ATTGCTTTTT TAAATTAATG CAGTGATTTT TCTTTAACAT CTAGTGACAG ACACTGGGGT CACATTTGCA GCTGGACCAT AATTAGGCTT CTGTTCTTCA   5911
GGAGACATTT GTTCAAAGTC ATTTGGGCAA CCATATTCTG AAAACAGCCC AGCCAGGGTG ATGGATCACT TTGCAAAGAT CCTCAATGAG CTATTTTCAA   6011
GTGATGACAA AGTGTGAAGT TAACCGCTCA ATTTGAGTTC TTTCTTTTTC ATCCAAAGTA AATTCAAATA TGATTAGAAA TCTGACCTTT TATTACTGGA   6111
ATTCTCTTGA CTAAAAGTAA AATTGAATTT TAATTCCTAA ATCTCCATGT GTATACAGTA CTGTGGGAAC ATCACAGATT TTGGCTCCAT GCCCTAAAGA   6211
GAAATTGGCT TTCAGATTAT TTGGATTAAA AACAAAGACT TTCTTAAGAG ATGTAAAATT TTCATGATGT TTTCTTTTTT GCTAAAACTA AAGAATTATT   6311
                 -17                                                                 -1  +1
                 Val Phe Leu Asp His Glu Asn Ala Asn Lys Ile Leu Asn Arg Pro Lys Arg Tyr Asn Ser Gly Lys Leu
CTTTTACATT TCAG TT TTT CTT GAT CAT GAA AAC GCC AAC AAA ATT CTG AAT CGG CCA AAG AGG TAT AAT TCA GGT AAA TTG   6393
               ↑

Glu Glu Phe Val Gln Gly Asn Leu Glu Arg Glu Cys Met Glu Glu Lys Cys Ser Phe Glu Glu Ala Arg Glu Val Phe Glu
GAA GAG TTT GTT CAA GGG AAC CTT GAG AGA GAA TGT ATG GAA GAA AAG TGT AGT TTT GAA GAA GCA CGA GAA GTT TTT GAA   6474
                    38
Asn Thr Glu Arg Thr
AAC ACT GAA AGA ACA G TGAGTATTTC CACATAATAC CCTTCAGATG CAGAGCATAG AATAGAAAAT CTTTAAAAAG ACACTTCTCT TTAAAATTTT   6570
                   ↑

AAAGCATCCA TATATATTTA TGTATGTTAA ATGTTATAAA AGATAGGAAA TCAATACCAA AACACTTTAG ATATTACCGT TAATTTGTCT TCTTTTATTC   6670
        39                      46
        Thr Glu Phe Trp Lys Gln Tyr Val
TTTATAG ACT GAA TTT TGG AAG CAG TAT GTT G G TAAGCAATTC ATTTTATCCT CTAGCTAATA TATGAAACAT ATGAGAATTA TGTGGGTTTT   6763
       ↑                                 ↑

TTCTCTGCAT AAATAGATAA TATATTAAAC TTTGTCAAAA GGACTCAGAA AGATCAGTCC AACCCTCTAA CCCATATTGG ATGGTGATAT ACTACAGGGT   6863
TATGCCAGTG TGGGAACTAT CGCTGGTAAA TAAGTTTAAT CCTCCCTAGG GCTTCACAAA GAACATTGTT CCACCCCAGG AGGGTGGAAG GAAGAAACTG   6963
AAATGATTGT GTCTTAGAAC CTAATGAAAG TTTGCATTCC TCAGTAAAAT CAGAGACTGC TGATTGACTT AAATGTTTAT AGCTTCAAAG TCCTCCTCAT   7063
TATCATGGCC CAGAAGCCCT TCCATGATTG TCCTTCCCCA CCCTCCCCAT TACCCTTCTT GCCTCCTCTG CTACTTCTCT CCTCGCACAC TGGGCTCCAG   7163
CCACCCTGGC CTTCCTGTCA CTTCTTGCAC ACTCTAGGAA TGCTCCCACT TTGGAGGCTT TATCTGGCTG TTTCTCTTAT TTGGCTGTTC CCAACTTCCT   7263
GTGGGCTGAC TCCCTCACCT CCTTCGGGTC TTTGCCCAAA TGTTACCATC TTAATGAGGC CTACCTTCAC CATCTATTAA TACTTCAACC TGCCCCAGTA   7363
GCCTTACCAC TCTAGACACC TGTACAGAAC TCCACTCTAC TTTTTAACAG AGCTTTTCAC CATCTAATGT ATCATATAAT TTCTTACTCA TACTATTTAT   7463
CATTTATTTT CTCCTACTCC ACTAAAATGC AAGTTTCATG TTGGCAGGGA TATTCAATTG TTTTGTTTAT TGATATATTC CTAGCACCTA GAACAGTATC   7563
TGGAAAAGAG GTACTCAGTA AATATTTATC AAATGAATTG ACCAAAAGAA GGAAAACTCA AAACTTTAAT GACAACTAAC TTTAAAGCTA CAATAACTTA   7663
AAATTCAGAG TAGGATTTTG AGGGAGGGTA AGTTTCAAAG ATTGACTTAC CTAAGACTAT CTGCATAAAT AAAAAGAAAT TAATCCAGAC AACAAATTCA   7763
```

FIG. 8D

```
CCAACTTCCA TCAATTGGAA ATCCAATTCT ATTTTCTACA GTTTATGTTC TGGAGACACT ACTGGACACT CTTTTACTCT CATAACTCAT AACTCCTCCA   7863
CTTTTGTTTT TAAATCATGA GAGAAAAAGA GTTGACTCTG TTATATTGTT TTATCTACCT TTCCTTGATC TTAGAAACGA ATACTACCAT ACCAGCTTCT   7963
ACTGAGGTGC CCCCTAAAGT TAGTCCAAAT AGGTCTTTGC AATCTCCATT CCCGCAGAAT TTAGAACTTT GAATCACATG ATTTATTTCT AAAAGTAAAT   8063
CCATGCCGAT TTTCCCCACC AAAAAATTCC TGACTATTAA ACTCCTACAA TCCCTTCATT GCTCACTCCC CACCCCCAGG ATCATATTTT AAAGTTGGGC   8163
CCTTGCCTTT TGGGTCACAT AGGTACACTG TTTGCTATAC CACAGGTATA GCTATCTGGA AAACATGGAG GGTATTATTC TGTTACTACT GCTTCGTCAA   8263
CCAAAAAATA AAACAAAACA AGAACAAAAA AGAAACAAAC TCCCTGCCTC TTTTCACTTG CAGTCAAGGT TCCTAACCAC TACAAAATTA GCCTATGTTT   8363
CTTCTTGCAC ATAGTAGAAA CCCAAGCTTC TCACTGCTGT GCTATTCTGT ACCATCAACT CATCACATAA AGAGCCTGGT TGAAGAATGA TTGTCCAACC   8463
ACATTACTAG CATCTGTCAA GACTTTCCAG TTTACAAAAG GCCTATCACA TTTAACCCTC ACACCATCCT TGTGACCAAA GCATTATTAA CTCCATTTTA   8563
CAGGAGAGTA AACTGAAGCT TAGGGAAGTT AAAAGAACTG CCAAAGGTCT CCCAGTTGGG GAGTCATGAA GCCCAGAAGA GAAGCCAAAT TCTCTGCTGC   8663
TCAACCCCTT GCTTTCACTA TTACACCTCA GGGCCTTCAA ATCTAAATGC AGTTATTCAT TAAACAGGAA CCTGGTAGTC TTAAACAGGA ATCTCTCACT   8763
TGGTAAGATC TTGTCTCTTG TTGTATTTGA CCCCAACTGT CTATGGCTTT GCCTGAACCC AAAGTACACA CAGCCTAGAA ACCAAAGGAG AACCAAATGT   8863
GGGATAAAAT GACACTCATT TTAACGACAT GTCTCAGCAA ATGAGTTCCT GTGTAGCTGG CTGAAAGCCC AGACCCTTTC AGTAAAACAT CCTGAATAAT   8963
TCACATTTGT TGGTCTATAA TATAAAGGGC AAATGTAGCT CATTTTTAGA CCAGTTCTGA ACATCAATAG TAACAAACCA GAGATAACCG ATTTTGTTTT   9063
CATAGAATTG GAACAAATTA GAGTATCTGT GCAAAAGCAT ATCAGATCTA GGAGCAGAGG GGACAAGGTG TAATTTTTAA ATAAGCAAAT TTTCCAGGGA   9163
GGGACTACTT ATGATAAAGG GATATTAGTC TCTTAGTCAA CGGAACCTGG ATACACGCTT CTGACAGAGA AGAGGGAGAA TAGGCAGGAA TCTACACACC   9263
AGATGTCAAG GAGATTTGCT TTAAAATACG ACTGATAATT AGAAATTTCT CAGTTTCCCC CTTTTCCCTC ATTCTTTGAT TCTTATTGTT ATCTTTATCT   9363
CTTACTCCTT TGTTTCTCAT ATATTGAGTC TTACAGATCA AGCTCCCATT TTTTTCTTCA GGGGTATTTT TCTAGTTCAA AGTGCCTACC ATCTCCCTTC   9463
TGGTTCTATT CATCCTTCTC TCCCAAAGCT CCTTTAGAAG TGTGGATTAA GGCAGAGCAC TAAGAAACCA GACTTAAAGA TTCCCTTCTC ATTCTGACTT   9563
TTCTCCTTTC ACCTATTCCT TCCTCCTGTT TTCTTACCAT CAGTGTCTTC AAAGGCTTTC AAGTACACGG TAAATGCAGA AACTTCAAGA AAGGCAGAAT   9663
GGAAACATAA CCAATGCATA CATAAATAAA GCACACTGTA GAATCTTTTT AAATTCTGTA TGATATATCG AATGCTGTCT CTCACATTAC CTAGACCATT   9763
TGAAACCGAA TTTGTAAAAC ATAGACTATC TTTAAGTAGT AACAGATGCT TCTGACATGT TTTCTATTGT CTTGAACCAT TACTGCATAT GATACATCAA   9863
AGTTAAGTGA CAATACAAGA AAGCAGATTC ATTTGCTCCC TGCCTAGGCC GTCAGTTCCT AAAGTGGAAA CGCCATATAT TATCTAGCTC AGTTTGCTCT   9963
ACAAGACCTG CAATAGAGCC TTGTGTGACA TAGAGATAAT ATTTGTTGAA GCAATTAAAT TTGACTTGGA ATTAACTCTG CCATCATTCT ATAAGGAAGG  10063
ATTGAAAATC CTTCTCACCC TGTGCTGATA TAGTACCTTT CTATACAAAA ACGTCCTTCT CCCTCTTCCC TTGGATTGCA TAAACTATGT ACATGCCTTC  10163
CTGAGGGGCA CTTTTCTAGG ACAGTGTCAG CCTAAGGATC TTTGTTTGGG TGGCTTTTAG AAACTCAGGA AGACAGGAGC ATCATATGCC TATAGGCAGC  10263
TGGCTTCCAG GTCAGTAGTT TTGCTCTGAC CCTAAAATCA GACTCCCATC CCAATGAGTA TCTACAGGGG AGGACCGGGC ATTCTAAGCA GTTTACGTGC  10363
                            47
                            Asp Gly Asp Gln Cys Glu Ser Asn Pro Cys Leu Asn Gly Gly Ser Cys Lys Asp Asp Ile
CAATTCAATT TCTTAACCTA TCTCAAAG AT GGA GAT CAG TGT GAG TCC AAT CCA TGT TTA AAT GGC GGC AGT TGC AAG GAT GAC ATT  10450
                              ↑                                   84
Asn Ser Tyr Glu Cys Trp Cys Pro Phe Gly Phe Glu Gly Lys Asn Cys Glu Leu
AAT TCC TAT GAA TGT TGG TGT CCC TTT GGA TTT GAA GGA AAG AAC TGT GAA TTA G GT AAGTAACTAT TTTTTGAATA CTCATGGTTC  10537
                                                                         ↑
```

FIG. 8E

```
AAAGTTTCCC TCTGAAACAA GTTGAAACTG GAAAATGCAA TATTGGTGTA TCATAATTTT TCTTAAAAAC ATACCTTTGA TGCTTATAAA CATTTCATTT 10637
GTAGTGATAG TTTTCAGGAT ATGAGTTCAA GAAGCTACAT TAAAATCAAT AACAATATTT GGTAACTAAT ATTAAGTAAT AATGATGTTC CGACTCACCT 10737
TATTAATCTT TAATACAACC GTATGTGGTT AGTACTATCA TTATGCGCAT TCTATGCAGA TGAGAAAACC GCAACTCCAA CGGCCAAAAA TTACAGAGGC 10837
ATAAATGGTT TAGACAGGAC TTAAACTTCA GTGTGACCAA AACCCATGCT TCTAACTACT ATATTCAAAA CTCAGAGAAA ACTGAACCCA GAAAATTGAA 10937
ATCATGACTA AATTGCTATC AACATAGGTG AAAGTCAATT AAGTACAGAA CTGGAGTATG ACTGGCCAAT TATCCCATAT AATGGGAATT CTCCACATGT 11037
ACAAACCACT TCATATGCTA AACTTGTTGA CAACATTCAA AGCTCATCCC TGAATTTGAC TATATTGATT ACATCGAAAA TGTTACATAG CAACCTTAGA 11137
ATCCTTGTGT ACCTTTTCTT CTCAAAGCCT AGATTATTTC TTTTTCCGAC GTTTTCAGTA ATTGGAGCAG TAAACCCCAG TGTCCCTTAC CTACTTGTTT 11237
ATTACCTCCA GATGCAATAT TACTGGTACT GTGATTGAGA AACGCACACA GTGCTAATGA GGAATTCACT TTCTACTCTG ACACTCTGGA AGAATAGAGA 11337
TGCAATCCTA AGGAAGAATT TAACACCACA GGCTACATGA CTAAGGATAA AGAGTAGAAA ATTAGCAGGA CTCTATTAAC CGATTACAGC AATCCACCTG 11437
ACAGATGAAA AAGGCATGAA ATGAAATGAA ATGTAGCAGC TACACTCGTC CTATTGAGAA AGGAAAAAAG TCACCTGTAA TGTTGTTCAG AAATCCTTTC 11537
AGTACTAAAA AATTCATTGA CCATCTTCCT TTAGTCTCGA AAATTTCTTA GAAGGTAAAA AAAGGAAAAG GTGACAGGGC AAAGACATTT GAAAAGAAAG 11637
AAAAGAGTGA ATGAACTTGC ACACCTGGCT TGGACTCCCC ATTCCCCTTA GGTTTCCATT GTGGGGGACA AACTAATGCC TGGGTTACCT TTCTTGAGAG 11737
TGTGTTAATT GATTCAATAT CTCTGAAGTG CTACTTTCAT CTGAAAGGTT ATAATTTGAA ATTCAGATTT ACCTGGATAA ATTTGATCTT GCTATTATGG 11837
AAACCTCTAG AAATCCTTGG AGTAGTTACT CATTATCAGC TTAAATAATA TAGCCGGTGG AGCTGAGGGA ATGAGTAACT CAATTAGTCT CAGTTACAAC 11937
TGAAGGGCAC ATTGTTGTAA ACTATAATTG AAAACATAAA TATCTTTACC TAGTTTAAAA AATAAAGATG CTTTAAAAGG AGGAAGGGAA TAGCCCTGAG 12037
GAATGTAAAT ATAAGCACAA AACTTCTACA ACAGAGTTTG CTACGTGTGT GGCTGTGTTC CACCCAGCAA AAATGCTAAG TCTACAACTG ACACAACTTG 12137
GATACTCTCA TGTTCCCACA TTTTGGTTTG GTCAAGGCTG TGCAGTTGTA CTGCAGGCCA CCACCACTCC TGGCCTCTAC AGTATATTGA TCTGACCCAC 12237
CAATCTGATC AAGGTTTAGA AAAATATTTT CAGCCCAGTT AGCTCACAAA CAAAATGAGA ATTCCCACAA ATTGCTCTTT ATCTCAGACA ACAGAGGAAA 12337
GCTACAGCAA AAGCATAAAC AAATTACCAT TTAAGTTTGT TGCTTCAAAT TAAAGACTAA TTGCAACAGC TACTAGATAG CACAGTTTAT GGGGCATCTC 12437
GGCCCCAAGT CTTTTGTCTT ATAAGGTCTT GAAAAAAAGA AAGGAGATTT TCATCAATAA GAGTTTTTTG TTATCTTTTT CCCTTGTTCA TCAGGCCCTT 12537
CACTGCGAGA GAGAGGTGTA AACGTTCAGG GCATGCATTC TAGTTAAAGA ATATTAATTG GCTATTGGGT CCCTTTGGTT AGAATAAAGA CCTCTGTATG 12637
ATGTCCCTAG CTGTACATCA AACCCAAATA TCTCTCAGAT AAATGAAGGT CTGTAAGAAT TTGGTCATTC CTGTCTCTTC TAAAGAGTAA CAGAGGCATT 12737
TTCCCGCAGT AAAGTAGAAT GGAAAGAAAA CAAAAATCAC AAGCCTATAA ACACCTTCTT CAATTTTCCC AGCATGTCAC AGACACTACT GTCTTATTTA 12837
CTACGTATTT CTGAGGAGTA AAAAAAGGAA ATATGTTGAG TTTAGCTGAA GCACAGCATA TTTTGTGGTA AACTTGTTAA ATAAAACATC TTTTGTCCAA 12937
GCTTTGGTTG TCACACAAGT GGATATATCA GGAAATATAA AGGCAGAATA AACTAAAGCA GAACATACTA ACATTTGTAG TAGGCATGAA GGGAATTAGA 13037
AAGTGTTTGT GTTAACATGG AGGGAGGGAG AACAGATGCT TTGAGATGTT CTTCAACAGA TATTCTAGGC ACTGAGACCC CCTTCGGGAC CAGAGAGAGC 13137
CCATATCCAC CACAGTACCT GACACATAAA TGCTCAGTAA TTGATAAATG AGTCCCATTC TAACTGTTCC TTAGCCCTGC TCTATGGAAC TCTCCCCTGA 13237
ATTCCTTGTG CCATTATTTT ATTTCTGGAA TCTTCAGCCT TTTAGCTGAG GGCAAAAGAT TGCTGATTAG GAAGCAATAT TTCCCACCTC CTGCGCAAAA 13337
CAAGCCAAAG ATCAACAGCA GCAGCAACAT ACTGAGCCCT AAAGGGCAAT GACAAATGTG GAGAATGATA CAGAGGTCTG GTTACTTCTT AGCCAATGAC 13437
ACAGAATCAC AATTGAGAAA ACACAGAGTT TATTCATTCC CATTGTGCAT GCCCTGGACA AACCAAGCTG CACCTTTCGT AACTTATCAC AATCTCATAT 13537
TGACGGAACA CTTTCTACAG GTAATGTTTG ATTTGGCTGA ACACTTTAGC ATTGCTTCGT AGCAACAAAA TGATAGCTAG TAACAGAAAA AGATCCAGGG 13637
ATATTACCAC TGTTAGTGAG GAGAAAGGCC TTTTAATTAA TTAATTAATT AATTAATAGG ACCAAGTGCC ATCTTTTTGG ATCATGCCCT TAGTGGATTA 13737
```

FIG. 8F

```
TTGGTAGCAA AGGTTAAAGC TCAAGCTGGT TCCTTTGTCC CCCTGGCAAC AGTTGATTTG CCTCCCTTAT CTCCTGAAGT ACCGTAAGGA CTAAGAGCCA  13837
ATTATTACAT TTGGCTATGC TAGCATATGT AAAATAGAGT TTAAAAGTTT AGATTCATCA CTCAAAAATT CATATTCTCC AAAACCATAC AGTCACTCTG  13937
TTAGCCTGTG TTCCCCCAGA AAAAAAGTCA CAAGCTTATT ATTAACATGT GCAATCCAGG GGCAAGAGAA AGGAACTGAA GATGAGGCAG AAAGGAAAAG  14037
AAAGCCAATA AGAGGATGAG TTATCAAACT ACTCGTTTCT TAACAGCAAC TGATTGCTTA ACTTCCTGGG ACTGTCTCCA ATAAGTCAAA TTGGCCTCAG  14137
GTTAGTCCAC CTGAGTGGGA AGAAGCGGTG AAAGAATTTG TCTGTCAGTA TCTGTCTCTC ATTGGTTAGA AGTTCGACTT ATGGGGAATT AACTCCCTCA  14237
CATTTCCTAG TTGGATAGCT TGGGTACCAG AGGCATATGG CATCCATGCT CAGCATGAAC AGGGAAGCTT CAAGGCAAAA GACACATAGT GCAGCTATGA  14337
GCCAAGGCAA TTCAAGGATA CACCCATAGG AGGCTGGTTG ACATCCACCC AGAGCTAATC ACCACCATGC TGGAAAAAGA CACAGGTGAA GCTGAGAAGA  14437
ATGAAGGTGG TGCATAGGAG GTATCTAATA CAGTCACTCA TTTTCAAACT TTCCATGTTA TGATTGCACT GACCACTGAG GATTTCTATT GAAAGTTTTA  14537
CTGTTGTCAA ACACGTACAC AAGGGGAAAG GTGTCTTACA TTGTTTATGT TCCTGTGCTG CTCTAGAAAC AGAAATAGGC TCAAGAGCAG AGCCTGTTTT  14637
TCTTAATTCA GCAGGTCTAA GCTAACAAGT CCTGAAACAT GGTACTTCCT GTTATTGGTA TTGCATAGGA GAAACAAAGG GAAAGCACAG TAATTAGAAA  14737
ATACAAACAA GATGGCAGGA ATAAGCCAAA AATATCAGGA AACACAATTA TTGTGAATTG GGATTAAACT AATCTATTAA TAATGACAAC TTTCAGCTTG  14837
GAGTTAAAAA TTTAATTGTA TACTGTTAAC GAAAGTGATA CCTAAAATAA AATTACACTG GGAGGCCAAA ATGAAGGGAT GTGAAAAGAA CTATCAGGTA  14937
AAAACTAACA AAAAGAAACT AGCAAAGCAA TCTTAATATC AGACAAAATA GAATCCAAGA GGAAAATCAT TTCAAAAGAC AAGAGATTTT TTTTATTAAT  15037
AAGGGGAATT GCATAGGAGA GTAAAGAAAA TGTGGGCCAC TGGAATGCTT AGCACTAATG ACATATTGGT CTTTGGTCTT CAGTTACCTT ACAGGACCCT  15137
ATTTCATTCT CTTATGTTTG ATATGTAACC ACCTCAGCCA GCTTCAAGTT GCTTTTTGGC CCTAATGGAC TTCCTAGCAC TATAATTTCT TTTTTTTTAA  15237
ATGTTTTATT TTAGGTTTAG GGGTACATGT GAAGGTTTGT TACATAGATA AACATGTGTC ACAGGGGTTT GTTGTACATA TTATTACATG ACGCAGATAT  15337
TCAGCTCAGT ACCAAATAGT GATCTTTTCT GCTCCTCTGC CTCATCCCAC CCTCCTCCCT CAAGTAGACT CCAGTATCTG TTGTTTCCTT CTTTGTGTTT  15437
ATAAGTTCTT AACACTTAGC TCCCGCTTAC AAGTGAGAAC CTGCAGTATT TGATTTTTGT TCCTACGCTA GTTTCCTAAG GATGATAGCC TCCAGCTCCA  15537
TTCATATTCC CACAAAAGAC ATAATCTCCT TCTTTTCTAT GGCTGCATAA TATTCCATGG TATATATGAA CCACATTTTC TTTATCCAGT CTGTCATTGA  15637
TGGGCATTTA GGTTGATTCC ATGTCTGCTA TTCTAACACT GTAATTTCTA AAGACTTCCA GATTCTACTT TTATAGGTAA CCTGTTAAAC AGTCTAGCTC  15737
TGGAAGCCAA GCAATTTCTA GAATAACTAA GCAATAGAAA TTACACTTCA ATGCAGAAAG GCAGTATCTA CATGAGATTA TGAAATTGCG GTTGCTTTTT  15837
GTGTTCACTG AAAAAAATAA GTAAAACTGT AACTTTCAGA AAAAATGATT GTACATATAG AAAACCCAAA GCATCTAAAC AATTAAAATA AATAAGTATA  15937
GAAAGATTAC TGGATACAGA GTCAACATAC AAATATCAAT TGTATGTCTA TATACCAGCA ACGATTCAAA AATGATTTTT ATAATAGCAT TAAAAATTAG  16037
ACGCTTAGTA ATAAATGTGA GAAAGATGTG CAAGAACTCT ACATAAAAAA TTATGAGACG TTATTGAGAA AAATTAAGGA AAACCTAAAT AAATGAATGA  16137
ATAGGCAATG TTTATCATTA AAGGATACAA TATAGTAAAT ATATCAAATG TTTACTAATG GATTCAATGC AATACCAAAG TGCCAGCAGG CTTTTTTGGT  16237
GGTGGGAGGT CGGGCAGGAT TCATAAGCTA ATTATAAAAT GCATATGGAA ATGCAAAGAG CCAAGGATAG CCAAGACAGT TTTGAGGAAG AATAAACTTG  16337
TACTACTTAC ACTACCAGAT GTCAAGACTT ATTATCGAGT TACATTTATT AAGACAGTGT GGTACTGACA CAAGGATAGA CAAATAGATC AGTGAAACAC  16437
ACTAGAGTGC TCAGAAGCAC ACCTGTACAT ATATAAAGGC TTGATTTATG ATAGAGGTGC CAGTGCAGTA GAGAAGGAAA TTATTGGTGT TTTCAATAAA  16537
AAGTGATAGG TCAATTAGAT ATTCATATGG CATGAAGTAT GAAACAATAA CAATTTATAT TCATAACTTG CAGAAAGCAA AAATTTCTTA AAATACAAAA  16637
AGTGATCACC ATAAAGGAAA AGATTGATAA ACTGGACTAT ATTAAAACTA AGGACTCCTG TTCAGCAAAA GACACTACTT CGACTGAAAA GACAAGTCAC  16737
AGAGTGAGAC AAGATATCTG CAATACAGAT ACCTAATAAC TGAACCCCAT ACAGTGATGG TGGGAATTTA AGTTCGTACA ATCATTTTAG AAAATTGCTT  16837
GGCAGTATCT ACTAGATCTG AACATGTGAT CCAGTAATTA CACTCATAAT TATAAGCCAG TAAAAAGGCA TGTTTATGTC ACCAAAAGAT ATATACAAGA  16937
```

FIG. 8G

```
ATGTTCATTA CACTATTATA CATAAGAGCC AAAAACTGGA AACAAACCAA ATATCCATTA ACAGTAGAAT GAATAAATAA AAGCTGTAAT AGTAATACAG  17037
TGGAATACTA CACAGCAATG TAAATGAACT ACTGCTGTAC AAAACAACAT GGTTTAATCT CACAGACAAA ATGTTAAATG AAAGACACAG ACGAGTACAT  17137
ATTGCGAACT TCTGTTTATA ATTCAAGAAC TGGCAAGAAC TGTTTACTGT GTTAGAAGTC CAGGTAATGG TAACCTATAA AAAGGAAAAA GGGTGGAATG  17237
ATTGGGAGGG GGCATCTTCT GGGGTCTTGA TAATGTGCTA TGTATTGGTC AGTTTAGTGT TTAAACAGGC TCATTTACTT TGTGAAAACT TACACTAAAA  17337
TTGTGTGTAT TTTTTGAATA TATGTTATAC ATTAATAAAT AGGGTTTTTA AACCTGTAGT TCATAATTTA GTGAAAGTAG AATATCCAAA CATTTAGTTT  17437
TAAACCAATC AATTATAGTG CTACCATCAT TTTTATGCAT TATTGAGAAG TTTATTTTAC CTTTCTTTCC ACTCTTATTT CAAGGCTCCA AAATTTCTCT  17537
CCCCAACGTA TATTGGGGGC AACATGAATG CCCCCAATGT ATATTTGACC CATACATGAG TCAGTAGTTC CATGTACTTT TTAGAAATGC ATGTTAAATG  17637
                                  85
                                 Asp Val Thr Cys Asn Ile Lys Asn Gly Arg Cys Glu Gln Phe Cys Lys Asn Ser Ala
ATGCTGTTAC TGTCTATTTT GCTTCTTTTA G AT GTA ACA TGT AAC ATT AAG AAT GGC AGA TGC GAG CAG TTT TGT AAA AAT AGT GCT  17724
                                 ↑                                                              127
Asp Asn Lys Val Val Cys Ser Cys Thr Glu Gly Tyr Arg Leu Ala Glu Asn Gln Lys Ser Cys Glu Pro Ala
GAT AAC AAG GTG GTT TGC TCC TGT ACT GAG GGA TAT CGA CTT GCA GAA AAC CAG AAG TCC TGT GAA CCA GCA G  GTCATAATCT  17807
                                                                                                  ↑
GAATAAGATT TTTTAAAGAA AATCTGTATC TGAAACTTCA GCATTTTAAC AAACCTACAT AATTTTAATT CCTACTTGAA TCTGCTTCCT TTTGAAATCA  17907
TAGAAAATAT CAGTAGCTTG AATTAGACCA ATTAATTTTC TAGATTGCAT CATATTTTAA ATATAACTAT GTAATCATCT ACAACCTGAA TTCTTTCTGT  18007
GTCCAATTTG TCCAATTTTT TTCTCTAACA TTTATATCAC AAAGCAATTA ATTTGTGTGA TTTCTGCATA TGTATTTGTA ATTCATCAAG TCAAATCAAT  18107
GTAGTAATAC TATATCATAA AATATACACA AATAATTGAG TGATAGGCTT CTAGTATAAG GACGGTAAGT TTGAAGCATG ATTCTATCTG GGCTGGCTAG  18207
TTTACTCTGA GAAAGTTATT TTTTATTGTT GGGTCTTAAG CTGAGTTTAC ACACTTGGTG TCAGAATGAT TCCGGCAATG AACTGTTTTA TGTTCTGCTA  18307
GGCTGATCAG CACAATCTAT ATGGCTGTGA ACAAAACAAT GTTTCCCAGT CATACCAACC ATGCCACCAT TTTAACAGCT GATTAGTGTA TTCAGAACAT  18407
CTCCACTCCA TGTTCGTATG GCTGTTATCT AAAGATGAAA GCAGTAGACA CTTTTATTTT TTGAAAAATT TAGGCTCTGC AGGGTCAATT ATATTTGATA  18507
AATGAGGGGC TTTTTTGAAG CAAACTAGAT ATAATTTCTT TTGCATTTCT AAAGCCTGAT ATCTTATTAA TTGGTACATT AAATTGTGCA CCATTTCTCT  18607
GTAACTGTTT CAGTACCTGT CTCAGCACTA TACCAGGCAG AAGAAATAAA GAAAGAACCA GTGCCAGATC AGCTTGGTCA GGAGACCCTA ATCCTGCGGC  18707
ACTAGAGGAA TTAAAGACAC ACACACAGAA ATATAGAGTA TGGAGTGGGA AATCAGGGGT CTCACAGCCT TCAGAGCTGA GAGCCCCGAA CAGAGATTTA  18807
CCCACATATT TATTGACAGC AAGCCAGTCA TAAGATTTAC TGAAAGTATT CCTTATGGGA AATAAAGGGA TGAGTCTGGC TAGTTATCTG CAGCAGGAAC  18907
ATGTCCTTAA GGCACAAATC ACTTATGCAA TTGTCTGTGG TTTAAGAACA CCTTTAAGCA GTTTTCCGCC CTGGGTGGGC CAGGTGTTCC TTGCCCTCAT  19007
TCTGGTAAAC CCACAACCTT CCAGTGTGGA TATCAAGGCC ATCACGAGCA TATCACAGTG CTGCAGAGAT TTTGTTTATG GCCAGTTTTG GGGCCAGTTT  19107
ATGGCCAGAT TTGGAGGCCT GTTCCCAACA AACCAGAAGC TAGGAATATA TATCCTGCAA ATAAAATGAA GAATCTCTAA GGCTTCAGGG CCTGCCCACT  19207
TGTTCTTCTG CCTGGTTCTT CACATACACT GTCTCAAAGC TAGTCTACCT TGAGAGGAGC ATGAATATGT GTGTGGGTGT GTGTCTGTGT ATTTTAACCT  19307
TAAAAACCTA ACTTCCAGTA TAGACAGATG GCATACTAGC TAAACCCTTA CAAGTTCTTC TATGCTATAA AAGAGAAACA GAATTGAGAA CCACCTCCAA  19407
CTATTAAGTG TTATATTTGA ATATAGCCTT AGCTTTAGCA GAATAAGTAG GCCAAACTTA AAATAAGCTT TTCTGCCTTT TCAATGATAA AGGTCCCTTT  19507
```

FIG. 8H

```
TCTGTAGCCA TTGTTGATTG TGTACACTTA TACATAAGTA TTTTGAACTA ATTTCCTGTT TTCTCAACCA CTTGCTGTCT TCATGATACT TTGTCGCAGC 19607
TGGTTGCTAT AGAAATGTCT GTTACAAGGA ATGTGGCTTG AAGGAAAGTG ATAAATGAAA ATGAAATGTG AAGTGACTTT GTTTGACTAC AAATTCCCAT 19707
TCTGGTAGTC CCCAGTGTAT CAATACATTA TTTTTCTTTA GAAAATAAAC CAACCCAAGG AAAAATGGTG GGCAGGTCCT GGTGAATATG GCTGTGATAA 19807
TTATATTAGC AATCTCTTTG GCTAATATTT GAAGCCCAAA TAATTGAATC ACAATGATCT CTCCCCAGAA AATATATAAA ATGCACCTTG GAATCTAGAA 19907
GGCCTTTTAG TCTGCAAAAG AAACCTTCTT AATCATAAGC AGCAGAAGTC CCATTTACCA AATTGGAAAG TTAAAGTTAC AAAGCATCAA TCATCAGACT 20007
TCCATTCAGG GATGGCAATT GGGAGTAAGA CTTTTTAGTA AAGAAACTAA ACACAAAGTC ATTAGACTCT GTAAAAGTCT TACCAAATTT GATTCTGGAA 20107
CACCTATTCT ATTTCCGTAA AGATGATGAA TTCGGAGCCA AATGTTCTTT TCATGAAGGA TTTGAAAACT GTCCATGAAA ATAACGCAAT CAACCTTTTA 20207
GCTTGAGACT CTATTCACTG ATTAGATTTT TTTAAATACT GATGGGCCTG CTTCTCAGAA GTGACAAGGA TGGGCCTCAA TCTCAATTTT TGTAATACAT 20307
                                                            128
                                                            Val Pro Phe Pro Cys Gly Arg Val Ser Val Ser Gln
GTTCCATTTG CCAATGAGAA ATATCAGGTT ACTAATTTTT CTTCTATTTT TCTAG TG CCA TTT CCA TGT GGA AGA GTT TCT GTT TCA CAA 20397
                                                            ↑

Thr Ser Lys Leu Thr Arg Ala Glu Ala Val Phe Pro Asp Val Asp Tyr Val Asn Ser Thr Glu Ala Glu Thr Ile Leu Asp
ACT TCT AAG CTC ACC CGT GCT GAG GCT GTT TTT CCT GAT GTG GAC TAT GTA AAT TCT ACT GAA GCT GAA ACC ATT TTG GAT 20478

Asn Ile Thr Gln Ser Thr Gln Ser Phe Asn Asp Phe Thr Arg Val Val Gly Gly Glu Asp Ala Lys Pro Gly Gln Phe Pro
AAC ATC ACT CAA AGC ACC CAA TCA TTT AAT GAC TTC ACT CGG GTT GTT GGT GGA GAA GAT GCC AAA CCA GGT CAA TTC CCT 20559
  195
Trp Gln
TGG CAG GT ACTTTATACT GATGGTGTGT CAAAACTGGA GCTCAGCTGG CAAGACACAG GCCAGGTGGG AGACTGAGGC TATTTTACTA GACAGACCTA 20657
       ↑

TTGGGATGTG AGAAGTATTT AGGCAAGTTT CAGCACTAAC CAATGTGAGA AGGCCTCCAG AGATGAGCAG TTGGTGAAAG AGAGGCTCAA AACCAGCTAC 20757
CATACAGGTC AAGAAGAATT TGGCATTAAG GAAACAGCAT AGCAGGATTC CAGACAGGCA ACTGGTCAAC AACATGAAGG TCTGGAAGAA AGGTCGCAGT 20857
ACTCAGGTTC AGGGCACTAC TTCAGCTTCA GCCCTTGCAA AAACTGGTGA GAGTTGGAAA GTCTTTAGGC TAAGAAAAAT TGGATTATTT AAAAGGGGTA 20957
AAGAAAGGGA CTCAAGGAGG AAGGATTAAG GCAAGAACTA GGTTCCAAGA AACAGGGCAT GAGAGAGAGT CTTGATCTAC CACTATAGTT CTCGTGGTAG 21057
CATCAGAATC ACCTGGGAAC GTAGAAATGC AAATTCTCCT GCTCTACACT AGACCTACCA AATCAGAATA TCTAGGGGGT GGGGCCCAGC AGTCTGTGCG 21157
CAAACAAGCA CTGCAGGTGA TTTTGATGCA CATTATAGTT TGAAAACTAG GCCAGGTGCA GTGGCTCATG CCAATAATCC CAGCACTTTG GGAGACTGAG 21257
ACGGGAGGAT TGCTTAAACC CAGGAGTTTG AGACCAGCCT GGGCAACACG GCGAAACCCC ACCTCTAATT AAAAAAAATA CAAAAATTAG CTAGGTGTGA 21357
TGGCTCCCAC CTGTGCTCCC AGCTATTCAG GAGGCTGAGG TGGGAGAATC ACCTGAGCCT GGAAAGTCGA GGCTGCAGTG AATTGTGATC ACACCACTGC 21457
ACTTCAGCCT GAGTGACAGA GTAAGACCCT ATCTCAAAAA ACAGAAAAAG AAAAACACTG GCCCAAAGGA AATGAACTTG TTACAGAAGC CGGGGTTCAA 21557
AACACCAAAT AATGCACTTG TACCTAGTCC TTCCCGGGTG CTCTGCAGAC ATTTCTCCAA GCGTAGTCTG CAAACAACCT ACATATGTAG AATTACCTAT 21657
GCACATTTTT CATTTAACAA CCAAGAGCTA CATTTGTAGC AAAATCTGGG TTGTAACTTA GCCTACAGCT GAAGCCTAAG AGATTCCGTC TGTGAGAAGA 21757
```

FIG. 8I

```
AATAACCCAC CTCTTTGGCC CCCCTCCCCA GGCAGGAAGC CAGGATGGTC CTTATATAAA GTTGTGCTGT CCAATAGGTA ACCACTAGCC ACATATGGCT  21857
ATTTAAATTT AAATTAACTA CAATTAAGAG AAATTAAAAA TTCAATTCCT CAATTGCACC TGCCAAATTT TAAGCACATA ACAACCACAT GTGGCTAGTA  21957
ACTACTGTAT TGGAGAGTGC AAGCGGAGAT AGAACACTCT ATTACTGCAG AAATTTCTAT TGGATAGCAC TTATAATAGT TTAGTGTAAC TTAAAACTCC  22057
CTAGTTGCCA CAGTCATGAT TTAGTAGTAA TTTCATGGAT TTCTCTACTG AGGTTAGAAT CTCTGCCATT AGAGACTGAT AAATTTAAAG TTTGCAATTA  22157
TCAAACTGGT GACAATTTAA GCCAGAATCA GGTAATGTCC TCAGTTTTAA CAGCATTGGA ATTTTCTGGG ACTAGCTGTG TATCTATCCA GGATTCTTGA  22257
GAATGCCTGC CATTTTTCAA CATAATGGAT GTAAGGTATT ACACATATAC CTGGGGATGG GGAGGTAGGT ATAATTGCAC AAGCATTGTG GAGAATGGTA  22357
TCAAAGAGTG GCAGAACATC ACAATCAAGG TTTTCCCTTT CTTTTACCTT TGCTTTTTAA AAAGACAATA TTTGCTGGAC CTGATCTTAT AACTCATAAA  22457
TGGGACACTG TATGTTCCTT TTTACCTCCT CTGTTTCTAC TTAATTGCAC CCTATGAGGA CTGCTTCCCT TACCTACCAT AACCCCTTCC TTCACTCATC  22557
CATATCTTTA CTCTTCTTCA CAACTCTGTA ATATTGACCT TCTTTATGAA CCTTTCCTGG AACAATCCCT CTTAATGCAA GCACTGTTAT TATGCCTTCA  22657
ATGTATTTAA TATCCATGTA TCTATTCTCT CTAATTTTGT CATTTTGTGT TCTCATGTAT TTTCATTCAT TATGTGTCCA ACTTCCATGG ATAACATGGT  22757
TACAACAAAA GATCCTACTT TATGACAATT ATCTTCCTTG GGTTTGTGGG ACATAGAACA GTGCACAGAG TAGGGGATCC AAGAACCCAG GAGAATATAT  22857
TAGCTAAGAA GATAACTTCC GTTTTTAAAA GTCCAAGATT CAGGAGATCA AAACCATCCT GGCTAACATA GTGAAACCCC GTCTCTTCCA AAAATACAAA  22957
AAATTAGCCC GGCGTGGTGG CAGGCGCCTA TAGTCCCAGC TACACGGGAG GCTGAGGCAG GAGAATGGCG TGAACCGGGG AGGCGGAGCT GGCAGTGAGC  23057
CGAGATCCCG CCACTGCACT CCAGCCTGGG CGACAGAGCG AGACTCCGTC TCAAAAAAAA AAAAAAAAAA AAAGTCCAAG ATTTTAAAAA AAAAAAAAAA  23157
AAGGATGTCT GCTTTGTGAG TTTAGCATTG TCTCCTTGTC ATTCCAGAAA TGAAATGGCA AATACATTTA AATCAGAACT AAAAAGGGGA ACAGGGTATA  23257
AAGGCTCAAT TTAGTCACAT CATTTCCGTT TCTCACCCAC CCCCTTTAAA CCAGATGTTT GCCAATGCAT TAACAATGCA GATGTTTCCT GAAAGAAAGT  23357
TTAGTAACTC AAGCAGACAC CTTATTTTCT TTTCAAGCAG AAAAGACTAT GAGATGGTGG TTGTGGTTGT TCCGGGAGGG AGAAGATATA AATGATACAC  23457
ATTATTTCAA ATCATTTCAT GACCTCACTG CACACTTATA GTTATTGTAC CTGTTGTCTT TTTGCTGTCA AGCCTAGCTA AGATCATTTG GAATGTTCAA  23557
GATCACTCAT ACATGCATGT GCACACATAC ACATGCACAT ATGTTCACTC CCTATTTCAT CCACATGAAC TAAGATTACT GATGTGTACA GATTCAAAGC  23657
ACTTTTATTC TTTTCCAAAG GCAAGAAGCT GAGCTACTTT CCAGAATAGT TGTGAAAGAC CCTGTCATAC TTCTGCATTG TTTCCTCCAC ACCACCTCCA  23757
TCCAGTTCCT TATGAATGGT TACTGGTTTT CAAAAATATG AGATAAATTG AGTGTATAAA AGTCATTTTT AGACAAAATG AAACAGGAAA TGAAAGAAAC  23857
CAGAATCTCT CCTCATTTGT GGATGGGCCA GCTCCACCAT GTCATGGTTA ATCTGCAGGG AGGAAATACT AGATTTGATT GCAGATCAGA CTGCAGCAAA  23957
CCTGCTGTGA CTAAGGCATC AAGAGAAAGC AAGCAACAGA CTGGGGCTTC AGTGGTGAAA ACATTATATA TCTAGCTTTG AAATATGAAA TACTGTTTAG  24057
CAGTGTCACC TAGAAAAGAG TGTTTCAAAA TGCTGATGCT TCATAAGAAC CTTTCTCTTC AGAGTTGGTT TCTTTTATCT TTCAAATTAG CCAGGGTGGG  24157
AAATAAAGTG ATCACTTGGT GAAGAAATCT CACAAAGAAG AACATAGAGA GTTCACTTTC ATCTGGAGTA ATGAACAGAT TGAACAAACT AGAAATGGTT  24257
AGTCTGTTAA AGAAAAGGTG TAGGTGAGCT GTTTGCAAGA GCCACAAGGG AAAGGGGAAG ACAACTTCTT TGTGGACTTA AGGGTGAAAG TTGCAAGCAG  24357
GCAAGACGAT TCTGACCTCC ATTAAGAAAG CCCAAACCAA CCAACAACCA CTGGGTTGGT TACGCAGGTT GGGCAGCATT GGGAGCAAAT GTTGATTGAA  24457
CAAATGTTTG TCGGAATTGT TGACTTAAAG AGCTGTTCTG TCACTGGGGA CAGCAGCGGC TAGATAGCCC CATTCAGGGA GAGGGCATTT GTTCACCTGG  24557
CCAGAGATCA GAGCAGGCTA AGGGACTGCT GGGATCCTGT CCAGCTTTGA GACCCTACAG AGCCATGTTC ACCTAGCACG TATCCCGTCT GCGGTCACGG  24657
TCATTTCTTA CCTTATTCCA GGGCTTTCAC CTCAGCTTGC CAGGCTGGAG CCAAGGGCCA ACGCAGCCGC GCCTTGTTCG CGATGGTAGC TTCCCAGGAG  24757
CCCCCTATGG TTCCGGAACG CGCTGCCGGC CCCATCCTGT TTGCTACCTC CTAAAGCCAA AGGCACTGGC GGGCCGGGCC AGCTTCTAAA GTCGCGCAAG  24857
GTTAGAAGGT TCCGGACAGG AACGGCGTGA GGCCAATGGA AGGAGGTACT TCAGTTTCCC TCCAGATGCC CAGCGATGGG CTCAGAGCTC CTTGAGAACT  24957
```

FIG. 8J

```
CGGGAAAGGA AGCAGGGTCT CTGAAGAAAT ACTTCAGGAG TAGAAAGAGG AAGCTAGAGG GTTAAATGCA CTACACAGGA ACAGAAATGA GTTTTTCTTA 25057
GAGTTAGTAT ATGTCTAGAG GTGTAGTAAA CTAAAACAAG TCTTGAATTG CATACCGCCA CGTAGGGAAG AAATGAAAAC CTTTGAATAT TAGTGAAAAA 25157
AGGGAAACTG CAACGCCTGT ATTACTAGAT AGCTTTCATC AACAGCTCAA AACCGACAGA TTTAAAGAAG CAACACCGCA TTTTGGCTTT CTAAAGCTTT 25257
AATTTGGTTT GGATCCCATG CCCATGACCC TGCCAGCTGA CAATTCTAAG CATGCGCAAA CTGGCCCCAA AAATTCCTCC CACATTTCCG AAGAACTATT 25357
TGGCCCTTTA TGTGAAGTAC CTGGTTTTTC CATTTTCTGT TTTACCATAG GCCTCAGTTC GGTGTGTGGC GTATTTATTC TACATTTAAC AATTTGAAGA 25457
TCATTCTATT AGATTAAAAA AAAAGAATAC AATGGAAGCC AAGTGATTAA GCTTTCCTTA TGCTTATATT AAGTTGTAGC ATATGCATTT ACCGATAGTT 25557
AACCGTATTA ACCTACAGAA AATGTCCAGG GAAATGGTCT ATTTCTTATT CTATTTTTGA CCTAAAGAAA ATCTTTAAAA TGTCTTAGCA TTTTCCCCAG 25657
TCTCCATCCA CTTCCCTCAG CTTTGGCCTG AAGCTATCTT TAAAGGTACC CTGTACAAGC TCTTGCCCTG TACAGCTAGC TACAGAGATT CAATCCTTTC 25757
TGTTCGATTA GGACACATCT CAGTGGCAGA TAACATGCAA AGTTATTATA TGTATGAACC AGAACTTGTT TTTCCTTAGG GGCCAGGATG TTACACTAAG 25857
GTCTTAAGAC TATAGTAATA TCTTCACTTG AAAAAGCCCT CTATTATTCC TATCTCAGAT GATAAAAATT CAATTAAGAG AAATAAGAAC GTGACATGTG 25957
TAATCGCACC TGGCTCTACA AAGCTAGTCT GGACAGACAT TTAAACAATT ATCCTCTAAG ATTATTTGAT GAAATGCATT TCAATGACTA GTTAACCATT 26057
AAAAACCAAA GTGAGCATCC CATCTGTTCC CAGTCAAATG ACCTAGAGCA AAGGACTAGG CAAACCACAT CTGTGGGCAT AGCAAGCTGT ACATCACAAA 26157
CAAATGAATT TGCTTTGTAT ATGAGTGAGA GCAAACACTC TTTATTGTAC AACTTGGGTG GGTAAGTAGG GAGAATAATG GTTTTACTGA AATCGCAGGT 26257
AACGGTTACG TTGGAGTTAA AGGTTAGGAA GAAAACCAAA GGGTAAGAGC TGTTGTTCTG GGCTGGCATT GTCAATGAAG AGCATAAATT CAGATGTGAA 26357
TGTATATTTT GTAGAAGCAT GTGTGTTGTT GGTTTTTGTG TATGTGTGAG TCTGAAAGAG GGAAAACAGG CTCCCATTAG ACTATGACTA ACAAAAATGT 26457
TTGACAGATT ATAACTCAGA TGTCTTACTC AGAGCATATG CCTTCCCATT TTCCCCATTA TTCCCCAACA TGATGTCTTT AAGAACTTGT CCTTGACCGA 26557
GCAGACATCT CATACCCCAA ATAGCTAATA TTTTGATAGC TATGATCCTG AACGGCCAAA CATTCCAAAA CCAAGTAGTT TGTAATATCT TTAATGCAAA 26657
TATATTTTAG GCCTTTTCCT TGGCAAGGAT GTTTGGTCAG GGGTTGGCAA AAATAATGCT CTTCAGACTT AAAAGAACAC AACCATATTT CTTAGCCATC 26757
CACCAGAAAG TAGTAGAACG CTCCAGGAAG CAAGTCTTTG TCAGGAGTCA GACTAGCTAC ATCATAATCT CTCTGCCCAG GGGCTGTGGA TGTCATCCAT 26857
CCTGGCCTAA CTAGCCTACT GAGCTGAGAG ATGTCCAATT TCCCCCCAAT ACACTAACCA GAGGAGAAGG ACCGTGATAT CATTGCATGT GAATTCTTAA 26957
TTCCAATTGC TTAAACAAAT ATGTTCAGTT GTAACTATCA ATACCAGTAT ATAACAGTGT TGGCCAAGTT TTATTGATGC TGACAATCAA TTGGAGTTAC 27057
AGCCAGACAC ATGGTCTTAT GACCGGCGTA CTTACGCAGG GCTTTGCACT GAGACAGGTC GTGCATCTGA GGTTTACTGC TTTGCATTTT TGTTTTGTAA 27157
CTGAAGTCTG ATGAGACAGC CAGAGCATGT GCTACCTAGG GACTTGAATC CCTGCAGCCC CATTTCACTT CTCACCACCT TCCGGGGTGG TTTCTCGACC 27257
TCCCACTCCC CTACCACCTG GTGCCTTAGC CAGCCCTGGC TCTCCCTCCA AACACCTGCC CAATGAGCAC TGCCACCCCA TGGTGCCCAG ACATGCTCTC 27357
CCTCCTCATC CCTACCTAGC TACCATTGCC ACTCCCCTCC CCCAGCGGGG ACATGGGCAT AGGAGCAGGG AGAGTTAAGG TTGGTCAGGT GCACGTGCCC 27457
TATGCTATCT TGGAAGGGGG CTTGGCCATG TGGCATCTCT GGACCAAGAA TGCGCCACAG CACATTTGGA GGGTGAATGG TGGGGGCACA CCCCTTGTCC 27557
ACCTCTATTT CAGGCATGGA ACACATCCTG GCATGAAAGT TGCAGTCCCT TGGGAATCAC CTCTCCACCT TGATTGCCAC AGTAGGCCAG TGACAAGGGA 27657
AGATTGACAC ATCATCCCTG CTGGGGCCCA GTGTCCTGTG GCTGGCAGGC AGGGGATCCT AAGGACATGT GGGTCTTAAA TTGTAGGGTG CACTTCCTGG 27757
GCACCTTTGA GGGTCTGCAC TGCCCCAGCA AATATCCCCA TGCTAGAAGG AGCAAAATAT TAAATGGCAA ATTTTAAAAA TGTAACAAGA TGGGTTGCAA 27857
AAGAGACTAC AGAGGAAAGC AAAAGTTTTG TATTTTAGTA TCTTCCATGG CACTTTTCTT CCTAGCTTTT GAACAAGGGG CCCCACATTT TTATTTCTCA 27957
CTGAGCCCCA CAAAGTATGT AGCCATTCCT GCCCGGAGTG AGGACTTTTA AAACATAAAG ATTATCAAGT CTTGGAAATT CTGATTCAGT AGATATATAA 28057
CAGGTCTCAA ACTTAATTAT GTAAAGAATA TTCTGGAGAG CTTCCTTTTA CCCAGTCCCA CCCACCAAAT ATTCTGATAA ATTAAGCTTC GATTAGCCCC 28157
```

FIG. 8K

```
CAGATCTGCA TTTTATAAGG ATCCCCAGAT GATTCTACTG CAATTGGTCC ACAGACCATG CCTGGACCGA ATTTGGGTGC TTAGGAGCAC AAATTCTGGA  28257
GCCGGGCAGA CTTGAGTTTG CTTCCTAGCT TTACCAACTG ATCTCAGGGG AGTTAATGTT TACCTCTAAA CTTTAGCTCA TGCATCTATA AATAAATATA  28357
TTAATATCAT GTCATAAGGA TATTATGTTG TATTAAATGT CTTTAAAACA CCACAATGAT TAGCCCAAAG TAAACACTCA ATAAATGTTC AAAAATTTAG  28457
GAAAATTGTT AAGACTGGGT TGTATGCACA CTGGTGTTTA TTATATTATG TAGTTTTTTC TGTATTTTTA CAACATTTCA GAATTAAAAG CAACAGCTAG  28557
AAAAAGAGGG AAATGGCCGG GTGCAGTCGT CACGCCTGTA ATCCCAGCAC TTTGGGAGGC CAAGGCGGGC GGATCACGAG GTCGAGAGAT CGAGACCATC  28657
CTGGCCAACA TGGTGAAACC CCATCTCTAC TAAAAATACA AAAATTAACT GGGCATGGTG GCATGCGCCT GTAGTCCCAG GAGAATTGCT TGAACCTGGG  28757
AGGCGGAGGT TGCAGTGAGC CAAGATCTCA CCACTGCTCT CCAGCCTGGT GACAGGGCAA GACTCCGTCA AAAAAAAAAA AGAGAGGGAG AGCCAGAGTA  28857
TGAAAAAGGA AGTCAGAGCC CTTTAATGAG TCAGCTTTGT AGGTCTCCAG GTAGGAGGCT AGTGCTTCAG TGTCTAGGAC ATAGTAGGTG TTCAGTAAAT  28957
TAAATTCAGG ACAAAAAGAA CATGCCCCAA GGACCATCTG ATATCCACTT AAAGTGATGG ACTACCTCGT TTCCCTTGTT TATGAATGGG TTCATGCCTA  29057
AGACTGTGTG CACTTTAATA CAAGGGCAGT CGTTCAGAAC TAGTCAGGTC CTGAAAAGGA TTTACCAAAT GTTGAGTGTG CCCTCTAGTG TTCACACTTC  29157
CCAGCTTTCT TCCTATAAAG GTGGATCAAG GCACTTGCTT ACAACTGGAA CTGAAATCCT CCAAGTCGAT CTAGACATTG AGATGGAGAA AATATTCATT  29257
GTCGACTGTA ATTATGCAAC GAATATCCAG TTGAGATAAT GGACTTGCCT CTTATCTAAT AATACCCAGG CTCAATGCGT CACTGCTTTG TCCACTTTGC  29357
CCAAAATTCA AGCACAGCTA AGTTGATATT TTAGGACAAA GGCAGCTTAC TATCCAGCCA GAGGGGAGTA GAATATGGTT AAGAGAGAGT GGAAAGAATG  29457
AATGAGCCCT GCTATTCCTC ACTGCCTGGA TGGCTATAAG CACAGCCCTT ATGGAGGCCT TAGGTCTTGC TTCACAATAT TCCAGTTTGA AAAGGGTTTG  29557
AAAAGACCTC CTAGAAAAAT CAGTAGTTTT TCTCTTTTGA GTAACATGTA GCAAAAAAAA TTTCATCATG TAGGTACAGG GAACACCCTA GTAACTATTA  29657
ATCTCAAGGA GTCAAGCCAG TGTGTTTCCT AATGTATCTG CTGTATCCCC ATGAAGCAAA TTTTGCCATC AGAGAAACTG ACTCATGGGG AAAAAATCCA  29757
AGGACCTCAA ATCACCAAAA GAAGCCATTC CTCAGATTTG CCTAAGCTTA AGCTTCCCTG TCTCTCATTG TGTGTTGCTT TCAATGCAGT TACATAAATG  29857
GCTTTTTTGT TTATGCACCA AAAACACTAA TTCATCTGCA AAGCTCACAT TTCCAGAAAC ATTCCATTTC TGCCAGCACC TAGAAGCCAA TATTTTGCCT  29957
                                                                                                                        196
                                                                                                                        Val Val Leu Asn Gly
ATTCCTGTAA CCAGCACACA TATTTATTTT TTTCTAGATC AAATGTATTA TGCAGTAAGA GTCTTAATTT TGTTTTCACA G GTT GTT TTG AAT GGT  30053
                                                                                         ↑
Lys Val Asp Ala Phe Cys Gly Gly Ser Ile Val Asn Glu Lys Trp Ile Val Thr Ala Ala His Cys Val Glu Thr Gly Val
AAA GTT GAT GCA TTC TGT GGA GGC TCT ATC GTT AAT GAA AAA TGG ATT GTA ACT GCT GCC CAC TGT GTT GAA ACT GGT GTT  30134
                    233
Lys Ile Thr Val Val Ala
AAA ATT ACA GTT GTC GCA G GTAAAT ACACAGAAAG AATAATAATC TGCAGCACCA CTAGCTCTTT AATATGATTG GTACACCATA TTTTACTAAG  30229
                         ↑
GTCTAATAAA ATTGTTGTTG AATAAATTGG GCTAAAGGCA GAAGGGTCAT AATTTCAGAA CCCACGTCGC ACCGTCCTCC AAGCATCCAT AGTTCTTTTG  30329
ATATACCCCT ATTATCACTC ATTTCAGTGA GGTACAATTA GTTCTTGATG TAGCCATTTC CATACCAGAA GGCCTTCCCA AAAATCAGTG TCATGTCACC  30429
GATCCTTTTA TCTCTGGTGC TTGGCACAAC CTGTAGCAGG TCCTCAGAAA ACAAACATTT GAATTAATGG CCAAATGAGT TTGTGCTCAA AAAAGGGGTG  30529
AGGATACTTG AAATTTGGAA AATCTAGGAT AATTCATGAC TAGTGGATTC ATTATCACCA ATGAAAGGCT TATAACAGCA TGAGTGAACA GAACCATCTC  30629
TATGATAGTC CTGAATGGCT TTTTGGTCTG AAAAATATGC ATTGGCTCTC ATTACATTTA ACCAAAATTA TCACAATATA AGAATGAGAT CTTTAACATT  30729
                                                                                                       234
```

FIG. 8L

```
                                                                                                        Gly Glu
GCCAATTAGG TCAGTGGTCC CAAGTAGTCA CTTAGAAAAT CTGTGTATGT GAAATACTGT TTGTGACTTA AAATGAAATT TATTTTTAAT AG GT GAA   30826
                                                                                                      ↑
His Asn Ile Glu Glu Thr Glu His Thr Glu Gln Lys Arg Asn Val Ile Arg Ile Ile Pro His His Asn Tyr Asn Ala Ala
CAT AAT ATT GAG GAG ACA GAA CAT ACA GAG CAA AAG CGA AAT GTG ATT CGA ATT ATT CCT CAC CAC AAC TAC AAT GCA GCT   30907
                                        •
Ile Asn Lys Tyr Asn His Asp Ile Ala Leu Leu Glu Leu Asp Glu Pro Leu Val Leu Asn Ser Tyr Val Thr Pro Ile Cys
ATT AAT AAG TAC AAC CAT GAC ATT GCC CTT CTG GAA CTG GAC GAA CCC TTA GTG CTA AAC AGC TAC GTT ACA CCT ATT TGC   30988

Ile Ala Asp Lys Glu Tyr Thr Asn Ile Phe Leu Lys Phe Gly Ser Gly Tyr Val Ser Gly Trp Gly Arg Val Phe His Lys
ATT GCT GAC AAG GAA TAC ACG AAC ATC TTC CTC AAA TTT GGA TCT GGC TAT GTA AGT GGC TGG GGA AGA GTC TTC CAC AAA   31069

Gly Arg Ser Ala Leu Val Leu Gln Tyr Leu Arg Val Pro Leu Val Asp Arg Ala Thr Cys Leu Arg Ser Thr Lys Phe Thr
GGG AGA TCA GCT TTA GTT CTT CAG TAC CTT AGA GTT CCA CTT GTT GAC CGA GCC ACA TGT CTT CGA TCT ACA AAG TTC ACC   31150

Ile Tyr Asn Asn Met Phe Cys Ala Gly Phe His Glu Gly Gly Arg Asp Ser Cys Gln Gly Asp Ser Gly Gly Pro His Val
ATC TAT AAC AAC ATG TTC TGT GCT GGC TTC CAT GAA GGA GGT AGA GAT TCA TGT CAA GGA GAT AGT GGG GGA CCC CAT GTT   31231

Thr Glu Val Glu Gly Thr Ser Phe Leu Thr Gly Ile Ile Ser Trp Gly Glu Glu Cys Ala Met Lys Gly Lys Tyr Gly Ile
ACT GAA GTG GAA GGG ACC AGT TTC TTA ACT GGA ATT ATT AGC TGG GGT GAA GAG TGT GCA ATG AAA GGC AAA TAT GGA ATA   31312
                                                                    415
Tyr Thr Lys Val Ser Arg Tyr Val Asn Trp Ile Lys Glu Lys Thr Lys Leu Thr STOP
TAT ACC AAG GTA TCC CGG TAT GTC AAC TGG ATT AAG GAA AAA ACA AAG CTC ACT TAA  TGAAAGATGG ATTTCCAAGG TTAATTCATT   31399

GGAATTGAAA ATTAACAGGG CCTCTCACTA ACTAATCACT TTCCCATCTT TTGTTAGATT TGAATATATA CATTCTATGA TCATTGCTTT TTCTCTTTAC   31499
AGGGGAGAAT TTCATATTTT ACCTGAGCAA ATTGATTAGA AAATGGAACC ACTAGAGGAA TATAATGTGT TAGGAAATTA CAGTCATTTC TAAGGGCCCA   31599
GCCCTTGACA AAATTGTGAA GTTAAATTCT CCACTCTGTC CATCAGATAC TATGGTTCTC CACTATGGCA ACTAACTCAC TCAATTTTCC CTCCTTAGCA   31699
GCATTCCATC TTCCCGATCT TCTTTGCTTC TCCAACCAAA ACATCAATGT TTATTAGTTC TGTATACAGT ACAGGATCTT TGGTCTACTC TATCACAAGG   31799
CCAGTACCAC ACTCATGAAG AAAGAACACA GGAGTAGCTG AGAGGCTAAA ACTCATCAAA AACACTACTC CTTTTCCTCT ACCCTATTCC TCAATCTTTT   31899
ACCTTTTCCA AATCCCAATC CCCAAATCAG TTTTTCTCTT TCTTACTCCC TCTCTCCCTT TTACCCTCCA TGGTCGTTAA AGGAGAGATG GGGAGCATCA   31999
TTCTGTTATA CTTCTGTACA CAGTTATACA TGTCTATCAA ACCCAGACTT GCTTCCATAG TGGAGACTTG CTTTTCAGAA CATAGGGATG AAGTAAGGTG   32099
CCTGAAAAGT TTGGGGGAAA AGTTTCTTTC AGAGAGTTAA GTTATTTTAT ATATATAATA TATATATAAA ATATATAATA TACAATATAA ATATATAGTG   32199
TGTGTGTGTA TGCGTGTGTG TAGACACACA CGCATACACA CATATAATGG AAGCAATAAG CCATTCTAAG AGCTTGTATG GTTATGGAGG TCTGACTAGG   32299
```

FIG. 8M

```
CATGATTTCA GGAAGGCAAG ATTGGCATAT CATTGTAACT AAAAAAGCTG ACATTGACCC AGACATATTG TACTCTTTCT AAAAATAATA ATAATAATGC 32399
TAACAGAAAG AAGAGAACCG TTCGTTTGCA ATCTACAGCT AGTAGAGACT TTGAGGAAGA ATTCAACAGT GTGTCTTCAG CAGTGTTCAG AGCCAAGCAA 32499
GAAGTTGAAG TTGCCTAGAC CAGAGGACAT AAGTATCATG TCTCCTTTAA CTAGCATACC CCGAAGTGGA GAAGGGTGCA GCAGGCTCAA AGGCATAAGT 32599
CATTCCAATC AGCCAACTAA GTTGTCCTTT TCTGGTTTCG TGTTCACCAT GGAACATTTT GATTATAGTT AATCCTTCTA TCTTGAATCT TCTAGAGAGT 32699
TGCTGACCAA CTGACGTATG TTTCCCTTTG TGAATTAATA AACTGGTGTT CTGGTTCATA CCTTGGCTTT TTGTGGATTC CATTGATGTG AATCAGTCAC 32799
CCTGTATTTG ATGATGCATG GGACTACTGA CAAAATCACT CTGACCCTGC CAAGCTGCTG CCTTCTCCTG CCCCAACCTC ACCCCCAGCC AGGCCTCACT 32899
CTTGCTAGTT CCTTTAGTTC TTTTAGTCAA TATATTTTTG TCTTCGCATA TAAGTATAAA TAAACATATT TTTAAATTTC TTGGCTGGGC CCAGTGGCTC 32999
ACGCCTATAA TCCCAGCACT TCTGGAGGCC AAGGTGGGCG GATCACCTGA GGTTAGGAGT TTCAGGCCAG CCTGGCCAAC ATGGTGAAAC CCTGTCTCTA 33099
CTAAAAATAG AACAATTAGC TGGGCTTGGT AATGTGCACC TATAATCCCA GCTACTGGGG AGGCTGAGGC AGGAGAATCA CTTGAGCCTG GGGAGCAGGG 33199
CGTGCGGGAG GTTGCAGTGA GACAAGATCG CACCAGTGCA CTCCCCATCC TGGGTGACAG AGTGAGACTC TGTCTCAAAG AAAATAAATA AATAAATACA 33299
TTTCTTGAGG CGTTTCTTGT TAAATCATTC ATGGAGAGGC ATCCCAAACA CCACATTCAA CAAAACACTC TGAAAAATGT TTTCAAATGC AATATAACAC 33399
AGCAGAGATT TGATGCTCTG TTATCCAGTT TTCATATAAG GCTGTGTGAG CTGTGTCCCA GAGAGGACAG TGGTCTGAAT CCACCTGAGA CAGAATTGGG 33499
TCTAACTAAC TGTGAGTATG GCCTTCAATA AGTCACTCTC CATTTGGGAA TTTGATTTCT CCACTTGTAT AATGAGAGTA TTTGACAGGA TGCTCTCCCA 33599
AATCCCTTGC AATTTTGTTA GTCTGTGATT TCATGTTTTT ATTTTTATTC CTTCATCCAA CAAATAGTCA AGGAGTAATT GCTGTGTGCC AAATACCAAC 33699
AGTATTCATT AAATTGTAAT TCAGATTTTA TATATATATA AATAATGTAT AATGTGTATA AATTGCTTTG TGAGTGCCTA CTACACTGCT AGACAGTAGT 33799
TGCTCAATAA CTTGTTAGCT GAATCAGAAT CCATGTTTAT CCCAGAGTAG CAATTAGTCT TGCATCGAGT ATCGTGAAAG AAGGCCACAC TTAAATAAGA 33899
ATAATGCCTG GGGTTTAGGT TTTATGAAAA AATGAAAGGA AATTAGTTCT GCTTTTGTTG ACTAAAGGAA GGGAAGAGAG AAGAGACACT ATAATTGTCT 33999
GCCTCAGATT TAAGGAGGAG GCTAATTCAT GCATTAAACA CGTTACTTCA AATTTGAATG ACCAAAGGTC TGTAGCCTCA GCACTTCAAA ATTGGTAAAA 34099
GTAAGACACT CTGGCCTTGT TTCCATAGAG ACCACCCCTT ACAAAGGCAC CAATGGGAAA CTGGCCTCAG GACTCCTGTT ATTGGTCTTC TCTGTGGCAG 34199
ACAAAGGAGC TCTTGGACCC ATAAATCTCT GAGCCACAGT TCTTTTTGCC ATGGGCTCAA AAATGATTGA ATTCATCATG AGCCACCTGT GGCATATTGC 34299
CACACTAAAC ATGTGGGGCC TTTAAGCTCA CTAAGAGCCA ATGTCTTCAG AGCCAGCCCT GGCTTGATTC TACCTAGGGC ATTTGCAGTT GCCATATAAG 34399
AATCATTAGT GCTTTCAAAA TTACTGTAGA TACTTTGCCT AAATAGACTA AAACATGCTG CCGTCATATT GGAAGTGACA GATTAAAATA GAACTCTTGC 34499
CAAGTGAAGG AAAGTGTGCT AATATAATGC AGTCATTTTA ACTTGCTGTT TAAGTGTGAT TGTTTTTAGT TCTTTTGAAT ATTATTTGTT TTATACTGAC 34599
AGGAACGAAG TACTGTCCAA TTTTCTCTGC CAAGGAAAAA AGAAAAGGTG TTCTTCCTTA CTTACCTGAA CCAAAACAGA CCAGTTTACA AAATTGCCTA 34699
ATTATAATTG CTAAACAAGT TCCGAATGCT TACAGTCTAA TCCAAGAATG TCAGAGCTGC AAGGGCCCTT AAACACCATC CAATCCACTC CACTCATTTA 34799
GCAGATGAAG AGATTGAGGG CAACATAAGG CCAGGCCCAA GATAACACAA TGACAGCCAG GACTAGAGCT CAAGTCTCCC ACCCTGCACT TTGAAAGAAT 34899
AATGCTTTCA ACTGGAGTAC ATTAACTCTA CTGTCTATAT TTTTAGGGCA GCTGGGGCAT TCTGCATTGG TGGCAATCCT CTCAACAACC CTGGGACTGA 34999
AAACTGCCTG GAATTCTTAC TAACAATTCT CTAATTGACC AAAAGGTGAC GAAATCAAGG AGACCAATAA GGTAGCCTTG GAAAGCAAGA GTGGC 35094
```

FIG. 8N

```
   1 gaattccgtg gatgtgcttt aaaaccacac ctaacgtttg agcacaagtc tcacgaactg
  61 gcgctacaac ttcatcagaa acgaagtctc caaatctgtc caacgcaaaa acacaaagga
 121 gtctaatgac taagtcttcc aaccacaact gtctgctgcg cccggaaaac aagccggggc
 181 tctggggacc cggggctcag gccgcctcgc tccggcctag ccccgccacc ttagttgtgt
 241 catcccccgg gcatgctgag catcccccg cggctccggc acagacgccc ggacctcagg
 301 tctctgcctc cgcgcggggg cccggccctg tggccggagg gagcggccgg atggagcgga
 361 ggatgaaagg cggatacttg gaccagcgag tgccctacac cttctgcagc aaatctcccg
 421 gaaatgggag cttgggcgaa gcgctgatgg tcccgcaggg aaagctcatg gacccgggct
 481 ccctgccgcc ttccgactca gaagatctct tccaggacct cagtcacttc caagagacgt
 541 ggctcgcaga agctcaggta ccggacagtg atgagcagtt tgttcctgat ttccattcag
 601 aaaacttagc tttccatagc cccaccacca ggatcaagaa ggaaccccag agtccccgca
 661 cagaccccgc cctgtcctgc agcaggaagc caccactccc ctaccaccat ggagagcagt
 721 gcctttactc cagacaaatc gccatcaagt cccccgctcc cggtgcccct ggacagtcgc
 781 ccctgcagcc cttttccagg gcagaacagc agcagagcct cctgagagcc tccagctctt
 841 cccagtccca ccctggccac gggtaccttg gtgagcacag ctccgtcttc cagcagcccg
 901 tggacatgtg ccactccttc acatctcctc agggaggggg ccgggaacct ctcccagccc
 961 cctatcaaca ccaactgtcg gagccctgcc caccctaccc ccagcagaac ttcaagcagg
1021 agtaccatga ccccctgtac gaacaggctg gccagcccgc ttcaagccag ggtggggtca
1081 gtgggcacag gtacccaggg gcgggggtgg tgatcaaaca ggagcgcaca gacttcgcct
1141 acgactcaga tgtccctgga tgtgcatcaa tgtacctcca cccagagggc ttctctggac
1201 cctctccagg tgatggagtg atgggttatg gctatgaaaa atcccttcga ccattcccag
1261 atgatgtctg cattgtccct aaaaaatttg aaggagacat caagcaggaa gggattggag
1321 ctttccggga ggggccaccc taccagcgcc ggggtgcctt acaactgtgg cagtttctgg
1381 tggccctgct ggatgaccca acaaatgctc atttcattgc ttggacaggc cggggaatgg
1441 agtttaaact aattgaacct gaagaggttg ccaggctctg ggtatccag aagaaccggc
1501 cagccatgaa ttatgacaag ctgagccgct cgctgcgata ctattatgag aaaggcatca
1561 tgcagaaggt ggctggcgaa cgctacgtgt acaagtttgt gtgcgagccg gaggccctgt
1621 tctctctggc cttcccagat aatcaacgtc cagctctgaa ggctgagttt gaccggccag
1681 tcagtgagga ggacacagtc cctttgtccc acttggatga gagtcctgcc tacctcccag
1741 aactcactgg ccccgctccg cccttcggcc acagaggtgg atattcttac taggcaccag
1801 tggcttcccc ttgacatggt ggggttgctc agtgtatata tcaactgatt tggtattggt
1861 gaaggccctc tttctgatgc ctgtagaagt ctctggggtc agagctccac tatcccatct
1921 gatactcctg gccagactca gctgctaacc agagtctgcg ggaaagacag tggaggcagg
1981 ccaaatctaa aggcagtagc tgaagttcgc tgtggctcac ctgtaccttc agttcagctt
2041 ggcctctgcc taggtcttgc tcagaggcca agttcctcac ccccaccaca gagatccagt
2101 gttctattct ggggacatac agggacttcc cttgtttatt atggcaacag ggccaagggg
2161 attctcagaa caccctgtgt ctcccctctc ccaacccccc atgggagaca aagttctgcc
2221 tggcttctgc cctgaacagg ggggtcctgt gttcttggtg ctgtgctctg ggaggcagga
2281 gcatgtgggc ggcagctggg gggggtgtg gaagtagaga tggctctctg ccctaggcct
2341 acccaggcct aattccacct ttgcctctta tgccagacct taataaagcc tctgcttctc
2401 cccggaattc
```

FIG. 9A

MTKSSNHNCLLRPENKPGLWGPGAQAASLRPSPATLVVSSPGHA
EHPPAAPAQTPGPQVSASARGPGPVAGGSGRMERRMKGGYLDQRVPYTFCSKSPGNGS
LGEALMVPQGKLMDPGSLPPSDSEDLFQDLSHFQETWLAEAQVPDSDEQFVPDFHSEN
LAFHSPTTRIKKEPQSPRTDPALSCSRKPPLPYHHGEQCLYSRQIAIKSPAPGAPGQS
PLQPFSRAEQQQSLLRASSSSQSHPGHGYLGEHSSVFQQPVDMCHSFTSPQGGGREPL
PAPYQHQLSEPCPPYPQQNFKQEYHDPLYEQAGQPASSQGGVSGHRYPGAGVVIKQER
TDFAYDSDVPGCASMYLHPEGFSGPSPGDGVMGYGYEKSLRPFPDDVCIVPKKFEGDI
KQEGIGAFREGPPYQRRGALQLWQFLVALLDDPTNAHFIAWTGRGMEFKLIEPEEVAR
LWGIQKNRPAMNYDKLSRSLRYYYEKGIMQKVAGERYVYKFVCEPEALFSLAFPDNQR
PALKAEFDRPVSEEDTVPLSHLDESPAYLPELTGPAPPFGHRGGYSY

FIG. 9B

```
   1 gaattccagg ttggaggggc ggcaacctcc tgccagcctt caggccactc tcctgtgcct
  61 gccagaagag acagagcttg aggagagctt gaggagagca ggaaaggtgg aacattgctg
 121 ctgctgctca ctcagttcca caggtgggag gaacagcagg gcttagagtg ggggtcattg
 181 tgcagatggg aaaacaaagg cccagagagg ggaagaaatg cctaggagct accgagggca
 241 ggcgacctca accacagccc agtgctggag ctgtgagtgg atgtagagca gcggaatatc
 301 cattcagcca gctcagggga aggacagggg ccctgaagcc aggggatgga gctgcaggga
 361 agggagctca gagagaaggg gaggggagtc tgagctcagt ttcccgctgc ctgaaaggag
 421 ggtggtacct actcccttca cagggtaact gaatgagaga ctgcctggag gaaagctctt
 481 caagtgtggc ccaccccacc ccagtgacac cagcccctga cacgggggag ggagggcagc
 541 atcaggaggg gctttctggg cacacccagt acccgtctct gagctttcct tgaactgttg
 601 cattttaatc ctcacagcag ctcaacaagg tacataccgt caccatcccc atttacaga
 661 tagggaaatt gaggctcgga gcggttaaac aactcacctg aggcctcaca gccagtaagt
 721 gggttccctg gtctgaatgt gtgtgctgga ggatcctgtg ggtcactcgc ctggtagagc
 781 cccaaggtgg aggcataaat gggactggtg aatgacagaa ggggcaaaaa tgcactcatc
 841 cattcactct gcaagtatct acggcacgta cgccagctcc caagcaggtt tgcgggttgc
 901 acagcggagc gatgcaatct gatttaggct tttaaaggat tgcaatcaag tgggacccac
 961 tagcctcaac cctgtacctc ccctcccctc cacccccagc agtctccaaa ggcctccaac
1021 aaccccagag tgggggccat gtatccaaag aaactccaag ctgtatacgg atcacactgg
1081 ttttccagga gcaaaaacag aaacagcctg aggctggtca aaattgaacc tcctcctgct
1141 ctgagcagcc taggggcag actaagcaga gggctgtgca gacccacata aagagcctac
1201 tgtgtgccag gcacttcacc cgaggcactt cacaagcatg cttgggaatg aaacttcca
1261 ctctttggga tgcaggtgaa acagttcctg gttcagagag gtgaagcggc ctgcctgagg
1321 cagcacagct cttctttaca gatgtgcttc cccacctcta ccctgtctca cggcccccca
1381 tgccagcctg acggttgtgt ctgcctcagt catgctccat ttttccatcg ggaccatcaa
1441 gagggtgttt gtgtctaagg ctgactgggt aactttggat gagcggtctc tccgctccga
1501 gcctgtttcc tcatctgtca aacgggctct aacccactct gatctcccag ggcggcagta
1561 agtcttcagc atcaggcatt ttggggtgac tcagtaaatg gtagatcttg ctaccagtgg
1621 aacagccact aaggattctg cagtgagagc agagggccag ctaagtggta ctctcccaga
1681 gactgtctga ctcacgccac cccctccacc ttggacacag gacgctgtgg tttctgagcc
1741 aggtacaatg actcctttcg gtaagtgcag tggaagctgt acactgccca ggcaaagcgt
1801 ccgggcagcg taggcgggcg actcagatcc cagccagtgg acttagcccc tgtttgctcc
1861 tccgataact ggggtgacct tggttaatat tcaccagcag cctcccccgt tgcccctctg
1921 gatccactgc ttaaatacgg acgaggacag ggccctgtct cctcagcttc aggcaccacc
1981 actgacctgg gacagtgaat cgtaagtatg cctttcactg cgaggggttc tggagaggct
2041 tccgagctcc ccatggccca ggcaggcagc aggtctgggg caggaggggg gttgtggagt
2101 gggtatccgc ctgctgaggt gcagggcaga tggagaggct gcagctgagc tcctattttc
2161 ataataacag cagccatgag ggttgtgtcc tgtttcccag tcctgcccgg tccccccctcg
2221 gtacctcctg gtggatacac tggttcctgt aagcagaagt ggatgagggt gtctaggtct
2281 gcagtcctgg caccccagga tgggggacac cagccaagat acagcaacag caacaaagcg
2341 cagccatttc tttctgtttg cacagctcct ctgtctgtcg gggctcctg tctgttgtct
2401 cctataagcc tcaccacctc tcctactgct tgggcatgca tctttctccc cttctataga
2461 tgaggaggtt aaggttcaga gaggggtggg gaggaacgcc ggctcacatt ctccatcccc
2521 tccagatatg accaggaaca gacctgtgcc agcctcagcc ttacatcaaa atgggcctcc
2581 ccatgcaccg tggacctctg ggccctcctg tcccagtgga ggacaggaag ctgtgagggg
2641 cactgtcacc cagggctcaa gctggcattc ctgaataatc gctctgcacc aggccacggc
2701 taagctcagt gcgtgattaa gcctcataac cctccaaggc agttactagt gtgattccca
```

FIG. 10A

```
2761 ttttacagat gaggaagatg gggacagaga ggtgaataac tggccccaaa tcacacacca
2821 tccataattc gggctcaggc acctggctcc agtccccaaa ctcttgaacc tggccctagt
2881 gtcactgttt ctcttgggtc tcaggcgctg gatggggaac aggaaacctg ggctgaactt
2941 gaggcctctc tgatgctcgg tgacttcaga cagttgctca acctctctgt tctcttgggc
3001 aaaacatgat aacctttgac ttctgtcccc tcccctcacc ccacccgacc ttgatctctg
3061 aagtgttgga aggatttaat ttttcctgca ctgagttttg gagacaggtc aaaaagatga
3121 ccaaggccaa ggtggccagt ttcctataga acgcctctaa aagacctgca gcaatagcag
3181 caagaactgg tattctcgag aacttgctgc gcagcaggca cttcttggca ttttatgtgt
3241 atttaatttc acaatagctc tatgacaaag tccacctttc tcatctccag gaaactgagg
3301 ttcagagagg ttaagtaact tgtccaaggt cacacagcta atagcaagtt gacgtggagc
3361 aatctggcct cagagccttt aattttagcc acagactgat gctcccctct tcatttagcc
3421 aggctgcctc tgaagttttc tgattcaaga cttctggctt cagctttgta cacagagatg
3481 attcaatgtc aggttttgga gcgaaatctg tttaatccca gacaaaacat ttaggattac
3541 atctcagttt tgtaagcaag tagctctgtg atttttagtg agttatttaa tgctctttgg
3601 ggctcaattt ttctatctat aaaatagggc taataatttg caccttatag ggtaagcttt
3661 gaggacagat tagatgatac ggtgcctgta aaacaccagg tgttagtaag tgtggcaatg
3721 atggtgacgc tgaggctgtg tttgcttagc atagggttag gcagctggca ggcagtaaac
3781 agttggataa tttaatggaa aatttgccaa actcagatgc tgttcactgc tgagcaggag
3841 ccccttcctg ctgaaatggt cctggggagt gcagcaggct ctccgggaag aaatctacca
3901 tctctcgggc aggagctcaa cctgtgtgca ggtacaggga gggcttcctc acctggtgcc
3961 cactcatgca ttacgtcagt tattcctcat ccctgtccaa aggattcttt tctccattgt
4021 acagctatga agctagtgct caaagaagtg aagtcattta ccccaggccc cctgccagta
4081 agtgacaggg cctggtcaca cttgggttta tttattgccc agttcaacag gttgtttgac
4141 cataggcgag attctcttcc ctgcaccctg ccgggttgct cttggtccct tattttatgc
4201 tcctgggtag aaatggtgcg agattaggca gggagtggac gcttccctgt ccctggcccc
4261 gcaaagagtg ctcccacctg ccccgatccc agaaatgtca ccatgaagcc ttcattcttt
4321 tggtttaaag cttggcctca gtgtccgtac accatggggt ccttggccag atggcgactt
4381 tctcctctcc agtcgccctc ccaggcacta gcttttagga gtgcagggtg ctgcctctga
4441 tagaagggcc aggagagagc aggttttgga gacctgatgt tataaggaac agcttgggag
4501 gcataatgaa cccaacatga tgcttgagac caatgtcaca gcccaattct gacattcatc
4561 atctgagatc tgaggacaca gctgtctcag ttcatgatct gagtgctggg aaagccaaga
4621 cttgttccag ctttgtcact gacttgctgt atagcctcaa caaggccctg accctctctg
4681 ggcttcaaac tcttcactgt gaaaggagga aaccagagta ggtgatgtga caccaggaaa
4741 gatggatggg tgtgggggaa tgtgctcctc ccagctgtca ccccctcgcc accctccctg
4801 caccagcctc tccacctcct ttgagcccag aattcccctg tctaggaggg cacctgtctc
4861 gtgcctagcc atgggaattc tccatctgtt ttgctacatt gaacccagat gccattctaa
4921 ccaagaatcc tggctgggtg caggggctct cgcctgtaac cccagcactt tgggaggcca
4981 aggcaggcgg atcaagaggt caggagttca agacctgcct ggccaacacg gtgaaacctc
5041 agctctacta aaaatacaaa aattagccag gcgtggtggc acacgcctgt aatcccagct
5101 atttgggaag ctgagacaga agaatttctt gaacccggga ggtggaggtt tcagtgagcc
5161 gagatcacgc cactgcactc caccctggcg gataaagcga gactctgtct caaaaaaaac
5221 ccaaaaacct atgttagtgt acagagggcc ccagtgaagt cttctcccag ccccactttg
5281 cacaactggg gagagtgagg ccccaggacc agaggattct tgctaaaggc caagtggata
5341 gtgatggccc tgccaggcta gaagccacaa cctctggccc tgaggccact cagcatattt
5401 agtgtcccca ccctgcagag gcccaactcc ctcctgacca ctgagccctg taatgatggg
5461 ggaatttcca taagccatga aggactgcac aaagttcagt tgggagtgaa agagaaatta
```

FIG. 10B

```
5521 aagggagatg gaaatataca gcactaattt tagcaccgtc ttcagttcta acaacactag
5581 ctagctgaag aaaatacaaa catgtattat gtaatgtgtg gtctgttcca tttggattac
5641 ttagaggcac gagggccaag gagaaaggtg gtggagagaa accagctttg cacttcattt
5701 gttgctttat tggaaggaaa cttttaaaag tccaaggggg ttgaagaatc tcaatatttg
5761 ttatttccag ctttttttct ccagtttttc atttcccaaa ttcaaggaca ccttttttctt
5821 tgtattttgt taagatgatg gttttggttt tgtgactagt agttaacaat gtggctgccg
5881 ggcatattct cctcagctag gacctcagtt ttcccatctg tgaagacggc aggttctacc
5941 taggggggctg caggcaggtg gtccgaagcc tgggcatatc tggagtagaa ggatcactgt
6001 ggggcagggc aggttctgtg ttgctgtgga tgacgttgac tttgaccatt gctcggcaga
6061 gcctgctctc gctggttcag ccacaggccc caccactccc tattgtctca gccccgggta
6121 tgaaacatgt attcctcact ggcctatcac ctgaagcctt tgaatttgca acacctgcca
6181 acccctccct caaaagagtt gccctctcta gatccttttg atgtaaggtt tggtgttgag
6241 acttatttca ctaaattctc atacataaac atcactttat gtatgaggca aaatgaggac
6301 cagggagatg aatgacttgt cctggctcat acacctggaa agtgacagag tcagattaga
6361 tcctaggtct atctgaagtt aaaagaggtg tcttttcact tcccacctcc tccatctact
6421 ttaaagcagc acaaacccct gctttcaagg agagatgagc gtctctaaag cccctgacag
6481 caagagccca gaactgggac accattagtg acccagacgg caggtaagct gactgcagga
6541 gcatcagcct attcttgtgt ctgggaccac agagcattgt ggggacagcc ccgtctcttg
6601 ggaaaaaaac cctaagggct gaggatcctt gtgagtgttg ggtgggaaca gctcccagga
6661 ggtttaatca cagcccctcc atgctctcta gctgttgcca ttgtgcaaga tgcatttccc
6721 ttctgtgcag cagtttccct ggccactaaa tagtgggatt agatagaagc cctccaaggg
6781 ctccagcttg acatgattct tgattctgat ctgacccgat tctgataatc gtgggcaggc
6841 ccattcctct tcttgtgcct catttcttc ttttgtaaaa caatggctgt accatttgca
6901 tcttagggtc attgcagatg aaagtgttgc tgtccagagc ctgggtgcag gacctagatg
6961 taggattctg gttctgctac ttcctcagtg acattgaata gctgacctaa tctctctggc
7021 tttggtttct tcatctgtaa aagaaggata ttagcattag cacctcacgg gattgttaca
7081 agaaaagcaat gaattaacac atgtgagcac ggagaacagt gcttggcata tggtaagcac
7141 tacgtacatt ttgctattct tctgattctt tcagtgttac tgatgtcggc aagtacttgg
7201 cacaggctgg tttaataatc cctaggcact ttcacgtggt gtcaatccct gatcactggg
7261 agtcatcatg tgccttgact cgggcctggc cccccatct ctgtcttgca ggacaatgcc
7321 gtcttctgtc tcgtggggca tcctcctgct ggcaggcctg tgctgcctgg tccctgtctc
7381 cctggctgag gatccccagg gagatgctgc ccagaagaca gatacatccc accatgatca
7441 ggatcaccca accttcaaca agatcacccc caacctggct gagttcgcct tcagcctata
7501 ccgccagctg gcacaccagt ccaacagcac caatatcttc ttctccccag tgagcatcgc
7561 tacagccttt gcaatgctct ccctggggac caaggctgac actcacgatg aaatcctgga
7621 gggcctgaat ttcaacctca cggagattcc ggaggctcag atccatgaag gcttccagga
7681 actcctccgt accctcaacc agccagacag ccagctccag ctgaccaccg gcaatggcct
7741 gttcctcagc gagggcctga agctagtgga taagtttttg gaggatgtta aaaagttgta
7801 ccactcagaa gccttcactg tcaacttcgg ggacaccgaa gaggccaaga aacagatcaa
7861 cgattacgtg gagaagggta ctcaagggaa aattgtggat ttggtcaagg agcttgacag
7921 agacacagtt tttgctctgg tgaattacat cttctttaaa ggtaaggttg ctcaaccagc
7981 ctgagctgtt tcccatagaa acaagcaaaa atatttctca aaccatcagt tcttgaactc
8041 tccttggcaa tgcattatgg gccatagcaa tgcttttcag cgtggattct tcagttttct
8101 acacacaaac actaaaatgt tttccatcat tgagtaattt gaggaaataa tagattaaac
8161 tgtcaaaact actgacgctc tgcagaactt ttcagagcct ttaatgtcct tgtgtatact
8221 gtatatgtag aatatataat gcttagaact atagaacaaa ttgtaataca ctgcataaag
8281 ggatagtttc atggaacata ctttacacga ctctagtgtc ccagaatcag tatcagtttt
```

FIG. 10C

```
8341 gcaatctgaa agacctgggt tcaaatcctg cctctaacac aattagcttt tgacaaaaac
8401 aatgcattct acctctttga ggtgctaatt tctcatctta gcatggacaa aataccattc
8461 ttgctgtcag gtttttttag gattaaacaa atgacaaaga ctgtggggat ggtgtgtggc
8521 atacagcagg tgatggactc ttctgtatct caggctgcct tcctgcccct gaggggttaa
8581 aatgccaggg tcctgggggc cccagggcat tctaagccag ctcccactgt cccaggaaaa
8641 cagcataggg gaggggaggt gggaggcaag gccaggggct gcttcctcca ctctgaggct
8701 cccttgctct tgaggcaaag gagggcagtg gaggcaagcc aggctgcagt cagcacagct
8761 aaagtcctgg ctctgctgtg gccttagtgg gggcccaggt ccctctccag ccccagtctc
8821 ctccttctgt ccaatgagaa agctgggatc aggggtccct gaggcccctg tccactctgc
8881 atgcctcgat ggtgaagctc tgttggtatg gcagagggga ggctgctcag gcatctgcat
8941 ttcccctgcc aatctagagg atgaggaaag ctctcaggaa tagtaagcag aatgtttgcc
9001 ctggatgaat aactgagctg ccaattaaca aggggcaggg agccttagac agaaggtacc
9061 aaatatgcct gatgctccaa cattttattt gtaatatcca agacaccctc aaataaacat
9121 atgattccaa taaaaatgca cagccacgat ggcatctctt agcctgacat cgccacgatg
9181 tagaaattct gcatcttcct ctagttttga attatcccca cacaatcttt ttcggcagct
9241 tggatggtca gtttcagcac cttttacaga tgatgaagct gagcctcgag ggatgtgtgt
9301 cgtcaagggg gctcagggct tctcagggag gggactcatg gtttcttatt ctgctacact
9361 cttccaaacc ttcactcacc cctggtgatg cccaccttcc cctctctcca ggcaaatggg
9421 agagacccctt tgaagtcaag gacaccgagg aagaggactt ccacgtggac caggtgacca
9481 ccgtgaaggt gcctatgatg aagcgtttag gcatgtttaa catccagcac tgtaagaagc
9541 tgtccagctg ggtgctgctg atgaaatacc tgggcaatgc caccgccatc ttcttcctgc
9601 ctgatgaggg gaaactacag cacctggtaa atgaactcac ccacgatatc atcaccaagt
9661 tcccctggaaaa tgaagacaga aggtgattcc ccaacctgag ggtgaccaag aagctgccca
9721 cacctcttag ccatgttggg actgaggccc atcaggactg gccagagggc tgaggagggt
9781 gaaccccaca tccctgggtc actgctactc tgtataaact tggcttccag aatgaggcca
9841 ccactgagtt caggcagcgc cgtccatgct ccatgaggag aacagtaccc agggtgagga
9901 ggtaaaggtc tcgtccctgg gaacttccca ctccagtgtg gacactgtcc cttcccaata
9961 tccagtgccc aaggcaggga cagcagcacc accacacgtt ctggcagaac caaaaaggaa
10021 cagatgggct tcctggcaaa ggcagcagtg gagtgtggag ttcaagggta gaatgtccct
10081 gggggacgg gggaagagcc tgtgtggcaa ggcccagaaa agcaaggttc ggaattggaa
10141 cagccaggcc atgttcgcag aaggcttgcg tttctctgtc actttatcgg tgctgttaga
10201 ttgggtgtcc tgtagtaagt gatacttaaa catgagccac acattagtgt atgtgtgtgc
10261 attcgtgatt atgcccatgc cctgctgatc tagttcgttt tgtacactgt aaaaccaaga
10321 tgaaaataca aaaggtgtcg ggttcataat aggaatcgag gctggaattt ctctgttcca
10381 tgccagcacc tcctgaggtc tctgctccag gggttgagaa agaacaaaga ggctgagagg
10441 gtaacggatc agagagccca gagccagctg ccgctcacac cagaccctgc tcagggtggc
10501 attgtctccc catggaaaac cagagaggag cactcagcct ggtgtggtca ctcttctctt
10561 atccactaaa cggttgtcac tgggcactgc caccagcccc gtgtttctct gggtgtaggg
10621 ccctggggat gttacaggct gggggccagg tgacccaaca ctacagggca agatgagaca
10681 ggcttccagg acacctagaa tatcagagga ggtggcattt caagcttttg tgattcattc
10741 gatgttaaca ttctttgact caatgtagaa gagctaaaag tagaacaaac caaagccgag
10801 ttcccatctt agtgtgggtg gaggacacag gagtaagtgg cagaaataat cagaaaagaa
10861 aacacttgca ctgtggtggg tcccagaaga acaagaggaa tgctgtgcca tgccttgaat
10921 ttcttttctg cacgacaggt ctgccagctt acatttaccc aaactgtcca ttactggaac
10981 ctatgatctg aagagcgtcc tgggtcaact gggcatcact aaggtcttca gcaatggggc
11041 tgacctctcc ggggtcacag aggaggcacc cctgaagctc tccaaggtga gatcaccctg
11101 acgaccttgt tgcaccatgg tatctgtagg gaagaatgtg tgggggctgc agcactgtcc
```

FIG. 10D

```
11161 tgaggctgag gaaggggccg agggaaacaa atgaagaccc aggctgagct cctgaagatg
11221 cccgtgattc actgacacgg gacggtgggc aaacagcaaa gccaggcagg ggctgctgtg
11281 cagctggcac tttcggggcc tcccttgagg ttgtgtcact gaccctgaat ttcaactttg
11341 cccaagacct tctagacatt gggccttgat ttatccatac tgacacagaa aggtttgggc
11401 taagttgttt caaaggaatt tctgactcct tcgatctgtg agatttggtg tctgaattaa
11461 tgaatgattt cagctaaagt gacacttatt ttggaaaact aaaggcgacc aatgaacaac
11521 ctgcagttcc atgaatggct gcattatctt ggggtctggg cactgtgaag gtcactgcca
11581 gggtccgtgt cctcaaggag cttcaagccg tgtactagaa aggagagagc cctggaggca
11641 gacgtggagt gacgatgctc ttccctgttc tgagttgtgg gtgcacctga gcaggggggag
11701 aggcgcttgt caggaagatg gacagagggg agccagcccc atcagccaaa gccttgagga
11761 ggagcaaggc ctatgtgaca gggagggaga ggatgtgcag ggccagggcc gtccaggggg
11821 agtgagcgct tcctgggagg tgtccacgtg agccttgctc gaggcctggg atcagcctta
11881 caacgtgtct ctgcttctct cccctccagg ccgtgcataa ggctgtgctg accatcgacg
11941 agaaagggac tgaagctgct ggggccatgt ttttagaggc catacccatg tctatccccc
12001 ccgaggtcaa gttcaacaaa ccctttgtct tcttaatgat tgaacaaaat accaagtctc
12061 ccctcttcat gggaaaagtg gtgaatccca cccaaaaata actgcctctc gctcctcaac
12121 ccctcccctc catccctggc cccctccctg gatgacatta aagaagggtt gagctggtcc
12181 ctgcctgcat gtgatctgta aatccctggg atgttttctc tg
```

FIG. 10E

```
   1 caccagcatc atctcctcca attcatccag ctactctgcc catgaagata atagttttca
  61 ggcggattgc ctcagatcac actatctcca cttgcccagc cctgtggaag attagcggcc
 121 atgtattcca atgtgatagg aactgtaacc tctggaaaaa ggaaggttta tctttgtcc
 181 ttgctgctca ttggcttctg ggactgcgtg acctgtcacg ggagccctgt ggacatctgc
 241 acagccaagc cgcgggacat tcccatgaat cccatgtgca tttaccgctc cccggagaag
 301 aaggcaactg aggatgaggg ctcagaacag aagatcccgg aggccaccaa ccggcgtgtc
 361 tgggaactgt ccaaggccaa ttcccgcttt gctaccactt tctatcagca cctggcagat
 421 tccaagaatg acaatgataa cattttcctg tcacccctga gtatctccac ggcttttgct
 481 atgaccaagc tgggtgcctg taatgacacc ctccagcaac tgatggaggt atttaagttt
 541 gacaccatat ctgagaaaac atctgatcag atccacttct tctttgccaa actgaactgc
 601 cgactctatc gaaaagccaa caaatcctcc aagttagtat cagccaatgc cctttttgga
 661 gacaaatccc ttaccttcaa tgagacctac caggacatca gtgagttggt atatggagcc
 721 aagctccagc ccctggactt caaggaaaat gcagagcaat ccagagcggc catcaacaa
 781 tgggtgtcca ataagaccga aggccgaatc accgatgtca ttccctcgga agccatcaat
 841 gagctcactg ttctggtgct ggttaacacc atttacttca agggcctgtg gaagtcaaag
 901 ttcagccctg agaacacaag gaaggaactg ttctacaagg ctgatggaga gtcgtgttca
 961 gcatctatga tgtaccagga aggcaagttc cgttatcggc gcgtggctga aggcacccag
1021 gtgcttgagt tgcccttcaa aggtgatgac atcaccatgg tcctcatctt gcccaagcct
1081 gagaagagcc tggccaaggt ggagaaggaa ctcaccccag aggtgctgca ggagtggctg
1141 gatgaattgg aggagatgat gctggtggtt cacatgcccc gcttccgcat tgaggacggc
1201 ttcagtttga aggagcagct gcaagacatg ggccttgtcg atctgttcag ccctgaaaag
1261 tccaaactcc caggtattgt tgcagaaggc cgagatgacc tctatgtctc agatgcattc
1321 cataaggcat ttcttgaggt aaatgaagaa ggcagtgaag cagctgcaag taccgctgtt
1381 gtgattgctg gccgttcgct aaacccccaac agggtgactt tcaaggccaa caggccctcc
1441 ctggttttta taagagaagt tcctctgaac actattatct tcatgggcag agtagccaac
1501 ccttgtgtta agtaaaatgt tcttattctt tgcacctctt cctatttttg gtttgtgaac
1561 agaagtaaaa ataaatacaa actacttcca tctcacatt
```

FIG. 11

```
   1 ctgcaggggg gggggggggg gggggctgtc atggcggcag gacggcgaac ttgcagtatc
  61 tccacgaccc gcccctacag gtgccagtgc ctccagaatg tggcagctca caagcctcct
 121 gctgttcgtg gccacctggg gaatttccgg cacaccagct cctcttgact cagtgttctc
 181 cagcagcgag cgtgcccacc aggtgctgcg gatccgcaaa cgtgccaact ccttcctgga
 241 ggagctccgt cacagcagcc tggagcggga gtgcatagag gagatctgtg acttcgagga
 301 ggccaaggaa attttccaaa atgtggatga cacactggcc ttctggtcca agcacgtcga
 361 cggtgaccag tgcttggtct tgcccttgga gcacccgtgc gccagcctgt gctgcgggca
 421 cggcacgtgc atcgacggca tcggcagctt cagctgcgac tgccgcagcg gctgggaggg
 481 ccgcttctgc cagcgcgagg tgagcttcct caattgctcg ctggacaacg gcggctgcac
 541 gcattactgc ctagaggagg tgggctggcg gcgctgtagc tgtgcgcctg gctacaagct
 601 gggggacgac ctcctgcagt gtcaccccgc agtgaagttc ccttgtggga ggccctggaa
 661 gcggatggag aagaagcgca gtcacctgaa acgagacaca gaagaccaag aagaccaagt
 721 agatccgcgg ctcattgatg ggaagatgac caggcgggga gacagcccct ggcaggtggt
 781 cctgctggac tcaaagaaga agctggcctg cggggcagtg ctcatccacc cctcctgggt
 841 gctgacagcg gcccactgca tggatgagtc caagaagctc cttgtcaggc ttggagagta
 901 tgacctgcgg cgctgggaga agtgggagct ggacctggac atcaaggagg tcttcgtcca
 961 ccccaactac agcaagagca ccaccgacaa tgacatcgca ctgctgcacc tggcccagcc
1021 cgccaccctc tcgcagacca tagtgcccat ctgcctcccg gacagcggcc ttgcagagcg
1081 cgagctcaat caggccggcc aggagaccct cgtgacgggc tggggctacc acagcagccg
1141 agagaaggag gccaagagaa accgcacctt cgtcctcaac ttcatcaaga ttcccgtggt
1201 cccgcacaat gagtgcagcg aggtcatgag caacatggtg tctgagaaca tgctgtgtgc
1261 gggcatcctc ggggaccggc aggatgcctg cgagggcgac agtggggggc ccatggtcgc
1321 ctccttccac ggcacctggt tcctggtggg cctggtgagc tggggtgagg gctgtgggct
1381 ccttcacaac tacggcgttt acaccaaagt cagccgctac ctcgactgga tccatggcca
1441 catcagagac aaggaagccc cccagaagag ctgggcacct tagcgaccct ccctgcaggg
1501 ctgggctttt gcatggcaat ggatgggaca ttaaagggac atgtaacaag cacaccggcc
1561 tgctgttctg tccttccatc cctcttttgg gctcttctgg agggaagtaa catttactga
1621 gcacctgttg tatgtcacat gccttatgaa tagaatctta actcctagag caactctgtg
1681 gggtggggag gagcagatcc aagttttgcg ggtctaaag ctgtgtgtgt tgagggggat
1741 actctgttta tgaaaaagaa taaaaaacac aaccacgaaa aaaaaaaaaa aaaaaaaaaa
1801 aaaaaaaaaa aaaaaaaccc cccccgcccc cccccccctg cag
```

FIG. 12A

```
   1 agtgaatctg ggcgagtaac acaaaacttg agtgtcctta cctgaaaaat agaggttaga
  61 gggatgctat gtgccattgt gtgtgtgtgt tgggggtggg gattgggggt gatttgtgag
 121 caattggagg tgagggtgga gcccagtgcc cagcacctat gcactgggga cccaaaaagg
 181 agcatcttct catgatttta tgtatcagaa attgggatgg catgtcattg ggacagcgtc
 241 tttttcttg tatggtggca cataaataca tgtgtcttat aattaatggt attttagatt
 301 tgacgaaata tggaatatta cctgttgtgc tgatcttggg caaactataa tatctctggg
 361 caaaaatgtc cccatctgaa aaacagggac aacgttcctc cctcagccag ccactatggg
 421 gctaaaatga gaccacatct gtcaagggtt ttgccctcac ctccctccct gctggatggc
 481 atccttggta ggcagaggtg ggcttcgggc agaacaagcc gtgctgagct aggaccagga
 541 gtgctagtgc cactgtttgt ctatggagag ggaggcctca gtgctgaggg ccaagcaaat
 601 atttgtggt atggattaac tcgaactcca ggctgtcatg gcggcaggac ggcgaacttg
 661 cagtatctcc acgacccgcc cctgtgagtc cccctccagg caggtctatg aggggtgtgg
 721 agggagggct gcccccggga gaagagagct aggtggtgat gagggctgaa tcctccagcc
 781 agggtgctca acaagcctga gcttggggta aaaggacaca aggccctcca caggccaggc
 841 ctggcagcca cagtctcagg tccctttgcc atgcgcctcc ctctttccag gccaagggtc
 901 cccaggccca gggccattcc aacagacagt ttggagccca ggaccctcca ttctccccac
 961 cccacttcca cctttggggg tgtcggattt gaacaaatct cagaagcggc ctcagaggga
1021 gtcggcaaga atggagagca gggtccggta gggtgtgcag aggccacgtg gcctatccac
1081 tggggagggt tccttgatct ctggccacca gggctatctc tgtggccttt tggagcaacc
1141 tggtggtttg gggcaggggt tgaatttcca ggcctaaac cacacaggcc tggccttgag
1201 tcctggctct gcgagtaatg catggatgta aacatggaga cccaggacct tgcctcagtc
1261 ttccgagtct ggtgcctgca gtgtactgat ggtgtgagac cctactcctg gaggatgggg
1321 gacagaatct gatcgatccc ctgggttggt gacttccctg tgcaatcaac ggagaccagc
1381 aagggttgga tttttaataa accacttaac tcctccgagt ctcagtttcc ccctctatga
1441 aatggggttg acagcattaa taactacctc ttgggtggtt gtgagcctta actgaagtca
1501 taatatctca tgtttactga gcatgagcta tgtgcaaagc ctgttttgag agctttatgt
1561 ggactaactc ctttaattct cacaacaccc tttaaggcac agatacacca cgttattcca
1621 tccattttac aaatgaggaa actgaggcat ggagcagtta agcatcttgc ccaacattgc
1681 cctccagtaa gtgctggagc tggaatttgc accgtgcagt ctggcttcat ggcctgccct
1741 gtgaatcctg taaaaattgt ttgaaagaca ccatgagtgt ccaatcaacg ttagctaata
1801 ttctcagccc agtcatcaga ccggcagagg cagccacccc actgtcccca gggaggacac
1861 aaacatcctg gcaccctctc cactgcattc tggagctgct ttctaggcag gcagtgtgag
1921 ctcagcccca cgtagagcgg gcagccgagg ccttctgagg ctatgtctct agcgaacaag
1981 gaccctcaat tccagcttcc gcctgacggc cagcacacag ggacagccct ttcattccgc
2041 ttccacctgg gggtgcaggc agagcagcag cgggggtagc actgcccgga gctcagaagt
2101 cctcctcaga caggtgccag tgcctccaga atgtggcagc tcacaagcct cctgctgttg
2161 gtggccacct ggggaatttc cggcacacca gctcctcttg gtaaggccac cccaccccta
2221 ccccgggacc cttgtggcct ctacaaggcc ctggtggcat ctgcccaggc cttcacagct
2281 tccaccatct ctctgagccc tgggtgaggt gaggggcaga tgggaatggc aggaatcaac
2341 tgacaagtcc caggtaggcc agctgccaga gtgccacaca ggggctgcca gggcaggcat
2401 gcgtgatggc agggagcccc gcgatgacct cctaaagctc cctcctccac acggggatgg
2461 tcacagagtc ccctgggcct tccctctcca cccactcact ccctcaactg tgaagacccc
2521 aggcccaggc taccgtccac actatccagc acagcctccc ctactcaaat gcacacyhhc
2581 ctcatggctg ccctgcccca accccttttcc tggtctccac agccaacggg aggaggccat
2641 gattcttggg gaggtccgca ggcacatggg cccctaaagc cacaccaggc tgttggtttc
2701 atttgtgcct ttatagagct gtttatctgc ttgggacctg cacctccacc ctttcccaag
```

FIG. 12B

```
2761 gtgccctcag ctcaggcata ccctcctcta ggatgccttt tcccccatcc cttcttgctc
2821 acacccccaa cttgatctct ccctcctaac tgtgccctgc accaagacag acacttcaca
2881 gagcccagga cacacctggg gacccttcct aggtgatagg tctgtctatc ctccaggtgt
2941 cctgcccaa ggggagaagc atggggaata cttggttggg ggaggaaagg aggactgggg
3001 ggatgtgtca agatggggct gcatgtggtg tactggcaga agagtgagag gatttaactt
3061 ggcagccttt acagcagcag ccagggcttg agtacttatc tctgggccag gctgtattgg
3121 atgttttaca tgacggtctc atccccatgt ttttggatga gtaaattgaa ccttagaaag
3181 gtaaagacac tggctcaagg tcacacagag atcggggtgg ggttcacagg gaggcctgtc
3241 catctcagag caaggcttcg tcctccaact gccatctgct tcctggggag gaaaagagca
3301 gaggacccct gcgccaagcc atgacctaga attagaatga gtcttgaggg ggcggagaca
3361 agaccttccc aggctctccc agctctgctt cctcagaccc cctcatggcc ccagcccctc
3421 ttaggcccct caccaaggtg agctcccctc cctccaaaac cagactcagt gttctccagc
3481 agcgagcgtg cccaccaggt gctgcggatc cgcaaacgtg ccaactcctt cctggaggag
3541 ctccgtcaca gcagcctgga gcgggagtgc atagaggaga tctgtgactt cgaggaggcc
3601 aaggaaattt tccaaaatgt ggatgacaca gtaaggccac catgggtcca gaggatgagg
3661 ctcaggggcg agctggtaac cagcaggggc ctcgaggagc aggtggggac tcaatgctga
3721 ggccctctta ggagttgtgg gggtggctga gtggagcgat taggatgctg gccctatgat
3781 gtcggccagg cacatgtgac tgcaagaaac agaattcagg aagaagctcc aggaaagagt
3841 gtggggtgac cctaggtggg gactcccaca gccacagtgt aggtggttca gtccaccctc
3901 cagccactgc tgagcaccac tgcctccccg tcccacctca caaagagggg acctaaagac
3961 caccctgctt ccacccatgc ctctgctgat cagggtgtgt gtgtgaccga aactcacttc
4021 tgtccacata aaatcgctca ctctgtgcct cacatcaaag ggagaaaatc tgattgttca
4081 gggggtcgga agacagggtc tgtgtcctat ttgtctaagg gtcagagtcc tttggagccc
4141 ccagagtcct gtggacgtgg ccctaggtag tagggtgagc ttggtaacgg ggctggcttc
4201 ctgagacaag gctcagaccc gctctgtccc tggggatcgc ttcagccacc aggacctgaa
4261 aattgtgcac gcctgggccc ccttccaagg catccaggga tgctttccag tggaggcttt
4321 cagggcagga gaccctctgg cctgcacct ctcttgccct cagcctccac ctccttgact
4381 ggacccccat ctggacctcc atccccacca cctctttccc cagtggcctc cctggcagac
4441 accacagtga ctttctgcag gcacatatct gatcacatca agtccccacc gtgctcccac
4501 ctcacccatg gtctctcagc cccagcagcc ttggctggcc tctctgatgg agcaggcatc
4561 aggcacaggc cgtgggtctc aacgtgggct gggtggtcct ggaccagcag cagccgccgc
4621 agcagcaacc ctggtacctg gttaggaacg cagaccctct gcccccatcc tcccaactct
4681 gaaaaacact ggcttaggga aaggcgcgat gctcaggggt cccccaaagc ccgcaggcag
4741 agggagtgat gggactggaa ggaggccgag tgacttggtg agggattcgg gtcccttgca
4801 tgcagaggct gctgtgggag cggacagtcg cgagagcagc actgcagctg catggggaga
4861 gggtgttgct ccagggacgt gggatggagg ctgggcgcgg gcgggtggcg ctggagggcg
4921 ggggaggggc agggagcacc agctcctagc agccaacgac catcgggcgt cgatccctgt
4981 ttgtctggaa gccctcccct cccctgcccg ctcacccgct gccctgcccc accgggcgc
5041 gcccctccgc acaccggctg caggagcctg acgctgcccg ctctctccgc agctggcctt
5101 ctggtccaag cacgtcggtg agtgcgttct agatccccgg ctggactacc ggcgcccgcg
5161 cccctcggga tctctggccg ctgacccccct accccgcctt gtgtcgcaga cggtgaccag
5221 tgcttggtct tgcccttgga gcacccgtgc gccagcctgt gctgcgggca cggcacgtgc
5281 atcgacggca tcggcagctt cagctgcgac tgccgcagcg gctgggaggg ccgcttctgc
5341 cagcgcggtg agggggagag gtggatgctg gcgggcggcg gggcggggct ggggccgggt
5401 tgggggcgcg gcaccagcac cagctgcccg cgccctcccc tgcccgcaga ggtgagcttc
5461 ctcaattgct ctctggacaa cggcggctgc acgcattact gcctagagga ggtgggctgg
```

FIG. 12C

```
5521 cggcgctgta gctgtgcgcc tggctacaag ctgggggacg acctcctgca gtgtcacccc
5581 gcaggtgaga agccccccaat acatcgccca ggaatcacgc tgggtgcggg gtgggcaggc
5641 ccctgacggg cgcggcgcgg ggggctcagg agggtttcta gggagggagc gaggaacaga
5701 gttgagcctt ggggcagcgg cagacgcgcc caacaccggg gccactgtta gcgcaatcag
5761 cccgggagct gggcgcgccc tccgctttcc ctgcttcctt tcttcctggc gtccccgctt
5821 cctccgggcg cccctgcgac ctggggccac ctcctggagc gcaagcccag tggtggctcc
5881 gctccccagt ctgagcgtat ctggggcgag gagtgcagcg tcctcctcca tgtagcctgg
5941 ctgcgttttt ctctgacgtt gtccggcgtg catcgcattt ccctctttac cccccttgctt
6001 ccttgaggag agaacagaat ccgattctg ccttcttcta tattttcctt tttatgcagg
6061 ttaatcaaat ttatatatgt atgaaacttt aaaaatcaga gttttacaac tcttacactt
6121 tcagcatgct gttccttggc atgggtcctt ttttcattca ttttcataaa aggtggaccc
6181 ttttaatgtg gaaattccta tcttctgcct ctagggcatt tatcacttat ttcttctaca
6241 atctcccctt tacttcctct attttctctt tctggacctc ccattattca gacctctttc
6301 ctctagtttt attgtctctt ctatttccca tctctttgac tttctctttt ctttcaggga
6361 actttctttt ttttcttttt ttttgagatg gagtttcact cttgttgtcc caggctggag
6421 tgcaatgacg tgatctcagc tcaccacaac cycchccycc tggattcaag cgattctcct
6481 gccgcagcct cccgagtagc tgggattaca ggcatgcgcc accacgccca gctaattttg
6541 tgtttttagt agagaagggg tttctccgtg ttggtcaagc tggtcttgaa ctcctgacct
6601 caggtgatcc acctgccttg gcctcctaaa gtgctgggat tacaggcgtg agccaccgcg
6661 cccagcctct ttcagggaac tttctccgtg tttataattc aattcttctg cagaaaaaaa
6721 tttttggcca ggctcagtag ctcagaccaa taattccagc actttgagag gctgaggtgg
6781 gaggattgct tgagcttggg agtttgagac tagcctgggc aacacagtga gaccctgtct
6841 ctatttttaa aaaaagtaaa aaaagatcta aaaatttaac tttttatttt gaaataatta
6901 gatatttcca ggaagctgca aagaaatgcc tggtgggcct gttggctgtgcg ggtttcctgc
6961 aaggccgtgg gaaggccctg tcattggcag aaccccagat tgagggct ttcctttag
7021 gctgctttct aagaggactc ctccaagctc ttggaggatg gaagacgctc acccatggtg
7081 ttcggcccct cagagcaggg tggggcaggg gagctggtgc ctgtgcaggc tgtggacatt
7141 tgcatgactc ccctgtggtca gctaagagca ccactccttc ctgaagcggg gcctgaagtc
7201 cctagtcaga gcctctggtt caccttctgc aggcagggag aggggagtca agtcagtgag
7261 gagggctttc gcagtttctc ttacaaactc tcaacatgcc ctcccacctg cactgccttc
7321 ctggaagccc cacagcctcc tctggttccg tggtccagtc cttcagcttc tgggcgcccc
7381 catcacgggc tgagattttt gctttccagt ctgccaagtc agttactgtg tccatccatc
7441 tgctgtcagc ttctggaatt gttgctgttg tgccctttcc attcttttgt tatgatgcag
7501 ctcccctgct gacgacgtcc cattgctctt ttaagtctag atatctggac tgggcattca
7561 aggcccattt tgagcagagt cgggctgacc tttcagccct cagttctcca tggagtatgc
7621 gctctcttct tggcagggag gcctcacaaa catgccatgc ctattgtagc agctctccaa
7681 gaatgctcac ctccttctcc ctgtaattcc tttcctctgt gaggagctca gcagcatccc
7741 attatgagac cttactaatc ccagggatca cccccaacag ccctggggta caatgagctt
7801 ttaagaagtt taaccaccta tgtaaggaga cacaggcagt gggcgatgct gcctggcctg
7861 actcttgcca ttgggtggta ctgtttgttg actgactgac tgactgactg gagggggttt
7921 gtaatttgta tctcagggat taccccccaac agccctgggg tacaatgagc cttcaagaag
7981 tttaacaacc tatgtaagga cacacagcca gtgggtgatg ctgcctggtc tgactcttgc
8041 cattcagtgg cactgtttgt tgactgactg actgactgac tggctgactg gagggggttc
8101 atagctaata ttaatggagt ggtctaagta tcattggttc cttgaaccct gcactgtggc
8161 aaagtggccc acaggctgga ggaggaccaa gacaggaggg cagtctcggg aggagtgcct
8221 ggcaggcccc tcaccacctc tgcctacctc agtgaagttc ccttgtggga ggccctggaa
8281 gcggatggag aataagcgca gtcacctgaa acgagacaca gaagaccaag aagaccaagt
```

FIG. 12D

```
8341 agatccgcgg ctcattgatg ggaagatgac caggcgggga gacagcccct ggcaggtggg
8401 aggcgaggca gcaccggctc gtcacgtgct gggtccggga tcactgagtc catcctggca
8461 gctatgctca gggtgcagaa accgagaggg aagcgctgcc attgcgtttg ggggatgatg
8521 aaggtggggg atgctcagg gaaagatgga cgcaacctga ggggagagga gcagccaggg
8581 tgggtgaggg gaggggcatg ggggcatgga ggggtctgca ggagggaggg ttacagtttc
8641 taaaaagagc tggaaagaca ctgctctgct ggcgggattt taggcagaag ccctgctgat
8701 gggagagggc taggagggag ggccgggcct gagtacccct ccagcctcca catgggaact
8761 gacacttact gggttcccct ctctgccagg catgggggag ataggaacca acaafrfffa
8821 gtatttgccc tggggactca gactctgcaa gggtcaggac cccaaagacc cggcagccca
8881 gtgggaccac agccaggacg gcccttcaag ataggggctg agggaggcca aggggaacat
8941 ccaggcagcc tgggggccac aaagtcttcc tggaagacac aaggcctgcc aagcctctaa
9001 ggatgagagg agctcgctgg gcgatgttgg tgtggctgag ggtgactgaa acagtatgaa
9061 cagtgcagga acagcatggg caaaggcagg aagacaccct gggacaggct gacactgtaa
9121 aatgggcaaa aatagaaaac gccagaaagg cctaagccta tgcccatatg accagggaac
9181 ccaggaaagt gcatatgaaa cccaggtgcc ctggactgga ggctgtcagg aggcagccct
9241 gtgatgtcat catcccaccc cattccaggt ggtcctgctg gactcaaaga agaagctggc
9301 ctgcggggca gtgctcatcc acccctcctg ggtgctgaca gcggcccact gcatggatga
9361 gtccaagaag ctccttgtca ggcttggtat gggctggagc caggcagaag gcatggatga
9421 gaggcctggg tagggggacc aggcaggctg ttcaggtttg ggggaccccg ggggctgcca
9481 gcttaagcaa gaggcttctt gagctccaca gaaggtgttt gggggggaaga ctccccaggt
9541 cccccaccct gcccacccat gtacacccag tattttgcag taggggggttc ggcctatgtg
9601 tcttcgaatc tgggcacagg tacctgcaca cacatgtttg tgagggcta tctggtgccc
9661 cacctctcca ctcccactca tgaggagcag gctgtgtggg cctcagcacc cacagacctt
9721 gagaccagca aggcctggcc tcagggctgt gcctcccaca gactgacagg cacagacctt
9781 tacagaggga gccctagcat ctgccaaagc cacaagctgc ttccctagca cttgggtgca
9841 tcctatgcat tggccccgat ctctggcaat ttctggaggg gggtctggc gatggagctg
9901 atgccaaaaa gaaggcaaag catattgaga aaggccaaat tcacatttcc ggctgggggga
9961 tctatgccag tggccccgtg gggcttggct tagaattccc aggtgctctt tcagcataa
10021 catcagtctg gactgagagg accttctctc tcaggtggga cccggccctg cccagggaac
10081 cagtgccgtg ttctgggggt cctcctctct gggtctcact gcccctgggg tcctccctgg
10141 tacctttgct ccatgttcct ttgtggctct ggtctgtgtc tggggtttcc tctctccagc
10201 ggcttccctg ctgcccattc cttctctggt ctcacggctc cgtgactcct aggggtctcg
10261 cagcatccta cccctttgga ttgacacctg ttggccactg cttctggcag gaaaagtcac
10321 cgttgatagg gttccacggc atagacaggt ggctccgcgc cagtgcctgg gacgtgtggg
10381 tgcacagtct ccgggtgaac cttcttcagg ccctctccca ggcctgcag ggcacagcag
10441 tgggtgggcc tcaggaaagt gccactgggg agaggctccc cgcagcccac tctgactgtg
10501 ccctctgccc tgcaggagag tatgacctgc ggcgctggga gaagtgggag ctggacctgg
10561 acatcaagga ggtcttcgtc caccccaact acagcaagag caccaccgac aatgacatcg
10621 cactgctgca cctggcccag cccgccaccc tgtcgcagac catagtgccc atctgcctcc
10681 cggacagcgg ccttgcagag cgcgagctca atcaggccgg ccaggagacc ctcgtgacgg
10741 gctggggcta ccacagcagc cgagagaagg aggccaagag aaaccgcacc ttcgtcctca
10801 acttcatcaa gattcccgtg gtcccgcaca atgagtgcag cgaggtcatg agcaacatgg
10861 tgtctgagaa catgctgtgt gcgggcatcc tcggggaccg gcaggatgcc tgcgagggcg
10921 acagtggggg gcccatggtc gccctccttcc acggcacctg gttcctggtg ggcctggtga
10981 gctggggtga gggctgtggg ctccttcaca actacggcgt ttacaccaaa gtcagccgct
11041 acctcgactg gatccatggg cacatcagag acaaggaagc cccccagaag agctgggcac
11101 cttagcgacc ctccctgcag ggctgggctt ttgcatggca atggatggga cattaaaggg
```

FIG. 12E

```
11161 acatgtaaca agcacaccgg cctgctgttc tgtccttcca tccctctttt gggctcttct
11221 ggagggaagt aacatttact gagcacctgt tgtatgtcac atgccttatg aatagaatct
11281 taactcctag agcaactctg tggggtgggg aggagcagat ccaagttttg cggggtctaa
11341 agctgtgtgt gttgaggggg atactctgtt tatgaaaaag aataaaaaac acaaccacga
11401 agccactaga gccttttcca gggctttggg aagagcctgt gcaagccggg gatgctgaag
11461 gtgaggattg accagctttc cagtctagcc agctatgagg tagacatgtt tagctcatat
11521 cacagaggag gaaactgagg ggtctgaaag gtttacatgg tggagccagg attcaaatct
11581 aggtctgact ccaaaaccca ggtgcttttt tctgttctcc acyhyccyhh aggacagctg
11641 tttcgacggt gctcagtgtg gaggccacta ttagctctgt agggaagcag ccagagaccc
11701 agaaagtgtt ggttcagccc agaat
```

FIG. 12F

SEQ ID NO:3

```
   ggcctctc actaactaat cactttccca tcttttgtta gatttgaata tatacattct
  atgatcattg ctttttctct ttacagggga gaatttcata ttttacctga gcaaattgat
  tagaaaatgg aaccactaga ggaatataat gtgttaggaa attacagtca tttctaaggg
  cccagccctt gacaaaattg tgaagttaaa ttctccactc tgtccatcag atactatggt
  tctccactat ggcaactaac tcactcaatt ttccctcctt agcagcattc catcttcccg
  atcttctttg cttctccaac caaaacatca atgtttatta gttctgtata cagtacagga
  tctttggtct actctatcac aaggccagta ccacactcat gaagaaagaa cacaggagta
  gctgagaggc taaaactcat caaaaacact actccttttc ctctacccta ttcctcaatc
  ttttaccttt tccaaatccc aatccccaaa tcagtttttc tctttcttac tccctctctc
  ccttttaccc tccatggtcg ttaaaggaga gatggggagc atcattctgt tatacttctg
  tacacagtta tacatgtcta tcaaacccag acttgcttcc atagtggaga cttgcttttc
  agaacatagg gatgaagtaa ggtgcctgaa aagtttgggg gaaaagtttc tttcagagag
  ttaagttatt ttatatatat aatatatata taaaatatat aatatacaat ataaatatat
  agtgtgtgtg tgtatgcgtg tgtgtagaca cacacgcata cacacatata atggaagcaa
  taagccattc taagagcttg tatggttatg gaggtctgac taggcatgat ttcacgaagg
  caagattggc atatcattgt aactaaaaaa gctgacattg acccagacat attgtactct
  ttctaaaaat aataataata atgctaacag aaagaagaga accgttcgtt tgcaatctac
  agctagtaga gactttgagg aagaattcaa cagtgtgtct tcagcagtgt tcagagccaa
  gcaagaagtt gaagttgcct agaccagagg acataagtat catgtctcct ttaactagca
  taccccgaag tggagaaggg tgcagcaggc tcaaaggcat aagtcattcc aatcagccaa
  ctaagttgtc cttttctggt ttcgtgttca ccatggaaca ttttgattat agttaatcct
  tctatcttga atctt
```

SEQ ID NO:76

```
   ggcctctg actaactaat cactttccca tcttttgtta gatttgaata tatacattct
  atgatcattg ctttttctct ttacagggga gaatttcata ttttacctga gcaaattgat
  tagaaaatgg aaccactaga ggaatataat gtgttaggaa attacagtca tttctaaggg
  cccagccctt gacaaaattg tgaagttaaa ttctccactc tgtccatcag atactatggt
  tctccactat ggcaactaac tcactcaatt ttccctcctt agcagcattc catcttcccg
  atcttctttg cttctccaac caaaacatca atgtttatta gttctgtata cagtacagga
  tctttggtct actctatcac aaggccagta ccacactcat gaagaaagaa cacaggacta
  gctgagaggc taaaactcat caaaaacact actccttttc ctctacccta ttcctcaatc
  ttttaccttt tccaaatccc aatccccaaa tcagtttttc tctttcttac tccctctctc
  ccttttaccc tccatggtcg ttaaaggaga gatggggagc atcattctgt tatacttctg
  tacacagtta tacatgtcta tcaaacccag acttgcttcc atagtggaga cttgcttttc
  agaacatagg gatgaagtaa ggtgcctgaa aagtttgggg gaaaagtttc tttcagagag
  ttaagttatt ttatatatat aatatatata taaaatatat aatatacaat ataaatatat
  agtgtgtgtg tgtatgcgtg tgtgtagaca cacacgcata cacacatata atggaagcaa
  taagccattc taagagcttg tatggttatg gaggtctgac taggcatgat ttcacgaagg
  caagattggc atatcattgt aactaaaaaa gctgacattg acccagacat attgtactct
  ttctaaaaat aataataata atgctaacag aaagaagaga accgttcgtt tgcaatctac
  agctagtaga gactttgagg aagaattcaa cagtgtgtct tcagcagtgt tcagagccaa
  gcaagaagtt gaagttgcct agaccagagg acataagtat catgtctcct ttaactagca
  taccccgaag tggagaaggg tgcagcaggc tcaaaggcat aagtcattcc aatcagccaa
  ctaagttgtc cttttctggt ttcgtgttca ccatggaaca ttttgattat agttaatcct
  tctatcttga atctt
```

FIG. 13A

SEQ ID NO:77

```
 ggcctctc actaactaat cactttccca tcttttgtta gatttgaata tatacattct
atgatcattg ctttttctct ttacagggga gaatttcata ttttacctga gcaaattgat
tagaaaatgg aaccactaga ggaatataat gtgttaggaa attacagtca tttctaaggg
cccagccctt gacaaaattg tgaagttaaa ttctccactc tgtccatcag atactatggt
tctccactat ggcaactaac tcactcaaat ttccctcctt agcagcattc catcttcccg
atcttctttg cttctccaac caaaacatca atgtttatta gttctgtata cagtacagga
tctttggtct actctatcac aaggccagta ccacactcat gaagaaagaa cacaggagta
gctgagaggc taaaactcat caaaaacact actccttttc ctctacccta ttcctcaatc
ttttaccttt tccaaatccc aatccccaaa tcagtttttc tctttcttac tccctctctc
ccttttaccc tccatggtcg ttaaaggaga gatggggagc atcattctgt tatacttctg
tacacagtta tacatgtcta tcaaacccag acttgcttcc atagtggaga cttgcttttc
agaacatagg gatgaagtaa ggtgcctgaa aagtttgggg gaaaagtttc tttcagagag
ttaagttatt ttatatatat aatatatata taaaatatat aatatacaat ataaatatat
agtgtgtgtg tgtatgcgtg tgtgtagaca cacacgcata cacacatata atggaagcaa
taagccattc taagagcttg tatggttatg gaggtctgac taggcatgat ttcacgaagg
caagattggc atatcattgt aactaaaaaa gctgacattg acccagacat attgtactct
ttctaaaaat aataataata atgctaacag aaagaagaga accgttcgtt tgcaatctac
agctagtaga gactttgagg aagaattcaa cagtgtgtct tcagcagtgt tcagagccaa
gcaagaagtt gaagttgcct agaccagagg acataagtat catgtctcct ttaactagca
taccccgaag tggagaaggg tgcagcaggc tcaaaggcat aagtcattcc aatcagccaa
ctaagttgtc cttttctggt ttcgtgttca ccatggaaca ttttgattat agttaatcct
tctatcttga atctt
```

SEQ ID NO:78

```
 ggcctctc actaactaat cactttccca tcttttgtta gatttgaata tatacattct
atgatcattg ctttttctct ttacagggga gaatttcata ttttacctga gcaaattgat
tagaaaatgg aaccactaga ggaatataat gtgttaggaa attacagtca tttctaaggg
cccagccctt gacaaaattg tgaagttaaa ttctccactc tgtccatcag atactatggt
tctccactat ggcaactaac tcactcaatt ttccctcctt agcagcattc catcttcccg
atcttctttg cttctccaac caaaacatca atgtttatta gttctgtata cagtacagga
tctttggtct actctatcac aaggccagta ccacactcat gaagaaagaa cacaggacta
gctgagaggc taaaactcat caaaaacact actccttttc ctctacccta ttcctcaatc
ttttaccttt tccaaatccc aatccccaaa tcagtttttc tctttcttac tccctctctc
ccttttaccc tccatggtcg ttaaaggaga gatggggacg atcattctgt tatacttctg
tacacagtta tacatgtcta tcaaacccag acttgcttcc atagtggaga cttgcttttc
agaacatagg gatgaagtaa ggtgcctgaa aagtttgggg gaaaagtttc tttcagagag
ttaagttatt ttatatatat aatatatata taaaatatat aatatacaat ataaatatat
agtgtgtgtg tgtatgcgtg tgtgtagaca cacacgcata cacacatata atggaagcaa
taagccattc taagagcttg tatggttatg gaggtctgac taggcatgat ttcacgaagg
caagattggc atatcattgt aactaaaaaa gctgacattg acccagacat attgtactct
ttctaaaaat aataataata atgctaacag aaagaagaga accgttcgtt tgcaatctac
agctagtaga gactttgagg aagaattcaa cagtgtgtct tcagcagtgt tcagagccaa
gcaagaagtt gaagttgcct agaccagagg acataagtat catgtctcct ttaactagca
taccccgaag tggagaaggg tgcagcaggc tcaaaggcat aagtcattcc aatcagccaa
ctaagttgtc cttttctggt ttcgtgttca ccatggaaca ttttgattat agttaatcct
tctatcttga atctt
```

FIG. 13B

SEQ ID NO:79

```
  ggcctctc actaactaat cactttccca tcttttgtta gatttgaata tatacattct
 atgatcattg ctttttctct ttacagggga gaatttcata ttttacctga gcaaattgat
 tagaaaatgg aaccactaga ggaatataat gtgttaggaa attacagtca tttctaaggg
 cccagccctt gacaaaattg tgaagttaaa ttctccactc tgtccatcag atactatggt
 tctccactat ggcaactaac tcactcaatt ttccctcctt agcagcattc catcttcccg
 atcttctttg cttctccaac caaaacatca atgtttatta gttctgtata cagtacagga
 tctttggtct actctatcac aaggccagta ccacactcat gaagaaagaa cacaggacta
 gctgagaggc taaaactcat caaaaacact actccttttc ctctacccta ttcctcaatc
 ttttaccttt tccaaatccc aatccccaaa tcagtttttc tctttcttac tccctctctc
 ccttttaccc tccatggtcg ttaaaggaga gatggggagc atcattctgt tatacttctg
 tacacagtta tacatgtcta tcaaacccag acttgcttcc atagtggaga cttgcttttc
 agaacatagg gatgaagtaa ggtgcctgaa aagtttgggg gaaaagtttc tttcagagag
 ttaagttatt ttatatatat aatatatata taaaatatat aatatacaat ataaatatat
 agtgtgtgtg tgtatgcgtg tgtgtagaca cacacgcatc cacacatata atggaagcaa
 taagccattc taagagcttg tatggttatg gaggtctgac taggcatgat ttcacgaagg
 caagattggc atatcattgt aactaaaaaa gctgacattg acccagacat attgtactct
 ttctaaaaat aataataata atgctaacag aaagaagaga accgttcgtt tgcaatctac
 agctagtaga gactttgagg aagaattcaa cagtgtgtct tcagcagtgt tcagagccaa
 gcaagaagtt gaagttgcct agaccagagg acataagtat gtactctcct ttaactagca
 taccccgaag tggagaaggg tgcagcaggc tcaaaggcat aagtcattcc aatcagccaa
 ctaagttgtc cttttctggt ttcgtgttca ccatggaaca ttttgattat agttaatcct
 tctatcttga atctt
```

SEQ ID NO:80

```
  ggcctctc actaactaat cactttccca tcttttgtta gatttgaata tatacattct
 atgatcattg ctttttctct ttacagggga gaatttcata ttttacctga gcaaattgat
 tagaaaatgg aaccactaga ggaatataat gtgttaggaa attacagtca tttctaaggg
 cccagccctt gacaaaattg tgaagttaaa ttctccactc tgtccatcag atactatggt
 tctccactat ggcaactaac tcactcaatt ttccctcctt agcagcattc catcttcccg
 atttcttctttg cttctccaac caaaacatca atgtttatta gttctgtata cagtacagga
 tctttggtct actctatcac aaggccagta ccacactcat gaagaaagaa cacaggacta
 gctgagaggc taaaactcat caaaaacact actccttttc ctctacccta ttcctcaatc
 ttttaccttt tccaaatccc aatccccaaa tcagtttttc tctttcttac tccctctctc
 ccttttaccc tccatggtcg ttaaaggaga gatggggagc atcattctgt tatacttctg
 tacacagtta tacatgtcta tcaaacccag acttgcttcc atagtggaga cttgcttttc
 agaacatagg gatgaagtaa ggtgcctgaa aagtttgggg gaaaagtttc tttcagagag
 ttaagttatt ttatatatat aatatatata taaaatatat aatatacaat ataaatatat
 agtgtgtgtg tgtatgcgtg tgtgtagaca cacacgcatc cacacatata atggaagcaa
 taagccattc taagagcttg tatggttatg gaggtctgac taggcatgat ttcacgaagg
 caagattggc atatcattgt aactaaaaaa gctgacattg acccagacat attgtactct
 ttctaaaaat aataataata atgctaacag aaagaagaga accgttcgtt tgcaatctac
 agctagtaga gactttgagg aagaattcaa cagtgtgtct tcagcagtgt tcagagccaa
 gcaagaagtt gaagttgcct agaccagagg acataagtat catgtctcct ttaactagca
 taccccgaag tggagaaggg tgcagcaggc tcaaaggcat aagtcattcc aatcagccaa
 ctaagttgtc cttttctggt ttcgtgttca ccatggaaca ttttgattat agttaatcct
 tctatcttga atctt
```

FIG. 13C

SEQ ID NO:81

```
  ggcctctc actaactaat cactttccca tcttttgtta gatttgaata tatacattct
atgatcattg cttttctct ttacagggga gaatttcata ttttacctga gcaaattgat
tagaaaatgg aaccactaga ggaatataat gtgttaggaa attacagtca tttctaaggg
cccagcccctt gacaaaattg tgaagttaaa ttctccactc tgtccatcag atactatggt
tctccactat ggcaactaac tcactcaatt ttccctcctt agcagcattc catcttcccg
atcttctttg cttctccaac caaaacatca atgtttatta gttctgtata cagtacagga
tctttggtct actctatcac aaggccagta ccacactcat gaagaaagaa cacaggacta
gctgagaggc taaaactcat caaaaacact actccttttc ctctacccta ttcctcaatc
ttttaccttt tccaaatccc aatccccaaa tcagtttttc tctttcttac tccctctctc
ccttttaccc tccatggtcg ttaaaggaga gatggggagc atcattctgt tatacttctg
tacacagtta tacatgtcta tcaaacccag acttgcttcc atagtggaga cttgcttttc
agaacatagg gatgaagtaa ggtgcctgaa aagtttgggg gaaaagtttc tttcagagag
ttaagttatt ttatatatat aatatatata taaaatatat aatatacaat ataaatatat
agtgtgtgtg tgtatgcgtg tgtgtagaca cacacgcatc cacacatata atggaagcaa
taagccattc taagagcttg tatggttatg gaggtctgac taggcatgat ttcacgaagg
caagattggc atatcattgt aactaaaaaa gctgacattg acccagacat attgtactct
ttctaaaaat aataataata atgctaacag aaagaagaga accgttcgtt tgcaatctac
agctagtaga gactttgagg aagaattcaa cagtgtgtct tcagcagtgt tcagagccaa
gcaagaagtt gaagttgcct agaccagagg acataagtat catgtctcct ttaactagca
taccccgaag tggagaaggg tgcagcaggc tcaaaggcat aagtcattcc aatcagccaa
ctgctaagttgtc cttttctggt ttcgtgttca ccatggaaca ttttgattat agttaatcct
tctatcttga atctt
```

SEQ ID NO:82

```
  ggcctctc actaactaat cactttccca tcttttgtta gatttgaata tatacattct
atgatcattg cttttctct ttacagggga gaatttcata ttttacctga gcaaattgat
tagaaaatgg aaccactaga ggaatataat gtgttaggaa attacagtca tttctaaggg
cccagcccctt gacaaaattg tgaagttaaa ttctccactc tgtccatcag atactatggt
tctccactat ggcaactaac tcactcaatt ttccctcctt agcagcattc catcttcccg
atcttctttg cttctccaac caaaacatca atgtttatta gttctgtata cagtacagga
tctttggtct actctatcac aaggccagta ccacactcat gaagaaagaa cacaggacta
gctgagaggc taaaactcat caaaaacact actccttttc ctctacccta ttcctcaatc
ttttaccttt tccaaatccc aatccccaaa tcagtttttc tctttcttac tccctctctc
ccttttaccc tccatggtcg ttaaaggaga gatggggagc atcattctgt tatacttctg
tacacagtta tacatgtcta tcaaacccag acttgcttcc atagtggaga cttgcttttc
agaacatagg gatgaagtaa ggtgcctgaa aagtttgggg gaaaagtttc tttcagagag
ttaagttatt ttatatatat aatatatata taaaatatat aatatacaat ataaatatat
agtgtgtgtg tgtatgcgtg tgtgtagaca cacacgcatc cacacatata atggaagcaa
taagccattc taagagcttg tatggttatg gaggtctgac taggcatgat ttcacgaagg
caagattggc atatcattgt aactaaaaaa gctgacattg acccagacat attgtactct
ttctaaaaat aataataata atgctaacag aaagaagaga accgttcgtt tgcaatctac
agctagtaga gactttgagg aagaattcaa cagtgtgtct tcagcagtgt tcagagccaa
gcaagaagtt gaagttgcct agaccagagg acataagtat catgtctcct ttaactagca
taccccgaag tggagaaggg tgcagcaggc tcaaaggcat aagtcattcc aatcagccaa
ctaagttgtc cttttctggt ttcgtgttca ccatggaaca ttttgattat agttaatcct
tctatcttga atctt
```

FIG. 13D

SEQ ID NO:83

```
   ggcctctc actaactaat cactttccca tcttttgtta gatttgaata tatacattct
  atgatcattg ctttttctct ttacagggga gaatttcata ttttacctga gcaaattgat
  tagaaaatgg aaccactaga ggaatataat gtgttaggaa attacagtca tttctaaggg
  cccagcccttt gacaaaattg tgaagttaaa ttctccactc tgtccatcag atactatggt
  tctccactat ggcaactaac tcactcaatt ttccctcctt agcagcattc catcttcccg
  atcttctttg cttctccaac caaaacatca atgtttatta gttctgtata cagtacagga
  tctttggtct actctatcac aaggccagta ccacactcat gaagaaagaa cacaggacta
  gctgagaggc taaaactcat caaaaacact actccttttc ctctacccta ttcctcaatc
  ttttaccttt tccaaatccc aatccccaaa tcagtttttc tctttcttac tccctctctc
  ccttttaccc tccatggtcg ttaaaggaga gatggggagc atcattctgt tatacttctg
  tacacagtta tacatgtcta tcaaacccag acttgcttcc atagtggaga cttgcttttc
  agaacatagg gatgaagtaa ggtgcctgaa aagtttgggg gaaaagtttc tttcagagag
  ttaagttatt ttatatatat aatatatata taaaatatat aatatacaat ataaatatat
  agtgtgtgtg tgtatgcgtg tgtgtagaca cacacgcatc cacacatata atggaagcaa
  taagccattc taagagcttg tatggttatg gaggtctgac taggcatgat ttcacgaagg
  caagattggc atatcattgt aactaaaaaa gctgacattg acccagacat attgtactct
  ttctaaaaat aataataata atgctaacag aaagaagaga accgttcgtt tgcaatctac
  agctagtaga gactttgagg aagaattcaa cagtgtgtct tcagcagtgt tcagagccaa
  gcaagaagtt gaagttgcct agaccagagg acataagtat catgtctcct ttaactagca
  taccccgaag tggagaaggg tgcagcaggc tcaaaggcat aagtcattcc aatcagccaa
  ctaagttgtc cttttctggt ttcgtgttca ccatggaaca ttttgattat agttaatcct
  tctatcttga atctt
```

FIG. 13E

SEQUENCE LISTING

```
<160> NUMBER OF SEQ ID NOS: 84

<210> SEQ ID NO 1
<211> LENGTH: 32
<212> TYPE: DNA
<213> ORGANISM: Homo sapiens

<400> SEQUENCE: 1

agccattcag tcgaggaagg atagggtggt at                                32


<210> SEQ ID NO 2
<211> LENGTH: 7
<212> TYPE: DNA
<213> ORGANISM: Homo sapiens

<400> SEQUENCE: 2

gaggaag                                                             7


<210> SEQ ID NO 3
<211> LENGTH: 1273
<212> TYPE: DNA
<213> ORGANISM: Homo sapiens

<400> SEQUENCE: 3

ggcctctcac taactaatca ctttcccatc ttttgttaga tttgaatata tacattctat    60
```

-continued gatcattgct ttttctcttt acaggggaga atttcatatt ttacctgagc aaattgatta 120
gaaaatggaa ccactagagg aatataatgt gttaggaaat tacagtcatt tctaagggcc 180
cagcccttga caaaattgtg aagttaaatt ctccactctg tccatcagat actatggttc 240
tccactatgg caactaactc actcaatttt ccctccttag cagcattcca tcttcccgat 300
cttctttgct tctccaacca aaacatcaat gtttattagt tctgtataca gtacaggatc 360
tttggtctac tctatcacaa ggccagtacc acactcatga agaaagaaca caggagtagc 420
tgagaggcta aaactcatca aaaacactac tccttttcct ctaccctatt cctcaatctt 480
ttaccttttc caaatcccaa tccccaaatc agtttttctc tttcttactc cctctctccc 540
ttttaccctc catggtcgtt aaaggagaga tggggagcat cattctgtta tacttctgta 600
cacagttata catgtctatc aaacccagac ttgcttccat agtggagact tgcttttcag 660
aacataggga tgaagtaagg tgcctgaaaa gtttgggga aaagtttctt tcagagagtt 720
aagttatttt atatatataa tatatatata aaatatataa tatacaatat aaatatatag 780
tgtgtgtgtg tatgcgtgtg tgtagacaca cacgcataca cacatataat ggaagcaata 840
agccattcta agagcttgta tggttatgga ggtctgacta ggcatgattt cacgaaggca 900
agattggcat atcattgtaa ctaaaaaagc tgacattgac ccagacatat tgtactcttt 960
ctaaaaataa taataataat gctaacagaa agaagagaac cgttcgtttg caatctacag 1020
ctagtagaga ctttgaggaa gaattcaaca gtgtgtcttc agcagtgttc agagccaagc 1080
aagaagttga agttgcctag accagaggac ataagtatca tgtctccttt aactagcata 1140
ccccgaagtg gagaagggtg cagcaggctc aaaggcataa gtcattccaa tcagccaact 1200
aagttgtcct tttctggttt cgtgttcacc atggaacatt ttgattatag ttaatccttc 1260
tatcttgaat ctt 1273

<210> SEQ ID NO 4
<211> LENGTH: 38059
<212> TYPE: DNA
<213> ORGANISM: Homo sapiens

<400> SEQUENCE: 4
gtatatctag aaaaccccat tgtctcattc caaaatcacc ttaagatgga taggcaactt 60
cagcaaagtc tcaggataac aaaatcaatg tgcaaaaatc acaggcattc ttatacacca 120
atagcagaca aacagacagc caaatcatga gtgaactccc attcacaatt gcttcaaaga 180
gaataaaata cctaggaatc ctacttacaa gggatgtgaa ggacctcttc aaggagaact 240
acaaaccact gctcaatgaa ataaaagagg atacaaacaa atggaagaac attacatgct 300
catgggtagg aagaatcaat atcatgaaaa tggccataat gcccaaggta atttatagat 360
tcaatgccat ccccatcaag ctaccaatga ctttcttcac agaattggaa aaaactactt 420
taaagttcat atggaaccaa aaaagagccc gcatcgccaa gtcaatccta agccaaaaga 480
acaaagctgg aggcatcatg ctacctgact tcaaactata ctacaaggct acagtaacca 540
aaacagcatg gtactggtac caaaacagag atacagacca atggaacaga acagagccct 600
cagaaataat gccacatatc tacaactatc tgatctttga aaaacctgac aaaaacaaga 660
aatggggaaa ggaatcccta attaataaat ggtgctggga aaactggcta gccatatgta 720
gaaagctgaa actggatccc ttccttatac cttatacaaa aattaattca agatggatta 780
aagacttcat tgttagacct aaaaccataa aaaccctaga agaaaaccta ggcaatacca 840
ttcaggacat aggcatgggc ttggacttca tgtctaaaac accaaaagca atggcaacaa 900

-continued

```
aagccaaaat tgacaaatgg gatcaaatga aactaaagag cttctgcaca gcaaaagaaa    960
ctaccatcag agtgaacagg caacctaaag aatgggagaa aatttttgca atctactcat   1020
ctgtccaagg gctaatatct agaatctaaa atgaactcaa acaaatttac agaaaaaaac   1080
aaacaacccc atcaacaagt gggtgaagga tatgaacaga cacttctcaa aagaagacat   1140
ttatgcagcc aacagacaca tgaaaaaatg ctcagcatca ccggccatca gagaaatgca   1200
aatcaaaacc acaatgagat accatctcac acaagttaga atggcgatca tcaaaaactc   1260
aggaagcaac aggtgctgga gaggatgtgg agaaatagga acactttgac actgttggtg   1320
ggactgtaaa ctagttcaac cattgtggaa gtcagtgtgg cgattcctca gggatctaga   1380
cctagaaata ccatctgacc cagccatccc attattgggt atataccaaa gtattataaa   1440
tcatgctgct ataaagacac atgcacacgt atgtttattg cggcactttt cacaatagca   1500
atgacttgga accaacccaa atgtccaaca atgatagact ggattaagaa aatgtggcac   1560
atatacacct aggaatacta ggcagccata aaaagaaaat gagttcatgt cctttgtagg   1620
gcatggatga agctagaaac catcattctc agcaaactat cgcaaggaca aaaaaccaaa   1680
caccgcatgt tctcactcat aggtgggaac tgaacaatga gaacacttgg acacaggaag   1740
gggaacatca cacaccgggg cctgttgtgg ggtggggggc gaggggaggg atagcattag   1800
gggatatacc taatgctaaa tgacgagtta atgggtacag cacaccaaca tggcacatgt   1860
atacatatgt aacaaacctg ctcgttgtgc acatgtaccc taaaacttaa agtataataa   1920
taaaaaaaag atcattctaa aatttataca agcccttaga acagttaaaa atatcttacc   1980
aaaagaagaa taaagttgga ggaatcactc tacctaatat aaagtcttac tacatagcta   2040
cagtaattat gacagtgtta tattggcaga gggataaata catcaatggc acaaagaata   2100
gatagagaaa ctggaagtag acccaaaaca atatggttaa ctgacttacg aaaaaaattc   2160
agaagccatt cagtcgagga aggatagggt ggtattgttg ttttttgttt taacaaattg   2220
tgctggataa attggacata cctatggaaa aaaaaatgaa gtttgaccta aacatcatac   2280
tttacacaaa tattaactca aaatggagca tgggcataaa tctaaaactt caaactgtaa   2340
aacatttaga aaaaaatagg aaaaaaacta tcaggatcta gtgttagtgg aagagttcta   2400
aatgtgatcc ataaaacaaa aacaaataaa ctggactaca tcaaaactaa aaaattctac   2460
tctgtgaaag acctaattaa gaggacaaaa gacaagctac aggctggaga caatatattt   2520
aatccacgta tctatgaaag gattcatatc tagaatatat aaacaacctt aagaatctga   2580
cagtaaaaaa aaaaaatcag actaactgga ccactcatac attgctgatg gaaatgtaaa   2640
gtggtacagc cattttggta aacatcattg ctctctgaca aagatacggt gggtcccact   2700
gatgaactgt gctgccacag taaatgtagc cactatgcct atctccattc tgaagatgtg   2760
tcacttcctg tttcagactc aaatcagcca cagtggcaga agcccacgaa atcagaggtg   2820
aaatttaata atgaccactg cccattctct tcacttgtcc caagaggcca ttggaaatag   2880
tccaaagacc cattgaggga gatggacatt atttcccaga agtaaataca gctcagcttg   2940
tactttggta caactaatcg accttaccac tttcacaatc tgctagcaaa ggttatgcag   3000
cgcgtgaaca tgatcatggc agaatcacca ggcctcatca ccatctgcct tttaggatat   3060
ctactcagtg ctgaatgtac aggtttgttt cctttttaa aatacattga gtatgcttgc    3120
cttttagata tagaaatatc tgatgctgtc ttcttcacta aattttgatt acatgatttg   3180
acagcaatat tgaagagtct aacagccagc acgcaggttg gtaagtactg gttctttgtt   3240
```

-continued

```
agctaggttt tcttcttctt catttttaaa actaaataga tcgacaatgc ttatgatgca   3300
tttatgttta ataaacactg ttcagttcat gatttggtca tgtaattcct gttagaaaac   3360
attcatctcc ttggtttaaa aaaattaaaa gtgggaaaac aaagaaatag cagaatatag   3420
tgaaaaaaaa taaccacatt atttttgttt ggacttacca ctttgaaatc aaaatgggaa   3480
acaaaagcac aaacaatggc cttatttaca caaaaagtct gattttaaga tatatgacat   3540
ttcaaggttt cagaagtatg taatgaggtg tgtctctaat tttttaaatt atatatcttc   3600
aatttaaagt tttagttaaa acataaagat taacctttca ttagcaagct gttagttatc   3660
accaaagctt ttcatggatt aggaaaaaat cattttgtct ctatgtcaaa catcttggag   3720
tttgattatt tggggaaaca caatactcag ttgagttccc taggggagaa aagcaagctt   3780
aagaattgac ataaagagta ggaagttagc taatgcaaca tatatcactt tgttttttca   3840
caactacagt gactttatgt atttcccaga ggaaggcata cagggaagaa attatcccat   3900
ttggacaaac agcatgttct cacaggaagc atttatcaca cttacttgtc aactttctag   3960
aatcaaatct agtagctgac agtaccagga tcaggggtgc caaccctaag cacccccaga   4020
aagctgactg gccctgtggt tcccactcca gacatgatgt cagctgtgaa atcagactga   4080
aatgctgaaa taacgataaa aaaaaataca gaggttaaac tagcaaagtg agtaaagtca   4140
agggataaag aaaatttgtt ggaaaactca caaagcagga cataaagcaa ggccattaga   4200
tatatctcat tagtgtgaca tctgggagga caaagcatcc aaaccctttc ttctatataa   4260
gtggtgagat gatgaaggtt gtaagaggct tctgcccccct tgaagacttc agatgctggg   4320
gaaaggatag ataagaataa ggatgaacct ggcttttgga gcctgggaaa taatgactag   4380
cgataaacct gaagggaagt taagtatacg atccccagat aatactaagg agaaaggcaa   4440
tgtgattctg cagccattgt agccagagat aataagccct tgaggaaggg gccaggggaa   4500
tttttctaag gatagacagt attaatgcag cactctcttc tgctattaaa ctctcattgg   4560
cttctaaaag gagtttcggt gagtgatttg ctgagatgtt tgcattttca tgctgctgcc   4620
tttaggttat tattgcaaca gtttggaatt ttgaaattaa aacagttctg taaaaccagt   4680
ttagttttgt aaagtgtatg catcaaagat gtccttcatt cagacattac tgagttacaa   4740
ctacggtgcc aggtactgtg tcagggtact aggggtatgg ggataaacca gactccctct   4800
ttgatctaaa gcagcatgag gccaggtgag aggtttcaat atatgtgata aaatgtgcac   4860
taggtactaa gggatcatag agaaaggaac acattaaatg ggaaacaat tgatagagag   4920
agaatatttt catctgggtc ttaaaagatg agtaggcgtt ctctctcttt aaatgtctga   4980
tataagggca ttttatgcaa agaaggatca ctcgtgcaaa gactcagctt tgcaagaacg   5040
tgaggtattt caggagtttt gtatggttcc atatggacta tgacaagtga gacaggtaaa   5100
ctaggcagag ctggtcatca gataatgaag tcattaacct aaggagattg gacaataaaa   5160
tgcaatatgg aggtatcgaa gtataaacat aaggagtacc actgatggct gatttaggat   5220
gcccagtctg gcaacacgct aatgaaatga tagtggggga gggggccgta ccaagactag   5280
gagagagcag tcctgagact attgcaatta tctgcgggag acataaaggc tagaacctga   5340
acagtagcag tacaaaaaaa gaggggagtt caaatgatat taaggaagta gaagtggtat   5400
gacttaacca tctgggtatg gaaggggaaa tggctagagt cttggggact ttgtgtttga   5460
tgtgattatg gaccacagaa taatgtctaa gagaactggc tctttagtct gactgccaga   5520
gtctgaatcc tgaatgtttt agtatgttac cttgcaaagc ccttagcctc tatgaatcta   5580
tcttcctcat ttataaaaat aagatgacag tgcctatctc gtgggacttt tgtgaggatg   5640
```

-continued

```
aagtgagata atggatgcaa agttactgag cacagtgtcc aacacagcag aagcattaca   5700
tatacattag ctattactgg ctacattatg atatacagtt agggagttgg aaagataatc   5760
tgaaattcag gagacgtatc tgactatagg tgagtatttg gaactcattg ttctgtaaac   5820
agtagttaca gcacgtgtgt gggcatctgg agagtgagca tggatattgt gatacctagt   5880
acagtgcctg gcagtagtgg ttgtatgctc agtaaatttt gttgacaggg tcagggccgg   5940
actagactgt ggtaagcaag gcctgtaggg cataaatata cttgtatgcc ccgagaagtg   6000
aggacctctt aaatattgtg ccctacatgc cttgtttggt tcactcttgt cccagcccta   6060
gcaagtatat ataaggtgaa aaaggaaaaa gctgaggctg gagcctggga gaaccctgga   6120
catttaaggg ccatggagag gaacaggagt taatcaattc aagtgctgga tggataacag   6180
gagttagagc aaagcgggga accagaatag agtgattatt ataaaaagag tttcctaaaa   6240
agggagagat caacaattag aaattattta gagcagccag taaatacata aactcaaaat   6300
tattctttag gtcattcctg attgtgacaa tagtcatttc attatataaa tgtgattaag   6360
gaaggaaaag agctacacag aagttattaa agagctaaag agaattgaga aatttaaaac   6420
agaagaaagt agggccaaca tgaaaggagt agggagaaaa agagataacc agcatattgt   6480
ctcactgatc ctgccaacac ctgtgagata gatattctta ttatactact gttaaaccta   6540
atttacattt gacaaagtta aggttcagag cttgtgtgac ttgtccaagg tcacaggtct   6600
agaggaggca gatacttgat tcaaacctat ttctgtctga tctgattcta aagtctgttt   6660
tttcactcaa ccacactgta cagtcagctc tccttgtgag ttccacagcc acagattcaa   6720
ttaactgcag atcaaaaata ttcaagaaaa aaatggatgg ttcgatctct actgaacatg   6780
tacagactct tttatctttc attattccct aaacaataca gcataacaac tatttacata   6840
gcatttacat tgtattagct attaagagaa acctagagat gatttaaagt acaaaggagg   6900
atgtgtttag gttatatgca aatagtaagc catttttata tcggagactt gagcatccac   6960
agatcttgat atttgcaggg ggtcttgcca ccaattttcc atggatactg aggaacgact   7020
gtaaatggat gcaggcatgg atgctattta ggagtgtcca gggccaagta aatgagttgc   7080
tgagcagaga ggtgggtgga ggctgtgagg catcaatatg tggtggcatc catctgcatt   7140
ttggtgattt ttttccttca cagtcctcgg ctgtctggga agagaaggat gaaggcagat   7200
ggctgctcca atttaggggc taggattgca gggtgggcac agcattgcaa acgagtgaag   7260
gaaattgaga aatatggcca atgaagagtt gaagagaggc ctggcatggt ggctcacacc   7320
tataatccca gcactttcag aggcccaggc aggcagatca cttgaggtca ggagttcgac   7380
accagcctgg ccaacaaggt gaaatggtga aaccccggct ttactaaaaa tacaaaaatt   7440
agctgggcat ggtggcgggt gcctgtaatc ccagctactt gggaggctga ggcaggagaa   7500
tagcttgaac ctgggagatg gaggttgcag tgagctgaga tcgcaccact gcactccagc   7560
ctgggcgaca gagcaagact ctgtcaaaaa aaaaagagtt gaagagaaaa agtctaggct   7620
aaattcaaag aaaaaaagtg agcccaaaag gaacttgcag agcaagggaa aagcagggat   7680
gtcaagggac tagaacactc cataaagtga acagctgcaa tgaaaataag ggaagaaagt   7740
ttagttcatc tccgtttctt tcctttcctt tttactttcc tttctcttcc tttttggagt   7800
tagtcaggaa gtagtcccaa ataccccaga aagttcatct tataagccct tggtcctctt   7860
gagatggtat cagatatatt gctagaccct tgaagaaagg aacaactcca ggcaacttct   7920
tgagtccctg ttattaattt tatacataca cacacatata tgtatataca tgaaaacaca   7980
```

-continued

```
caaacacatg tgtgtgtata cagccatgca ttccttaaca atggggatat attctgagaa   8040
atgtgtcatt aagcaatttc atcattgtgc gaacataata gagtgtactt acctaaacct   8100
aaatggtata gcttactaca tacctaggtt gtattgatgt ggcctattgc tcctaggctc   8160
ctgggctgca aacctgtaca gcatgtgact gtactgaaca ctgtaggcaa tggtaacagt   8220
ggtatttgtg tatctaaaca tagaaaaggt acagtgaaaa tacagtatta taaccttatg   8280
ggaccactgt cgtataatgt ggtccatcat tgaccaaaat gtcattgtgc agcaaatgat   8340
tatctcatat atatatatat atgatatgat atatatgata tatatgtgtg tgtatatatg   8400
tatacatata tatgtgtaca tatatgtata catatataca cacacatata tatgtacaca   8460
catatatgta tatatatgta cacacatata tgtatatata tgtacacaca tatatgtata   8520
tatatatgta cacacatata tgtatatata tatgtacaca cacacacata gagagagaga   8580
gagaggagag gagaggaagg agggagggaa ggagaaatat gattcagata gagacatcta   8640
tcctccagag ttcaggagtg tctcttcaga ctaggtagat gtagcttaaa aaaaacatat   8700
cctggaattc tagagagatg cttaaatcac tgcaattcct ataacacttg ccaaccaaag   8760
gtgctgttga tctgaaattg ctttttaaa ttaatgcagt gatttttctt taacatctag   8820
tgacagacac tggggtcaca tttgcagctg gaccataatt aggcttctgt tcttcaggag   8880
acatttgttc aaagtcattt gggcaaccat attctgaaaa cagcccagcc agggtgatgg   8940
atcactttgc aaagatcctc aatgagctat tttcaagtga tgacaaagtg tgaagttaac   9000
cgctcaattt gagttctttc tttttcatcc aaagtaaatt caaatatgat tagaaatctg   9060
accttttatt actggaattc tcttgactaa aagtaaaatt gaattttaat tcctaaatct   9120
ccatgtgtat acagtactgt gggaacatca cagattttgg ctccatgccc taaagagaaa   9180
ttggctttca gattatttgg attaaaaaca aagactttct taagagatgt aaaattttca   9240
tgatgttttc ttttttgcta aaactaaaga attattcttt tacatttcag tttttcttga   9300
tcatgaaaac gccaacaaaa ttctgaatcg gccaaagagg tataattcag gtaaattgga   9360
agagtttgtt caagggaacc ttgagagaga atgtatggaa gaaaagtgta gttttgaaga   9420
agcacgagaa gtttttgaaa acactgaaag aacagtgagt atttccacat aataccccttc   9480
agatgcagag catagaatag aaaatcttta aaaagacact tctctttaaa attttaaagc   9540
atccatatat atttatgtat gttaaatgtt ataaaagata ggaaatcaat accaaaacac   9600
tttagatatt accgttaatt tgtcttcttt tattctttat agactgaatt ttggaagcag   9660
tatgttggta agcaattcat tttatcctct agctaatata tgaaacatat gagaattatg   9720
tgggtttttt ctctgcataa atagataata tattaaactt tgtcaaaagg actcagaaag   9780
atcagtccaa ccctctaacc catattggat ggtgatatac tacagggtta tgccagtgtg   9840
ggaactatcg ctggtaaata agtttaatcc tccctagggc ttcacaaaga acattgttcc   9900
accccaggag ggtggaagga agaaactgaa atgattgtgt cttagaacct aatgaaagtt   9960
tgcattcctc agtaaaatca gagactgctg attgacttaa atgtttatag cttcaaagtc  10020
ctcctcatta tcatggccca gaagcccttc catgattgtc cttccccacc ctccccatta  10080
cccttcttgc ctcctctgct acttctctcc tcgcacactg ggctccagcc accctggcct  10140
tcctgtcact tcttgcacac tctaggaatg ctcccacttt ggaggcttta tctggctgtt  10200
tctcttattt ggctgttccc aacttcctgt gggctgactc cctcacctcc ttcgggtctt  10260
tgcccaaatg ttaccatctt aatgaggcct accttcacca tctattaata cttcaacctg  10320
ccccagtagc cttaccactc tagacacctg tacagaactc cactctactt tttaacagag  10380
```

-continued

```
cttttcacca tctaatgtat catataattt cttactcata ctatttatca tttattttct  10440
cctactccac taaaatgcaa gtttcatgtt ggcagggata ttcaattgtt ttgtttattg  10500
atatattcct agcacctaga acagtatctg gaaaagaggt actcagtaaa tatttatcaa  10560
atgaattgac caaaagaagg aaaactcaaa actttaatga caactaactt taaagctaca  10620
ataacttaaa attcagagta ggattttgag ggagggtaag tttcaaagat tgacttacct  10680
aagactatct gcataaataa aaagaaatta atccagacaa caaattcacc aacttccatc  10740
aattggaaat ccaattctat tttctacagt ttatgttctg gagacactac tggacactct  10800
tttactctca taactcataa ctcctccact tttgttttta aatcatgaga gaaaaagagt  10860
tgactctgtt atattgtttt atctaccttt ccttgatctt agaaacgaat actaccatac  10920
cagcttctac tgaggtgccc cctaaagtta gtccaaatag gtctttgcaa tctccattcc  10980
cgcagaattt agaactttga atcacatgat ttatttctaa aagtaaatcc atgccgattt  11040
tccccaccaa aaaattcctg actattaaac tcctacaatc ccttcattgc tcactcccca  11100
cccccaggat catattttaa agttgggccc ttgccttttg ggtcacatag gtacactgtt  11160
tgctatacca caggtatagc tatctggaaa acatggaggg tattattctg ttactactgc  11220
ttcgtcaacc aaaaaataaa acaaaacaag aacaaaaaag aaacaaactc cctgcctctt  11280
ttcacttgca gtcaaggttc ctaaccacta caaaattagc ctatgtttct tcttgcacat  11340
agtagaaacc caagcttctc actgctgtgc tattctgtac catcaactca tcacataaag  11400
agcctggttg aagaatgatt gtccaaccac attactagca tctgtcaaga ctttccagtt  11460
tacaaaaggc ctatcacatt taaccctcac accatccttg tgaccaaagc attattaact  11520
ccattttaca ggagagtaaa ctgaagctta gggaagttaa aagaactgcc aaaggtctcc  11580
cagttgggga gtcatgaagc ccagaagaga agccaaattc tctgctgctc aaccccttgc  11640
tttcactatt acacctcagg gccttcaaat ctaaatgcag ttattcatta aacaggaacc  11700
tggtagtctt aaacaggaat ctctcacttg gtaagatctt gtctcttgtt gtatttgacc  11760
ccaactgtct atggctttgc ctgaacccaa agtacacaca gcctagaaac caaaggagaa  11820
ccaaatgtgg gataaaatga cactcatttt aacgacatgt ctcagcaaat gagttcctgt  11880
gtagctggct gaaagcccag accctttcag taaaacatcc tgaataattc acatttgttg  11940
gtctataata taaagggcaa atgtagctca tttttagacc agttctgaac atcaatagta  12000
acaaaccaga gataaccgat tttgttttca tagaattgga acaaattaga gtatctgtgc  12060
aaaagcatat cagatctagg agcagagggg acaaggtcta atttttaaat aagcaaattt  12120
tccagggagg gactacttat gataaaggga tattagtctc ttagtcaacg gaacctggat  12180
acacgcttct gacagagaag agggagaata ggcaggaatc tacacaccag atgtcaagga  12240
gatttgcttt aaaatacgac tgataattag aaatttctca gtttccccct tttccctcat  12300
tctttgattc ttattgttat ctttatctct tactcctttg tttctcatat attgagtctt  12360
acagatcaag ctcccatttt tttcttcagg ggtatttttc tagttcaaag tgcctaccat  12420
ctcccttctg gttctattca tccttctctc ccaaagctcc tttagaagtg tggattaagg  12480
cagagcacta agaaaccaga cttaaagatt cccttctcat tctgactttt ctcctttcac  12540
ctattccttc ctcctgtttt cttaccatca gtgtcttcaa aggctttcaa gtacacggta  12600
aatgcagaaa cttcaagaaa ggcagaatgg aaacataacc aatgcataca taaataaagc  12660
acactgtaga atctttttaa attctgtatg atatatcgaa tgctgtctct cacattacct  12720
```

-continued

```
agaccatttg aaaccgaatt tgtaaaacat agactatctt taagtagtaa cagatgcttc  12780

tgacatgttt tctattgtct tgaaccatta ctgcatatga tacatcaaag ttaagtgaca  12840

atacaagaaa gcagattcat ttgctccctg cctaggccgt cagttcctaa agtggaaacg  12900

ccatatatta tctagctcag tttgctctac aagacctgca atagagcctt gtgtgacata  12960

gagataatat ttgttgaagc aattaaattt gacttggaat taactctgcc atcattctat  13020

aaggaaggat tgaaaatcct tctcaccctg tgctgatata gtacctttct atacaaaaac  13080

gtccttctcc ctcttccctt ggattgcata aactatgtac atgccttcct caggggcact  13140

tttctaggac agtgtcagcc taaggatctt tgtttgggtg gcttttagaa actcaggaag  13200

acaggagcat catatgccta taggcagctg gcttccaggt cagtagtttt gctctgaccc  13260

taaaatcaga ctcccatccc aatgagtatc tacaggggag gaccgggcat tctaagcagt  13320

ttacgtgcca attcaatttc ttaacctatc tcaaagatgg agatcagtgt gagtccaatc  13380

catgtttaaa tggcggcagt tgcaaggatg acattaattc ctatgaatgt tggtgtccct  13440

ttggatttga aggaaagaac tgtgaattag gtaagtaact attttttgaa tactcatggt  13500

tcaaagtttc cctctgaaac aagttgaaac tggaaaatgc aatattggtg tatcataatt  13560

tttcttaaaa acatacettt gatgcttata aacatttcat ttgtagtgat agttttcagg  13620

atatgagttc aagaagctac attaaaatca ataacaatat ttggtaacta atattaagta  13680

ataatgatgt tccgactcac cttattaatc tttaatacaa ccgtatgtgg ttagtactat  13740

cattatgcgc attctatgca gatgagaaaa ccgcaactcc aacggccaaa aattacagag  13800

gcataaatgg tttagacagg acttaaactt cagtgtgacc aaaacccatg cttctaacta  13860

ctatattcaa aactcagaga aaactgaacc cagaaaattg aaatcatgac taaattgcta  13920

tcaacatagg tgaaagtcaa ttaagtacag aactggagta tgactggcca attatcccat  13980

ataatgggaa ttctccacat gtacaaacca cttcatatgc taaacttgtt gacaacattc  14040

aaagctcatc cctgaatttg actatattga ttacatcgaa aatgttacat agcaacctta  14100

gaatccttgt gtacctttc ttctcaaagc ctagattatt tctttttccg acgttttcag  14160

taattggagc agtaaacccc agtgtccctt acctacttgt ttattacctc cagatgcaat  14220

attactggta ctgtgattga gaaacgcaca cagtgctaat gaggaattca ctttctactc  14280

tgacactctg gaagaataga gatgcaatcc taaggaagaa tttaacacca caggctacat  14340

gactaaggat aaagagtaga aaattagcag gactctatta accgattaca gcaatccacc  14400

tgacagatga aaaaggcatg aaatgaaatg aaatgtagca gctacactcg tcctattgag  14460

aaaggaaaaa agtcacctgt aatgttgttc agaaatcctt tcagtactaa aaaattcatt  14520

gaccatcttc ctttagtctc gaaaatttct tagaaggtaa aaaaaggaaa aggtgacagg  14580

gcaaagacat ttgaaaagaa agaaaagagt gaatgaactt gcacacctgg cttggactcc  14640

ccattcccct taggtttcca ttgtggggga caaactaatg cctgggttac ctttcttgag  14700

agtgtgttaa ttgattcaat atctctgaag tgctactttc atctgaaagg ttataatttg  14760

aaattcagat ttacctggat aaatttgatc ttgctattat ggaaacctct agaaatcctt  14820

ggagtagtta ctcattatca gcttaaataa tatagccggt ggagctgagg gaatgagtaa  14880

ctcaattagt ctcagttaca actgaagggc acattgttgt aaactataat tgaaaacata  14940

aatatcttta cctagtttaa aaaataaaga tgctttaaaa ggaggaaggg aatagccctg  15000

aggaatgtaa atataagcac aaaacttcta caacagagtt tgctacgtgt gtggctgtgt  15060

tccacccagc aaaaatgcta agtctacaac tgacacaact tggatactct catgttccca  15120
```

-continued

```
cattttggtt tggtcaaggc tgtgcagttg tactgcaggc caccaccact cctggcctct  15180
acagtatatt gatctgaccc accaatctga tcaaggttta gaaaaatatt ttcagcccag  15240
ttagctcaca aacaaaatga gaattcccac aaattgctct ttatctcaga caacagagga  15300
aagctacagc aaaagcataa acaaattacc atttaagttt gttgcttcaa attaaagact  15360
aattgcaaca gctactagat agcacagttt atggggcatc tcggccccaa gtcttttgtc  15420
ttataaggtc ttgaaaaaaa gaaaggagat tttcatcaat aagagttttt tgttatcttt  15480
ttcccttgtt catcaggccc ttcactgcga gagagaggtg taaacgttca gggcatgcat  15540
tctagttaaa gaatattaat tggctattgg gtccctttgg ttagaataaa gacctctgta  15600
tgatgtccct agctgtacat caaacccaaa tatctctcag ataaatgaag gtctgtaaga  15660
atttggtcat tcctgtctct tctaaagagt aacagaggca ttttcccgca gtaaagtaga  15720
atggaaagaa aacaaaaatc acaagcctat aaacaccttc ttcaattttc ccagcatgtc  15780
acagacacta ctgtcttatt tactacgtat ttctgaggag taaaaaaagg aaatatgttg  15840
agtttagctg aagcacagca tattttgtgg taaacttgtt aaataaaaca tcttttgtcc  15900
aagctttggt tgtcacacaa gtggatatat caggaaatat aaaggcagaa taaactaaag  15960
cagaacatac taacatttgt agtaggcatg aagggaatta gaaagtgttt gtgttaacat  16020
ggagggaggg agaacagatg ctttgagatg ttcttcaaca gatattctag gcactgagac  16080
ccccttcggg accagagaga gcccatatcc accacagtac ctgacacata aatgctcagt  16140
aattgataaa tgagtcccat tctaactgtt ccttagccct gctctatgga actctcccct  16200
gaattccttg tgccattatt ttatttctgg aatcttcagc cttttagctg agggcaaaag  16260
attgctgatt aggaagcaat atttcccacc tcctgcgcaa aacaagccaa agatcaacag  16320
cagcagcaac atactgagcc ctaaagggca atgacaaatg tggagaatga tacagaggtc  16380
tggttacttc ttagccaatg acacagaatc acaattgaga aaacacagag tttattcatt  16440
cccattgtgc atgccctgga caaaccaagc tgcacctttc gtaacttatc acaatctcat  16500
attgacggaa cactttctac aggtaatgtt tgatttggct gaacacttta gcattgcttc  16560
gtagcaacaa aatgatagct agtaacagaa aaagatccag ggatattacc actgttagtg  16620
aggagaaagg ccttttaatt aattaattaa ttaattaata ggaccaagtg ccatcttttt  16680
ggatcatgcc cttagtggat tattggtagc aaaggttaaa gctcaagctg gttcctttgt  16740
ccccctggca acagttgatt tgcctccctt atctcctgaa gtaccgtaag gactaagagc  16800
caattattac atttggctat gctagcatat gtaaaataga gtttaaaagt ttagattcat  16860
cactcaaaaa ttcatattct ccaaaaccat acagtcactc tgttagcctg tgttccccca  16920
gaaaaaaagt cacaagctta ttattaacat gtgcaatcca ggggcaagag aaaggaactg  16980
aagatgaggc agaaaggaaa agaaagccaa taagaggatg agttatcaaa ctactcgttt  17040
cttaacagca actgattgct taacttcctg ggactgtctc caataagtca aattggcctc  17100
aggttagtcc acctgagtgg gaagaagcgg tgaaagaatt tgtctgtcag tatctgtctc  17160
tcattggtta gaagttcgac ttatggggaa ttaactccct cacatttcct agttggatag  17220
cttgggtacc agaggcatat ggcatccatg ctcagcatga acagggaagc ttcaaggcaa  17280
aagacacata gtgcagctat gagccaaggc aattcaagga tacacccata ggaggctggt  17340
tgacatccac ccagagctaa tcaccaccat gctggaaaaa gacacaggtg aagctgagaa  17400
gaatgaaggt ggtgcatagg aggtatctaa tacagtcact cattttcaaa ctttccatgt  17460
```

-continued

```
tatgattgca ctgaccactg aggatttcta ttgaaagttt tactgttgtc aaacacgtac  17520
acaaggggaa aggtgtctta cattgtttat gttcctgtgc tgctctagaa acagaaatag  17580
gctcaagagc agagcctgtt tttcttaatt cagcaggtct aagctaacaa gtcctgaaac  17640
atggtacttc ctgttattgg tattgcatag gagaaacaaa gggaaagcac agtaattaga  17700
aaatacaaac aagatggcag gaataagcca aaaatatcag gaaacacaat tattgtgaat  17760
tgggattaaa ctaatctatt aataatgaca actttcagct tggagttaaa aatttaattg  17820
tatactgtta acgaaagtga tacctaaaat aaaattacac tgggaggcca aaatgaaggg  17880
atgtgaaaag aactatcagg taaaaactaa caaaaagaaa ctagcaaagc aatcttaata  17940
tcagacaaaa tagaatccaa gaggaaaatc atttcaaaag acaagagatt tttttattta  18000
ataaggggaa ttgcatagga gagtaaagaa aatgtgggcc actggaatgc ttagcactaa  18060
tgacatattg gtctttggtc ttcagttacc ttacaggacc ctatttcatt ctcttatgtt  18120
tgatatgtaa ccacctcagc cagcttcaag ttgctttttg gccctaatgg acttcctagc  18180
actataattt cttttttttt aaatgtttta ttttaggttt aggggtacat gtgaaggttt  18240
gttacataga taaacatgtg tcacaggggt ttgttgtaca tattattaca tgacgcagat  18300
attcagctca gtaccaaata gtgatctttt ctgctcctct gcctcatccc accctcctcc  18360
ctcaagtaga ctccagtatc tgttgtttcc ttctttgtgt ttataagttc ttaacactta  18420
gctcccgctt acaagtgaga acctgcagta tttgattttt gttcctacgc tagtttccta  18480
aggatgatag cctccagctc cattcatatt cccacaaaag acataatctc cttcttttct  18540
atggctgcat aatattccat ggtatatatg aaccacattt tctttatcca gtctgtcatt  18600
gatgggcatt taggttgatt ccatgtctgc tattctaaca ctgtaatttc taaagacttc  18660
cagattctac ttttataggt aacctgttaa acagtctagc tctggaagcc aagcaatttc  18720
tagaataact aagcaataga aattacactt caatgcagaa aggcagtatc tacatgagat  18780
tatgaaattg cggttgcttt ttgtgttcac tgaaaaaaat aagtaaaact gtaactttca  18840
gaaaaaatga ttgtacatat agaaaaccca aagcatctaa acaattaaaa taaataagta  18900
tagaaagatt actggataca gagtcaacat acaaatatca attgtatgtc tatataccag  18960
caacgattca aaaatgattt ttataatagc attaaaaatt agacgcttag taataaatgt  19020
gagaaagatg tgcaagaact ctacataaaa aattatgaga cgttattgag aaaaattaag  19080
gaaaacctaa ataaatgaat gaataggcaa tgtttatcat taaaggatac aatatagtaa  19140
atatatcaaa tgtttactaa tggattcaat gcaataccaa agtgccagca ggcttttttg  19200
gtggtgggag gtcgggcagg attcataagc taattataaa atgcatatgg aaatgcaaag  19260
agccaaggat agccaagaca gttttgagga agaataaact tgtactactt acactaccag  19320
atgtcaagac ttattatcga gttacattta ttaagacagt gtggtactga cacaaggata  19380
gacaaataga tcagtgaaac acactagagt gctcagaagc acacctgtac atatataaag  19440
gcttgattta tgatagaggt gccagtgcag tagagaagga aattattggt gttttcaata  19500
aaaagtgata ggtcaattag atattcatat ggcatgaagt atgaaacaat aacaatttat  19560
attcataact tgcagaaagc aaaaatttct taaaatacaa aaagtgatca ccataaagga  19620
aaagattgat aaactggact atattaaaac taaggactcc tgttcagcaa aagacactac  19680
ttcgactgaa aagacaagtc acagagtgag acaagatatc tgcaatacag atacctaata  19740
actgaacccc atacagtgat ggtgggaatt taagttcgta caatcatttt agaaaattgc  19800
ttggcagtat ctactagatc tgaacatgtg atccagtaat tacactcata attataagcc  19860
```

-continued

```
agtaaaaagg catgtttatg tcaccaaaag atatatacaa gaatgttcat tacactatta  19920
tacataagag ccaaaaactg gaaacaaacc aaatatccat taacagtaga atgaataaat  19980
aaaagctgta atagtaatac agtggaatac tacacagcaa tgtaaatgaa ctactgctgt  20040
acaaaacaac atggtttaat ctcacagaca aaatgttaaa tgaaagacac agacgagtac  20100
atattgcgaa cttctgttta taattcaaga actggcaaga actgtttact gtgttagaag  20160
tccaggtaat ggtaacctat aaaaaggaaa aagggtggaa tgattgggag ggggcatctt  20220
ctggggtctt gataatgtgc tatgtattgg tcagtttagt gtttaaacag gctcatttac  20280
tttgtgaaaa cttacactaa aattgtgtgt attttttgaa tatatgttat acattaataa  20340
atagggtttt taaacctgta gttcataatt tagtgaaagt agaatatcca aacatttagt  20400
tttaaaccaa tcaattatag tgctaccatc atttttatgc attattgaga agtttatttt  20460
acctttcttt ccactcttat ttcaaggctc caaaatttct ctccccaacg tatattgggg  20520
gcaacatgaa tgccccccaat gtatatttga cccatacatg agtcagtagt tccatgtact  20580
ttttagaaat gcatgttaaa tgatgctgtt actgtctatt ttgcttcttt tagatgtaac  20640
atgtaacatt aagaatggca gatgcgagca gttttgtaaa aatagtgctg ataacaaggt  20700
ggtttgctcc tgtactgagg gatatcgact tgcagaaaac cagaagtcct gtgaaccagc  20760
aggtcataat ctgaataaga ttttttaaag aaaatctgta tctgaaactt cagcatttta  20820
acaaacctac ataattttaa ttcctacttg aatctgcttc cttttgaaat catagaaaat  20880
atcagtagct tgaattagac caattaattt tctagattgc atcatatttt aaatataact  20940
atgtaatcat ctacaacctg aattctttct gtgtccaatt tgtccaattt ttttctctaa  21000
catttatatc acaaagcaat taatttgtgt gatttctgca tatgtatttg taattcatca  21060
agtcaaatca atgtagtaat actatatcat aaaatataca caaataattg agtgataggc  21120
ttctagtata aggacggtaa gtttgaagca tgattctatc tgggctggct agtttactct  21180
gagaaagtta ttttttattg ttgggtctta agctgagttt acacacttgg tgtcagaatg  21240
attccggcaa tgaactgttt tatgttctgc taggctgatc agcacaatct atatggctgt  21300
gaacaaaaca atgtttccca gtcataccaa ccatgccacc attttaacag ctgattagtg  21360
tattcagaac atctccactc catgttcgta tggctgttat ctaaagatga aagcagtaga  21420
cacttttatt ttttgaaaaa tttaggctct gcagggtcaa ttatatttga taaatgaggg  21480
gctttttttga agcaaactag atataatttc ttttgcattt ctaaagcctg atatcttatt  21540
aattggtaca ttaaattgtg caccatttct ctgtaactgt ttcagtacct gtctcagcac  21600
tataccaggc agaagaaata aagaaagaac cagtgccaga tcagcttggt caggagaccc  21660
taatcctgcg gcactagagg aattaaagac acacacacag aaatatagag tatggagtgg  21720
gaaatcaggg gtctcacagc cttcagagct gagagccccg aacagagatt tacccacata  21780
tttattgaca gcaagccagt cataagattt actgaaagta ttccttatgg gaaataaagg  21840
gatgagtctg gctagttatc tgcagcagga acatgtcctt aaggcacaaa tcacttatgc  21900
aattgtctgt ggtttaagaa cacctttaag cagttttccg ccctgggtgg gccaggtgtt  21960
ccttgccctc attctggtaa acccacaacc ttccagtgtg gatatcaagg ccatcacgag  22020
catatcacag tgctgcagag attttgttta tggccagttt tggggccagt ttatggccag  22080
atttggaggc ctgttcccaa caaaccagaa gctaggaata tatatcctgc aaataaaatg  22140
aagaatctct aaggcttcag ggcctgccca cttgttcttc tgcctggttc ttcacataca  22200
```

-continued

```
ctgtctcaaa gctagtctac cttgagagga gcatgaatat gtgtgtgggt gtgtgtctgt  22260
gtattttaac cttaaaaacc taacttccag tatagacaga tggcatacta gctaaaccct  22320
tacaagttct tctatgctat aaaagagaaa cagaattgag aaccacctcc aactattaag  22380
tgttatattt gaatatagcc ttagctttag cagaataagt aggccaaact taaaataagc  22440
ttttctgcct tttcaatgat aaaggtccct tttctgtagc cattgttgat tgtgtacact  22500
tatacataag tattttgaac taatttcctg ttttctcaac cacttgctgt cttcatgata  22560
ctttgtcgca gctggttgct atagaaatgt ctgttacaag gaatgtggct tgaaggaaag  22620
tgataaatga aaatgaaatg tgaagtgact ttgtttgact acaaattccc attctggtag  22680
tccccagtgt atcaatacat tatttttctt tagaaaataa accaacccaa ggaaaaatgg  22740
tgggcaggtc ctggtgaata tggctgtgat aattatatta gcaatctctt tggctaatat  22800
ttgaagccca aataattgaa tcacaatgat ctctccccag aaaatatata aaatgcacct  22860
tggaatctag aaggcctttt agtctgcaaa agaaaccttc ttaatcataa gcagcagaag  22920
tcccatttac caaattggaa agttaaagtt acaaagcatc aatcatcaga cttccattca  22980
gggatggcaa ttgggagtaa gactttttag taaagaaact aaacacaaag tcattagact  23040
ctgtaaaagt cttaccaaat ttgattctgg aacacctatt ctatttccgt aaagatgatg  23100
aattcggagc caaatgttct tttcatgaag gatttgaaaa ctgtccatga aaataacgca  23160
atcaaccttt tagcttgaga ctctattcac tgattagatt tttttaaata ctgatgggcc  23220
tgcttctcag aagtgacaag gatgggcctc aatctcaatt tttgtaatac atgttccatt  23280
tgccaatgag aaatatcagg ttactaattt ttcttctatt tttctagtgc catttccatg  23340
tggaagagtt tctgtttcac aaacttctaa gctcacccgt gctgaggctg tttttcctga  23400
tgtggactat gtaaattcta ctgaagctga aaccattttg gataacatca ctcaaagcac  23460
ccaatcattt aatgacttca ctcgggttgt tggtggagaa gatgccaaac caggtcaatt  23520
cccttggcag gtactttata ctgatggtgt gtcaaaactg gagctcagct ggcaagacac  23580
aggccaggtg ggagactgag gctattttac tagacagacc tattgggatg tgagaagtat  23640
ttaggcaagt ttcagcacta accaatgtga gaaggcctcc agagatgagc agttggtgaa  23700
agagaggctc aaaaccagct accatacagg tcaagaagaa tttggcatta aggaaacagc  23760
atagcaggat tccagacagg caactggtca acaacatgaa ggtctggaag aaaggtcgca  23820
gtactcaggt tcagggcact acttcagctt cagcccttgc aaaaaactggt gagagttgga  23880
aagtctttag gctaagaaaa attggattat ttaaaagggg taaagaaagg gactcaagga  23940
ggaaggatta aggcaagaac taggttccaa gaaacagggc atgagagaga gtcttgatct  24000
accactatag ttctcgtggt agcatcagaa tcacctggga acgtagaaat gcaaattctc  24060
ctgctctaca ctagacctac caaatcagaa tatctagggg gtggggccca gcagtctgtg  24120
cgcaaacaag cactgcaggt gattttgatg cacattatag tttgaaaact aggccaggtg  24180
cagtggctca tgccaataat cccagcactt tgggagactg agacgggagg attgcttaaa  24240
cccaggagtt tgagaccagc ctgggcaaca cggcgaaacc ccacctctaa ttaaaaaaaa  24300
tacaaaaatt agctaggtgt gatggctccc acctgtgctc ccagctattc aggaggctga  24360
ggtgggagaa tcacctgagc ctggaaagtc gaggctgcag tgaattgtga tcacaccact  24420
gcacttcagc ctgagtgaca gagtaagacc ctatctcaaa aaacagaaaa agaaaaacac  24480
tggcccaaag gaaatgaact tgttacagaa gccggggttc aaaacaccaa ataatgcact  24540
tgtacctagt ccttcccggg tgctctgcag acatttctcc aagcgtagtc tgcaaacaac  24600
```

-continued

```
ctacatatgt agaattacct atgcacattt ttcatttaac aaccaagagc tacatttgta  24660
gcaaaatctg ggttgtaact tagcctacag ctgaagccta agagattccg tctgtgagaa  24720
gaaataaccc acctctttgg ccccccctccc caggcaggaa gccaggatgg tccttatata  24780
aagttgtgct gtccaatagg taaccactag ccacatatgg ctatttaaat ttaaattaac  24840
tacaattaag agaaattaaa aattcaattc ctcaattgca cctgccaaat tttaagcaca  24900
taacaaccac atgtggctag taactactgt attggagagt gcaagcggag atagaacact  24960
ctattactgc agaaatttct attggatagc acttataata gtttagtgta acttaaaact  25020
ccctagttgc cacagtcatg atttagtagt aatttcatgg atttctctac tgaggttaga  25080
atctctgcca ttagagactg ataaatttaa agtttgcaat tatcaaactg gtgacaattt  25140
aagccagaat caggtaatgt cctcagtttt aacagcattg gaattttctg ggactagctg  25200
tgtatctatc caggattctt gagaatgcct gccatttttc aacataatgg atgtaaggta  25260
ttacacatat acctggggat ggggaggtag gtataattgc acaagcattg tggagaatgg  25320
tatcaaagag tggcagaaca tcacaatcaa ggttttccct ttcttttacc tttgcttttt  25380
aaaaagacaa tatttgctgg acctgatctt ataactcata aatgggacac tgtatgttcc  25440
tttttacctc ctctgtttct acttaattgc accctatgag gactgcttcc cttacctacc  25500
ataacccctt ccttcactca tccatatctt tactcttctt cacaactctg taatattgac  25560
cttctttatg aacctttcct ggaacaatcc ctcttaatgc aagcactgtt attatgcctt  25620
caatgtattt aatatccatg tatctattct ctctaatttt gtcattttgt gttctcatgt  25680
attttcattc attatgtgtc caacttccat ggataacatg gttacaacaa aagatcctac  25740
tttatgacaa ttatcttcct tgggtttgtg ggacatagaa cagtgcacag agtaggggat  25800
ccaagaaccc aggagaatat attagctaag aagataactt ccgtttttaa aagtccaaga  25860
ttcaggagat caaaaccatc ctggctaaca tagtgaaacc ccgtctcttc caaaaataca  25920
aaaaattagc ccggcgtggt ggcaggcgcc tatagtccca gctacacggg aggctgaggc  25980
aggagaatgg cgtgaaccgg ggaggcggag ctggcagtga gccgagatcc cgccactgca  26040
ctccagcctg ggcgacagag cgagactccg tctcaaaaaa aaaaaaaaaa aaaaagtcca  26100
agattttaaa aaaaaaaaaa aaaaggatgt ctgctttgtg agtttagcat tgtctccttg  26160
tcattccaga aatgaaatgg caaatacatt taaatcagaa ctaaaaaggg gaacagggta  26220
taaaggctca atttagtcac atcatttccg tttctcaccc acccccttta aaccagatgt  26280
ttgccaatgc attaacaatg cagatgtttc ctgaaagaaa gtttagtaac tcaagcagac  26340
accttatttt cttttcaagc agaaaagact atgagatggt ggttgtggtt gttccgggag  26400
ggagaagata taaatgatac acattatttc aaatcatttc atgacctcac tgcacactta  26460
tagttattgt acctgttgtc tttttgctgt caagcctagc taagatcatt tggaatgttc  26520
aagatcactc atacatgcat gtgcacacat acacatgcac atatgttcac tccctatttc  26580
atccacatga actaagatta ctgatgtgta cagattcaaa gcacttttat tcttttccaa  26640
aggcaagaag ctgagctact ttccagaata gttgtgaaag accctgtcat acttctgcat  26700
tgtttcctcc acaccacctc catccagttc cttatgaatg gttactggtt ttcaaaaata  26760
tgagataaat tgagtgtata aaagtcattt ttagacaaaa tgaaacagga aatgaaagaa  26820
accagaatct ctcctcattt gtggatgggc cagctccacc atgtcatggt taatctgcag  26880
ggaggaaata ctagatttga ttgcagatca gactgcagca aacctgctgt gactaaggca  26940
```

-continued

```
tcaagagaaa gcaagcaaca gactggggct tcagtggtga aaacattata tatctagctt  27000
tgaaatatga aatactgttt agcagtgtca cctagaaaag agtgtttcaa aatgctgatg  27060
cttcataaga acctttctct tcagagttgg tttcttttat ctttcaaatt agccagggtg  27120
ggaaataaag tgatcacttg gtgaagaaat ctcacaaaga agaacataga gagttcactt  27180
tcatctggag taatgaacag attgaacaaa ctagaaatgg ttagtctgtt aaagaaaagg  27240
tgtaggtgag ctgtttgcaa gagccacaag ggaaagggga agacaacttc tttgtggact  27300
taagggtgaa agttgcaagc aggcaagacg attctgacct ccattaagaa agcccaaacc  27360
aaccaacaac cactgggttg gttacgcagg ttgggcagca ttgggagcaa atgttgattg  27420
aacaaatgtt tgtcggaatt gttgacttaa agagctgttc tgtcactggg gacagcagcg  27480
gctagatagc cccattcagg gagagggcat ttgttcacct ggccagagat cagagcaggc  27540
taagggactg ctgggatcct gtccagcttt gagaccctac agagccatgt tcacctagca  27600
cgtatcccgt ctgcggtcac ggtcatttct taccttattc cagggctttc acctcagctt  27660
gccaggctgg agccaagggc caacgcagcc gcgccttgtt cgcgatggta gcttcccagg  27720
agccccctat ggttccggaa cgcgctgccg gccccatcct gtttgctacc tcctaaagcc  27780
aaaggcactg gcgggccggg ccagcttcta aagtcgcgca aggttagaag gttccggaca  27840
ggaacggcgt gaggccaatg gaaggaggta cttcagtttc cctccagatg cccagcgatg  27900
ggctcagagc tccttgagaa ctcgggaaag gaagcagggt ctctgaagaa atacttcagg  27960
agtagaaaga ggaagctaga gggttaaatg cactacacag gaacagaaat gagtttttct  28020
tagagttagt atatgtctag aggtgtagta aactaaaaca agtcttgaat tgcataccgc  28080
cacgtaggga agaaatgaaa acctttgaat attagtgaaa aaagggaaac tgcaacgcct  28140
gtattactag atagctttca tcaacagctc aaaaccgaca gatttaaaga agcaacaccg  28200
cattttggct ttctaaagct ttaatttggt ttggatccca tgcccatgac cctgccagct  28260
gacaattcta agcatgcgca aactggcccc aaaaattcct cccacatttc cgaagaacta  28320
tttggccctt tatgtgaagt acctggtttt tccattttct gttttaccat aggcctcagt  28380
tcggtgtgtg gcgtatttat tctacattta acaatttgaa gatcattcta ttagattaaa  28440
aaaaaagaat acaatggaag ccaagtgatt aagctttcct tatgcttata ttaagttgta  28500
gcatatgcat ttaccgatag ttaaccgtat taacctacag aaaatgtcca gggaaatggt  28560
ctatttctta ttctattttt gacctaaaga aaatctttaa aatgtcttag cattttcccc  28620
agtctccatc cacttccctc agctttggcc tgaagctatc tttaaaggta ccctgtacaa  28680
gctcttgccc tgtacagcta gctacagaga ttcaatcctt tctgttcgat taggacacat  28740
ctcagtggca gataacatgc aaagttatta tatgtatgaa ccagaacttg tttttcctta  28800
ggggccagga tgttacacta aggtcttaag actatagtaa tatcttcact tgaaaaagcc  28860
ctctattatt cctatctcag atgataaaaa ttcaattaag agaaataaga acgtgacatg  28920
tgtaatcgca cctggctcta caaagctagt ctggacagac atttaaacaa ttatcctcta  28980
agattatttg atgaaatgca tttcaatgac tagttaacca ttaaaaacca aagtgagcat  29040
cccatctgtt cccagtcaaa tgacctagag caaaggacta ggcaaaccac atctgtgggc  29100
atagcaagct gtacatcaca aacaaatgaa tttgctttgt atatgagtga gagcaaacac  29160
tctttattgt acaacttggg tgggtaagta gggagaataa tggttttact gaaatcgcag  29220
gtaacggtta cgttggagtt aaaggttagg aagaaaacca aagggtaaga gctgttgttc  29280
tgggctggca ttgtcaatga agagcataaa ttcagatgtg aatgtatatt ttgtagaagc  29340
```

-continued

```
atgtgtgttg ttggtttttg tgtatgtgtg agtctgaaag agggaaaaca ggctcccatt  29400
agactatgac taacaaaaat gtttgacaga ttataactca gatgtcttac tcagagcata  29460
tgccttccca ttttccccat tattccccaa catgatgtct ttaagaactt gtccttgacc  29520
gagcagacat ctcatacccc aaatagctaa tattttgata gctatgatcc tgaacggcca  29580
aacattccaa aaccaagtag tttgtaatat ctttaatgca aatatatttt aggccttttc  29640
cttggcaagg atgtttggtc aggggttggc aaaaataatg ctcttcagac ttaaaagaac  29700
acaaccatat ttcttagcca tccaccagaa agtagtagaa cgctccagga agcaagtctt  29760
tgtcaggagt cagactagct acatcataat ctctctgccc aggggctgtg gatgtcatcc  29820
atcctggcct aactagccta ctgagctgag agatgtccaa tttcccccca atacactaac  29880
cagaggagaa ggaccgtgat atcattgcat gtgaattctt aattccaatt gcttaaacaa  29940
atatgttcag ttgtaactat caataccagt atataacagt gttggccaag ttttattgat  30000
gctgacaatc aattggagtt acagccagac acatggtctt atgaccggcg tacttacgca  30060
gggctttgca ctgagacagg tcgtgcatct gaggtttact gctttgcatt tttgttttgt  30120
aactgaagtc tgatgagaca gccagagcat gtgctaccta gggacttgaa tccctgcagc  30180
cccatttcac ttctcaccac cttccggggt ggtttctcga cctcccactc ccctaccacc  30240
tggtgcctta gccagccctg gctctccctc caaacacctg cccaatgagc actgccaccc  30300
catggtgccc agacatgctc tccctcctca tccctaccta gctaccattg ccactcccct  30360
cccccagcgg ggacatgggc ataggagcag ggagagttaa ggttggtcag gtgcacgtgc  30420
cctatgctat cttggaaggg ggcttggcca tgtggcatct ctggaccaag aatgcgccac  30480
agcacatttg gagggtgaat ggtgggggca cacccccttgt ccacctctat ttcaggcatg  30540
gaacacatcc tggcatgaaa gttgcagtcc cttgggaatc acctctccac cttgattgcc  30600
acagtaggcc agtgacaagg gaagattgac acatcatccc tgctggggcc cagtgtcctg  30660
tggctggcag gcaggggatc ctaaggacat gtgggtctta aattgtaggg tgcacttcct  30720
gggcaccttt gagggtctgc actgccccag caaatatccc catgctagaa ggagcaaaat  30780
attaaatggc aaattttaaa aatgtaacaa gatgggttgc aaaagagact acagaggaaa  30840
gcaaaagttt tgtattttag tatcttccat ggcacttttc ttcctagctt ttgaacaagg  30900
ggccccacat ttttatttct cactgagccc cacaaagtat gtagccattc ctgcccggag  30960
tgaggacttt taaaacataa agattatcaa gtcttggaaa ttctgattca gtagatatat  31020
aacaggtctc aaacttaatt atgtaaagaa tattctggag agcttccttt tacccagtcc  31080
cacccaccaa atattctgat aaattaagct tcgattagcc cccagatctg cattttataa  31140
ggatccccag atgattctac tgcaattggt ccacagacca tgcctggacc gaatttgggt  31200
gcttaggagc acaaattctg gagccgggca gacttgagtt tgcttcctag ctttaccaac  31260
tgatctcagg ggagttaatg tttacctcta aactttagct catgcatcta taaataaata  31320
tattaatatc atgtcataag gatattatgt tgtattaaat gtctttaaaa caccacaatg  31380
attagcccaa agtaaacact caataaatgt tcaaaaattt aggaaaattg ttaagactgg  31440
gttgtatgca cactggtgtt tattatatta tgtagttttt tctgtatttt tacaacattt  31500
cagaattaaa agcaacagct agaaaaagag ggaaatggcc gggtgcagtc gtcacgcctg  31560
taatcccagc actttgggag gccaaggcgg gcggatcacg aggtcgagag atcgagacca  31620
tcctggccaa catggtgaaa ccccatctct actaaaaata caaaaattaa ctgggcatgg  31680
```

-continued

```
tggcatgcgc ctgtagtccc aggagaattg cttgaacctg ggaggcggag gttgcagtga  31740
gccaagatct caccactgct ctccagcctg gtgacagggc aagactccgt caaaaaaaaa  31800
aaagagaggg agagccagag tatgaaaaag gaagtcagag ccctttaatg agtcagcttt  31860
gtaggtctcc aggtaggagg ctagtgcttc agtgtctagg acatagtagg tgttcagtaa  31920
attaaattca ggacaaaaag aacatgcccc aaggaccatc tgatatccac ttaaagtgat  31980
ggactacctc gtttcccttg tttatgaatg ggttcatgcc taagactgtg tgcactttaa  32040
tacaagggca gtcgttcaga actagtcagg tcctgaaaag gatttaccaa atgttgagtg  32100
tgccctctag tgttcacact tcccagcttt cttcctataa aggtggatca aggcacttgc  32160
ttacaactgg aactgaaatc ctccaagtcg atctagacat tgagatggag aaaatattca  32220
ttgtcgactg taattatgca acgaatatcc agttgagata atggacttgc ctcttatcta  32280
ataataccca ggctcaatgc gtcactgctt tgtccacttt gcccaaaatt caagcacagc  32340
taagttgata ttttaggaca aaggcagctt actatccagc cagaggggag tagaatatgg  32400
ttaagagaga gtggaaagaa tgaatgagcc ctgctattcc tcactgcctg gatggctata  32460
agcacagccc ttatggaggc cttaggtctt gcttcacaat attccagttt gaaaagggtt  32520
tgaaaagacc tcctagaaaa atcagtagtt tttctctttt gagtaacatg tagcaaaaaa  32580
aatttcatca tgtaggtaca gggaacaccc tagtaactat taatctcaag gagtcaagcc  32640
agtgtgtttc ctaatgtatc tgctgtatcc ccatgaagca aattttgcca tcagagaaac  32700
tgactcatgg ggaaaaaatc caaggacctc aaatcaccaa aagaagccat tcctcagatt  32760
tgcctaagct taagcttccc tgtctctcat tgtgtgttgc tttcaatgca gttacataaa  32820
tggctttttt gtttatgcac caaaaacact aattcatctg caaagctcac atttccagaa  32880
acattccatt tctgccagca cctagaagcc aatattttgc ctattcctgt aaccagcaca  32940
catatttatt tttttctaga tcaaatgtat tatgcagtaa gagtcttaat tttgttttca  33000
caggttgttt tgaatggtaa agttgatgca ttctgtggag gctctatcgt taatgaaaaa  33060
tggattgtaa ctgctgccca ctgtgttgaa actggtgtta aaattacagt tgtcgcaggt  33120
aaatacacag aaagaataat aatctgcagc accactagct ctttaatatg attggtacac  33180
catattttac taaggtctaa taaaattgtt gttgaataaa ttgggctaaa ggcagaaggg  33240
tcataatttc agaacccacg tcgcaccgtc ctccaagcat ccatagttct tttgatatac  33300
ccctattatc actcatttca gtgaggtaca attagttctt gatgtagcca tttccatacc  33360
agaaggcctt cccaaaaatc agtgtcatgt caccgatcct tttatctctg gtgcttggca  33420
caacctgtag caggtcctca gaaaacaaac atttgaatta atggccaaat gagtttgtgc  33480
tcaaaaaagg ggtgaggata cttgaaattt ggaaaatcta ggataattca tgactagtgg  33540
attcattatc accaatgaaa ggcttataac agcatgagtg aacagaacca tctctatgat  33600
agtcctgaat ggctttttgg tctgaaaaat atgcattggc tctcattaca tttaaccaaa  33660
attatcacaa tataagaatg agatctttaa cattgccaat taggtcagtg gtcccaagta  33720
gtcacttaga aaatctgtgt atgtgaaata ctgtttgtga cttaaaatga aatttatttt  33780
taataggtga acataatatt gaggagacag aacatacaga gcaaaagcga aatgtgattc  33840
gaattattcc tcaccacaac tacaatgcag ctattaataa gtacaaccat gacattgccc  33900
ttctggaact ggacgaaccc ttagtgctaa acagctacgt tacacctatt tgcattgctg  33960
acaaggaata cacgaacatc ttcctcaaat ttggatctgg ctatgtaagt ggctggggaa  34020
gagtcttcca caaagggaga tcagctttag ttcttcagta ccttagagtt ccacttgttg  34080
```

-continued

```
accgagccac atgtcttcga tctacaaagt tcaccatcta taacaacatg ttctgtgctg  34140
gcttccatga aggaggtaga gattcatgtc aaggagatag tgggggaccc catgttactg  34200
aagtggaagg gaccagtttc ttaactggaa ttattagctg ggtgaagag tgtgcaatga  34260
aaggcaaata tggaatatat accaaggtat cccggtatgt caactggatt aaggaaaaaa  34320
caaagctcac ttaatgaaag atggatttcc aaggttaatt cattggaatt gaaaattaac  34380
agggcctctc actaactaat cactttccca tcttttgtta gatttgaata tatacattct  34440
atgatcattg ctttttctct ttacagggga gaatttcata ttttacctga gcaaattgat  34500
tagaaaatgg aaccactaga ggaatataat gtgttaggaa attacagtca tttctaaggg  34560
cccagccctt gacaaaattg tgaagttaaa ttctccactc tgtccatcag atactatggt  34620
tctccactat ggcaactaac tcactcaatt ttccctcctt agcagcattc catcttcccg  34680
atcttctttg cttctccaac caaaacatca atgtttatta gttctgtata cagtacagga  34740
tctttggtct actctatcac aaggccagta ccacactcat gaagaaagaa cacaggagta  34800
gctgagaggc taaaactcat caaaaacact actccttttc ctctacccta ttcctcaatc  34860
ttttaccttt tccaaatccc aatccccaaa tcagttttc tctttcttac tccctctctc  34920
ccttttaccc tccatggtcg ttaaaggaga gatggggagc atcattctgt tatacttctg  34980
tacacagtta tacatgtcta tcaaacccag acttgcttcc atagtggaga cttgcttttc  35040
agaacatagg gatgaagtaa ggtgcctgaa aagtttgggg gaaaagtttc tttcagagag  35100
ttaagttatt ttatatatat aatatatata taaaatatat aatatacaat ataaatatat  35160
agtgtgtgtg tgtatgcgtg tgtgtagaca cacacgcata cacacatata atggaagcaa  35220
taagccattc taagagcttg tatggttatg gaggtctgac taggcatgat ttcacgaagg  35280
caagattggc atatcattgt aactaaaaaa gctgacattg acccagacat attgtactct  35340
ttctaaaaat aataataata atgctaacag aaagaagaga accgttcgtt tgcaatctac  35400
agctagtaga gactttgagg aagaattcaa cagtgtgtct tcagcagtgt tcagagccaa  35460
gcaagaagtt gaagttgcct agaccagagg acataagtat catgtctcct ttaactagca  35520
taccccgaag tggagaaggg tgcagcaggc tcaaaggcat aagtcattcc aatcagccaa  35580
ctaagttgtc cttttctggt ttcgtgttca ccatggaaca ttttgattat agttaatcct  35640
tctatcttga atcttctaga gagttgctga ccaactgacg tatgtttccc tttgtgaatt  35700
aataaactgg tgttctggtt catacettgg ctttttgtgg attccattga tgtgaatcag  35760
tcaccctgta tttgatgatg catgggacta ctgacaaaat cactctgacc ctgccaagct  35820
gctgccttct cctgccccaa cctcaccccc agccaggcct cactcttgct agttccttta  35880
gttcttttag tcaatatatt tttgtcttcg catataagta taaataaaca tatttttaaa  35940
tttcttggct gggcccagtg gctcacgcct ataatcccag cacttctgga ggccaaggtg  36000
ggcggatcac ctgaggttag gagtttcagg ccagcctggc caacatggtg aaaccctgtc  36060
tctactaaaa atagaacaat tagctgggct tggtaatgtg cacctataat cccagctact  36120
ggggaggctg aggcaggaga atcacttgag cctggggagc agggggtgcg ggaggttgca  36180
gtgagacaag atcgcaccag tgcactcccc atcctgggtg acagagtgag actctgtctc  36240
aaagaaaata aataaataaa tacatttctt gaggcgtttc ttgttaaatc attcatggag  36300
aggcatccca aacaccacat tcaacaaaac actctgaaaa atgttttcaa atgcaatata  36360
acacagcaga gatttgatgc tctgttatcc agttttcata taaggctgtg tgagctgtgt  36420
```

-continued

```
cccagagagg acagtggtct gaatccacct gagacagaat tgggtctaac taactgtgag  36480

tatggccttc aataagtcac tctccatttg ggaatttgat ttctccactt gtataatgag  36540

agtatttgac aggatgctct cccaaatccc ttgcaatttt gttagtctgt gatttcatgt  36600

ttttattttt attccttcat ccaacaaata gtcaaggagt aattgctgtg tgccaaatac  36660

caacagtatt cattaaattg taattcagat tttatatata tataaataat gtataatgtg  36720

tataaattgc tttgtgagtg cctactacac tgctagacag tagttgctca ataacttgtt  36780

agctgaatca gaatccatgt ttatcccaga gtagcaatta gtcttgcatc gagtatcgtg  36840

aaagaaggcc acacttaaat aagaataatg cctggggttt aggttttatg aaaaaatgaa  36900

aggaaattag ttctgctttt gttgactaaa ggaagggaag agagaagaga cactataatt  36960

gtctgcctca gatttaagga ggaggctaat tcatgcatta aacacgttac ttcaaatttg  37020

aatgaccaaa ggtctgtagc ctcagcactt caaaattggt aaaagtaaga cactctggcc  37080

ttgtttccat agagaccacc ccttacaaag gcaccaatgg gaaactggcc tcaggactcc  37140

tgttattggt cttctctgtg gcagagaaag gagctcttgg acccataaat ctctgagcca  37200

cagttctttt tgccatgggc tcaaaaatga ttgaattcat catgagccac ctgtggcata  37260

ttgccacact aaacatgtgg ggcctttaag ctcactaaga gccaatgtct tcagagccag  37320

ccctggcttg attctaccta gggcatttgc agttgccata taagaatcat tagtgctttc  37380

aaaattactg tagatacttt gcctaaatag actaaaacat gctgccgtca tattggaagt  37440

gacagattaa aatagaactc ttgccaagtg aaggaaagtg tgctaatata atgcagtcat  37500

tttaacttgc tgtttaagtg tgattgtttt tagttctttt gaatattatt tgttttatac  37560

tgacaggaac gaagtactgt ccaattttct ctgccaagga aaaaagaaaa ggtgttcttc  37620

cttacttacc tgaaccaaaa cagaccagtt tacaaaattg cctaattata attgctaaac  37680

aagttccgaa tgcttacagt ctaatccaag aatgtcagag ctgcaagggc ccttaaacac  37740

catccaatcc actccactca tttagcagat gaagagattg agggcaacat aaggccaggc  37800

ccaagataac acaatgacag ccaggactag agctcaagtc tcccaccctg cactttgaaa  37860

gaataatgct ttcaactgga gtacattaac tctactgtct atatttttag ggcagctggg  37920

gcattctgca ttggtggcaa tcctctcaac aaccctggga ctgaaaactg cctggaattc  37980

ttactaacaa ttctctaatt gaccaaaagg tgacgaaatc aaggagacca ataaggtagc  38040

cttggaaagc aagagtggc                                                38059
```

<210> SEQ ID NO 5
<211> LENGTH: 29
<212> TYPE: PRT
<213> ORGANISM: Homo sapiens

<400> SEQUENCE: 5

```
Met Gln Arg Val Asn Met Ile Met Ala Glu Ser Pro Gly Leu Ile Thr
  1               5                  10                  15

Ile Cys Leu Leu Gly Tyr Leu Leu Ser Ala Glu Cys Thr
             20                  25
```

<210> SEQ ID NO 6
<211> LENGTH: 55
<212> TYPE: PRT
<213> ORGANISM: Homo sapiens

<400> SEQUENCE: 6

```
Val Phe Leu Asp His Glu Asn Ala Asn Lys Ile Leu Asn Arg Pro Lys
```

```
  1               5                  10                 15

Arg Tyr Asn Ser Gly Lys Leu Glu Glu Phe Val Gln Gly Asn Leu Glu
             20                  25                  30

Arg Glu Cys Met Glu Glu Lys Cys Ser Phe Glu Glu Ala Arg Glu Val
         35                  40                  45

Phe Glu Asn Thr Glu Arg Thr
     50                  55


<210> SEQ ID NO 7
<211> LENGTH: 8
<212> TYPE: PRT
<213> ORGANISM: Homo sapiens

<400> SEQUENCE: 7

Thr Glu Phe Trp Lys Gln Tyr Val
  1               5


<210> SEQ ID NO 8
<211> LENGTH: 38
<212> TYPE: PRT
<213> ORGANISM: Homo sapiens

<400> SEQUENCE: 8

Asp Gly Asp Gln Cys Glu Ser Asn Pro Cys Leu Asn Gly Gly Ser Cys
  1               5                  10                  15

Lys Asp Asp Ile Asn Ser Tyr Glu Cys Trp Cys Pro Phe Gly Phe Glu
             20                  25                  30

Gly Lys Asn Cys Glu Leu
         35


<210> SEQ ID NO 9
<211> LENGTH: 43
<212> TYPE: PRT
<213> ORGANISM: Homo sapiens

<400> SEQUENCE: 9

Asp Val Thr Cys Asn Ile Lys Asn Gly Arg Cys Glu Gln Phe Cys Lys
  1               5                  10                  15

Asn Ser Ala Asp Asn Lys Val Val Cys Ser Cys Thr Glu Gly Tyr Arg
             20                  25                  30

Leu Ala Glu Asn Gln Lys Ser Cys Glu Pro Ala
         35                  40


<210> SEQ ID NO 10
<211> LENGTH: 68
<212> TYPE: PRT
<213> ORGANISM: Homo sapiens

<400> SEQUENCE: 10

Val Pro Phe Pro Cys Gly Arg Val Ser Val Ser Gln Thr Ser Lys Leu
  1               5                  10                  15

Thr Arg Ala Glu Ala Val Phe Pro Asp Val Asp Tyr Val Asn Ser Thr
             20                  25                  30

Glu Ala Glu Thr Ile Leu Asp Asn Ile Thr Gln Ser Thr Gln Ser Phe
         35                  40                  45

Asn Asp Phe Thr Arg Val Val Gly Gly Glu Asp Ala Lys Pro Gly Gln
     50                  55                  60

Phe Pro Trp Gln
 65
```

<210> SEQ ID NO 11
<211> LENGTH: 38
<212> TYPE: PRT
<213> ORGANISM: Homo sapiens

<400> SEQUENCE: 11

```
Val Val Leu Asn Gly Lys Val Asp Ala Phe Cys Gly Gly Ser Ile Val
  1               5                  10                  15

Asn Glu Lys Trp Ile Val Thr Ala Ala His Cys Val Glu Thr Gly Val
             20                  25                  30

Lys Ile Thr Val Val Ala
         35
```

<210> SEQ ID NO 12
<211> LENGTH: 182
<212> TYPE: PRT
<213> ORGANISM: Homo sapiens

<400> SEQUENCE: 12

```
Gly Glu His Asn Ile Glu Glu Thr Glu His Thr Glu Gln Lys Arg Asn
  1               5                  10                  15

Val Ile Arg Ile Ile Pro His His Asn Tyr Asn Ala Ala Ile Asn Lys
             20                  25                  30

Tyr Asn His Asp Ile Ala Leu Leu Glu Leu Asp Glu Pro Leu Val Leu
         35                  40                  45

Asn Ser Tyr Val Thr Pro Ile Cys Ile Ala Asp Lys Glu Tyr Thr Asn
     50                  55                  60

Ile Phe Leu Lys Phe Gly Ser Gly Tyr Val Ser Gly Trp Gly Arg Val
 65                  70                  75                  80

Phe His Lys Gly Arg Ser Ala Leu Val Leu Gln Tyr Leu Arg Val Pro
                 85                  90                  95

Leu Val Asp Arg Ala Thr Cys Leu Arg Ser Thr Lys Phe Thr Ile Tyr
            100                 105                 110

Asn Asn Met Phe Cys Ala Gly Phe His Glu Gly Gly Arg Asp Ser Cys
        115                 120                 125

Gln Gly Asp Ser Gly Gly Pro His Val Thr Glu Val Glu Gly Thr Ser
    130                 135                 140

Phe Leu Thr Gly Ile Ile Ser Trp Gly Glu Glu Cys Ala Met Lys Gly
145                 150                 155                 160

Lys Tyr Gly Ile Tyr Thr Lys Val Ser Arg Tyr Val Asn Trp Ile Lys
                165                 170                 175

Glu Lys Thr Lys Leu Thr
            180
```

<210> SEQ ID NO 13
<211> LENGTH: 2410
<212> TYPE: DNA
<213> ORGANISM: Mus musculus

<400> SEQUENCE: 13

```
gaattccgtg gatgtgcttt aaaaccacac ctaacgtttg agcacaagtc tcacgaactg      60

gcgctacaac ttcatcagaa acgaagtctc caaatctgtc caacgcaaaa acacaaagga     120

gtctaatgac taagtcttcc aaccacaact gtctgctgcg cccggaaaac aagccggggc     180

tctggggacc cggggctcag gccgcctcgc tccggcctag ccccgccacc ttagttgtgt     240

catcccccgg gcatgctgag catccccccg cggctccggc acagacgccc ggacctcagg     300
```

-continued

```
tctctgcctc cgcgcggggg cccggccctg tggccggagg gagcggccgg atggagcgga    360

ggatgaaagg cggatacttg gaccagcgag tgccctacac cttctgcagc aaatctcccg    420

gaaatgggag cttgggcgaa gcgctgatgg tcccgcaggg aaagctcatg gacccgggct    480

ccctgccgcc ttccgactca gaagatctct tccaggacct cagtcacttc caagagacgt    540

ggctcgcaga agctcaggta ccggacagtg atgagcagtt tgttcctgat ttccattcag    600

aaaacttagc tttccatagc cccaccacca ggatcaagaa ggaaccccag agtccccgca    660

cagaccccgc cctgtcctgc agcaggaagc caccactccc ctaccaccat ggagagcagt    720

gcctttactc cagacaaatc gccatcaagt cccccgctcc cggtgcccct ggacagtcgc    780

ccctgcagcc cttttccagg gcagaacagc agcagagcct cctgagagcc tccagctctt    840

cccagtccca ccctggccac gggtaccttg gtgagcacag ctccgtcttc cagcagcccg    900

tggacatgtg ccactccttc acatctcctc agggaggggg ccgggaacct ctcccagccc    960

cctatcaaca ccaactgtcg gagccctgcc caccctaccc ccagcagaac ttcaagcagg   1020

agtaccatga ccccctgtac gaacaggctg gccagcccgc ttcaagccag ggtggggtca   1080

gtgggcacag gtacccaggg gcgggggtgg tgatcaaaca ggagcgcaca gacttcgcct   1140

acgactcaga tgtccctgga tgtgcatcaa tgtacctcca cccagagggc ttctctggac   1200

cctctccagg tgatggagtg atgggttatg gctatgaaaa atcccttcga ccattcccag   1260

atgatgtctg cattgtccct aaaaaatttg aaggagacat caagcaggaa gggattggag   1320

ctttccggga ggggccaccc taccagcgcc ggggtgcctt acaactgtgg cagtttctgg   1380

tggccctgct ggatgaccca acaaatgctc atttcattgc ttggacaggc cggggaatgg   1440

agtttaaact aattgaacct gaagaggttg ccaggctctg gggtatccag aagaaccggc   1500

cagccatgaa ttatgacaag ctgagccgct cgctgcgata ctattatgag aaaggcatca   1560

tgcagaaggt ggctggcgaa cgctacgtgt acaagtttgt gtgcgagccg gaggccctgt   1620

tctctctggc cttcccagat aatcaacgtc cagctctgaa ggctgagttt gaccggccag   1680

tcagtgagga ggacacagtc cctttgtccc acttggatga gagtcctgcc tacctcccag   1740

aactcactgg ccccgctccg cccttcggcc acagaggtgg atattcttac taggcaccag   1800

tggcttcccc ttgacatggt ggggttgctc agtgtatata tcaactgatt tggtattggt   1860

gaaggccctc tttctgatgc ctgtagaagt ctctggggtc agagctccac tatcccatct   1920

gatactcctg gccagactca gctgctaacc agagtctgcg ggaaagacag tggaggcagg   1980

ccaaatctaa aggcagtagc tgaagttcgc tgtggctcac ctgtaccttc agttcagctt   2040

ggcctctgcc taggtcttgc tcagaggcca agttcctcac ccccaccaca gagatccagt   2100

gttctattct ggggacatac agggacttcc cttgtttatt atggcaacag ggccaagggg   2160

attctcagaa caccctgtgt ctcccctctc ccaacccccc atgggagaca aagttctgcc   2220

tggcttctgc cctgaacagg ggggtcctgt gttcttggtg ctgtgctctg ggaggcagga   2280

gcatgtgggc ggcagctggg ggggggtgtg gaagtagaga tggctctctg ccctaggcct   2340

acccaggcct aattccacct ttgcctctta tgccagacct taataaagcc tctgcttctc   2400

cccggaattc                                                          2410
```

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic -continued

<400> SEQUENCE: 14
taacaggatc cggcctctca ctaactaatc ac 32

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic

<400> SEQUENCE: 15
caactggatc caagattcaa gatagaagga t 31

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic

<400> SEQUENCE: 16
ggacaggatc ccccaaactt ttcaggcac 29

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic

<400> SEQUENCE: 17
caagcatgca tctagtgtta gtggaagag 29

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic

<400> SEQUENCE: 18
caagcatgca aatattaact caaaatgga 29

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic

<400> SEQUENCE: 19
caagcatgct gttgtttttt gttttaac 28

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic

<400> SEQUENCE: 20
caagcatgca gccattcagt cgaggaagg 29

<210> SEQ ID NO 21

<211> LENGTH: 27
<212> TYPE: DNA
<213> ORGANISM: Artificial Sequence
<220> FEATURE:
<223> OTHER INFORMATION: Description of Artificial Sequence: Synthetic

<400> SEQUENCE: 21
caagcatgcg atcccttcct tatacct 27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic

<400> SEQUENCE: 22
taagcttaac ctttgctagc agattgt 27

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic

<400> SEQUENCE: 23
cttggtacca gccattcagt cgaggaagg 29

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic

<400> SEQUENCE: 24
cttggtacca tatgaatcct ttcatagat 29

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 25
ctgtgggaac acacagattt tgg 23

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 26
ggaataattc gaatcacat 19

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 27
ccaatctgct cacacaggat 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 28
ccttgaggct gtccaagtga 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 29
atggttaact gacttacgaa 20

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 30
gctccatttt gagttaatat ttgtgt 26

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 31
ttcagtcgag gaaggatagg gt 22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 32
ttcagtcggt tggtgatagg gt 22

<210> SEQ ID NO 33
<211> LENGTH: 11
<212> TYPE: DNA
<213> ORGANISM: Homo sapiens

<400> SEQUENCE: 33
tcgaggaagg a 11

<210> SEQ ID NO 34
<211> LENGTH: 15
<212> TYPE: DNA
<213> ORGANISM: Homo sapiens

<400> SEQUENCE: 34
agtcgaggaa ggata 15

<210> SEQ ID NO 35
<211> LENGTH: 19
<212> TYPE: DNA
<213> ORGANISM: Homo sapiens

<400> SEQUENCE: 35
tcagtcgagg aaggatagg 19

<210> SEQ ID NO 36
<211> LENGTH: 23
<212> TYPE: DNA
<213> ORGANISM: Homo sapiens

<400> SEQUENCE: 36
attcagtcga ggaaggatag ggt 23

<210> SEQ ID NO 37
<211> LENGTH: 27
<212> TYPE: DNA
<213> ORGANISM: Homo sapiens

<400> SEQUENCE: 37
ccattcagtc gaggaaggat agggtgg 27

<210> SEQ ID NO 38
<211> LENGTH: 30
<212> TYPE: DNA
<213> ORGANISM: Homo sapiens

<400> SEQUENCE: 38
gccattcagt cgaggaagga tagggtggta 30

<210> SEQ ID NO 39
<211> LENGTH: 7
<212> TYPE: DNA
<213> ORGANISM: Artificial Sequence
<220> FEATURE:
<223> OTHER INFORMATION: Description of Artificial Sequence: Synthetic

<400> SEQUENCE: 39 gaggatg 7

<210> SEQ ID NO 40
<211> LENGTH: 7
<212> TYPE: DNA
<213> ORGANISM: Artificial Sequence
<220> FEATURE:
<223> OTHER INFORMATION: Description of Artificial Sequence: Synthetic

<400> SEQUENCE: 40 caggaag 7

<210> SEQ ID NO 41
<211> LENGTH: 7
<212> TYPE: DNA
<213> ORGANISM: Artificial Sequence
<220> FEATURE:
<223> OTHER INFORMATION: Description of Artificial Sequence: Synthetic

<400> SEQUENCE: 41 caggatg 7

<210> SEQ ID NO 42
<211> LENGTH: 12222
<212> TYPE: DNA
<213> ORGANISM: Homo sapiens

<400> SEQUENCE: 42
gaattccagg ttggaggggc ggcaacctcc tgccagcctt caggccactc tcctgtgcct 60
gccagaagag acagagcttg aggagagctt gaggagagca ggaaaggtgg aacattgctg 120
ctgctgctca ctcagttcca caggtgggag gaacagcagg gcttagagtg gggtcattg 180 tgcagatggg aaaacaaagg cccagagagg ggaagaaatg cctaggagct accgagggca 240
ggcgacctca accacagccc agtgctggag ctgtgagtgg atgtagagca gcggaatatc 300
cattcagcca gctcagggga aggacagggg ccctgaagcc aggggatgga gctgcaggga 360
agggagctca gagagaaggg gaggggagtc tgagctcagt ttcccgctgc ctgaaaggag 420
ggtggtacct actcccttca cagggtaact gaatgagaga ctgcctggag gaaagctctt 480
caagtgtggc ccaccccacc ccagtgacac cagcccctga cacgggggag ggagggcagc 540
atcaggaggg gctttctggg cacacccagt acccgtctct gagctttcct tgaactgttg 600
cattttaatc ctcacagcag ctcaacaagg tacataccgt caccatcccc attttacaga 660
tagggaaatt gaggctcgga gcggttaaac aactcacctg aggcctcaca gccagtaagt 720
gggttccctg gtctgaatgt gtgtgctgga ggatcctgtg ggtcactcgc ctggtagagc 780
cccaaggtgg aggcataaat gggactggtg aatgacagaa ggggcaaaaa tgcactcatc 840
cattcactct gcaagtatct acggcacgta cgccagctcc caagcaggtt tgcgggttgc 900
acagcggagc gatgcaatct gatttaggct tttaaaggat tgcaatcaag tgggacccac 960
tagcctcaac cctgtacctc ccctcccctc cacccccagc agtctccaaa ggcctccaac 1020
aaccccagag tgggggccat gtatccaaag aaactccaag ctgtatacgg atcacactgg 1080
ttttccagga gcaaaaacag aaacagcctg aggctggtca aaattgaacc tcctcctgct 1140
ctgagcagcc tagggggcag actaagcaga gggctgtgca gacccacata aagagcctac 1200
tgtgtgccag gcacttcacc cgaggcactt cacaagcatg cttgggaatg aaacttccaa 1260
ctctttggga tgcaggtgaa acagttcctg gttcagagag gtgaagcggc ctgcctgagg 1320
cagcacagct cttctttaca gatgtgcttc cccacctcta ccctgtctca cggcccccca 1380
tgccagcctg acggttgtgt ctgcctcagt catgctccat ttttccatcg ggaccatcaa 1440
gagggtgttt gtgtctaagg ctgactgggt aactttggat gagcggtctc tccgctccga 1500
gcctgtttcc tcatctgtca aacgggctct aacccactct gatctcccag ggcggcagta 1560
agtcttcagc atcaggcatt ttggggtgac tcagtaaatg gtagatcttg ctaccagtgg 1620
aacagccact aaggattctg cagtgagagc agagggccag ctaagtggta ctctcccaga 1680
gactgtctga ctcacgccac cccctccacc ttggacacag gacgctgtgg tttctgagcc 1740
aggtacaatg actcctttcg gtaagtgcag tggaagctgt acactgccca ggcaaagcgt 1800
ccgggcagcg taggcgggcg actcagatcc cagccagtgg acttagcccc tgtttgctcc 1860
tccgataact ggggtgacct tggttaatat tcaccagcag cctcccccgt tgcccctctg 1920
gatccactgc ttaaatacgg acgaggacag ggccctgtct cctcagcttc aggcaccacc 1980
actgacctgg gacagtgaat cgtaagtatg cctttcactg cgaggggttc tggagaggct 2040
tccgagctcc ccatggccca ggcaggcagc aggtctgggg caggaggggg gttgtggagt 2100

-continued

```
gggtatccgc ctgctgaggt gcagggcaga tggagaggct gcagctgagc tcctattttc   2160

ataataacag cagccatgag ggttgtgtcc tgtttcccag tcctgcccgg tcccccctcg   2220

gtacctcctg gtggatacac tggttcctgt aagcagaagt ggatgagggt gtctaggtct   2280

gcagtcctgg caccccagga tgggggacac cagccaagat acagcaacag caacaaagcg   2340

cagccatttc tttctgtttg cacagctcct ctgtctgtcg gggctcctg tctgttgtct   2400

cctataagcc tcaccacctc tcctactgct tgggcatgca tctttctccc cttctataga   2460

tgaggaggtt aaggttcaga gaggggtggg gaggaacgcc ggctcacatt ctccatcccc   2520

tccagatatg accaggaaca gacctgtgcc agcctcagcc ttacatcaaa atgggcctcc   2580

ccatgcaccg tggacctctg ggccctcctg tcccagtgga ggacaggaag ctgtgagggg   2640

cactgtcacc cagggctcaa gctggcattc ctgaataatc gctctgcacc aggccacggc   2700

taagctcagt gcgtgattaa gcctcataac cctccaaggc agttactagt gtgattccca   2760

ttttacagat gaggaagatg gggacagaga ggtgaataac tggccccaaa tcacacacca   2820

tccataattc gggctcaggc acctggctcc agtccccaaa ctcttgaacc tggccctagt   2880

gtcactgttt ctcttgggtc tcaggcgctg gatggggaac aggaaacctg ggctgaactt   2940

gaggcctctc tgatgctcgg tgacttcaga cagttgctca acctctctgt tctcttgggc   3000

aaaacatgat aacctttgac ttctgtcccc tcccctcacc ccacccgacc ttgatctctg   3060

aagtgttgga aggatttaat ttttcctgca ctgagttttg gagacaggtc aaaaagatga   3120

ccaaggccaa ggtggccagt ttcctataga acgcctctaa aagacctgca gcaatagcag   3180

caagaactgg tattctcgag aacttgctgc gcagcaggca cttcttggca ttttatgtgt   3240

atttaatttc acaatagctc tatgacaaag tccacctttc tcatctccag gaaactgagg   3300

ttcagagagg ttaagtaact tgtccaaggt cacacagcta atagcaagtt gacgtggagc   3360

aatctggcct cagagccttt aattttagcc acagactgat gctcccctct tcatttagcc   3420

aggctgcctc tgaagttttc tgattcaaga cttctggctt cagctttgta cacagagatg   3480

attcaatgtc aggttttgga gcgaaatctg tttaatccca gacaaaacat ttaggattac   3540

atctcagttt tgtaagcaag tagctctgtg atttttagtg agttatttaa tgctctttgg   3600

ggctcaattt ttctatctat aaaatagggc taataatttg caccttatag ggtaagcttt   3660

gaggacagat tagatgatac ggtgcctgta aaacaccagg tgttagtaag tgtggcaatg   3720

atggtgacgc tgaggctgtg tttgcttagc atagggttag gcagctggca ggcagtaaac   3780

agttggataa tttaatggaa aatttgccaa actcagatgc tgttcactgc tgagcaggag   3840

ccccttcctg ctgaaatggt cctggggagt gcagcaggct ctccgggaag aaatctacca   3900

tctctcgggc aggagctcaa cctgtgtgca ggtacaggga gggcttcctc acctggtgcc   3960

cactcatgca ttacgtcagt tattcctcat ccctgtccaa aggattcttt tctccattgt   4020

acagctatga agctagtgct caaagaagtg aagtcattta ccccaggccc cctgccagta   4080

agtgacaggg cctggtcaca cttgggttta tttattgccc agttcaacag gttgtttgac   4140

cataggcgag attctcttcc ctgcaccctg ccgggttgct cttggtccct tattttatgc   4200

tcctgggtag aaatggtgcg agattaggca gggagtggac gcttccctgt ccctggcccc   4260

gcaaagagtg ctcccacctg ccccgatccc agaaatgtca ccatgaagcc ttcattcttt   4320

tggtttaaag cttggcctca gtgtccgtac accatggggt ccttggccag atggcgactt   4380

tctcctctcc agtcgccctc ccaggcacta gcttttagga gtgcagggtg ctgcctctga   4440

tagaagggcc aggagagagc aggttttgga gacctgatgt tataaggaac agcttgggag   4500
```

-continued

```
gcataatgaa cccaacatga tgcttgagac caatgtcaca gcccaattct gacattcatc   4560
atctgagatc tgaggacaca gctgtctcag ttcatgatct gagtgctggg aaagccaaga   4620
cttgttccag ctttgtcact gacttgctgt atagcctcaa caaggccctg accctctctg   4680
ggcttcaaac tcttcactgt gaaaggagga aaccagagta ggtgatgtga caccaggaaa   4740
gatggatggg tgtgggggaa tgtgctcctc ccagctgtca ccccctcgcc accctccctg   4800
caccagcctc tccacctcct ttgagcccag aattcccctg tctaggaggg cacctgtctc   4860
gtgcctagcc atgggaattc tccatctgtt ttgctacatt gaacccagat gccattctaa   4920
ccaagaatcc tggctgggtg caggggctct cgcctgtaac cccagcactt tgggaggcca   4980
aggcaggcgg atcaagaggt caggagttca agacctgcct ggccaacacg gtgaaacctc   5040
agctctacta aaaatacaaa aattagccag gcgtggtggc acacgcctgt aatcccagct   5100
atttgggaag ctgagacaga agaatttctt gaacccggga ggtggaggtt tcagtgagcc   5160
gagatcacgc cactgcactc caccctggcg gataaagcga gactctgtct caaaaaaaac   5220
ccaaaaacct atgttagtgt acagagggcc ccagtgaagt cttctcccag ccccactttg   5280
cacaactggg gagagtgagg ccccaggacc agaggattct tgctaaaggc caagtggata   5340
gtgatggccc tgccaggcta gaagccacaa cctctggccc tgaggccact cagcatattt   5400
agtgtcccca ccctgcagag gcccaactcc ctcctgacca ctgagccctg taatgatggg   5460
ggaatttcca taagccatga aggactgcac aaagttcagt tgggagtgaa agagaaatta   5520
aagggagatg gaaatataca gcactaattt tagcaccgtc ttcagttcta acaacactag   5580
ctagctgaag aaaatacaaa catgtattat gtaatgtgtg gtctgttcca tttggattac   5640
ttagaggcac gagggccaag gagaaaggtg gtggagagaa accagctttg cacttcattt   5700
gttgctttat tggaaggaaa cttttaaaag tccaaggggg ttgaagaatc tcaatatttg   5760
ttatttccag ctttttttct ccagtttttc atttcccaaa ttcaaggaca ccttttttctt   5820
tgtattttgt taagatgatg gttttggttt tgtgactagt agttaacaat gtggctgccg   5880
ggcatattct cctcagctag gacctcagtt ttcccatctg tgaagacggc aggttctacc   5940
tagggggctg caggcaggtg gtccgaagcc tgggcatatc tggagtagaa ggatcactgt   6000
ggggcagggc aggttctgtg ttgctgtgga tgacgttgac tttgaccatt gctcggcaga   6060
gcctgctctc gctggttcag ccacaggccc caccactccc tattgtctca gccccgggta   6120
tgaaacatgt attcctcact ggcctatcac ctgaagcctt tgaatttgca acacctgcca   6180
acccctccct caaaagagtt gccctctcta gatccttttg atgtaaggtt tggtgttgag   6240
acttatttca ctaaattctc atacataaac atcactttat gtatgaggca aaatgaggac   6300
cagggagatg aatgacttgt cctggctcat acacctggaa agtgacagag tcagattaga   6360
tcctaggtct atctgaagtt aaaagaggtg tcttttcact tcccacctcc tccatctact   6420
ttaaagcagc acaaacccct gctttcaagg agagatgagc gtctctaaag cccctgacag   6480
caagagccca gaactgggac accattagtg acccagacgg caggtaagct gactgcagga   6540
gcatcagcct attcttgtgt ctgggaccac agagcattgt ggggacagcc ccgtctcttg   6600
ggaaaaaaac cctaagggct gaggatcctt gtgagtgttg ggtgggaaca gctcccagga   6660
ggtttaatca cagcccctcc atgctctcta gctgttgcca ttgtgcaaga tgcatttccc   6720
ttctgtgcag cagtttccct ggccactaaa tagtgggatt agatagaagc cctccaaggg   6780
ctccagcttg acatgattct tgattctgat ctgacccgat tctgataatc gtgggcaggc   6840
```

-continued

```
ccattcctct tcttgtgcct cattttcttc ttttgtaaaa caatggctgt accatttgca   6900
tcttagggtc attgcagatg aaagtgttgc tgtccagagc ctgggtgcag gacctagatg   6960
taggattctg gttctgctac ttcctcagtg acattgaata gctgacctaa tctctctggc   7020
tttggtttct tcatctgtaa aagaaggata ttagcattag cacctcacgg gattgttaca   7080
agaaagcaat gaattaacac atgtgagcac ggagaacagt gcttggcata tggtaagcac   7140
tacgtacatt ttgctattct tctgattctt tcagtgttac tgatgtcggc aagtacttgg   7200
cacaggctgg tttaataatc cctaggcact ttcacgtggt gtcaatccct gatcactggg   7260
agtcatcatg tgccttgact cgggcctggc ccccccatct ctgtcttgca ggacaatgcc   7320
gtcttctgtc tcgtggggca tcctcctgct ggcaggcctg tgctgcctgg tccctgtctc   7380
cctggctgag gatccccagg gagatgctgc ccagaagaca gatacatccc accatgatca   7440
ggatcaccca accttcaaca agatcacccc caacctggct gagttcgcct tcagcctata   7500
ccgccagctg gcacaccagt ccaacagcac caatatcttc ttctccccag tgagcatcgc   7560
tacagccttt gcaatgctct ccctggggac caaggctgac actcacgatg aaatcctgga   7620
gggcctgaat ttcaacctca cggagattcc ggaggctcag atccatgaag gcttccagga   7680
actcctccgt accctcaacc agccagacag ccagctccag ctgaccaccg gcaatggcct   7740
gttcctcagc gagggcctga agctagtgga taagtttttg gaggatgtta aaaagttgta   7800
ccactcagaa gccttcactg tcaacttcgg ggacaccgaa gaggccaaga aacagatcaa   7860
cgattacgtg gagaagggta ctcaagggaa aattgtggat ttggtcaagg agcttgacag   7920
agacacagtt tttgctctgg tgaattacat cttctttaaa ggtaaggttg ctcaaccagc   7980
ctgagctgtt tcccatagaa acaagcaaaa atatttctca aaccatcagt tcttgaactc   8040
tccttggcaa tgcattatgg gccatagcaa tgcttttcag cgtggattct tcagttttct   8100
acacacaaac actaaaatgt tttccatcat tgagtaattt gaggaaataa tagattaaac   8160
tgtcaaaact actgacgctc tgcagaactt ttcagagcct ttaatgtcct tgtgtatact   8220
gtatatgtag aatatataat gcttagaact atagaacaaa ttgtaataca ctgcataaag   8280
ggatagtttc atggaacata ctttacacga ctctagtgtc ccagaatcag tatcagtttt   8340
gcaatctgaa agacctgggt tcaaatcctg cctctaacac aattagcttt tgacaaaaac   8400
aatgcattct acctctttga ggtgctaatt tctcatctta gcatggacaa aataccattc   8460
ttgctgtcag gtttttttag gattaaacaa atgacaaaga ctgtggggat ggtgtgtggc   8520
atacagcagg tgatggactc ttctgtatct caggctgcct tcctgcccct gaggggttaa   8580
aatgccaggg tcctgggggc cccagggcat tctaagccag ctcccactgt cccaggaaaa   8640
cagcataggg gaggggaggt gggaggcaag gccaggggct gcttcctcca ctctgaggct   8700
cccttgctct tgaggcaaag gagggcagtg gaggcaagcc aggctgcagt cagcacagct   8760
aaagtcctgg ctctgctgtg gccttagtgg gggcccaggt ccctctccag ccccagtctc   8820
ctccttctgt ccaatgagaa agctgggatc aggggtccct gaggcccctg tccactctgc   8880
atgcctcgat ggtgaagctc tgttggtatg gcagaggggga ggctgctcag gcatctgcat   8940
ttcccctgcc aatctagagg atgaggaaag ctctcaggaa tagtaagcag aatgtttgcc   9000
ctggatgaat aactgagctg ccaattaaca aggggcaggg agccttagac agaaggtacc   9060
aaatatgcct gatgctccaa cattttattt gtaatatcca agacaccctc aaataaacat   9120
atgattccaa taaaaatgca cagccacgat ggcatctctt agcctgacat cgccacgatg   9180
tagaaattct gcatcttcct ctagttttga attatcccca cacaatcttt ttcggcagct   9240
```

-continued

```
tggatggtca gtttcagcac cttttacaga tgatgaagct gagcctcgag ggatgtgtgt   9300
cgtcaagggg gctcagggct tctcagggag gggactcatg gtttcttatt ctgctacact   9360
cttccaaacc ttcactcacc cctggtgatg cccaccttcc cctctctcca ggcaaatggg   9420
agagaccctt tgaagtcaag gacaccgagg aagaggactt ccacgtggac caggtgacca   9480
ccgtgaaggt gcctatgatg aagcgtttag gcatgtttaa catccagcac tgtaagaagc   9540
tgtccagctg ggtgctgctg atgaaatacc tgggcaatgc caccgccatc ttcttcctgc   9600
ctgatgaggg gaaactacag cacctggtaa atgaactcac ccacgatatc atcaccaagt   9660
tcctggaaaa tgaagacaga aggtgattcc ccaacctgag ggtgaccaag aagctgccca   9720
cacctcttag ccatgttggg actgaggccc atcaggactg gccagagggc tgaggagggt   9780
gaaccccaca tccctgggtc actgctactc tgtataaact tggcttccag aatgaggcca   9840
ccactgagtt caggcagcgc cgtccatgct ccatgaggag aacagtaccc agggtgagga   9900
ggtaaaggtc tcgtccctgg gaacttccca ctccagtgtg gacactgtcc cttcccaata   9960
tccagtgccc aaggcaggga cagcagcacc accacacgtt ctggcagaac caaaaaggaa  10020
cagatgggct tcctggcaaa ggcagcagtg gagtgtggag ttcaagggta gaatgtccct  10080
ggggggacgg gggaagagcc tgtgtggcaa ggcccagaaa agcaaggttc ggaattggaa  10140
cagccaggcc atgttcgcag aaggcttgcg tttctctgtc actttatcgg tgctgttaga  10200
ttgggtgtcc tgtagtaagt gatacttaaa catgagccac acattagtgt atgtgtgtgc  10260
attcgtgatt atgcccatgc cctgctgatc tagttcgttt tgtacactgt aaaaccaaga  10320
tgaaaataca aaaggtgtcg ggttcataat aggaatcgag gctggaattt ctctgttcca  10380
tgccagcacc tcctgaggtc tctgctccag gggttgagaa agaacaaaga ggctgagagg  10440
gtaacggatc agagagccca gagccagctg ccgctcacac cagaccctgc tcagggtggc  10500
attgtctccc catggaaaac cagagaggag cactcagcct ggtgtggtca ctcttctctt  10560
atccactaaa cggttgtcac tggcactgc caccagcccc gtgtttctct gggtgtaggg  10620
ccctggggat gttacaggct gggggccagg tgacccaaca ctacagggca agatgagaca  10680
ggcttccagg acacctagaa tatcagagga ggtggcattt caagcttttg tgattcattc  10740
gatgttaaca ttctttgact caatgtagaa gagctaaaag tagaacaaac caaagccgag  10800
ttcccatctt agtgtgggtg gaggacacag gagtaagtgg cagaaataat cagaaaagaa  10860
aacacttgca ctgtggtggg tcccagaaga acaagaggaa tgctgtgcca tgccttgaat  10920
ttcttttctg cacgacaggt ctgccagctt acatttaccc aaactgtcca ttactggaac  10980
ctatgatctg aagagcgtcc tgggtcaact gggcatcact aaggtcttca gcaatggggc  11040
tgacctctcc ggggtcacag aggaggcacc cctgaagctc tccaaggtga gatcaccctg  11100
acgaccttgt tgcaccatgg tatctgtagg gaagaatgtg tgggggctgc agcactgtcc  11160
tgaggctgag gaaggggccg agggaaacaa atgaagaccc aggctgagct cctgaagatg  11220
cccgtgattc actgacacgg gacggtgggc aaacagcaaa gccaggcagg ggctgctgtg  11280
cagctggcac tttcggggcc tcccttgagg ttgtgtcact gaccctgaat ttcaactttg  11340
cccaagacct tctagacatt gggccttgat ttatccatac tgacacagaa aggtttgggc  11400
taagttgttt caaaggaatt tctgactcct tcgatctgtg agatttggtg tctgaattaa  11460
tgaatgattt cagctaaagt gacacttatt ttggaaaact aaaggcgacc aatgaacaac  11520
ctgcagttcc atgaatggct gcattatctt ggggtctggg cactgtgaag gtcactgcca  11580
```

-continued

```
gggtccgtgt cctcaaggag cttcaagccg tgtactagaa aggagagagc cctggaggca  11640

gacgtggagt gacgatgctc ttccctgttc tgagttgtgg gtgcacctga gcagggggag  11700

aggcgcttgt caggaagatg gacagagggg agccagcccc atcagccaaa gccttgagga  11760

ggagcaaggc ctatgtgaca gggagggaga ggatgtgcag ggccagggcc gtccaggggg  11820

agtgagcgct tcctgggagg tgtccacgtg agccttgctc gaggcctggg atcagcctta  11880

caacgtgtct ctgcttctct cccctccagg ccgtgcataa ggctgtgctg accatcgacg  11940

agaaagggac tgaagctgct ggggccatgt ttttagaggc catacccatg tctatccccc  12000

ccgaggtcaa gttcaacaaa ccctttgtct tcttaatgat tgaacaaaat accaagtctc  12060

ccctcttcat gggaaaagtg gtgaatccca cccaaaaata actgcctctc gctcctcaac  12120

ccctcccctc catccctggc cccctccctg gatgacatta aagaagggtt gagctggtcc  12180

ctgcctgcat gtgatctgta aatccctggg atgttttctc tg                     12222
```

<210> SEQ ID NO 43
<211> LENGTH: 1599
<212> TYPE: DNA
<213> ORGANISM: Artificial Sequence
<220> FEATURE:
<223> OTHER INFORMATION: Description of Artificial Sequence:  Synthetic

<400> SEQUENCE: 43

```
caccagcatc atctcctcca attcatccag ctactctgcc catgaagata atagttttca    60

ggcggattgc ctcagatcac actatctcca cttgcccagc cctgtggaag attagcggcc   120

atgtattcca atgtgatagg aactgtaacc tctggaaaaa ggaaggttta tcttttgtcc   180

ttgctgctca ttggcttctg ggactgcgtg acctgtcacg ggagccctgt ggacatctgc   240

acagccaagc cgcgggacat tcccatgaat cccatgtgca tttaccgctc cccggagaag   300

aaggcaactg aggatgaggg ctcagaacag aagatcccgg aggccaccaa ccggcgtgtc   360

tgggaactgt ccaaggccaa ttcccgcttt gctaccactt tctatcagca cctggcagat   420

tccaagaatg acaatgataa cattttcctg tcacccctga gtatctccac ggcttttgct   480

atgaccaagc tgggtgcctg taatgacacc ctccagcaac tgatggaggt atttaagttt   540

gacaccatat ctgagaaaac atctgatcag atccacttct tctttgccaa actgaactgc   600

cgactctatc gaaaagccaa caaatcctcc aagttagtat cagccaatcg cctttttgga   660

gacaaatccc ttaccttcaa tgagacctac caggacatca gtgagttggt atatggagcc   720

aagctccagc ccctggactt caaggaaaat gcagagcaat ccagagcggc catcaacaaa   780

tgggtgtcca ataagaccga aggccgaatc accgatgtca ttccctcgga agccatcaat   840

gagctcactg ttctggtgct ggttaacacc atttacttca agggcctgtg gaagtcaaag   900

ttcagccctg agaacacaag gaaggaactg ttctacaagg ctgatggaga gtcgtgttca   960

gcatctatga tgtaccagga aggcaagttc cgttatcggc gcgtggctga aggcacccag  1020

gtgcttgagt tgcccttcaa aggtgatgac atcaccatgg tcctcatctt gcccaagcct  1080

gagaagagcc tggccaaggt ggagaaggaa ctcaccccag aggtgctgca ggagtggctg  1140

gatgaattgg aggagatgat gctggtggtt cacatgcccc gcttccgcat tgaggacggc  1200

ttcagtttga aggagcagct gcaagacatg ggccttgtcg atctgttcag ccctgaaaag  1260

tccaaactcc caggtattgt tgcagaaggc cgagatgacc tctatgtctc agatgcattc  1320

cataaggcat ttcttgaggt aaatgaagaa ggcagtgaag cagctgcaag taccgctgtt  1380

gtgattgctg gccgttcgct aaaccccaac agggtgactt tcaaggccaa caggcccttc  1440
```

ctggttttta taagagaagt tcctctgaac actattatct tcatgggcag agtagccaac 1500
ccttgtgtta agtaaaatgt tcttattctt tgcacctctt cctatttttg gtttgtgaac 1560
agaagtaaaa ataaatacaa actacttcca tctcacatt 1599

<210> SEQ ID NO 44
<211> LENGTH: 23
<212> TYPE: DNA
<213> ORGANISM: T7 virus

<400> SEQUENCE: 44
taatacgact cactataggg cga 23

<210> SEQ ID NO 45
<211> LENGTH: 24
<212> TYPE: DNA
<213> ORGANISM: T3 virus

<400> SEQUENCE: 45
ttattaaccc tcactaaagg gaag 24

<210> SEQ ID NO 46
<211> LENGTH: 23
<212> TYPE: DNA
<213> ORGANISM: SP6 virus

<400> SEQUENCE: 46
atttaggtga cactatagaa tac 23

<210> SEQ ID NO 47
<211> LENGTH: 555
<212> TYPE: PRT
<213> ORGANISM: Mus musculus

<400> SEQUENCE: 47

Met Thr Lys Ser Ser Asn His Asn Cys Leu Leu Arg Pro Glu Asn Lys
1 5 10 15

Pro Gly Leu Trp Gly Pro Gly Ala Gln Ala Ala Ser Leu Arg Pro Ser
20 25 30

Pro Ala Thr Leu Val Val Ser Ser Pro Gly His Ala Glu His Pro Pro
35 40 45

Ala Ala Pro Ala Gln Thr Pro Gly Pro Gln Val Ser Ala Ser Ala Arg
50 55 60

Gly Pro Gly Pro Val Ala Gly Gly Ser Gly Arg Met Glu Arg Arg Met
65 70 75 80

Lys Gly Gly Tyr Leu Asp Gln Arg Val Pro Tyr Thr Phe Cys Ser Lys
85 90 95

Ser Pro Gly Asn Gly Ser Leu Gly Glu Ala Leu Met Val Pro Gln Gly
100 105 110

Lys Leu Met Asp Pro Gly Ser Leu Pro Pro Ser Asp Ser Glu Asp Leu
115 120 125

Phe Gln Asp Leu Ser His Phe Gln Glu Thr Trp Leu Ala Glu Ala Gln
130 135 140

Val Pro Asp Ser Asp Glu Gln Phe Val Pro Asp Phe His Ser Glu Asn
145 150 155 160

Leu Ala Phe His Ser Pro Thr Thr Arg Ile Lys Lys Glu Pro Gln Ser
165 170 175

Pro Arg Thr Asp Pro Ala Leu Ser Cys Ser Arg Lys Pro Pro Leu Pro

-continued

```
            180                 185                 190

Tyr His His Gly Glu Gln Cys Leu Tyr Ser Arg Gln Ile Ala Ile Lys
        195                 200                 205

Ser Pro Ala Pro Gly Ala Pro Gly Gln Ser Pro Leu Gln Pro Phe Ser
    210                 215                 220

Arg Ala Glu Gln Gln Gln Ser Leu Leu Arg Ala Ser Ser Ser Ser Gln
225                 230                 235                 240

Ser His Pro Gly His Gly Tyr Leu Gly Glu His Ser Ser Val Phe Gln
                245                 250                 255

Gln Pro Val Asp Met Cys His Ser Phe Thr Ser Pro Gln Gly Gly Gly
            260                 265                 270

Arg Glu Pro Leu Pro Ala Pro Tyr Gln His Gln Leu Ser Glu Pro Cys
        275                 280                 285

Pro Pro Tyr Pro Gln Gln Asn Phe Lys Gln Glu Tyr His Asp Pro Leu
    290                 295                 300

Tyr Glu Gln Ala Gly Gln Pro Ala Ser Ser Gln Gly Gly Val Ser Gly
305                 310                 315                 320

His Arg Tyr Pro Gly Ala Gly Val Val Ile Lys Gln Glu Arg Thr Asp
                325                 330                 335

Phe Ala Tyr Asp Ser Asp Val Pro Gly Cys Ala Ser Met Tyr Leu His
            340                 345                 350

Pro Glu Gly Phe Ser Gly Pro Ser Pro Gly Asp Gly Val Met Gly Tyr
        355                 360                 365

Gly Tyr Glu Lys Ser Leu Arg Pro Phe Pro Asp Asp Val Cys Ile Val
    370                 375                 380

Pro Lys Lys Phe Glu Gly Asp Ile Lys Gln Glu Gly Ile Gly Ala Phe
385                 390                 395                 400

Arg Glu Gly Pro Pro Tyr Gln Arg Arg Gly Ala Leu Gln Leu Trp Gln
                405                 410                 415

Phe Leu Val Ala Leu Leu Asp Asp Pro Thr Asn Ala His Phe Ile Ala
            420                 425                 430

Trp Thr Gly Arg Gly Met Glu Phe Lys Leu Ile Glu Pro Glu Glu Val
        435                 440                 445

Ala Arg Leu Trp Gly Ile Gln Lys Asn Arg Pro Ala Met Asn Tyr Asp
    450                 455                 460

Lys Leu Ser Arg Ser Leu Arg Tyr Tyr Tyr Glu Lys Gly Ile Met Gln
465                 470                 475                 480

Lys Val Ala Gly Glu Arg Tyr Val Tyr Lys Phe Val Cys Glu Pro Glu
                485                 490                 495

Ala Leu Phe Ser Leu Ala Phe Pro Asp Asn Gln Arg Pro Ala Leu Lys
            500                 505                 510

Ala Glu Phe Asp Arg Pro Val Ser Glu Glu Asp Thr Val Pro Leu Ser
        515                 520                 525

His Leu Asp Glu Ser Pro Ala Tyr Leu Pro Glu Leu Thr Gly Pro Ala
    530                 535                 540

Pro Pro Phe Gly His Arg Gly Gly Tyr Ser Tyr
545                 550                 555
```

<210> SEQ ID NO 48
<211> LENGTH: 8
<212> TYPE: DNA
<213> ORGANISM: Artificial Sequence
<220> FEATURE:
<223> OTHER INFORMATION: Description of Artificial Sequence: Synthetic

<400> SEQUENCE: 48 cccggaag 8

<210> SEQ ID NO 49
<211> LENGTH: 1843
<212> TYPE: DNA
<213> ORGANISM: Homo sapiens

<400> SEQUENCE: 49
ctgcaggggg gggggggggg gggggctgtc atggcggcag gacggcgaac ttgcagtatc 60
tccacgaccc gcccctacag gtgccagtgc ctccagaatg tggcagctca caagcctcct 120
gctgttcgtg gccacctggg gaatttccgg cacaccagct cctcttgact cagtgttctc 180
cagcagcgag cgtgcccacc aggtgctgcg gatccgcaaa cgtgccaact ccttcctgga 240
ggagctccgt cacagcagcc tggagcggga gtgcatagag gagatctgtg acttcgagga 300
ggccaaggaa attttccaaa atgtggatga cacactggcc ttctggtcca agcacgtcga 360
cggtgaccag tgcttggtct tgcccttgga gcacccgtgc gccagcctgt gctgcgggca 420
cggcacgtgc atcgacggca tcggcagctt cagctgcgac tgccgcagcg gctgggaggg 480
ccgcttctgc cagcgcgagg tgagcttcct caattgctcg ctggacaacg gcggctgcac 540
gcattactgc ctagaggagg tgggctggcg gcgctgtagc tgtgcgcctg gctacaagct 600
gggggacgac ctcctgcagt gtcaccccgc agtgaagttc ccttgtggga ggccctggaa 660
gcggatggag aagaagcgca gtcacctgaa acgagacaca gaagaccaag aagaccaagt 720
agatccgcgg ctcattgatg ggaagatgac caggcgggga gacagcccct ggcaggtggt 780
cctgctggac tcaaagaaga agctggcctg cggggcagtg ctcatccacc cctcctgggt 840
gctgacagcg gcccactgca tggatgagtc caagaagctc cttgtcaggc ttggagagta 900
tgacctgcgg cgctgggaga agtgggagct ggacctggac atcaaggagg tcttcgtcca 960
ccccaactac agcaagagca ccaccgacaa tgacatcgca ctgctgcacc tggcccagcc 1020
cgccaccctc tcgcagacca tagtgcccat ctgcctcccg gacagcggcc ttgcagagcg 1080
cgagctcaat caggccggcc aggagaccct cgtgacgggc tggggctacc acagcagccg 1140
agagaaggag gccaagagaa accgcacctt cgtcctcaac ttcatcaaga ttcccgtggt 1200
cccgcacaat gagtgcagcg aggtcatgag caacatggtg tctgagaaca tgctgtgtgc 1260
gggcatcctc ggggaccggc aggatgcctg cgagggcgac agtggggggc ccatggtcgc 1320
ctccttccac ggcacctggt tcctggtggg cctggtgagc tggggtgagg gctgtgggct 1380
ccttcacaac tacggcgttt acaccaaagt cagccgctac ctcgactgga tccatgggca 1440
catcagagac aaggaagccc cccagaagag ctgggcacct tagcgaccct ccctgcaggg 1500
ctgggctttt gcatggcaat ggatgggaca ttaaagggac atgtaacaag cacaccggcc 1560
tgctgttctg tccttccatc cctcttttgg gctcttctgg agggaagtaa catttactga 1620
gcacctgttg tatgtcacat gccttatgaa tagaatctta actcctagag caactctgtg 1680
gggtggggag gagcagatcc aagttttgcg gggtctaaag ctgtgtgtgt tgagggggat 1740
actctgttta tgaaaaagaa taaaaaacac aaccacgaaa aaaaaaaaaa aaaaaaaaaa 1800
aaaaaaaaaa aaaaaaaccc ccccccgccc ccccccctg cag 1843

<210> SEQ ID NO 50
<211> LENGTH: 11725
<212> TYPE: DNA
<213> ORGANISM: Homo sapiens -continued

<400> SEQUENCE: 50

```
agtgaatctg ggcgagtaac acaaaacttg agtgtcctta cctgaaaaat agaggttaga     60
gggatgctat gtgccattgt gtgtgtgtgt tgggggtggg gattgggggt gatttgtgag    120
caattggagg tgagggtgga gcccagtgcc cagcacctat gcactgggga cccaaaaagg    180
agcatcttct catgatttta tgtatcagaa attgggatgg catgtcattg ggacagcgtc    240
ttttttcttg tatggtggca cataaataca tgtgtcttat aattaatggt attttagatt    300
tgacgaaata tggaatatta cctgttgtgc tgatcttggg caaactataa tatctctggg    360
caaaaatgtc cccatctgaa aaacagggac aacgttcctc cctcagccag ccactatggg    420
gctaaaatga gaccacatct gtcaagggtt ttgccctcac ctccctccct gctggatggc    480
atccttggta ggcagaggtg ggcttcgggc agaacaagcc gtgctgagct aggaccagga    540
gtgctagtgc cactgtttgt ctatggagag ggaggcctca gtgctgaggg ccaagcaaat    600
atttgtggtt atggattaac tcgaactcca ggctgtcatg gcggcaggac ggcgaacttg    660
cagtatctcc acgacccgcc cctgtgagtc cccctccagg caggtctatg aggggtgtgg    720
agggagggct gcccccggga gaagagagct aggtggtgat gagggctgaa tcctccagcc    780
agggtgctca acaagcctga gcttggggta aaaggacaca aggccctcca caggccaggc    840
ctggcagcca cagtctcagg tccctttgcc atgcgcctcc ctctttccag gccaagggtc    900
cccaggccca gggccattcc aacagacagt ttggagccca ggaccctcca ttctccccac    960
cccacttcca cctttggggg tgtcggattt gaacaaatct cagaagcggc ctcagaggga   1020
gtcggcaaga atggagagca gggtccggta gggtgtgcag aggccacgtg gcctatccac   1080
tggggagggt tccttgatct ctggccacca gggctatctc tgtggccttt tggagcaacc   1140
tggtggtttg gggcaggggt tgaatttcca ggcctaaaac cacacaggcc tggccttgag   1200
tcctggctct gcgagtaatg catggatgta aacatggaga cccaggacct tgcctcagtc   1260
ttccgagtct ggtgcctgca gtgtactgat ggtgtgagac cctactcctg gaggatgggg   1320
gacagaatct gatcgatccc ctgggttggt gacttccctg tgcaatcaac ggagaccagc   1380
aagggttgga tttttaataa accacttaac tcctccgagt ctcagtttcc ccctctatga   1440
aatggggttg acagcattaa taactacctc ttgggtggtt gtgagcctta actgaagtca   1500
taatatctca tgtttactga gcatgagcta tgtgcaaagc ctgttttgag agctttatgt   1560
ggactaactc ctttaattct cacaacaccc tttaaggcac agatacacca cgttattcca   1620
tccattttac aaatgaggaa actgaggcat ggagcagtta agcatcttgc ccaacattgc   1680
cctccagtaa gtgctggagc tggaatttgc accgtgcagt ctggcttcat ggcctgccct   1740
gtgaatcctg taaaaattgt ttgaaagaca ccatgagtgt ccaatcaacg ttagctaata   1800
ttctcagccc agtcatcaga ccggcagagg cagccacccc actgtcccca gggaggacac   1860
aaacatcctg gcaccctctc cactgcattc tggagctgct ttctaggcag gcagtgtgag   1920
ctcagcccca cgtagagcgg gcagccgagg ccttctgagg ctatgtctct agcgaacaag   1980
gaccctcaat tccagcttcc gcctgacggc cagcacacag ggacagccct ttcattccgc   2040
ttccacctgg gggtgcaggc agagcagcag cgggggtagc actgcccgga gctcagaagt   2100
cctcctcaga caggtgccag tgcctccaga atgtggcagc tcacaagcct cctgctgttc   2160
gtggccacct ggggaatttc cggcacacca gctcctcttg gtaaggccac cccacccct a   2220
ccccgggacc cttgtggcct ctacaaggcc ctggtggcat ctgcccaggc cttcacagct   2280
```

-continued

```
tccaccatct ctctgagccc tgggtgaggt gaggggcaga tgggaatggc aggaatcaac   2340
tgacaagtcc caggtaggcc agctgccaga gtgccacaca ggggctgcca gggcaggcat   2400
gcgtgatggc agggagcccc gcgatgacct cctaaagctc cctcctccac acggggatgg   2460
tcacagagtc ccctgggcct tccctctcca cccactcact ccctcaactg tgaagacccc   2520
aggcccaggc taccgtccac actatccagc acagcctccc ctactcaaat gcacactggc   2580
ctcatggctg ccctgcccca accccttcc tggtctccac agccaacggg aggaggccat    2640
gattcttggg gaggtccgca ggcacatggg cccctaaagc cacaccaggc tgttggtttc   2700
atttgtgcct ttatagagct gtttatctgc ttgggacctg cacctccacc ctttcccaag   2760
gtgccctcag ctcaggcata ccctcctcta ggatgccttt tcccccatcc cttcttgctc   2820
acacccccaa cttgatctct ccctcctaac tgtgccctgc accaagacag acacttcaca   2880
gagcccagga cacacctggg gacccttcct gggtgatagg tctgtctatc ctccaggtgt   2940
ccctgcccaa ggggagaagc atggggaata cttggttggg ggaggaaagg aagactgggg   3000
ggatgtgtca agatggggct gcatgtggtg tactggcaga agagtgagag gatttaactt   3060
ggcagccttt acagcagcag ccagggcttg agtacttatc tctgggccag gctgtattgg   3120
atgttttaca tgacggtctc atccccatgt ttttggatga gtaaattgaa ccttagaaag   3180
gtaaagacac tggctcaagg tcacacagag atcggggtgg ggttcacagg gaggcctgtc   3240
catctcagag caaggcttcg tcctccaact gccatctgct tcctggggag gaaaagagca   3300
gaggacccct gcgccaagcc atgacctaga attagaatga gtcttgaggg ggcggagaca   3360
agaccttccc aggctctccc agctctgctt cctcagaccc cctcatggcc ccagcccctc   3420
ttaggcccct caccaaggtg agctcccctc cctccaaaac cagactcagt gttctccagc   3480
agcgagcgtg cccaccaggt gctgcggatc cgcaaacgtg ccaactcctt cctggaggag   3540
ctccgtcaca gcagcctgga gcgggagtgc atagaggaga tctgtgactt cgaggaggcc   3600
aaggaaattt tccaaaatgt ggatgacaca gtaaggccac catgggtcca gaggatgagg   3660
ctcaggggcg agctggtaac cagcaggggc ctcgaggagc aggtggggac tcaatgctga   3720
ggccctctta ggagttgtgg gggtggctga gtggagcgat taggatgctg gccctatgat   3780
gtcggccagg cacatgtgac tgcaagaaac agaattcagg aagaagctcc aggaaagagt   3840
gtggggtgac cctaggtggg gactcccaca gccacagtgt aggtggttca gtccaccctc   3900
cagccactgc tgagcaccac tgcctccccg tcccacctca caaagagggg acctaaagac   3960
caccctgctt ccacccatgc ctctgctgat cagggtgtgt gtgtgaccga aactcacttc   4020
tgtccacata aaatcgctca ctctgtgcct cacatcaaag ggagaaaatc tgattgttca   4080
gggggtcgga agacagggtc tgtgtcctat ttgtctaagg gtcagagtcc tttggagccc   4140
ccagagtcct gtggacgtgg ccctaggtag tagggtgagc ttggtaacgg ggctggcttc   4200
ctgagacaag gctcagaccc gctctgtccc tggggatcgc ttcagccacc aggacctgaa   4260
aattgtgcac gcctgggccc ccttccaagg catccaggga tgctttccag tggaggcttt   4320
cagggcagga gaccctctgg cctgcaccct ctcttgccct cagcctccac ctccttgact   4380
ggacccccat ctggacctcc atccccacca cctctttccc cagtggcctc cctggcagac   4440
accacagtga ctttctgcag gcacatatct gatcacatca agtccccacc gtgctcccac   4500
ctcacccatg gtctctcagc cccagcagcc ttggctggcc tctctgatgg agcaggcatc   4560
aggcacaggc cgtgggtctc aacgtgggct gggtggtcct ggaccagcag cagccgccgc   4620
agcagcaacc ctggtacctg gttaggaacg cagaccctct gcccccatcc tcccaactct   4680
```

-continued

```
gaaaaacact ggcttaggga aaggcgcgat gctcaggggt cccccaaagc ccgcaggcag   4740
agggagtgat gggactggaa ggaggccgag tgacttggtg agggattcgg gtcccttgca   4800
tgcagaggct gctgtgggag cggacagtcg cgagagcagc actgcagctg catggggaga   4860
gggtgttgct ccagggacgt gggatggagg ctgggcgcgg gcgggtggcg ctggagggcg   4920
ggggaggggc agggagcacc agctcctagc agccaacgac catcgggcgt cgatccctgt   4980
ttgtctggaa gccctcccct cccctgcccg ctcacccgct gccctgcccc acccgggcgc   5040
gcccctccgc acaccggctg caggagcctg acgctgcccg ctctctccgc agctggcctt   5100
ctggtccaag cacgtcggtg agtgcgttct agatccccgg ctggactacc ggcgcccgcg   5160
cccctcggga tctctggccg ctgacccccct accccgcctt gtgtcgcaga cggtgaccag   5220
tgcttggtct tgcccttgga gcacccgtgc gccagcctgt gctgcgggca cggcacgtgc   5280
atcgacggca tcggcagctt cagctgcgac tgccgcagcg gctgggaggg ccgcttctgc   5340
cagcgcggtg agggggagag gtggatgctg gcgggcggcg gggcggggct ggggccgggt   5400
tgggggcgcg gcaccagcac cagctgcccg cgccctcccc tgcccgcaga ggtgagcttc   5460
ctcaattgct ctctggacaa cggcggctgc acgcattact gcctagagga ggtgggctgg   5520
cggcgctgta gctgtgcgcc tggctacaag ctgggggacg acctcctgca gtgtcacccc   5580
gcaggtgaga agcccccaat acatcgccca ggaatcacgc tgggtgcggg gtgggcaggc   5640
ccctgacggg cgcggcgcgg ggggctcagg agggtttcta gggagggagc gaggaacaga   5700
gttgagcctt ggggcagcgg cagacgcgcc caacaccggg gccactgtta gcgcaatcag   5760
cccgggagct gggcgcgccc tccgctttcc ctgcttcctt tcttcctggc gtccccgctt   5820
cctccgggcg cccctgcgac ctggggccac ctcctggagc gcaagcccag tggtggctcc   5880
gctccccagt ctgagcgtat ctggggcgag gcgtgcagcg tcctcctcca tgtagcctgg   5940
ctgcgttttt ctctgacgtt gtccggcgtg catcgcattt ccctctttac cccccttgctt  6000
ccttgaggag agaacagaat cccgattctg ccttcttcta tattttcctt tttatgcatt   6060
ttaatcaaat ttatatatgt atgaaacttt aaaaatcaga gttttacaac tcttacactt   6120
tcagcatgct gttccttggc atgggtcctt ttttcattca ttttcataaa aggtggaccc   6180
ttttaatgtg gaaattccta tcttctgcct ctagggcatt tatcacttat ttcttctaca   6240
atctcccctt tacttcctct attttctctt tctggacctc ccattattca gacctctttc   6300
ctctagtttt attgtctctt ctatttccca tctctttgac tttgtgtttt ctttcaggga   6360
actttctttt ttttcttttt ttttgagatg gagtttcact cttgttgtcc caggctggag   6420
tgcaatgacg tgatctcagc tcaccacaac ctccgcctcc tggattcaag cgattctcct   6480
gccgcagcct cccgagtagc tgggattaca ggcatgcgcc accacgccca gctaattttg   6540
tgtttttagt agagaagggg tttctccgtg ttggtcaagc tggtcttgaa ctcctgacct   6600
caggtgatcc acctgccttg gcctcctaaa gtgctgggat tacaggcgtg agccaccgcg   6660
cccagcctct ttcagggaac tttctacaac tttataattc aattcttctg cagaaaaaaa   6720
tttttggcca ggctcagtag ctcagaccaa taattccagc actttgagag gctgaggtgg   6780
gaggattgct tgagcttggg agtttgagac tagcctgggc aacacagtga gaccctgtct   6840
ctatttttaa aaaaagtaaa aaaagatcta aaaatttaac tttttatttt gaaataatta   6900
gatatttcca ggaagctgca aagaaatgcc tggtgggcct gttggctgtg ggtttcctgc   6960
aaggccgtgg gaaggccctg tcattggcag aaccccagat cgtgagggct ttccttttag   7020
```

-continued

```
gctgctttct aagaggactc ctccaagctc ttggaggatg gaagacgctc acccatggtg   7080
ttcggcccct cagagcaggg tggggcaggg gagctggtgc ctgtgcaggc tgtggacatt   7140
tgcatgactc cctgtggtca gctaagagca ccactccttc ctgaagcggg gcctgaagtc   7200
cctagtcaga gcctctggtt caccttctgc aggcagggag aggggagtca agtcagtgag   7260
gagggctttc gcagtttctc ttacaaactc tcaacatgcc ctcccacctg cactgccttc   7320
ctggaagccc cacagcctcc tatggttccg tggtccagtc cttcagcttc tgggcgcccc   7380
catcacgggc tgagattttt gctttccagt ctgccaagtc agttactgtg tccatccatc   7440
tgctgtcagc ttctggaatt gttgctgttg tgccctttcc attcttttgt tatgatgcag   7500
ctcccctgct gacgacgtcc cattgctctt ttaagtctag atatctggac tgggcattca   7560
aggcccattt tgagcagagt cggctgacc tttcagccct cagttctcca tggagtatgc   7620
gctctcttct tggcagggag gcctcacaaa catgccatgc ctattgtagc agctctccaa   7680
gaatgctcac ctccttctcc ctgtaattcc tttcctctgt gaggagctca gcagcatccc   7740
attatgagac cttactaatc ccagggatca cccccaacag ccctggggta caatgagctt   7800
ttaagaagtt taaccaccta tgtaaggaga cacaggcagt gggcgatgct gcctggcctg   7860
actcttgcca ttgggtggta ctgtttgttg actgactgac tgactgactg gagggggttt   7920
gtaatttgta tctcagggat tacccccaac agccctgggg tacaatgagc cttcaagaag   7980
tttaacaacc tatgtaagga cacacagcca gtgggtgatg ctgcctggtc tgactcttgc   8040
cattcagtgg cactgtttgt tgactgactg actgactgac tggctgactg gagggggttc   8100
atagctaata ttaatggagt ggtctaagta tcattggttc cttgaaccct gcactgtggc   8160
aaagtggccc acaggctgga ggaggaccaa gacaggaggg cagtctcggg aggagtgcct   8220
ggcaggcccc tcaccacctc tgcctacctc agtgaagttc ccttgtggga ggccctggaa   8280
gcggatggag aagaagcgca gtcacctgaa acgagacaca gaagaccaag aagaccaagt   8340
agatccgcgg ctcattgatg ggaagatgac caggcgggga gacagcccct ggcaggtggg   8400
aggcgaggca gcaccggctc gtcacgtgct gggtccggga tcactgagtc catcctggca   8460
gctatgctca gggtgcagaa accgagaggg aagcgctgcc attgcgtttg ggggatgatg   8520
aaggtggggg atgcttcagg gaaagatgga cgcaacctga ggggagagga gcagccaggg   8580
tgggtgaggg gaggggcatg gggcatgga ggggtctgca ggagggaggg ttacagtttc   8640
taaaaagagc tggaaagaca ctgctctgct ggcgggattt taggcagaag ccctgctgat   8700
gggagagggc taggagggag ggccgggcct gagtacccct ccagcctcca catgggaact   8760
gacacttact gggttcccct ctctgccagg catgggggag ataggaacca acaagtggga   8820
gtatttgccc tggggactca gactctgcaa gggtcaggac cccaaagacc cggcagccca   8880
gtgggaccac agccaggacg gcccttcaag ataggggctg agggaggcca aggggaacat   8940
ccaggcagcc tgggggccac aaagtcttcc tggaagacac aaggcctgcc aagcctctaa   9000
ggatgagagg agctcgctgg gcgatgttgg tgtggctgag ggtgactgaa acagtatgaa   9060
cagtgcagga acagcatggg caaaggcagg aagacaccct gggacaggct gacactgtaa   9120
aatgggcaaa aatagaaaac gccagaaagg cctaagccta tgcccatatg accagggaac   9180
ccaggaaagt gcatatgaaa cccaggtgcc ctggactgga ggctgtcagg aggcagccct   9240
gtgatgtcat catcccaccc cattccaggt ggtcctgctg gactcaaaga agaagctggc   9300
ctgcggggca gtgctcatcc acccctcctg ggtgctgaca gcggcccact gcatggatga   9360
gtccaagaag ctccttgtca ggcttggtat gggctggagc caggcagaag gggctgcca   9420
```

-continued

```
gaggcctggg tagggggacc aggcaggctg ttcaggtttg ggggaccccg ctccccaggt   9480
gcttaagcaa gaggcttctt gagctccaca gaaggtgttt ggggggaaga ggcctatgtg   9540
cccccaccct gcccacccat gtacacccag tattttgcag tagggggttc tctggtgccc   9600
tcttcgaatc tgggcacagg tacctgcaca cacatgtttg tgaggggcta cacagacctt   9660
cacctctcca ctcccactca tgaggagcag gctgtgtggg cctcagcacc cttgggtgca   9720
gagaccagca aggcctggcc tcagggctgt gcctccccaca gactgacagg gatggagctg   9780
tacagaggga gccctagcat ctgccaaagc cacaagctgc ttccctagca ggctgggggc   9840
tcctatgcat tggccccgat ctatggcaat ttctggaggg ggggtctggc tcaactcttt   9900
atgccaaaaa gaaggcaaag catattgaga aaggccaaat tcacatttcc tacagcataa   9960
tctatgccag tggccccgtg gggcttggct tagaattccc aggtgctctt cccagggaac  10020
catcagtctg gactgagagg accttctctc tcaggtggga cccggccctg tcctccctgg  10080
cagtgccgtg ttctgggggt cctcctctct gggtctcact gcccctgggg tctctccagc  10140
tacctttgct ccatgttcct ttgtggctct ggtctgtgtc tggggtttcc aggggtctcg  10200
ggcttccctg ctgcccattc cttctctggt ctcacggctc cgtgactcct gaaaaccaac  10260
cagcatccta ccccttttgga ttgacacctg ttggccactc cttctggcag gaaaagtcac  10320
cgttgatagg gttccacggc atagacaggt ggctccgcgc cagtgcctgg gacgtgtggg  10380
tgcacagtct ccgggtgaac cttcttcagg ccctctccca ggcctgcagg ggcacagcag  10440
tgggtgggcc tcaggaaagt gccactgggg agaggctccc cgcagcccac tctgactgtg  10500
ccctctgccc tgcaggagag tatgacctgc ggcgctggga gaagtgggag ctggacctgg  10560
acatcaagga ggtcttcgtc caccccaact acagcaagag caccaccgac aatgacatcg  10620
cactgctgca cctggcccag cccgccaccc tctcgcagac catagtgccc atctgcctcc  10680
cggacagcgg ccttgcagag cgcgagctca atcaggccgg ccaggagacc ctcgtgacgg  10740
gctggggcta ccacagcagc cgagagaagg aggccaagag aaaccgcacc ttcgtcctca  10800
acttcatcaa gattcccgtg gtcccgcaca atgagtgcag cgaggtcatg agcaacatgg  10860
tgtctgagaa catgctgtgt gcgggcatcc tcggggaccg gcaggatgcc tgcgagggcg  10920
acagtggggg gcccatggtc gcctccttcc acggcacctg gttcctggtg ggcctggtga  10980
gctggggtga gggctgtggg ctccttcaca actacggcgt ttacaccaaa gtcagccgct  11040
acctcgactg gatccatggg cacatcagag acaaggaagc cccccagaag agctgggcac  11100
cttagcgacc ctccctgcag ggctgggctt ttgcatggca atggatggga cattaaaggg  11160
acatgtaaca agcacaccgg cctgctgttc tgtccttcca tccctctttt gggctcttct  11220
ggagggaagt aacatttact gagcacctgt tgtatgtcac atgccttatg aatagaatct  11280
taactcctag agcaactctg tggggtgggg aggagcagat ccaagttttg cggggtctaa  11340
agctgtgtgt gttgaggggg atactctgtt tatgaaaaag aataaaaaac acaaccacga  11400
agccactaga gcctttttcca gggctttggg aagagcctgt gcaagccggg gatgctgaag  11460
gtgaggcttg accagctttc cagctagccc agctatgagg tagacatgtt tagctcatat  11520
cacagaggag gaaactgagg ggtctgaaag gtttacatgg tggagccagg attcaaatct  11580
aggtctgact ccaaaaccca ggtgcttttt tctgttctcc actgtcctgg aggacagctg  11640
tttcgacggt gctcagtgtg gaggccacta ttagctctgt agggaagcag ccagagaccc  11700
agaaagtgtt ggttcagccc agaat                                         11725
```

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic

<400> SEQUENCE: 51
ttattttata tatataatat atatataaaa ta 32

<210> SEQ ID NO 52
<211> LENGTH: 9
<212> TYPE: DNA
<213> ORGANISM: Artificial Sequence
<220> FEATURE:
<223> OTHER INFORMATION: Description of Artificial Sequence: Synthetic

<400> SEQUENCE: 52 tataatata 9

<210> SEQ ID NO 53
<211> LENGTH: 16
<212> TYPE: DNA
<213> ORGANISM: Artificial Sequence
<220> FEATURE:
<223> OTHER INFORMATION: Description of Artificial Sequence: Synthetic

<400> SEQUENCE: 53
caatataaat atatag 16

<210> SEQ ID NO 54
<211> LENGTH: 44
<212> TYPE: DNA
<213> ORGANISM: Artificial Sequence
<220> FEATURE:
<223> OTHER INFORMATION: Description of Artificial Sequence: Synthetic

<400> SEQUENCE: 54
tgtgtgtgta tgcgtgtgtg tagacacaca cgcatacaca cata 44

<210> SEQ ID NO 55
<211> LENGTH: 41
<212> TYPE: DNA
<213> ORGANISM: Artificial Sequence
<220> FEATURE:
<223> OTHER INFORMATION: Description of Artificial Sequence: Synthetic

<400> SEQUENCE: 55
ttattttata tatataatat atatataaaa tatataatat a 41

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic

<400> SEQUENCE: 56
tataatatac aatataaata tatag 25

<210> SEQ ID NO 57
<211> LENGTH: 60
<212> TYPE: DNA
<213> ORGANISM: Artificial Sequence
<220> FEATURE:
<223> OTHER INFORMATION: Description of Artificial Sequence: Synthetic

<400> SEQUENCE: 57
caatataaat atatagtgtg tgtgtatgcg tgtgtgtaga cacacacgca tacacacata 60

<210> SEQ ID NO 58
<211> LENGTH: 101
<212> TYPE: DNA
<213> ORGANISM: Artificial Sequence
<220> FEATURE:
<223> OTHER INFORMATION: Description of Artificial Sequence: Synthetic

<400> SEQUENCE: 58
ttattttata tatataatat atatataaaa tatataatat acaatataaa tatatagtgt 60
gtgtgtatgc gtgtgtgtag acacacacgc atacacacat a 101

<210> SEQ ID NO 59
<211> LENGTH: 723
<212> TYPE: DNA
<213> ORGANISM: Homo sapiens

<400> SEQUENCE: 59
tttaggaaaa ttgttaagac tgggttgtat gcacactggt gtttattata ttatgtagtt 60
ttttctgtat ttttacaaca tttcagaatt aaaagcaaca gctagaaaaa gagggaaatg 120
gccgggtgca gtcgtcacgc ctgtaatccc agcactttgg gaggccaagg cgggcggatc 180
acgaggtcga gagatcgaga ccatcctggc caacatggtg aaaccccatc tctactaaaa 240
atacaaaaat taactgggca tggtggcatg cgcctgtagt cccaggagaa ttgcttgaac 300
ctgggaggcg gaggttgcag tgagccaaga tctcaccact gctctccagc ctggtgacag 360
ggcaagactc cgtcaaaaaa aaaaaagaga gggagagcca gagtatgaaa aaggaagtca 420
gagcccttta atgagtcagc tttgtaggtc tccaggtagg aggctagtgc ttcagtgtct 480
aggacatagt aggtgttcag taaattaaat tcaggacaaa aagaacatgc cccaaggacc 540
atctgatatc cacttaaagt gatggactac ctcgtttccc ttgtttatga atgggttcat 600
gcctaagact gtgtgcactt taatacaagg gcagtcgttc agaactagtc aggtcctgaa 660
aaggatttac caaatgttga gtgtgccctc tagtgttcac acttcccagc tttcttccta 720
taa 723

<210> SEQ ID NO 60
<211> LENGTH: 447
<212> TYPE: DNA
<213> ORGANISM: Homo sapiens

<400> SEQUENCE: 60
aatatccagt tgagataatg gacttgcctc ttatctaata atacccaggc tcaatgcgtc 60
actgctttgt ccactttgcc caaaattcaa gcacagctaa gttgatattt taggacaaag 120
gcagcttact atccagccag aggggagtag aatatggtta agagagagtg gaaagaatga 180
atgagccctg ctattcctca ctgcctggat ggctataagc acagccctta tggaggcctt 240
aggtcttgct tcacaatatt ccagtttgaa aagggtttga aaagacctcc tagaaaaatc 300
agtagttttt ctcttttgag taacatgtag caaaaaaaat ttcatcatgt aggtacaggg 360
aacaccctag taactattaa tctcaaggag tcaagccagt gtgtttccta atgtatctgc 420
tgtatcccca tgaagcaaat tttgcca 447

<210> SEQ ID NO 61

-continued

```
<211> LENGTH: 103
<212> TYPE: DNA
<213> ORGANISM: Homo sapiens

<400> SEQUENCE: 61

aggtggatca aggcacttgc ttacaactgg aactgaaatc ctccaagtcg atctagacat     60

tgagatggag aaaatattca ttgtcgactg taattatgca acg                      103


<210> SEQ ID NO 62
<211> LENGTH: 7
<212> TYPE: DNA
<213> ORGANISM: Artificial Sequence
<220> FEATURE:
<223> OTHER INFORMATION: Description of Artificial Sequence:  Synthetic

<400> SEQUENCE: 62

gtggaag                                                                7


<210> SEQ ID NO 63
<211> LENGTH: 7
<212> TYPE: DNA
<213> ORGANISM: Artificial Sequence
<220> FEATURE:
<223> OTHER INFORMATION: Description of Artificial Sequence:  Synthetic

<400> SEQUENCE: 63

gtggatg                                                                7


<210> SEQ ID NO 64
<211> LENGTH: 7
<212> TYPE: DNA
<213> ORGANISM: Artificial Sequence
<220> FEATURE:
<223> OTHER INFORMATION: Description of Artificial Sequence:  Synthetic

<400> SEQUENCE: 64

ctggaag                                                                7


<210> SEQ ID NO 65
<211> LENGTH: 7
<212> TYPE: DNA
<213> ORGANISM: Artificial Sequence
<220> FEATURE:
<223> OTHER INFORMATION: Description of Artificial Sequence:  Synthetic

<400> SEQUENCE: 65

ctggatg                                                                7


<210> SEQ ID NO 66
<211> LENGTH: 32
<212> TYPE: DNA
<213> ORGANISM: Artificial Sequence
<220> FEATURE:
<223> OTHER INFORMATION: Description of Artificial Sequence:  Synthetic

<400> SEQUENCE: 66

acccattcag tcgaggaagg atagggtggt at                                   32


<210> SEQ ID NO 67
<211> LENGTH: 32
<212> TYPE: DNA
<213> ORGANISM: Artificial Sequence
<220> FEATURE:
<223> OTHER INFORMATION: Description of Artificial Sequence:  Synthetic

<400> SEQUENCE: 67
```

agccattgag tcgaggaagg atagggtggt at 32

<210> SEQ ID NO 68
<211> LENGTH: 32
<212> TYPE: DNA
<213> ORGANISM: Artificial Sequence
<220> FEATURE:
<223> OTHER INFORMATION: Description of Artificial Sequence: Synthetic

<400> SEQUENCE: 68
agccattcag acgaggaagg atagggtggt at 32

<210> SEQ ID NO 69
<211> LENGTH: 32
<212> TYPE: DNA
<213> ORGANISM: Artificial Sequence
<220> FEATURE:
<223> OTHER INFORMATION: Description of Artificial Sequence: Synthetic

<400> SEQUENCE: 69
agccattcag tcgaggaagg atagggtggt tt 32

<210> SEQ ID NO 70
<211> LENGTH: 32
<212> TYPE: DNA
<213> ORGANISM: Artificial Sequence
<220> FEATURE:
<223> OTHER INFORMATION: Description of Artificial Sequence: Synthetic

<400> SEQUENCE: 70
agccattcag tcgaggatcc caagggtggt at 32

<210> SEQ ID NO 71
<211> LENGTH: 32
<212> TYPE: DNA
<213> ORGANISM: Artificial Sequence
<220> FEATURE:
<223> OTHER INFORMATION: Description of Artificial Sequence: Synthetic

<400> SEQUENCE: 71
agccattcag tcgaggaagg atagggccta at 32

<210> SEQ ID NO 72
<211> LENGTH: 33
<212> TYPE: DNA
<213> ORGANISM: Artificial Sequence
<220> FEATURE:
<223> OTHER INFORMATION: Description of Artificial Sequence: Synthetic

<400> SEQUENCE: 72
agaccattca gtcgaggaag gatagggtgg tat 33

<210> SEQ ID NO 73
<211> LENGTH: 33
<212> TYPE: DNA
<213> ORGANISM: Artificial Sequence
<220> FEATURE:
<223> OTHER INFORMATION: Description of Artificial Sequence: Synthetic

<400> SEQUENCE: 73
agccattcag tcgaggaagg atagcggtgg tat 33

<210> SEQ ID NO 74
<211> LENGTH: 25
<212> TYPE: DNA

-continued

```
<213> ORGANISM: Artificial Sequence
<220> FEATURE:
<223> OTHER INFORMATION: Description of Artificial Sequence:  Synthetic

<400> SEQUENCE: 74

agccattcag tcgaggaagg ataat                                          25


<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence:  Synthetic

<400> SEQUENCE: 75

agccattcga ggaaggatag ggtggtat                                       28


<210> SEQ ID NO 76
<211> LENGTH: 1273
<212> TYPE: DNA
<213> ORGANISM: Artificial Sequence
<220> FEATURE:
<223> OTHER INFORMATION: Description of Artificial Sequence:  Synthetic

<400> SEQUENCE: 76

ggcctctgac taactaatca ctttcccatc ttttgttaga tttgaatata tacattctat     60

gatcattgct ttttctcttt acaggggaga atttcatatt ttacctgagc aaattgatta    120

gaaaatggaa ccactagagg aatataatgt gttaggaaat tacagtcatt tctaagggcc    180

cagcccttga caaaattgtg aagttaaatt ctccactctg tccatcagat actatggttc    240

tccactatgg caactaactc actcaatttt ccctccttag cagcattcca tcttcccgat    300

cttctttgct tctccaacca aaacatcaat gtttattagt tctgtataca gtacaggatc    360

tttggtctac tctatcacaa ggccagtacc acactcatga agaaagaaca caggagtagc    420

tgagaggcta aaactcatca aaaacactac tccttttcct ctaccctatt cctcaatctt    480

ttacctttc caaatcccaa tccccaaatc agtttttctc tttcttactc cctctctccc     540

ttttaccctc catggtcgtt aaaggagaga tggggagcat cattctgtta tacttctgta    600

cacagttata catgtctatc aaacccagac ttgcttccat agtggagact tgcttttcag    660

aacataggga tgaagtaagg tgcctgaaaa gtttggggga aaagtttctt tcagagagtt    720

aagttatttt atatatataa tatatatata aaatatataa tatacaatat aaatatatag    780

tgtgtgtgtg tatgcgtgtg tgtagacaca cacgcataca cacatataat ggaagcaata    840

agccattcta agagcttgta tggttatgga ggtctgacta ggcatgattt cacgaaggca    900

agattggcat atcattgtaa ctaaaaaagc tgacattgac ccagacatat tgtactcttt    960

ctaaaaataa taataataat gctaacagaa agaagagaac cgttcgtttg caatctacag   1020

ctagtagaga ctttgaggaa gaattcaaca gtgtgtcttc agcagtgttc agagccaagc   1080

aagaagttga agttgcctag accagaggac ataagtatca tgtctccttt aactagcata   1140

ccccgaagtg gagaagggtg cagcaggctc aaaggcataa gtcattccaa tcagccaact   1200

aagttgtcct tttctggttt cgtgttcacc atggaacatt ttgattatag ttaatccttc   1260

tatcttgaat ctt                                                      1273


<210> SEQ ID NO 77
<211> LENGTH: 1273
<212> TYPE: DNA
<213> ORGANISM: Artificial Sequence
```

<220> FEATURE:
<223> OTHER INFORMATION: Description of Artificial Sequence: Synthetic

<400> SEQUENCE: 77

```
ggcctctcac taactaatca ctttcccatc ttttgttaga tttgaatata tacattctat     60

gatcattgct ttttctcttt acaggggaga atttcatatt ttacctgagc aaattgatta    120

gaaaatggaa ccactagagg aatataatgt gttaggaaat tacagtcatt tctaagggcc    180

cagcccttga caaaattgtg aagttaaatt ctccactctg tccatcagat actatggttc    240

tccactatgg caactaactc actcaaattt ccctccttag cagcattcca tcttcccgat    300

cttctttgct tctccaacca aaacatcaat gtttattagt tctgtataca gtacaggatc    360

tttggtctac tctatcacaa ggccagtacc acactcatga agaaagaaca caggagtagc    420

tgagaggcta aaactcatca aaaacactac tccttttcct ctaccctatt cctcaatctt    480

ttacctttc caaatcccaa tccccaaatc agtttttctc tttcttactc cctctctccc     540

ttttaccctc catggtcgtt aaaggagaga tggggagcat cattctgtta tacttctgta    600

cacagttata catgtctatc aaacccagac ttgcttccat agtggagact tgcttttcag    660

aacataggga tgaagtaagg tgcctgaaaa gtttgggggga aaagtttctt tcagagagtt   720

aagttatttt atatatataa tatatatata aaatatataa tatacaatat aaatatatag    780

tgtgtgtgtg tatgcgtgtg tgtagacaca cacgcataca cacatataat ggaagcaata    840

agccattcta agagcttgta tggttatgga ggtctgacta ggcatgattt cacgaaggca    900

agattggcat atcattgtaa ctaaaaaagc tgacattgac ccagacatat tgtactcttt    960

ctaaaaataa taataataat gctaacagaa agaagagaac cgttcgtttg caatctacag   1020

ctagtagaga ctttgaggaa gaattcaaca gtgtgtcttc agcagtgttc agagccaagc   1080

aagaagttga agttgcctag accagaggac ataagtatca tgtctccttt aactagcata   1140

ccccgaagtg gagaagggtg cagcaggctc aaaggcataa gtcattccaa tcagccaact   1200

aagttgtcct tttctggttt cgtgttcacc atggaacatt ttgattatag ttaatccttc   1260

tatcttgaat ctt                                                      1273
```

<210> SEQ ID NO 78
<211> LENGTH: 1273
<212> TYPE: DNA
<213> ORGANISM: Artificial Sequence
<220> FEATURE:
<223> OTHER INFORMATION: Description of Artificial Sequence: Synthetic

<400> SEQUENCE: 78

```
ggcctctcac taactaatca ctttcccatc ttttgttaga tttgaatata tacattctat     60

gatcattgct ttttctcttt acaggggaga atttcatatt ttacctgagc aaattgatta    120

gaaaatggaa ccactagagg aatataatgt gttaggaaat tacagtcatt tctaagggcc    180

cagcccttga caaaattgtg aagttaaatt ctccactctg tccatcagat actatggttc    240

tccactatgg caactaactc actcaatttt ccctccttag cagcattcca tcttcccgat    300

cttctttgct tctccaacca aaacatcaat gtttattagt tctgtataca gtacaggatc    360

tttggtctac tctatcacaa ggccagtacc acactcatga agaaagaaca caggagtagc    420

tgagaggcta aaactcatca aaaacactac tccttttcct ctaccctatt cctcaatctt    480

ttacctttc caaatcccaa tccccaaatc agtttttctc tttcttactc cctctctccc     540

ttttaccctc catggtcgtt aaaggagaga tggggacgat cattctgtta tacttctgta    600
```

-continued

```
cacagttata catgtctatc aaacccagac ttgcttccat agtggagact tgcttttcag    660

aacataggga tgaagtaagg tgcctgaaaa gtttggggga aaagtttctt tcagagagtt    720

aagttatttt atatatataa tatatatata aaatatataa tatacaatat aaatatatag    780

tgtgtgtgtg tatgcgtgtg tgtagacaca cacgcataca cacatataat ggaagcaata    840

agccattcta agagcttgta tggttatgga ggtctgacta ggcatgattt cacgaaggca    900

agattggcat atcattgtaa ctaaaaaagc tgacattgac ccagacatat tgtactcttt    960

ctaaaaataa taataataat gctaacagaa agaagagaac cgttcgtttg caatctacag   1020

ctagtagaga ctttgaggaa gaattcaaca gtgtgtcttc agcagtgttc agagccaagc   1080

aagaagttga agttgcctag accagaggac ataagtatca tgtctccttt aactagcata   1140

ccccgaagtg gagaagggtg cagcaggctc aaaggcataa gtcattccaa tcagccaact   1200

aagttgtcct tttctggttt cgtgttcacc atggaacatt ttgattatag ttaatccttc   1260

tatcttgaat ctt                                                      1273
```

<210> SEQ ID NO 79
<211> LENGTH: 1273
<212> TYPE: DNA
<213> ORGANISM: Artificial Sequence
<220> FEATURE:
<223> OTHER INFORMATION: Description of Artificial Sequence: Synthetic

<400> SEQUENCE: 79

```
ggcctctcac taactaatca ctttcccatc ttttgttaga tttgaatata tacattctat     60

gatcattgct ttttctcttt acaggggaga atttcatatt ttacctgagc aaattgatta    120

gaaaatggaa ccactagagg aatataatgt gttaggaaat tacagtcatt tctaagggcc    180

cagcccttga caaaattgtg aagttaaatt ctccactctg tccatcagat actatggttc    240

tccactatgg caactaactc actcaatttt ccctccttag cagcattcca tcttcccgat    300

cttctttgct tctccaacca aaacatcaat gtttattagt tctgtataca gtacaggatc    360

tttggtctac tctatcacaa ggccagtacc acactcatga agaaagaaca caggagtagc    420

tgagaggcta aaactcatca aaaacactac tccttttcct ctaccctatt cctcaatctt    480

ttaccttttc caaatcccaa tccccaaatc agtttttctc tttcttactc cctctctccc    540

ttttaccctc catggtcgtt aaaggagaga tggggagcat cattctgtta tacttctgta    600

cacagttata catgtctatc aaacccagac ttgcttccat agtggagact tgcttttcag    660

aacataggga tgaagtaagg tgcctgaaaa gtttggggga aaagtttctt tcagagagtt    720

aagttatttt atatatataa tatatatata aaatatataa tatacaatat aaatatatag    780

tgtgtgtgtg tatgcgtgtg tgtagacaca cacgcataca cacatataat ggaagcaata    840

agccattcta agagcttgta tggttatgga ggtctgacta ggcatgattt cacgaaggca    900

agattggcat atcattgtaa ctaaaaaagc tgacattgac ccagacatat tgtactcttt    960

ctaaaaataa taataataat gctaacagaa agaagagaac cgttcgtttg caatctacag   1020

ctagtagaga ctttgaggaa gaattcaaca gtgtgtcttc agcagtgttc agagccaagc   1080

aagaagttga agttgcctag accagaggac ataagtatgt actctccttt aactagcata   1140

ccccgaagtg gagaagggtg cagcaggctc aaaggcataa gtcattccaa tcagccaact   1200

aagttgtcct tttctggttt cgtgttcacc atggaacatt ttgattatag ttaatccttc   1260

tatcttgaat ctt                                                      1273
```

```
<210> SEQ ID NO 80
<211> LENGTH: 1275
<212> TYPE: DNA
<213> ORGANISM: Artificial Sequence
<220> FEATURE:
<223> OTHER INFORMATION: Description of Artificial Sequence:  Synthetic

<400> SEQUENCE: 80

ggcctctcac taactaatca ctttcccatc ttttgttaga tttgaatata tacattctat      60

gatcattgct ttttctcttt acaggggaga atttcatatt ttacctgagc aaattgatta     120

gaaaatggaa ccactagagg aatataatgt gttaggaaat tacagtcatt tctaagggcc     180

cagcccttga caaaattgtg aagttaaatt ctccactctg tccatcagat actatggttc     240

tccactatgg caactaactc actcaatttt ccctccttag cagcattcca tcttcccgat     300

ttcttctttg cttctccaac caaaacatca atgtttatta gttctgtata cagtacagga     360

tctttggtct actctatcac aaggccagta ccacactcat gaagaaagaa cacaggagta     420

gctgagaggc taaaactcat caaaaacact actccttttc ctctacccta ttcctcaatc     480

ttttaccttt tccaaatccc aatccccaaa tcagttttc tctttcttac tccctctctc      540

ccttttaccc tccatggtcg ttaaaggaga gatggggagc atcattctgt tatacttctg     600

tacacagtta tacatgtcta tcaaacccag acttgcttcc atagtggaga cttgcttttc     660

agaacatagg gatgaagtaa ggtgcctgaa aagtttgggg gaaaagtttc tttcagagag     720

ttaagttatt ttatatatat aatatatata taaaatatat aatatacaat ataaatatat     780

agtgtgtgtg tgtatgcgtg tgtgtagaca cacacgcata cacacatata atggaagcaa     840

taagccattc taagagcttg tatggttatg gaggtctgac taggcatgat ttcacgaagg     900

caagattggc atatcattgt aactaaaaaa gctgacattg acccagacat attgtactct     960

ttctaaaaat aataataata atgctaacag aaagaagaga accgttcgtt tgcaatctac    1020

agctagtaga gactttgagg aagaattcaa cagtgtgtct tcagcagtgt tcagagccaa    1080

gcaagaagtt gaagttgcct agaccagagg acataagtat catgtctcct ttaactagca    1140

taccccgaag tggagaaggg tgcagcaggc tcaaaggcat aagtcattcc aatcagccaa    1200

ctaagttgtc cttttctggt ttcgtgttca ccatggaaca ttttgattat agttaatcct    1260

tctatcttga atctt                                                     1275


<210> SEQ ID NO 81
<211> LENGTH: 1276
<212> TYPE: DNA
<213> ORGANISM: Artificial Sequence
<220> FEATURE:
<223> OTHER INFORMATION: Description of Artificial Sequence:  Synthetic

<400> SEQUENCE: 81

ggcctctcac taactaatca ctttcccatc ttttgttaga tttgaatata tacattctat      60

gatcattgct ttttctcttt acaggggaga atttcatatt ttacctgagc aaattgatta     120

gaaaatggaa ccactagagg aatataatgt gttaggaaat tacagtcatt tctaagggcc     180

cagcccttga caaaattgtg aagttaaatt ctccactctg tccatcagat actatggttc     240

tccactatgg caactaactc actcaatttt ccctccttag cagcattcca tcttcccgat     300

cttctttgct tctccaacca aaacatcaat gtttattagt tctgtataca gtacaggatc     360

tttggtctac tctatcacaa ggccagtacc acactcatga agaaagaaca caggagtagc     420

tgagaggcta aaactcatca aaaacactac tccttttcct ctaccctatt cctcaatctt     480
```

-continued

```
ttacctttc caaatcccaa tccccaaatc agtttttctc tttcttactc cctctctccc    540

ttttaccctc catggtcgtt aaaggagaga tggggagcat cattctgtta tacttctgta    600

cacagttata catgtctatc aaacccagac ttgcttccat agtggagact tgcttttcag    660

aacataggga tgaagtaagg tgcctgaaaa gtttgggga aaagtttctt tcagagagtt    720

aagttatttt atatatataa tatatatata aaatatataa tatacaatat aaatatatag    780

tgtgtgtgtg tatgcgtgtg tgtagacaca cacgcataca cacatataat ggaagcaata    840

agccattcta agagcttgta tggttatgga ggtctgacta ggcatgattt cacgaaggca    900

agattggcat atcattgtaa ctaaaaaagc tgacattgac ccagacatat tgtactcttt    960

ctaaaaataa taataataat gctaacagaa agaagagaac cgttcgtttg caatctacag   1020

ctagtagaga ctttgaggaa gaattcaaca gtgtgtcttc agcagtgttc agagccaagc   1080

aagaagttga agttgcctag accagaggac ataagtatca tgtctccttt aactagcata   1140

ccccgaagtg gagaagggtg cagcaggctc aaaggcataa gtcattccaa tcagccaact   1200

gctaagttgt ccttttctgg tttcgtgttc accatggaac attttgatta tagttaatcc   1260

ttctatcttg aatctt                                                   1276
```

<210> SEQ ID NO 82
<211> LENGTH: 1272
<212> TYPE: DNA
<213> ORGANISM: Artificial Sequence
<220> FEATURE:
<223> OTHER INFORMATION: Description of Artificial Sequence: Synthetic

<400> SEQUENCE: 82

```
ggcctctcac taactaatca ctttcccatc ttttgttaga tttgaatata tacattctat     60

gatcattgct ttttctcttt acaggggaga atttcatatt ttacctgagc aaattgatta    120

gaaaatggaa ccactagagg aatataatgt gttaggaaat tacagtcatt tctaagggcc    180

cagcccttga caaaattgtg aagttaaatt ctccactctg tccatcagat actatggttc    240

tccactatgg caactaactc actcaatttt ccctccttag cagcattcca tcttcccgat    300

cttctttgct tctccaacca aaacatcaat gtttattagt tctgtataca gtacaggatc    360

tttggtctac tctatcacaa ggccagtacc acactcatga agaaagaaca caggagtagc    420

tgagaggcta aaactcatca aaaacactac tccttttcct ctaccctatt cctcaatctt    480

ttacctttc caaatcccaa tccccaaatc agtttttctc tttcttactc cctctctccc    540

ttttaccctc catggtcgtt aaaggagaga tggggagcat cattctgtta tacttctgta    600

cacagttata catgtctatc aaacccagac ttgcttccat agtggagact tgcttttcag    660

aacataggga tgaagtaagg tgcctgaaaa gtttgggga aaagtttctt tcagagagtt    720

aagttatttt atatatataa tatatatata aaatatataa tatacaatat aaatatatag    780

tgtgtgtgtg tatgcgtgtg tgtagacaca cacgcataca cacatataat ggaagcaata    840

agccattcta agagcttgta tggttatgga ggtctgacta ggcatgattt cacgaaggca    900

agattggcat atcattgtaa ctaaaaaagc tgacattgac ccagacatat tgtactcttt    960

ctaaaaataa taataataat gctaacagaa agaagagaac cgttcgtttg caatctacag   1020

ctagtagaga ctttgaggaa gaattcaaca gtgtgtcttc agcagtgttc agagccaagc   1080

aagaagttga agttgcctag accagaggac ataagtatca tgtctccttt aactagcata   1140

ccccgaagtg gagaagggtg cagcaggctc aaaggcataa gtcattccaa tcagccaact   1200

aagttgtcct tttctggttt cgtgttcacc atggaacatt ttgattatag ttatccttct   1260
```

atcttgaatc tt 1272

<210> SEQ ID NO 83
<211> LENGTH: 1272
<212> TYPE: DNA
<213> ORGANISM: Artificial Sequence
<220> FEATURE:
<223> OTHER INFORMATION: Description of Artificial Sequence: Synthetic

<400> SEQUENCE: 83
gcctctcact aactaatcac tttcccatct tttgttagat ttgaatatat acattctatg 60
atcattgctt tttctcttta caggggagaa tttcatattt tacctgagca aattgattag 120
aaaatggaac cactagagga atataatgtg ttaggaaatt acagtcattt ctaagggccc 180
agcccttgac aaaattgtga agttaaattc tccactctgt ccatcagata ctatggttct 240
ccactatggc aactaactca ctcaattttc cctccttagc agcattccat cttcccgatc 300
ttctttgctt ctccaaccaa aacatcaatg tttattagtt ctgtatacag tacaggatct 360
ttggtctact ctatcacaag gccagtacca cactcatgaa gaaagaacac aggagtagct 420
gagaggctaa aactcatcaa aaacactact ccttttcctc taccctattc ctcaatcttt 480
taccttttcc aaatcccaat ccccaaatca gtttttctct ttcttactcc ctctctccct 540
tttaccctcc atggtcgtta aaggagagat ggggagcatc attctgttat acttctgtac 600
acagttatac atgtctatca aacccagact tgcttccata gtggagactt gcttttcaga 660
acatagggat gaagtaaggt gcctgaaaag tttgggggaa aagtttcttt cagagagtta 720
agttatttta tatatataat atatatataa aatatataat atacaatata aatatatagt 780
gtgtgtgtgt atgcgtgtgt gtagacacac acgcatacac acatataatg gaagcaataa 840
gccattctaa gagcttgtat ggttatggag gtctgactag gcatgatttc acgaaggcaa 900
gattggcata tcattgtaac taaaaaagct gacattgacc cagacatatt gtactctttc 960
taaaaataat aataataatg ctaacagaaa gaagagaacc gttcgtttgc aatctacagc 1020
tagtagagac tttgaggaag aattcaacag tgtgtcttca gcagtgttca gagccaagca 1080
agaagttgaa gttgcctaga ccagaggaca taagtatcat gtctccttta actagcatac 1140
cccgaagtgg agaagggtgc agcaggctca aaggcataag tcattccaat cagccaacta 1200
agttgtcctt ttctggtttc gtgttcacca tggaacattt tgattatagt taatccttct 1260
atcttgaatc tt 1272

<210> SEQ ID NO 84
<211> LENGTH: 7
<212> TYPE: DNA
<213> ORGANISM: Artificial Sequence
<220> FEATURE:
<223> OTHER INFORMATION: Description of Artificial Sequence: Synthetic

<400> SEQUENCE: 84 gcggaag 7

NUCLEOTIDE SEQUENCES FOR GENE REGULATION AND METHODS OF USE THEREOF

This Application for patent under 35 U.S.C. § 111(a) is a Continuation of application Ser. No. 10/032,084 filed on Dec. 19, 2001 (now abandoned) which is a Continuation of patent application Ser. No. 09/328,925 filed on Jun. 09, 1999 (now issued as U.S. Pat. No. 6,610,906).

This work was made, in part, with Government support by the National Institutes of Health grant numbers HL38644 and HL53713. The Government has certain rights in this invention.

FIELD OF THE INVENTION

The invention relates to nucleic acid sequences which regulate expression of a nucleotide sequence of interest. In particular, the invention relates to nucleic acid sequences which regulate expression of a nucleotide sequence of interest in an age-related manner and/or in a liver-specific manner. The invention further relates to methods of using the regulatory nucleic acid sequences provided herein for age-related and/or liver-specific expression of nucleotides sequences of interest. The invention also relates to host cells and to transgenic non-human animals which harbor the regulatory nucleic acid sequences of the invention. The compositions and methods of the invention are useful in regulating expression of a nucleotide sequence of interest in an age-related and/or liver-specific manner.

BACKGROUND OF THE INVENTION

A multitude of human diseases (e.g., thrombosis, cardiovascular diseases, diabetes, Alzheimer's disease, cancer, osteoporosis, osteoarthritis, Parkinson's disease, dementia) are associated with increasing age and result in serious effects on the quality of life and on the life expectancy of individuals suffering from such diseases. Other diseases (e.g., cirrhosis, primary and metastatic neoplasia, Wilson disease, hepachromatosis, infectious hepatitis, hepatic necrosis, Gilbert disease, Criggler-Najar disease) which afflict the liver also have serious clinical manifestations and are responsible for high morbidity and mortality.

The treatment of age-related diseases (i.e., diseases whose prevalence and/or severity of clinical manifestations increases with the age of the patient) and diseases afflicting the liver focuses on the alleviation of the general symptoms of the disease using one or a combination of two modalities, i.e., non-pharmacological treatment and pharmacological treatment. Non-pharmacological treatment include, for example, periods of bed rest and dietary changes. Non-pharmacological treatment is often used as an adjunct to pharmacological treatment which involves the use of drugs. Unfortunately, many of the commonly used pharmacological agents have numerous side effects and their use is further exacerbated by the non-responsiveness by many patients with severe disease, who, paradoxically, are in most need of treatment. Both non-pharmacological and pharmacological treatments provide unsatisfactory approaches to treating age-related and liver-associated diseases because these approaches are often ineffective, their effects are inconsistent, and are directed to alleviating the general symptoms of disease, rather than to specifically addressing the source of morbidity and mortality. Moreover, no suitable animal models are currently available to rationally design drugs which target specific biochemical and physiological pathways which are associated with age-related and with liver-associated diseases.

What is needed are methods for age-related and liver-specific gene expression and models for age-related and liver-specific diseases.

SUMMARY OF THE INVENTION

The invention provides nucleic acid sequences which regulate expression of a nucleotide sequence of interest in an age-related manner, as well as nucleic acid sequences which direct liver-specific expression of a gene of interest. Further provided by the invention are transgenic animals which may be used as models for age-related and/or liver specific diseases.

In one embodiment, the invention provides a recombinant expression vector comprising in operable combination i) a nucleic acid sequence of interest, ii) a promoter sequence, and iii) one or more age regulatory sequences selected from SEQ ID NO:1, SEQ ID NO:3, a portion of SEQ ID NO:1, and a portion of SEQ ID NO:3. Without intending to limit the invention to any particular type or source of nucleic acids sequence of interest, in a preferred embodiment, the nucleic acid sequence of interest encodes a protein selected from factor VIII, factor VII, factor IX, factor X, prothrombin, protein C, antithrombin III, tissue factor pathway inhibitor, LDL-receptor, human α1-antitrypsin, antithrombin III, PEA-3 protein, β-galactosidase, and luciferase. While it is not intend ed that the invention be restricted to any particular type or source of promoter sequence, in an alternative preferred embodiment, the promoter sequence is selected from human factor IX promoter, cytomegalovirus promoter, tRNA promoter, 5S rRNA promoters, histone gene promoters, RSV promoter, retrovirus LTR promoter, SV40 promoter, PEPCK promoter, MT promoter, SRα promoter, P450 family promoters, GAL7 promoter, T7 promoter, T3 promoter, SP6 promoter, K11 promoter, and HIV promoter. It is not contemplated that the invention be limited to any particular age regulatory sequence which is a portion of SEQ ID NO:1. However, in another preferred embodiment, the age regulatory sequence which is a portion of SEQ ID NO:1 is selected from SEQ ID NO:2, SEQ ID NO:33, SEQ ID NO:34, SEQ ID NO:35, SEQ ID NO:36, SEQ ID NO:37, and SEQ ID NO:38. Without intending to limit the invention to any particular rage regulatory sequence which s a portion of SEQ ID NO:3, in yet another preferred embodiment, the age regulatory sequence which is a portion of SEQ ID NO:3 is selected from SEQ ID NO:51, SEQ ID NO:52, SEQ ID NO:53, SEQ ID NO:54, SEQ ID NO:55, and SEQ ID NO:56.

Also provided by the invention is a host cell containing a recombinant expression vector comprising in operable combination i) a nucleic acid sequence of interest, ii) a promoter sequence, and iii) one or more age regulatory sequences selected from SEQ ID NO:1, SEQ ID NO:3, a portion of SEQ ID NO:1, and a portion of SEQ ID NO:3. Without intending to limit the invention to the environment in which the host cell is contained, in one preferred embodiment, the host cell is comprised in a tissue or organ in a living animal. In another preferred embodiment, the host cell is a gamete. In yet another preferred embodiment, the host cell is selected from bacterial cell, yeast cell, plant cell, insect cell, and mammalian cell.

The invention also provides a recombinant expression vector comprising in operable combination i) a nucleic acid sequence of interest, ii) a promoter sequence, and iii) a functional homolog of one or more age regulatory sequences selected from SEQ ID NO:1, SEQ ID NO:3, a portion of SEQ ID NO:1, and a portion of SEQ ID NO:3. Without limiting the invention to the type or source of the nucleic acid sequence of interest, in one preferred embodiment, the nucleic acid sequence of interest encodes a protein selected from factor VIII, factor VII, factor IX, factor X, prothrombin, protein C, antithrombin III, tissue factor pathway inhibitor, LDL-receptor, human a $\alpha$1-antitrypsin, antithrombin III, PEA-3 protein, $\beta$-galactosidase, and luciferase. While it is not intended that the invention be limited to the type or source of the promoter sequence, in an alternative preferred embodiment, the promoter sequence is selected from human factor IX promoter, cytomegalovirus promoter, tRNA promoter, 5S rRNA promoters, histone gene promoters, RSV promoter, retrovirus LTR promoter, SV40 promoter, PEPCK promoter, MT promoter, SR$\alpha$ promoter, P450 family promoters, GAL7 promoter, T7 promoter, T3 promoter, SP6 promoter, K11 promoter, and HIV promoter. Though it is not contemplated that the invention be limited to the portion of SEQ lID NO:1 which has age-related regulatory activity, in another preferred embodiment, the age regulatory sequence which is a portion of SEQ ID NO:1 is selected from SEQ ID NO:2, SEQ ID NO:33, SEQ ID NO:34, SEQ ID NO:35, SEQ ID NO:36, SEQ ID NO:37, and SEQ ID NO:38. Without intending to limit the invention the portion of SEQ ID NO:3 which has age-related regulatory activity, in yet another preferred embodiment, the age regulatory sequence which is a portion of SEQ ID NO:3 is selected from SEQ ID NO:51, SEQ ID NO:52, SEQ iD NO:53, SEQ lID NO:54, SEQ lID NO:55, and SEQ lID NO:56.

Also provided herein is a host cell containing recombinant expression vector comprising in operable combination i) a nucleic acid sequence of interest, ii) a promoter sequence, and iii) a functional homolog of one or more age regulatory sequences selected from SEQ ID NO:1, SEQ ID NO:3, a portion of SEQ ID NO:1, and a portion of SEQ ID NO:3. Without intending to limit the invention to the environment in which the host cell is contained, in one preferred embodiment, the host cell is comprised in a tissue or organ in a living animal. In an alternative preferred embodiment, the host cell is a gamete. In another preferred embodiment, the host cell is selected from bacterial cell, yeast cell, plant cell, insect cell, and mammalian cell.

The invention also provides a method, comprising: a) providing: i) a cell, ii) a nucleic acid sequence of interest, iii) a promoter sequence, and iv) one or more age regulatory sequences selected from SEQ ID NO:1, SEQ ID NO:3, a portion of SEQ ID NO:1, and a portion of SEQ ID NO:3; b) operably linking the nucleic acid sequence of interest, the promoter sequence, and the one or more age regulatory sequences to produce a transgene; and c) introducing the transgene into the cell to create a treated cell under conditions such that the nucleic acid sequence of interest is expressed in the treated cell. Without intending to limit the treated cell to any particular environment, in one preferred embodiment, the treated cell is comprised in a tissue or organ in a living animal.

The invention further provides a substantially purified nucleic acid sequence comprising a nucleotide sequence selected from a functional homolog of SEQ ID NO:1 and of the complement thereof.

Also provided herein is a substantially purified nucleic acid sequence comprising a nucleotide sequence selected from a functional homolog of SEQ ID NO:3 and of the complement thereof.

Also provided by the present invention is a substantially purified nucleic acid sequence comprising a portion of a nucleotide sequence selected from a functional homolog of SEQ ID NO:1 and of the complement thereof. In one embodiment, the portion is SEQ ID NO:2. In an alternative embodiment, the portion is selected from SEQ ID NO:33, SEQ ID NO:34, SEQ ID NO:35, SEQ ID NO:36, SEQ ID NO:37 and SEQ ID NO:38.

The invention also provides a substantially purified nucleic acid sequence comprising a portion of a nucleotide sequence selected from a functional homolog of SEQ ID NO:3 and of the complement thereof. In one embodiment, the portion is selected from SEQ ID NO:51, SEQ ID NO:52, SEQ ID NO:53, SEQ lID NO:54, SEQ lID NO:55, and SEQ ID NO:56.

Also provided herein is a substantially purified nucleic acid sequence which hybridizes under stringent hybridization conditions with SEQ ID NO:1 or with the complement thereof, wherein the nucleic acid sequence is characterized by having age-related regulatory activity, and by having greater than 63% and less than 100% homology to the SEQ ID NO:1.

The invention also provides a substantially purified nucleic acid sequence which hybridizes under stringent hybridization conditions with SEQ ID NO:3 or with the complement thereof, wherein the nucleic acid sequence is characterized by having age-related regulatory activity, and by having greater than 60% and less than 100% homology to the SEQ ID NO:3.

The invention additionally provides a recombinant expression vector comprising at least a portion of a nucleotide sequence selected from a functional homolog of SEQ ID NO:1 and of the complement thereof.

Also provided herein is a recombinant expression vector comprising at least a portion of a nucleotide sequence selected from a functional homolog of SEQ ID NO:3 and of the complement thereof.

The invention also provides a transgenic cell comprising at least a portion of a nucleotide sequence selected from a functional homolog of SEQ ID NO:1 and of the complement thereof. In one embodiment, the nucleotide sequence is operably linked to a promoter and to a nucleic acid sequence of interest. In a preferred embodiment, the transgenic cell is comprised in an animal. In a more preferred embodiment, the nucleic acid sequence of interest is expressed in an age-related manner in the transgenic cell.

The invention additionally provides a transgenic cell comprising at least a portion of a nucleotide sequence selected from a functional homolog of SEQ ID NO:3 and of the complement thereof. In one embodiment, the nucleotide sequence is operably linked to a promoter and to a nucleic acid sequence of interest. In a preferred embodiment, the transgenic cell is comprised in an animal. In a more preferred embodiment, the nucleic acid sequence of interest is expressed in an age-related manner in the transgenic cell.

The invention also provides a method for expressing a nucleic acid sequence of interest in a cell, comprising: a) providing: i) a cell; ii) a nucleic acid sequence of interest; iii) a promoter sequence; iv) SEQ ID NO:1; and v) SEQ ID NO:3; b) operably linking the nucleic acid sequence of interest, the promoter sequence, the SEQ ID NO:1 and the SEQ ID NO:3 to produce a transgene; and c) introducing the transgene into the cell to produce a transgenic cell under conditions such that the nucleic acid sequence of interest is expressed in the transgenic cell. In one embodiment, the cell expresses a recombinant protein identified as SEQ ID NO:47. In an alternative embodiment, the cell is selected from HepG2 cell, fibroblast cell, myoblast cell, and endothelial cell. In another embodiment, the cell is a fertilized egg cell, and the transgenic cell is a transgenic fertilized egg cell. In a preferred embodiment, the method further comprises d) introducing the transgenic fertilized egg cell into a non-human animal and permitting the animal to deliver progeny containing the transgene. In a more preferred embodiment, the progeny is characterized by age-related expression of the nucleic acid sequence of interest. In an alternative more preferred embodiment, the progeny is characterized by liver-specific expression of the nucleic acid sequence of interest. In another preferred embodiment, the fertilized egg cell is derived from a mammal of the order Rodentia. In a more preferred embodiment, the fertilized egg cell is a mouse fertilized egg cell. In yet another embodiment, the promoter is selected from human factor IX promoter, cytomegalovirus promoter, tRNA promoter, 5S rRNA promoters, histone gene promoters, RSV promoter, retrovirus LTR promoter, SV40 promoter, PEPCK promoter, MT promoter, SRα promoter, P450 family promoters, GAL7 promoter, $T_7$ promoter, $T_3$ promoter, SP6 promoter, K11 promoter, and HIV promoter. In a further embodiment, the nucleic acid sequence of interest encodes a protein selected from factor VIII, factor VII, factor IX, factor X, prothrombin, protein C, antithrombin III, tissue factor pathway inhibitor, LDL-receptor, human α1-antitrypsin, antithrombin III, PEA-3 protein, β-galactosidase, and luciferase.

The invention also provides a method for expressing a nucleic acid sequence of interest in a cell, comprising: a) providing: i) a cell; ii) a nucleic acid sequence of interest; iii) a promoter sequence; iv) a portion of SEQ ID NO:1; and v) a portion of SEQ ID NO:3; b) operably linking the nucleic acid sequence of interest, the promoter sequence, the portion of SEQ ID NO:1 and the portion of SEQ ID NO:3 to produce a transgene; and c) introducing the transgene into the cell to produce a transgenic cell under conditions such that the nucleic acid sequence of interest is expressed in the transgenic cell.

Additionally provided by the invention is a method for expressing a nucleic acid sequence of interest in a cell, comprising: a) providing: i) a cell; ii) a nucleic acid sequence of interest; iii) a promoter sequence; and iv) SEQ ID NO:1; b) operably linking the nucleic acid sequence of interest, the promoter sequence, and the SEQ ID NO:1 to produce a transgene; and c) introducing the transgene into the cell to produce a transgenic cell under conditions such that the nucleic acid sequence of interest is expressed in the transgenic cell.

Also provided herein is a method for expressing a nucleic acid sequence of interest in a cell, comprising: a) providing: i) a cell; ii) a nucleic acid sequence of interest; iii) a promoter sequence; and iv) a portion of SEQ ID NO:1; b) operably linking the nucleic acid sequence of interest, the promoter sequence, and the portion of SEQ ID NO:1 to produce a transgene; and c) introducing the transgene into the cell to produce a transgenic cell under conditions such that the nucleic acid sequence of interest is expressed in the transgenic cell.

The invention further provides a method for expressing a nucleic acid sequence of interest in a cell, comprising: a) providing: i) a cell; ii) a nucleic acid sequence of interest; iii) a promoter sequence; and iv) SEQ ID NO:3; b) operably linking the nucleic acid sequence of interest, the promoter sequence, and the SEQ ID NO:3 to produce a transgene; and c) introducing the transgene into the cell to produce a transgenic cell under conditions such that the nucleic acid sequence of interest is expressed in the transgenic cell.

Further provided by the invention is a method for expressing a nucleic acid sequence of interest in a cell, comprising: a) providing: i) a cell; ii) a nucleic acid sequence of interest; iii) a promoter sequence; and iv) a portion of SEQ ID NO:3; b) operably linking the nucleic acid sequence of interest, the promoter sequence, and the portion of SEQ ID NO:3 to produce a transgene; and c) introducing the transgene into the cell to produce a transgenic cell under conditions such that the nucleic acid sequence of interest is expressed in the transgenic cell.

BRIEF DESCRIPTION OF THE DRAWINGS

FIG. 8A-N shows the nucleotide sequence (SEQ ID NO:4) of, and eight amino acid sequences (SEQ ID NOs:5 to 12) which together form, the human factor IX (GenBank accession number K02402). The initiation transcription site (nucleotide 1) and the poly-A addition site (nucleotide 32,757) are identified by solid circles. The solid vertical arrows indicate the intron-exon splice junction. The five Alu repetitive sequences have been underlined, while the 5-base insert in intron A and the AATAAA sequence in exon VIII are boxed. The cleavage or termination site at the 3' end of the gene (CATTG) is underlined with a dashed line.

FIG. 9 shows the cDNA sequence (SEQ ID NO:13) (A) and encoded polypeptide sequence (SEQ ID NO:47) (B) of mouse PEA-3 (GenBank accession number X63190).

FIG. 10 A-E shows the cDNA sequence (SEQ ID NO:42) of the human α1-antitrypsin gene (GenBank accession number K02212).

FIG. 11 shows the DNA sequence (SEQ ID NO:43) of human antithrombin III (GenBank accession number A06100).

FIG. 12 shows the cDNA sequence (A) (SEQ ID NO:49) (GenBank accession number X02750) and genomic DNA sequence (B-F) (SEQ ID NO:50) (GenBank accession number M11228) of human protein C.

FIG. 13 (A-E) shows the nucleic acid sequences (SEQ ID NOs:76-83) of exemplary homologs of AE3' (SEQ ID NO:3).

DEFINITIONS

Figure 1:
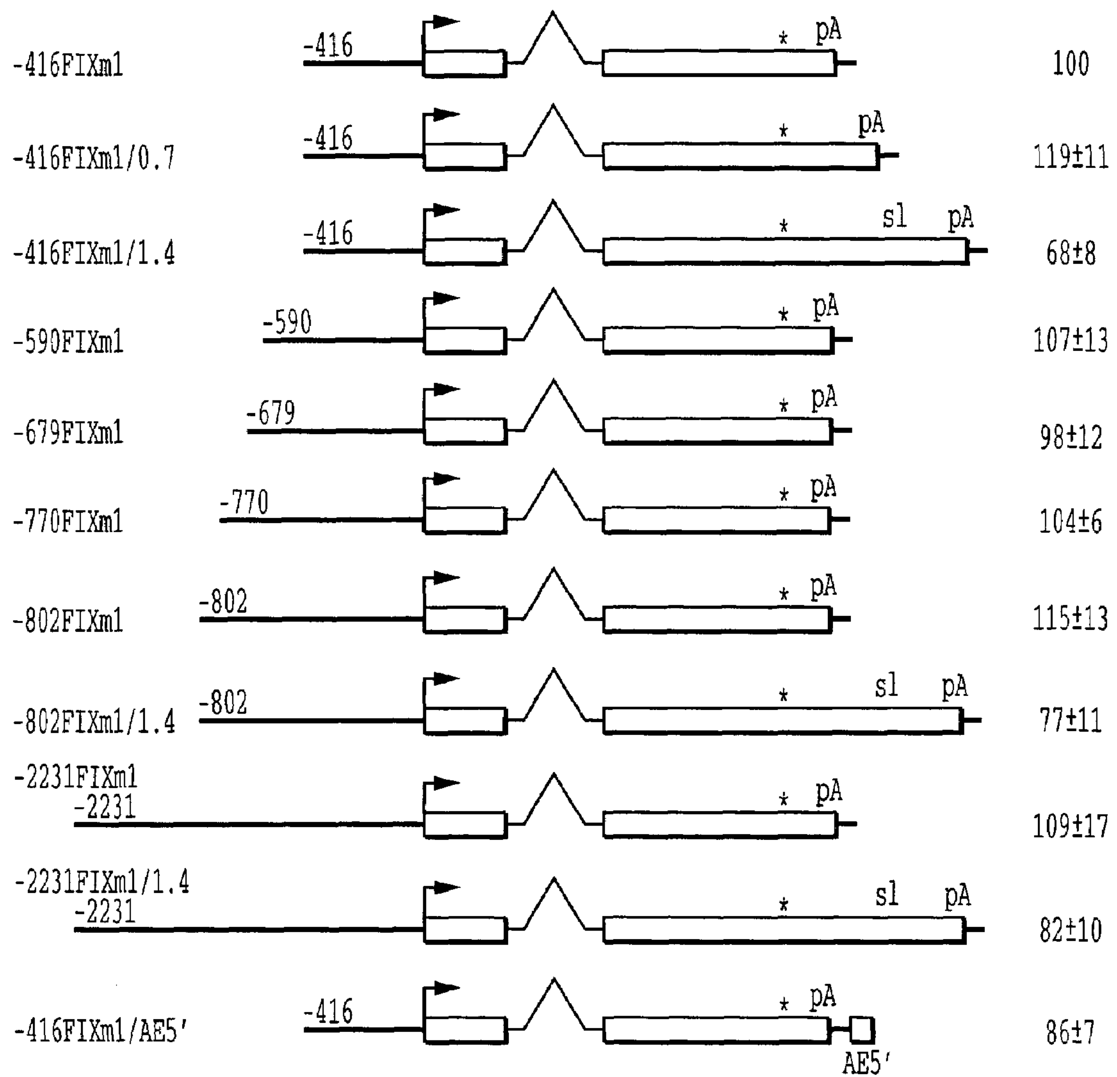
FIG. 1 shows the structure of eleven exemplary human FIX minigene expression constructs and relative in vitro transient expression activities (ng hFIX/$10^6$ cells/48 hr).

To facilitate understanding of the invention, a number of terms are defined below.

The term "isolated" when used in relation to a nucleic acid, as in "an isolated nucleic acid sequence" refers to a nucleic acid sequence that is identified and separated from at least one contaminant nucleic acid with which it is ordinarily associated in its natural state, or when obtained from its actual source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, an isolated nucleic acid sequence comprising SEQ ID NO:1 includes, by way of example, such nucleic acid sequences in cells which ordinarily contain SEQ ID NO:1 where the nucleic acid sequence is in a chromosomal or extrachromosomal location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain (at a minimum) at least a portion of the sense or coding strand (i.e., the nucleic acid sequence may be single-stranded). Alternatively, it may contain both the sense and anti-sense strands (i.e., the nucleic acid sequence may be double-stranded).

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

The term "recombinant" when made in reference to a DNA sequence refers to a DNA sequence which is comprised of segments of DNA joined together by means of molecular biological techniques. The term "recombinant" when made in reference to a polypeptide sequence refers to a polypeptide sequence which is expressed using a recombinant DNA sequence.

As used herein, the terms "vector" and "vehicle" are used interchangeably in reference to nucleic acid molecules that transfer DNA segment(s) from one cell to another.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals.

The term "transgenic" when used in reference to a cell refers to a cell which contains a transgene, or whose genome has been altered by the introduction of a transgene. The term "transgenic" when used in reference to a tissue or animal refers to a tissue or animal, respectively, which comprises one or more cells that contain a transgene, or whose genome has been altered by the introduction of a transgene. Transgenic cells, tissues and animals may be produced by several methods including the introduction of a "transgene" comprising nucleic acid (usually DNA) into a target cell or integration of the transgene into a chromosome of a target cell by way of human intervention, such as by the methods described herein.

A "non-human animal" refers to any animal which is not a human and includes vertebrates such as rodents, non-human primates, ovines, bovines, ruminants, lagomorphs, porcines, caprines, equines, canines, felines, aves, etc. Preferred non-human animals are selected from the order Rodentia. The term "order Rodentia" refers to rodents i.e., placental mammals (class Euthria) which include the family Muridae (e.g., rats and mice), most preferably mice.

The term "nucleotide sequence of interest" refers to any nucleotide sequence, the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the terms "complementarity," or "complementary" are used in reference to nucleotide sequences related by the base-pairing rules. For example, the sequence 5'-AGT-3' is complementary to the sequence 5'-ACT-3'. Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands.

A "complement" of a nucleic acid sequence as used herein refers to a nucleotide sequence whose nucleic acids show total complementarity to the nucleic acids of the nucleic acid sequence.

The term "homology" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid sequence and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

When used in reference to a single-stranded nucleic acid sequence, the term "substantially homologous" refers to any probe which can hybridize to the single-stranded nucleic acid sequence under conditions of low stringency as described infra.

The term "hybridization" as used herein includes "any process by which a strand of nucleic acid joins with a complementary strand through base pairing." [Coombs J (1994) *Dictionary of Biotechnology*, Stockton Press, New York N.Y.]. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m$=81.5+0.41(% G+C), when a nucleic acid is in aqueous solution at 1 M NaCl [see e.g., Anderson and Young, Quantitative Filter Hybridization, in *Nucleic Acid Hybridization* (1985)]. Other references include more sophisticated computations which take structural as well as sequence characteristics into account for the calculation of $T_m$.

Low stringency conditions when used in reference to nucleic acid hybridization comprise conditions equivalent to binding or hybridization at 68° C. in a solution consisting of 5×SSPE (43.8 g/l NaCl, 6.9 g/l $NaH_2PO_4.H_2O$ and 1.85 g/l EDTA, pH adjusted to 7.4 with NaOH), 1% SDS, 5× Denhardt's reagent [50× Denhardt's contains the following per 500 ml: 5 g Ficoll (Type 400, Pharmacia), 5 g BSA (Fraction V; Sigma)] and 100 μg/ml denatured salmon sperm DNA followed by washing in a solution comprising 0.2× SSPE, and 0.1% SDS at room temperature when a DNA probe of about 100 to about 1000 nucleotides in length is employed.

High stringency conditions when used in reference to nucleic acid hybridization comprise conditions equivalent to binding or hybridization at 68° C. in a solution consisting of 5×SSPE, 1% SDS, 5× Denhardt's reagent and 100 μg/ml denatured salmon sperm DNA followed by washing in a solution comprising 0.1×SSPE, and 0.1% SDS at 68° C. when a probe of about 100 to about 1000 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 50% to 70% homology to the first nucleic acid sequence, then another hybridization condition is said to be equivalent to the hybridization condition of interest if this other hybridization condition also results in hybridization of the first nucleic acid sequence with other nucleic acid sequences that have from 50% to 70% homology to the first nucleic acid sequence.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above-listed conditions.

Those skilled in the art know that whereas higher stringencies may be preferred to reduce or eliminate non-specific binding of the nucleotide sequence of SEQ ID NOs:1 or 3 with other nucleic acid sequences, lower stringencies may be preferred to detect a larger number of nucleic acid sequences having different homologies to the nucleotide sequence of SEQ ID NOs:1 and 3.

As used herein, the terms "regulatory element" and "regulatory sequence" interchangeably refer to a nucleotide sequence which does not encode RNA or a protein and which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. In contrast, the term "regulatory gene" refers to a DNA sequence which encodes RNA or a protein (e.g., transcription factor) that controls the expression of other genes.

Regulatory elements may be tissue specific or cell specific. The term "tissue specific" as it applies to a regulatory element refers to a regulatory element that is capable of directing selective expression of a nucleotide sequence of interest to a specific type of tissue (e.g., liver) in the relative absence of expression of the same nucleotide sequence of interest in a different type of tissue (e.g., lung).

Tissue specificity of a regulatory element may be evaluated by, for example, operably linking a reporter gene to a promoter sequence (which is not tissue-specific) and to the regulatory element to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the regulatory element is "specific" for the tissues in which greater levels of expression are detected. Thus, the term "tissue-specific" (e.g., liver-specific) as used herein is a relative term that does not require absolute specificity of expression. In other words, the term "tissue-specific" does not require that one tissue have extremely high levels of expression and another tissue have no expression. It is sufficient that expression is greater in one tissue than another. By contrast, "strict" or "absolute"

tissue-specific expression is meant to indicate expression in a single tissue type (e.g., liver) with no detectable expression in other tissues.

The term "cell type specific" as applied to a regulatory element refers to a regulatory element which is capable of directing selective expression of a nucleotide sequence of interest in a specific type of cell in the relative absence of expression of the same nucleotide sequence of interest in a different type of cell within the same tissue. The term "cell type specific" when applied to a regulatory element also means a regulatory element capable of promoting selective expression of a nucleotide sequence of interest in a region within a single tissue.

Cell type specificity of a regulatory element may be assessed using methods well known in the art, e.g., immunohistochemical staining and/or Northern blot analysis. Briefly, for immunohistochemical staining, tissue sections are embedded in paraffin, and paraffin sections are reacted with a primary antibody which is specific for the polypeptide product encoded by the nucleotide sequence of interest whose expression is regulated by the regulatory element. A labeled (e.g., peroxidase conjugated) secondary antibody which is specific for the primary antibody is allowed to bind to the sectioned tissue and specific binding detected (e.g., with avidin/biotin) by microscopy. Briefly, for Northern blot analysis, RNA is isolated from cells and electrophoresed on agarose gels to fractionate the RNA according to size followed by transfer of the RNA from the gel to a solid support, such as nitrocellulose or a nylon membrane. The immobilized RNA is then probed with a labeled oligo-deoxyribonucleotide probe or DNA probe to detect RNA species complementary to the probe used. Northern blots are a standard tool of molecular biologists.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, etc.). In contrast, a "regulatable" promoter is one which is capable of directing a level of transcription of an operably linked nucleic acid sequence in the presence of a stimulus (e.g., heat shock, chemicals, etc.) which is different from the level of transcription of the operably linked nucleic acid sequence in the absence of the stimulus.

DESCRIPTION OF THE INVENTION

The invention provides nucleic acid sequences which regulate expression of a nucleotide sequence of interest. In on embodiment, the invention provides nucleic acid sequences which regulate expression of a nucleotide sequence of interest in an age-related manner. Yet more particularly, the exemplary age-regulatory element 5' (AE5') has been discovered to regulate stable gene expression over time in vivo, while the exemplary age-regulatory element 3' (AE3') has been discovered to regulate increased gene expression over time in vivo. In another embodiment, the invention provides nucleic acid sequences (e.g., AE5') which direct liver-specific expression of a gene of interest. In yet another embodiment, the invention provides transgenic animals which harbor the nucleic acid sequences provided herein and which expres a nucleotide sequence of interest in an age-related and/or liver-specific manner. The nucleic acid sequences provided herein are useful in, for example, identifying and isolating functional homologs of AE5' and AE3', and amplifying at least a portion of AE5' and AE3'. Importantly, the nucleic acid sequences of the invention are also useful in age-related expression and/or liver-specific expression of a nucleotide sequence of interest in an animal, in gene therapy, and in reducing expression of factor IX in an animal.

The invention is further discussed under (A) Regulatory Nucleic Acid Sequences, (B) Using Probes To Identify And Isolate Homologs Of AE5' and AE3', (C) Using Primers to Amplify At Least A Portion Of AE5' And AE3', (D) Methods For Regulating Gene Expression, (E) Gene Therapy, and (F) Reducing Expression Of Factor IX In An Animal.

A. Regulatory Nucleic Acid Sequences

The regulatory nucleic acid sequences of the invention and their surprising properties in regulating gene expression were discovered during the inventor's investigation of the mechanisms underlying age-associated regulation of the human factor IX, which is involved in blood coagulation. Blood coagulation plays a critical role not only in homeostasis, but also in many physiological and pathological conditions [Saito in *Disorders of Hemostasis*, O. D. Ratnoff and C. D. Forbes, Eds., Sauders, Philadelphia, ed. 2 (1991), pp. 18-47; Kurachi et al. (1993) Blood Coagul. Fibrinol. 4:953-974]. Blood coagulation potential in humans as well as in other mammals reaches the young adult level around the age of weaning [Yao et al. (1991) Thromb. Haemost. 65:52-58; Andrew et al. (1992) Blood 80:1998-2005; Andrew et al. Blood (1987) 70:165-172; Andrew et al. (1988) Blood 72:1651-1657]. This is followed by a gradual increase in coagulation potential during young adulthood, and an almost two-fold increase by old age [Sweeney and Hoemig (1993) Am. J. Clin. Pathol. 99:687-688; Kurachi et al. (1996) Thromb. Haemost. 76:965-969]. This age-associated increase in coagulation potential takes place in healthy centenarians [Marie et al. (1995) Blood 85:3144-3149], indicating that the increase is a normal phenomenon associated with aging.

It is the inventors' consideration that this increase in coagulation potential may make a crucial contribution to the development and progression of age-associated diseases such as cardiovascular and thrombotic disorders [Conlan et al. (1993) The Atherosclerosis Risk in Communities (ARIC) Study 70:380-385; Balleisen et al. (1985) Thromb. Haemost. 54:475-479; Rode et al. (1996) Nat. Med. 2:293-298; Woodward et al. (1997) Brit. J. Haemat. 97:785-797]. The inventors' consideration was based on the observation that this increase in blood coagulation potential coincides with plasma level increases of pro-coagulant factors such as factor IX, whereas plasma levels of anti-coagulation factors (such as antithrombin III and protein C) or of factors involved in fibrinolysis are only marginally affected [Conlan et al. (1994) The Atherosclerosis Risk in Committees (ARIC) Study 72:551-556; Lowe et al. (1997) Brit. J. Haemat. 97:775-784]. These facts strongly suggested to the inventors that the observed increase in blood coagulation activity with advancing age is due to regulated events. Plasma levels of each protein factor involved in blood coagulation, fibrinolysis and their regulatory systems are presumably determined by the balance of the many processes involved. At present, little is known about why an advancing age-associated increase in blood coagulation activity exists, or what molecular mechanisms are involved in age-dependent regulation (homeostasis) of blood coagulation [Finch in *Longevity, Senescence, and the Genome*, The University of Chicago Press, Chicago, 1990].

Blood coagulation factor IX (FIX) occupies a key position in the blood coagulation cascade where the intrinsic and extrinsic pathways merge [Saito in *Disorders of Hemostasis*, O. D. Ratnoff and C. D. Forbes, Eds., Sauders, Philadelphia, ed. 2 (1991), pp. 18-47; Kurachi et al. (1993) Blood Coagul. Fibrinol. 4:953-974]. FIX is synthesized in the liver with strict tissue-specificity, and its deficiency results in the bleeding disorder hemophilia B. In normal humans the plasma activity and protein concentration levels of human FIX (hFIX) increase with advancing age [Sweeney and Hoemig (1993) Am. J. Clin. Pathol. 99:687-688; Kurachi et al. (1996) Thromb. Haemost. 76:965-969]. Mouse FIX (mFIX) plasma activity also increases with age in a manner similar to hFIX, and is directly correlated with an increase in liver mFIX messenger RNA (mRNA) level [Sweeney and Hoemig (1993) Am. J. Clin. Pathol. 99:687-688; Kurachi et al. (1996) Thromb. Haemost. 76:965-969]. However, nothing else is known about the molecular mechanisms underlying such an increase. In investigating the basic molecular mechanisms responsible for age-associated regulation of hFIX, the inventors discovered the nucleotide sequences which regulate age-associated expression, and which direct liver-specific expression, of the exemplary hFIX gene.

The discovery of the invention sequences was made possible, in part, by the inventors' use of the hFIX promoter in combination with the coding sequence for hFIX instead of with the coding sequence for commonly used reporter proteins. The discovery of the surprising functions of the nucleotide sequences provided herein was also made possible by the inventors' use of longitudinal in vivo analyses, rather than of in vitro analyses. In particular, the inventors' earlier studies used reporter genes (including bacterial β-galactosidase and chloramphenicol acetyltransferase [CAT]) which are heterologous to the factor IX promoter. In these earlier studies, the factor IX promoter showed only very weak expression activity in vitro [Kurachi et al. (1995) J. Biol. Chem. 270:5276-5281]. Use of such heterologous reporter genes made it impossible to reliably and quantitatively perform longitudinal analyses of transgene expression in animals. The inventors unexpectedly observed that the use of hFIX minigene expression vectors which contained the hFIX promoter and its homologous hFIX gene were capable of producing high level plasma hFIX in vivo. This unexpected observation not only solved the problems associated with the use of genes which are heterologous to the hFIX promoter by providing a reliable animal assay system, but also provided multiple unexpected critical insights into the regulatory mechanisms of the hFIX gene, including the determination of nucleotide sequences which regulate the stability and age-related increased expression of the exemplary hFIX gene.

The present invention provides the 32-nucleotide nucleic acid sequence (SEQ ID NO:1) of AE5' which corresponds to the sequence from 2164 to 2195 of the hFIX gene deposited in GenBank as accession number K02402, and which corresponds to the sequence from −802 to −771 of GenBank accession number K02402 when in relation to the hFIX start codon (ATG) in which the adenine is designated as position +30.

The present invention also provides the 1273-nucleotide nucleic acid sequence (SEQ ID NO:3) (FIG. 13) of AE3' which corresponds to the sequence from 34,383 to 35,655 of GenBank accession number K02402, and which corresponds to the sequence from 31,418 to 32,690 of FIG. 8 when in relation to the hFIX start codon (ATG) in which the adenine is designated as position zero.

The terms "age-related regulatory activity" and "age-related activity" when made in reference to a nucleic acid sequence refer to the ability of the nucleic acid sequence to alter in an age-related manner (e.g., increase over a period of time) the level of transcription into mRNA and/or the synthesis of a polypeptide encoded by nucleotide sequence of interest which is operably linked to a promoter sequence as compared to the level of transcription into mRNA of the nucleotide sequence of interest which is operably linked to the promoter sequence in the absence of the nucleic acid sequence which has age-related regulatory activity. An "age regulatory sequence" is herein used to refer to a nucleic acid sequence which has age-related regulatory activity.

To illustrate, where expression levels of a gene of interest decrease over a period of time, a nucleic acid sequence is said to have age-related regulatory activity if (when operably linked to the gene of interest) it results in (a) a smaller decrease in expression levels of the gene over the same period of time as compared to the decrease in expression levels in the absence of the nucleic acid sequence, (b) relatively constant (i.e., unchanged) expression levels over the same period of time, or (c) increased expression levels over the same period of time.

The terms "operably linked," "in operable combination," and "in operable order" as used herein refer to the linkage of nucleic acid sequences such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest and/or the synthesis of a polypeptide encoded by the nucleotide sequence of interest. Similarly, operably linking a nucleic acid sequence having age-related regulatory activity to a promoter sequence and to a nucleotide sequence of interest means linking the nucleic acid sequence having age-related regulatory activity, the promoter sequence and the nucleotide sequence of interest in a manner such that the nucleic acid sequence having age-related regulatory activity is capable of altering over a period of time the level of transcription into mRNA of the nucleotide sequence of interest and/or the synthesis of a polypeptide encoded by the nucleotide sequence of interest.

Methods for determining age-related regulatory activity of a candidate nucleic acid sequence, given the teachings of the present specification, are within the ordinary skill in the art and are exemplified by the methods disclosed herein. For example, a test vector is constructed in which the candidate nucleic acid sequence is linked upstream or downstream of a promoter sequence which is operably linked to a nucleotide sequence of interest (e.g., Example 1). A control vector which is similar to the test vector but which lacks the candidate nucleic acid sequence is also constructed. The test vector and control vector are separately introduced into a host cell. It is preferred that the host cell (e.g., fertilized egg) be capable of generating a transgenic multicellular organism, e.g., a transgenic mouse (e.g., Example 3) and that transgenic multicellular organisms are generated. Longitudinal analyses of the expression of mRNA which is encoded by the nucleotide sequence of interest (e.g., by Northern blot hybridization) over a period of time in, and preferably over the entire life span of, founders and successive generations of the transgenic multicellular organism are carried out (e.g., Example 3). The detection in any tissue of mRNA and/or protein levels which are encoded by the nucleotide sequence of interest and which are greater in transgenic animals harboring the test vector as compared to the mRNA and/or protein levels in transgenic animals harboring the control vector at least one point in time indicates that the candidate nucleic acid sequence has age-related regulatory activity.

Figure 2B:
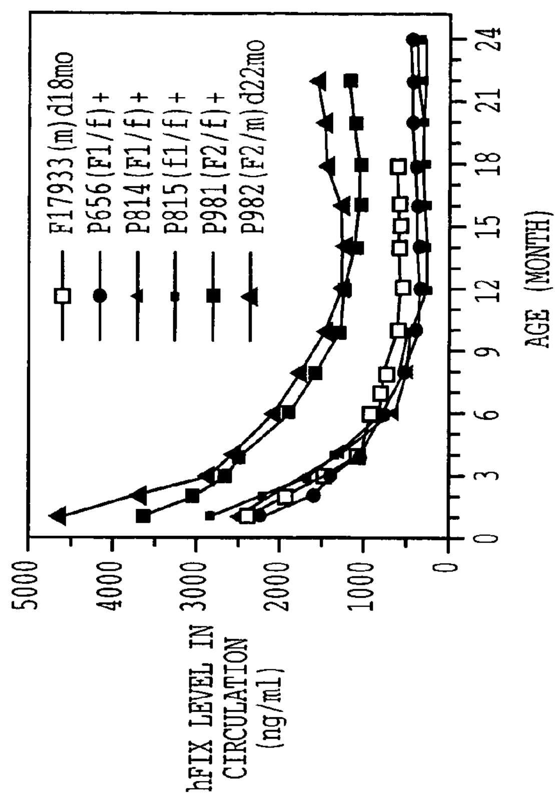
FIG. 2 shows graphs of longitudinal analyses of transgenic mice which carry −416FIXm1 (A), −416FIXm1/1.4 (B), −590FIXm1 (C), −679FIXm1 (D), and −770FIXm1 (E) expression vectors and which produce high initial prepubertal, but rapidly decreasing, hFIX expression levels with age.
Figure 2A:
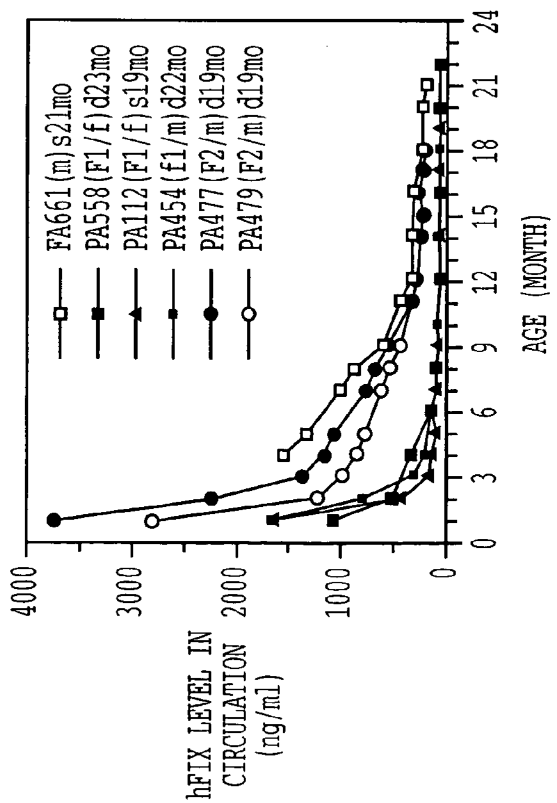
Figures 2C, 2D, 2E:
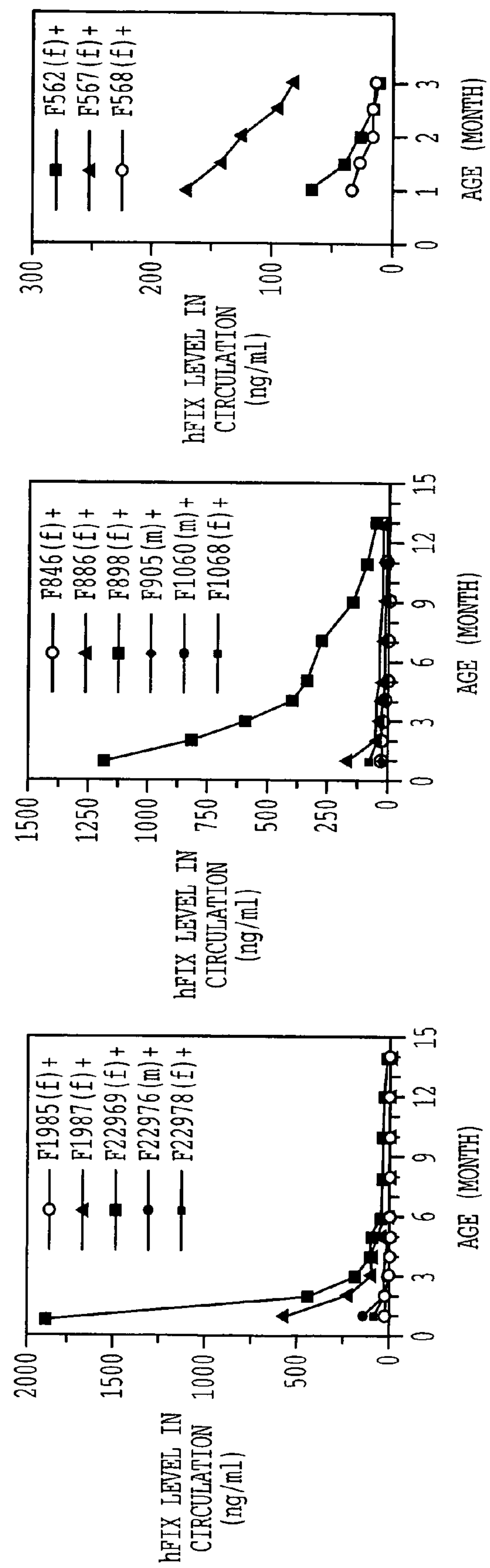

For example, evidence provided herein shows the surprising result that AE5' (SEQ ID NO:1) alone has age-related regulatory activity in that AE5' stabilizes hFIX mRNA whereby hFIX mRNA levels are essentially unchanged at different time points over the entire life span of transgenic animals (FIG. 4, A, C and E) as compared to the declining hFIX mRNA levels in transgenic animals which harbor vectors that lack AE5' (FIGS. 2A and 2E). The age-related regulatory activity of AE5' was observed regardless whether AE5' was placed upstream (FIG. 4A) or downstream (FIG. 4E) of the promoter sequence in the expression construct.

Figure 5:
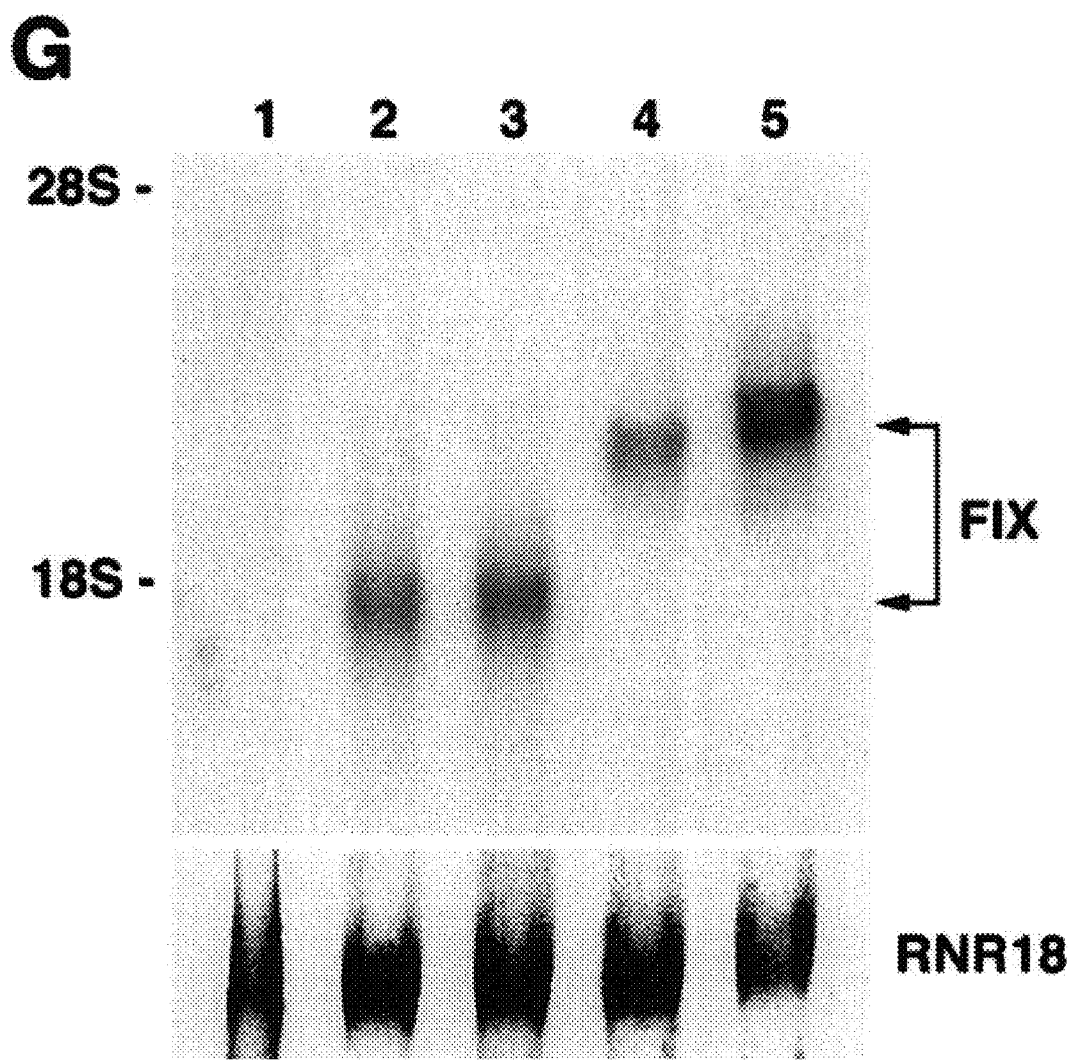
FIG. 5 shows a Northern blot of transgenic mice carrying −802FIXm1 and −802FIXm1/1.4 expression vectors.

Furthermore, data provided herein demonstrates the unexpected result that AE3' (SEQ ID NO:3) alone has age-related regulatory activity in that AE3' increases hFIX mRNA at several time points during the life of transgenic animals (FIG. 2B) relative to the hFIX mRNA levels at the same time points in transgenic animals harboring vectors that lack AE3' (FIG. 2A). AE3' substantially increased the steady state hFIX mRNA levels (FIG. 5). This result which was observed in vivo was surprising in part because AE3' exhibited weak down regulatory effects on hFIX production in vitro. Without limiting the invention to any particular mechanism, these results suggest that AE3' functions by increasing hFIX mRNA stability which directly correlates with an increase in the hFIX protein level in the circulation. Also without intending to limit the invention to any particular theory, it is the inventors' consideration that the age-related regulatory activity of AE3' is due to the sl structure-forming dinucleotide repeats present in the 3'UTR; the sl region is the 103 bp sequence (SEQ ID NO:61) from nt 32,141 through nt 32,243 of FIG. 8. This consideration is based on the inventors' observation that dinucleotide repeats, such as $(AT)_n$ of the 3' UTR of various genes, can form sl structures in mRNA, which upon binding specific proteins are known to modulate mRNA stability, mostly to a less stable state [Ross (1995) Microbiol. Rev. 59:423-450].

Importantly, the invention demonstrates the surprising synergistic action of AE5' and AE3' which together result in hFIX mRNA levels which not only are greater at each time point tested over the life span of transgenic animals (FIGS. 4 B and D) as compared to hFIX mRNA levels in transgenic animals harboring vectors that lack both AE5' and AE3', but also that the profile of increased human FIX mRNA levels over the life span of transgenic mouse recapitulates the profile of increased mouse FIX mRNA levels as a wild-type mouse ages.

Data presented herein further demonstrate that the age-related regulatory activity of AE5' alone, of AE3' alone, and of the combination of AE5' and AE3' is independent of the level of expression of the transgenes harboring them, sex, generation or zygosity status of the transgenic animals.

The present invention is not limited to SEQ ID NOs:1 and 3 but specifically contemplates portions thereof. As used herein the term "portion" when made in reference to a nucleic acid sequence refers to a fragment of that sequence. The fragment may range in size from five (5) contiguous nucleotide residues to the entire nucleic acid sequence minus one nucleic acid residue. Thus, a nucleic acid sequence comprising "at least a portion of" a nucleotide sequence comprises from five (5) contiguous nucleotide residues of the nucleotide sequence to the entire nucleotide sequence.

In a preferred embodiment, portions of SEQ ID NO:1 contemplated to be within the scope of the invention include, but are not limited to, the 7-nucleotide nucleic acid sequence of the polyomavirus enhance activator 3 (PEA-3) (5'-GAGGAAG-3') (SEQ ID NO:2) which corresponds to the sequence from 2176 to 2182 of GenBank accession number K02402, and which corresponds to the sequence from −790 to −784 of GenBank accession number K02402 when in relation to the hFIX start codon (ATG) in which the adenine is designated as position zero. A nucleotide sequence [5'-CAGGAAG-3' (SEQ ID NO:40)] which is homologous to the invention's PEA-3 nucleotide sequence was initially reported in the art as a polyoma virus enhancer, and was reported to be involved in the regulation of expression of various genes (e.g., collagen gene and c-fos) in several tissues [Martin et al. (1988) Proc. Natl. Acad. Sci. 85:5839-5843; Xin et al. (1992) Genes & Develop. 6:481-496; Chotteau-Lelievre et al. (1997) Oncogene 15:937-952; Gutman and Wasylyk (1990) EMBO J. 9:2241-2246]. However, the PEA-3 protein sequence [or PEA-3 related protein(s)] which binds to nucleotide sequences which are homologous to the invention's PEA-3 nucleotide sequence has not been reported to be either liver-specific or enriched in the liver.

Other portions of SEQ ID NO: 1 included within the scope of the invention include, for example, SEQ ID NO:33 [5'-tcgaggaagga-3'], SEQ ID NO:34 [5'-agtcgaggaaggata-3'], SEQ ID NO:35 [5'-tcagtcgaggaaggatagg-3'], SEQ ID NO:36 [5'-attcagtcgaggaaggatagggt-3'], SEQ ID NO:37 [5'-ccattcagtcgaggaaggatagggtgg-3'], and SEQ ID NO:38 [5'-gccattcagtcgaggaaggatagggtggta-3'], all of which include the PEA-3 nucleotide sequence.

In a preferred embodiment, portions of SEQ ID NO:3 contemplated to be within the scope of the invention include, but are not limited to, SEQ ID NO:51 [5'-TTATTTTATATATATAATATATATATAAAATA-3'], SEQ ID NO:52 [5'-TAT AATATA-3'], SEQ ID NO:53 [5'-CAATATAAATATATAG-3'], SEQ ID NO:54 [5'-TGTGTGTGTATGCGTGTGTGTAGACACACACG-CATACACACATA-3'], the combination of SEQ ID NOs:51 and 52, i.e., SEQ ID NO:55 [5'-TTATTTTATA TATATAATATATATATAAAATATATAATATA-3'], the combination of SEQ ID NOs:52 and 53, i.e., SEQ ID NO:56 [5'-TATAATATACAATATAAATATATAG-3'], the combination of SEQ ID NOs:53 and 54, i.e., SEQ ID NO:57 [5'-CAATATAAAT ATATAGTGTGTGTGTATGCGTGTGTGTAGACACACACGCATACACACATA-3'], the combination of SEQ ID NOs:51, 52, 53, and 54, i.e., SEQ ID NO:58 [5'-TTAT TTTATATATATAATATATATATAAAATATATAATATACA ATATAAATATATAG TGTGTGTGTATGCGTGTGTGTA-GACACACACGCATACACACATA-3'], the 723 bp sequence (SEQ ID NO:59) from nt 31,418 through nt 32,140 of FIG. 8, the 447 bp sequence (SEQ ID NO:60) from nt 32,244 through nt 32,690 of FIG. 8, and the 103 bp sequence (SEQ ID NO:61) (i.e., the sl region of the 3' UTR) from nt 32,141 through nt 32,243 of FIG. 8.

The nucleotide sequence of portions of SEQ ID NOs:1 and 3 which exhibit age-related regulatory activity may be determined using methods known in the art, e.g., using deletion constructs (e.g., see Yang et al. (1998) J. Biol. Chem. 273:891-897). Briefly, several expression plasmids are constructed to contain a reporter gene under the control of a promoter and of different candidate nucleotide sequences which are obtained either by restriction enzyme deletion of internal sequences in SEQ ID NOs:1 and 3, restriction enzyme truncation of sequences at the 5' and/or 3' end of SEQ ID NOs:1 and 3, by the introduction of single nucleic acid base changes by PCR into SEQ ID NOs:1 and 3, or by chemical synthesis. The gene-related regulatory activity of the different constructs is determined as described supra in order to determine whether the candidate nucleotide sequence exhibits age-related regulatory activity.

The sequences of the present invention are not limited to SEQ ID NOs: 1 and 3 and portions thereof, but also include homologs of SEQ ID NOs:1 and 3, and homologs of portions thereof. Homologs of SEQ ID NOs:1 and 3, and of portions thereof, include, but are not limited to, nucleotide sequences having deletions, insertions or substitutions of different nucleotides or nucleotide analogs as compared to SEQ ID NOs: 1 and 3, and of portions thereof, respectively. Such homologs may be produced using methods well known in the art.

A “homolog” of SEQ ID NO:1 is defined as a nucleotide sequence having more than 63% identity and less than 100% identity with SEQ ID NO:1. Homologs of SEQ ID NO:1 are exemplified, but not limited to, SEQ ID NO:66 (5'-acccatt cagtcgagga aggatagggt ggtat-3') which is the sequence from nt 2,164 to nt 2,195 of GenBank accession number k02402, except that the G at nt 1,265 is replaced with a C; SEQ ID NO:67 (5'-agccatt gagtcgagga aggatagggt ggtat-3') which is the sequence from nt 2,164 to nt 2,195 of GenBank accession number k02402, except that the C at nt 2,171 is replaced with a G; SEQ ID NO:68 (5'-agccatt cagacgagga aggatagggt ggtat-3') is the sequence from nt 2,164 to nt 2,195 of GenBank accession number k02402, except that the T at nt 2,174 is replaced with a A; SEQ ID NO:69 (5'-agccatt cagtcgagga aggatagggt ggttt-3') which is the sequence from nt 2,164 to nt 2,195 of GenBank accession number k02402, except that the A at nt 2,194 is replaced with a T; SEQ ID NO:70 (5'-agccatt cagtcgagga tcccaagggt ggtat-3') which is the sequence from nt 2,164 to nt 2,195 of GenBank accession number k02402, except that AGGGT beginning at nt 2,186 is replaced with TCCCA; SEQ ID NO:71 (5'-agccatt cagtcgagga aggatagggcctaat-3') which is the sequence from nt 2,164 to nt 2,195 of GenBank accession number k02402, except that TGGT beginnining at nt 2,190 is replaced with CCTA; SEQ ID NO:72 (5'-agaccatt cagtcgagga aggatagggt ggtat-3') which is the sequence from nt 2,164 to nt 2,195 of GenBank accession number k02402, except that a A is inserted after nt 2,165; SEQ ID NO:73 (5'-agccatt cagtcgagga aggatagcggt ggtat-3') which is the sequence from nt 2,164 to nt 2,195 of GenBank accession number k02402, except that a C is inserted after nt 2,187; SEQ ID NO:74 (5'-agccatt cagtcgagga aggataat-3') which is the sequence from nt 2,164 to nt 2,195 of GenBank accession number k02402, except that GGGTGGT beginning at nt 12,187 is deleted; and SEQ ID NO:75 (5'-agccatt cgagga aggatagggt ggtat-3') which is the sequence from nt 2,164 to nt 2,195 of GenBank accession number k02402, except that CAGT beginning at nt 2,171 is deleted.

A “homolog” of SEQ ID NO:2 is defined as a nucleotide sequence having more than 75% identity and less than 100% identity with SEQ ID NO:2. Homologs of SEQ ID NO:2 include, for example, GAGGATG (SEQ ID NO:39), CAGGAAG (SEQ ID NO:40), CAGGATG (SEQ ID NO:41), GTGGAAG (SEQ ID NO:62), GTGGATG (SEQ ID NO:63), CTGGAAG (SEQ ID NO:64), CTGGATG (SEQ ID NO:65), and CAGGAAG (SEQ ID NO:84).

A “homolog” of SEQ ID NO:3 is defined as a nucleotide sequence having less than 100% and more than 60% identity with SEQ ID NO:3. Homologs of SEQ ID NO:3 are exemplified, but not limited to, SEQ ID NOs:76-83 shown in FIG. 13. Specifically, SEQ ID NO:76 is the sequence from nt 34,383 to nt 35,655 of GenBank accession number k02402, except that the C at nt 34,390 has been replaced with a G. SEQ ID NO:77 is the sequence from nt 34,383 to nt 35,655 of GenBank accession number k02402, except that the T at nt 34,649 has been replaced with a A. SEQ ID NO:78 is the sequence from nt 34,383 to nt 35,655 of GenBank accession number k02402, except that the GC beginning at nt 34,959 has been replaced with a CG. SEQ ID NO:79 is the sequence from nt 34,383 to nt 35,655 of GenBank accession number k02402, except that the CATG beginning at nt 35,501 has been replaced with a GTAC. SEQ ID NO:80 is the sequence from nt 34,383 to nt 35,655 of GenBank accession number k02402, except that TT is inserted after the A at nt 34,681. SEQ ID NO:81 is the sequence from nt 34,383 to nt 35,655 of GenBank accession number k02402, except that TGC is inserted after the C at nt 35,581. SEQ ID NO:82 is the sequence from nt 34,383 to nt 35,655 of GenBank accession number k02402, except that A at nt 35,636 is deleted. SEQ ID NO:83 is the sequence from nt 34,383 to nt 35,655 of GenBank accession number k02402, except that the G at nt 34,383 is deleted.

A “homolog” of SEQ ID NO:59 is defined as a nucleotide sequence having less than 100% and more than 62% identity with SEQ ID NO:59.

A “homolog” of SEQ ID NO:60 is defined as a nucleotide sequence having less than 100% and more than 60% identity with SEQ ID NO:60.

A “homolog” of SEQ ID NO:61 is defined as a nucleotide sequence having less than 100% and more than 60% identity with SEQ ID NO:61.

Homologs of a portion of SEQ ID NO: 1 are exemplified by homologs of the PEA-3 nucleotide sequence (SEQ ID NO:2), which include, for example, GAGGATG (SEQ ID NO:39), CAGGAAG (SEQ ID NO:40), CAGGATG (SEQ ID NO:41), GTGGAAG (SEQ ID NO:62), GTGGATG (SEQ ID NO:63), CTGGAAG (SEQ ID NO:64), CTGGATG (SEQ ID NO:65), and CAGGAAG (SEQ ID NO:84).

The present invention also contemplates functioning or functional homologs of SEQ ID NO:1, of portions of SEQ ID NO:1 (e.g., functional portions of SEQ ID NOs:2, and 33-38), of SEQ ID NO:3, and of portions of SEQ ID NO:3 (e.g., functional portions of SEQ ID NOs:51-61).

A “functional homolog” of SEQ ID NO: 1 is defined as a nucleotide sequence having more than 63% identity and less than 100% identity with SEQ ID NO:1, and which has age-related regulatory activity. Alternatively, a functional homolog of SEQ ID NO:1 is a nucleotide sequence having more than 63% identity and less than 100% identity with SEQ ID NO:1, and having liver-specific activity.

A “functional homolog” of SEQ ID NO:2 is defined as a nucleotide sequence having more than 75% identity and less than 100% identity with SEQ ID NO:2, and which has age-related regulatory activity. Alternatively, a functional homolog of SEQ ID NO:2 is a nucleotide sequence having more than 75% identity and less than 100% identity with SEQ ID NO:2, and having liver-specific activity.

A “functional homolog” of SEQ ID NO:3 is defined as a nucleotide sequence having less than 100% and more than 60% identity with SEQ ID NO:3, and which has age-related regulatory activity.

A “functional homolog” of SEQ ID NO:59 is defined as a nucleotide sequence having less than 100% and more than 62% identity with SEQ ID NO:59, and which has age-related regulatory activity.

A "functional homolog" of SEQ ID NO:60 is defined as a nucleotide sequence having less than 100% and more than 60% identity with SEQ ID NO:60, and which has age-related regulatory activity.

A "functional homolog" of SEQ ID NO:61 is defined as a nucleotide sequence having less than 100% and more than 60% identity with SEQ ID NO:61, and which has age-related regulatory activity.

The present invention is not limited to sense molecules of SEQ ID NOs: 1 and 3 but contemplates within its scope antisense molecules comprising a nucleic acid sequence complementary to at least a portion (e.g., a portion greater than 10 nucleotide bases in length and more preferably greater than 100 nucleotide bases in length) of the nucleotide sequence of SEQ ID NOs:1 and 3. These antisense molecules find use in, for example, reducing or preventing expression of a gene (e.g. hFIX) whose expression is regulated by SEQ ID NOs:1 and 3.

The nucleotide sequence of SEQ ID NOs:1 and 3, portions, homologs and antisense sequences thereof may be synthesized by synthetic chemistry techniques which are commercially available and well known in the art [see Caruthers M H et al., (1980) Nuc. Acids Res. Symp. Ser. 215-223; Horn T. et al., (1980) Nuc. Acids Res. Symp. Ser. 225-232]. Additionally, fragments of SEQ ID NOs:1 and 3 can be made by treatment of SEQ ID NOs:1 and 3 with restriction enzymes followed by purification of the fragments by gel electrophoresis. Alternatively, sequences may also be produced using the polymerase chain reaction (PCR) as described by Mullis [U.S. Pat. Nos. 4,683,195, 4,683,202 and 4,965,188, all of which are hereby incorporated by reference]. SEQ ID NOs:1 and 3, portions, homologs and antisense sequences thereof may be ligated to each other or to heterologous nucleic acid sequences using methods well known in the art.

The nucleotide sequence of synthesized sequences may be confirmed using commercially available kits as well as using methods well known in the art which utilize enzymes such as the Klenow fragment of DNA polymerase I, Sequenase®, Taq DNA polymerase, or thermostable T7 polymerase. Capillary electrophoresis may also be used to analyze the size and confirm the nucleotide sequence of the products of nucleic acid synthesis, restriction enzyme digestion or PCR amplification.

It is readily appreciated by those in the art that the sequences of the present invention may be used in a variety of ways. For example, the nucleic acid sequences of the invention and portions thereof can be used as probes for the detection and isolation of functional homologs of AE5' and AE3', amplification of homologous nucleotide sequences, age-related and/or liver-specific expression of a nucleotide sequence of interest in an animal, gene therapy, and reducing factor IX levels in an animal.

B. Using Probes to Identify and Isolate Homologs of AE5' and AE3'

The invention provided herein is not limited to SEQ ID NO:1 and 3, homologs and portions thereof having age-related regulatory activity, but includes sequences having no age-related regulatory activity (i.e., non-functional homologs and non-functional portions of homologs). The use of such sequences may be desirable, for example, where a portion of SEQ ID NOs:1 and 3 is used as a probe to detect the presence of SEQ ID NOs:1 and 3, respectively, or of portions thereof in a sample.

As used herein, the term "probe" refers to an oligonucleotide, whether occurring naturally as in a purified restriction digest or produced synthetically, recombinantly or by PCR amplification, which is capable of hybridizing to a nucleotide sequence of interest. A probe may be single-stranded or double-stranded. It is contemplated that any probe used in the present invention will be labelled with any "reporter molecule," so that it is detectable in any detection system including, but not limited to enzyme (e.g., ELISA, as well as enzyme-based histochemical assays), fluorescent, radioactive, calorimetric, gravimetric, magnetic, and luminescent systems. It is not intended that the present invention be limited to any particular detection system or label.

The probes provided herein are useful in the detection, identification and isolation of, for example, sequences such as those listed as SEQ ID NOs:1 and 3 as well as of homologs thereof. Preferred probes are of sufficient length (e.g., from about 9 nucleotides to about 20 nucleotides or more in length) such that high stringency hybridization may be employed. In one embodiment, probes from 20 to 50 nucleotide bases in length are employed.

C. Using Primers to Amplify at Least a Portion of AE5' and AE3'

The invention provided herein is not limited to SEQ ID NOs:1 and 3, homologs and portions thereof having age-related regulatory activity, but includes sequences having no age-related regulatory activity. This may be desirable, for example, where a portion of the nucleic acid sequences set forth as SEQ ID NOs:1 and 3 is used as a primer for the amplification of nucleic acid sequences by, for example, polymerase chain reactions (PCR) or reverse transcription-polymerase chain reactions (RT-PCR). The term "amplification" is defined as the production of additional copies of a nucleic acid sequence and is generally carried out using polymerase chain reaction technologies well known in the art [Dieffenbach C W and G S Dveksler (1995) *PCR Primer, a Laboratory Manual*, Cold Spring Harbor Press, Plainview N.Y.]. As used herein, the term "polymerase chain reaction" ("PCR") refers to the method of K. B. Mullis disclosed in U.S. Pat. Nos. 4,683,195, 4,683,202 and 4,965,188, all of which are hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are the to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}P$-labeled deoxyribonucleotide triphosphates, such as dCTP or dATP, into the amplified segment). In addition to genomic DNA, any nucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long (e.g., from about 9 nucleotides to about 20 nucleotides or more in length) to prime the synthesis of extension products in the presence of the inducing agent. Suitable lengths of the primers may be empirically determined and depend on factors such as temperature, source of primer and the use of the method. In one embodiment, the present invention employs primers from 20 to 50 nucleotide bases in length.

The primers contemplated by the invention are useful in, for example, identifying sequences which are homologous to AE5' and AE3' in mammals, yeast, bacteria, and in other organisms.

D. Methods for Regulating Gene Expression

The present invention provides methods for regulating expression of a nucleotide sequence of interest over a period of time in a cell or multicellular organism. Specifically, gene expression is preferably regulated in a multicellular organism. In one embodiment, expression of a nucleotide sequence of interest is stabilized such that the level of mRNA and/or protein encoded by the nucleotide sequence of interest remains relatively unchanged at different times during the life of the organism. In an alternative embodiment, expression of a nucleotide sequence of interest is increased. Increased expression means that the level of mRNA and/or protein encoded by the nucleotide sequence of interest at a given time point is greater than the level of mRNA and/or protein, respectively, at an earlier time point during the life of the organism or cell. Alternatively, increased expression means that the level of mRNA and/or protein encoded by the nucleotide sequence of interest is greater than the level of mRNA and/or protein, respectively, at the same time point in the life of the organism or cell as compared to the level of mRNA and/or protein when expressed in the absence of the sequences of the invention.

In one embodiment, regulating expression of a nucleotide sequence of interest over a period of time is accomplished by introducing into a host cell a vector that contains a nucleotide sequence of interest operably linked to a promoter sequence and to sequences provided herein which have age-related regulatory activity. The transfected host cell is allowed to develop into a transgenic animal in which the nucleotide sequence of interest is expressed in at least one tissue. These steps are further described below for specific embodiments.

1. Expression Constructs

In one embodiment of the methods of the invention for regulating expression of a nucleotide sequence of interest in an age-related manner and/or to liver tissue, a vector is constructed in which the nucleic acid sequences of the invention (e.g., AE5' alone, AE3' alone, or a combination of AE5' and AE3') are operably linked to a promoter sequence and to a nucleotide sequence of interest. In one embodiment, the nucleotide sequence of interest is the coding region of the hFIX gene (Example 1). In another embodiment the nucleotide sequence of interest is the coding region of the protein C gene (Example 7).

The invention is not limited to coding sequences of the hFIX gene or protein C gene. Rather, any nucleotide acid sequence whose expression is desired to be regulated by sequences provided herein are contemplated to be within the scope of this invention. Such nucleotide sequences include, but are not limited to, coding sequences of structural genes which encode a protein [e.g., reporter genes, selection marker genes, oncogenes, drug resistance genes, growth factor genes, activator protein 1 gene, activator protein 2 gene, Sp1 gene, etc.]. In one preferred embodiment, the structural gene is the human α1-antitrypsin gene (FIG. 10) (SEQ ID NO:42) which encodes a plasma proteinase inhibitor used for treating emphysema. In another preferred embodiment, the structural gene is one encoding the human antithrombin III (FIG. 11) (SEQ ID NO:43) which is a plasma proteinase inhibitor for activated blood coagulation factors and whose activity is increased by heparin. In yet another preferred embodiment, the structural gene is the gene encoding the PEA-3 protein (FIG. 9) (SEQ ID NO:47) and/or its related protein, which has been shown to bind specifically to homologs of the PEA-3 nucleotide sequence (SEQ ID NO:2) disclosed herein.

The invention is not limited to using a single nucleotide sequence of interest in operable combination with the sequences of the invention. Rather, a plurality (i.e., more than one) of nucleotide sequences of interest may be ligated in tandem such that their expression is regulated by the regulatory sequences of the invention. A plurality of coding sequences may be desirable, for example, where it is useful to express a transcription product of more than one gene to permit interaction of these transcriptional products. Alternatively, a plurality of coding sequences may be desirable where one of the gene sequences is a reporter gene sequence. For example, it may be advantageous to place a coding sequence of a reporter gene in tandem with the coding sequence of a gene of interest such that expression of the coding region of both the reporter gene and the gene of interest is regulated by the sequences of the invention. Expression of the reporter gene usually correlates with expression of the gene of interest. Examples of reporter gene sequences include the sequences encoding the enzymes β-galactosidase and luciferase. Fusion genes may also be desirable to facilitate purification of the expressed protein. For example, the heterologous sequence which encodes protein A allows purification of the fusion protein on immobilized immunoglobulin. Other affinity traps are well known in the art and can be utilized to advantage in purifying the expressed fusion protein. For example, pGEX vectors (Promega, Madison Wis.) may be used to express the polypeptides of interest as a fusion protein with glutathione S-transferase (GST). In general, such fusion proteins are soluble and can easily be purified from lysed cells by adsorption to glutathione-agarose beads followed by elution in the presence of free glutathione. Other fusion polypeptides useful in the purification of proteins of interest are commercially available, including histidine tails (which bind to $Ni^{2+}$), biotin (which binds to streptavidin), and maltose-binding protein (MBP) (which binds to amylose). Proteins made in such systems may be designed to include heparin, thrombin or factor XA protease cleavage sites so that the cloned polypeptide of interest can be released at will from the heterologous polypeptide moiety to which it is fused.

One of skill in the art would understand that where a plurality of nucleotide sequences of interest is operably linked to sequences of the present invention, the nucleotide sequences of interest may be either contiguous or separated by intervening polynucleotide sequences, so long as the nucleic acid sequences of interest are operably linked to the promoter sequence, and so long as the sequences of the invention are operably linked to the promoter sequence.

While specific preferred embodiments used herein disclose the use of the hFIX promoter and the CMV promoter, it is not intended that the invention be limited to the type or source of the promoter sequence which is operably linked to the sequences of the invention. Any promoter whose activity is desired to be regulated by the sequences provided herein is contemplated to be within the scope of the invention. Exemplary promoters include the tRNA promoter, 5S rRNA promoters, histone gene promoters, RSV promoter (can be isolated from vector plasmid pRc/RSV from Invitrogen), retrovirus LTR promoter (can be isolated from vector plasmid pLXSN from Clontech) SV40 promoter (located between positions +3530 to +3192 in vector plasmid pCR3 from Invitrogen), PEPCK promoter, MT promoter, SRα promoter, P450 family promoters, GAL7 promoter, $T_7$ promoter having the 23-bp sequence (SEQ ID NO:44) 5'-TAATACGACTCACTATAGGGCGA-3', $T_3$ promoter having the 24-bp sequence (SEQ ID NO:45) 5'-TTATTAACCCTCACTAAAGGGAAG-3', SP6 promoter having the 23-bp sequence (SEQ ID NO:46) 5'-ATTTAGGTGACACTATAGAATAC-3', and K11 promoter. The $T_7$ promoter, $T_3$ promoter, SP6 promoter and K11 promoter have been described in U.S. Pat. No. 5,591,601, the entire contents of which are incorporated by reference.

Nor is the invention intended to be limited to the use of a single promoter. For example, chimeric promoters (i.e., two or more promoters which are derived from at least one gene) are expressly contemplated to be within the scope of the invention. Such chimeric promoters may be desirable where, for example, chimeric promoters result in increased levels of expression of an operably linked downstream coding sequence. Chimeric promoters are known in the art and include, for example, the double Tet promoter [Kistner et al. (1996) Proc. Natl. Acad. Sci. USA 93:10933-10938], and the U1 snRNA promoter-CMV promoter/enhancer [Bartlett et al. (1996) Proc. Natl. Acad. Sci. USA 93:8852-8857].

Expression vectors in which expression of a nucleic acid sequence of interest is regulated by sequences of the invention may be constructed using the teachings of the present invention in conjunction with techniques well known in the art. [Sambrook et al. (1989) *Molecular Cloning, A Laboratory Manual*, Cold Spring Harbor Press, Plainview N.Y.; Ausubel et al. (1989) *Current Protocols in Molecular Biology*, John Wiley & Sons, New York N.Y.]. Briefly, the nucleic acid sequence of interest is placed in operable combination with a promoter sequence and sequences of the invention in the presence of transcription and translation regulatory sequences, including initiation signals such as a start codon (i.e., ATG), enhancers, and transcription termination signals. The ATG initiation codon must be in the correct reading frame to ensure translation of the entire heterologous nucleotide sequence. Transcription termination signals are placed downstream of the heterologous nucleic acid sequence and include polyadenylation sequences which are exemplified by, but not limited to, SV40 poly-A sequence, hINV poly-A sequence, or bovine growth hormone poly-A sequence, etc.

Other regulatory sequences which may affect RNA stability as well as enhancers (i.e., a sequence which when activated results in an increase in the basal rate of transcription of a gene) and silencers (i.e., a sequence involved in reducing expression of a gene) may also be included. These regulatory sequences may be relatively position-insensitive, i.e., the regulatory element will function correctly even if positioned differently in relation to the heterologous nucleotide sequence in the construct as compared to its position in relation to the corresponding heterologous nucleotide sequence in the genome. For example, an enhancer may be located at different distances from the promoter sequence, in a different orientation, and/or in a different linear order. Thus, an enhancer that is located 3' to a promoter sequence in germline configuration might be located 5' to the promoter sequence in the construct.

2. Host Cells

Host cells are transformed with expression vectors which contain the sequences of the invention in operable combination with a nucleic acid sequence of interest using methods known in the art. The term "transformation" as used herein refers to the introduction of a transgene into a cell. The term "transgene" as used herein refers to any nucleic acid sequence which is introduced into the genome of a cell by experimental manipulations.

The term "transgene" as used herein refers to any nucleic acid sequence which is introduced into the genome of a cell by experimental manipulations. A transgene may be an "endogenous DNA sequence," or a "heterologous DNA sequence." The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The terms "heterologous DNA sequence" and "foreign DNA sequence" refer to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification (e.g., a point mutation, the presence of a selectable marker gene, etc.) relative to the naturally-occurring gene. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

Transformation may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like.

Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA) which detects the presence of a polypeptide encoded by one or more of the transgenes. Alternatively, transient transformation may be detected by detecting the activity of the protein encoded by the transgene. For example, the activity of β-glucuronidase (GUS) which is encoded by the uid A gene may be detected using either a histochemical assay of GUS enzyme activity by staining with X-gluc which gives a blue precipitate in the presence of the GUS enzyme, or a chemiluminescent assay using the GUS-Light kit (Tropix). The term "transient transformant" refers to a cell which has transiently incorporated one or more transgenes. In contrast, the term "stable transformation" or "stably transformed" refers to the introduction and integration of one or more transgenes into the genome of a cell. Stable transformation of a cell may be detected by Southern blot hybridization of genomic DNA of the cell with nucleic acid sequences which are capable of binding to one or more of the transgenes. Alternatively, stable transformation of a cell may also be detected by the polymerase chain reaction (PCR) of genomic DNA of the cell to amplify transgene sequences. The term "stable transformant" refers to a cell which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene.

Suitable host cells include bacterial, yeast, plant, insect, and mammalian cells. In one embodiment the host cell is mammalian. In a preferred embodiment, the mammalian host cell is a mouse fertilized egg cell. In an alternative embodiment, the mammalian host cell is a HepG2 cell (ATCC number HB8065), a fibroblast cell (e.g., ATCC number CCL 110), a myoblast cell (e.g., Clonetics, catalog # SkMC), and an endothelial cell (e.g., human umbilical cord endothelial cells; ATCC number CRL 1730).

In one embodiment, the host cell is transformed both with an expression vector which contains the sequences of the invention in operable combination with the nucleic acid sequences of interest, as well as with an expression vector which expresses the PEA-3 protein (Example 6). Such co-transformation may be desirable, for example, where expression of the nucleotide sequence of interest is regulated by AE5' or portions or homologs thereof which contain homologs of the PEA-3 nucleotide sequence to which the PEA-3 protein binds. In one embodiment, expression of the PEA-3 protein is under the control of the LTR promoter of the Moloney murine leukemia virus (MOLV) which is capable of driving expression of operably linked genes in several cell types. Transient expression assays are suitable for determining the relative promoter activities in expressing desirable PEA-3 protein levels.

Any number of selection systems may be used to recover transfected cells. These include, but are not limited to, the herpes simplex virus thymidine kinase (Wigler M et al. (1977) Cell 11:223-32) and adenine phosphoribosyltransferase (Lowy I et al. (1980) Cell 22:817-23) genes which can be employed in $tk^-$ or $aprt^-$ cells, respectively. Also, antimetabolite, antibiotic or herbicide resistance can be used as the basis for selection; for example, dhfr which confers resistance to methotrexate [Wigler M et al., (1980) Proc Natl Acad Sci 77:3567-70]; npt, which confers resistance to the aminoglycosides neomycin and G-418 [Colbere-Garapin F et al., (1981) J. Mol. Biol. 150:1-14] and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine [Hartman S C and R C Mulligan (1988) Proc Natl Acad Sci 85:8047-51]. Recently, the use of a reporter gene system which expresses visible markers has gained popularity with such markers as β-glucuronidase and its substrate (GUS), luciferase and its substrate (luciferin), and β-galactosidase and its substrate (X-Gal) being widely used not only to identify transformants, but also to quantify the amount of transient or stable protein expression attributable to a specific vector system [Rhodes C A et al. (1995) Methods Mol Biol 55:121-131].

The presence or expression of the reporter gene usually indicates the presence or expression, respectively, of the tandem heterologous nucleic acid sequence as well. However, it is preferred that the presence and expression of the desired heterologous nucleic acid sequence be confirmed. This is accomplished by procedures known in the art which include DNA-DNA or DNA-RNA hybridization or amplification using probes, or fragments of the heterologous nucleic acid sequence. For example, Fluorescent In Situ Hybridization (FISH) can be used to detect the heterologous nucleic acid sequence in cells. Several guides to FISH techniques are available, e.g., Gall et al. Meth. Enzymol. 21:470-480 (1981); Angerer et al., in "Genetic Engineering: Principles and Methods," Setlow & Hollaender, Eds. Vol. 7 pp. 43-65, Plenum Press, New York (1985). Alternatively, DNA or RNA can be isolated from cells for detection of the transgene by Southern or Northern hybridization or by amplification based assays. Nucleic acid amplification based assays involve the use of oligonucleotides or oligomers based on the nucleotide sequence of interest in order to detect cells and tissues which contain the DNA or RNA encoding the transgene of interest. As used herein, the terms "oligonucleotides" and "oligomers" refer to a nucleic acid sequence of at least about five (5) contiguous nucleotide residues and as many as about sixty (60) nucleotides, preferably about 15 to 30 nucleotides, and more preferably about 20-25 nucleotides, which can be used as a probe or amplimer. Standard PCR methods useful in the present invention are described by Innis et al. (Eds.), "PCR Protocols: A Guide to Methods and Applications," Academic Press, San Diego (1990).

Yet another alternative for the detection of heterologous nucleic acid sequences includes detecting the polypeptide product of transcription of the heterologous nucleotide sequence. A variety of protocols which employ polyclonal or monoclonal antibodies specific for the protein product are known in the art. Examples include enzyme-linked immunosorbent assay (ELISA), radioimmunoassay (RIA) and fluorescent activated cell sorting (FACS). A competitive binding assay may also be used. Alternatively, a two-site, monoclonal-based immunoassay which utilizes monoclonal antibodies that are reactive to two non-interfering epitopes on the protein of interest may be employed. These and other assays are described in, among other places, Hampton R et al. (1990), *Serological Methods a Laboratory Manual*, APS Press, St Paul Minn.), and Maddox D E et al. (1983), J. Exp. Med. 158:1211.

A wide variety of labels and conjugation techniques are known by those skilled in the art and can be used in various nucleic acid and amino acid assays. Means for producing labeled hybridization or PCR probes for detecting related sequences include oligolabeling, nick translation, end-labeling or PCR amplification using a labeled nucleotide. Alternatively, the nucleotide sequence of interest, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides. A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like.

Host cells transformed with expression vectors containing the sequences provided herein are useful for age-related expression of recombinant proteins of interest. Host cells transformed with expression vectors containing the invention's sequences may be part of a tissue or organ of a living animal. A "living animal" as used herein refers to any multicellular animal (e.g., humans, non-human primates, ovines, bovines, ruminants, lagomorphs, porcines, caprines, equines, canines, felines, aves, etc.) into whose cells the sequences provided herein may be introduced. Where the host cells (e.g., fertilized egg cells) are capable of generating a multicellular organism, these cells when transformed with expression vectors containing the sequences of the invention are useful in generating transgenic animals which exhibit age-related and/or liver-specific expression of nucleotide sequences of interest.

3. Transgenic Animals

The present invention provides transgenic non-human animals which express a nucleotide sequence of interest in an age-related manner. These animals provide useful models for diseases (e.g., thrombosis, cardiovascular diseases, diabetes, Alzheimer's disease, cancer, osteoporosis, osteoarthritis, Parkinson's disease, dementia) which are associated with increasing age, as well a for screening candidate therapeutic agents against such diseases. These transgenic animals are also useful in studies of normal phenomena, such as ageing, gene regulation, etc. In one embodiment, the invention discloses transgenic mice which express in an age-related manner the exemplary hFIX coding sequence under the control of AE5' and/or AE3' (Example 3).

The term "age-related manner" when made in reference to the expression of a nucleotide sequence of interest is a relative term which refers to an increase over a period of time in the quantity of mRNA and/or protein encoded by the nucleotide sequence of interest when the nucleotide sequence of interest is operably linked to a promoter and to a nucleic acid sequence which has age-related regulatory activity, as compared to the quantity of mRNA and/or protein, respectively, encoded by the nucleotide sequence of interest when the nucleotide sequence of interest is operably linked to the promoter in the absence of the nucleic acid sequence which has age-related regulatory activity. Thus, the term "age-related" when made in reference to expression of a nucleotide sequence of interest by a transgenic animal means that the transgenic animal expresses the nucleotide sequence of interest in an age-related manner.

For example, in one embodiment, the invention demonstrates that hFIX is expressed in an age-related manner in transgenic mice which harbor a transgene (−416FIXm1/1.4) (FIG. 2B) which contains hFIX under the control of the hFIX promoter and the regulatory control of AE3' as compared to expression of hFIX in transgenic mice which harbor a transgene (−416FIXm1) (FIG. 2A) in which hFIX is under the control of the hFIX promoter in the absence of AE3'. While transgenic mice harboring the −416FIXm1/1.4 construct showed decreasing hFIX activity levels over a period of time (e.g., from 1 to 9 months of age), this decrease was less than the decrease in hFIX activity levels which was observed in transgenic mice harboring the −416FIXm1 construct over the same period of time.

In another embodiment, the invention discloses that hFIX is expressed in an age-related manner in transgenic mice which harbor transgenes (−802FIXm1, −2231FIXm1, and −416FIXm1/AE5') (FIGS. 4A, C and E) each of which contains hFIX under the control of the hFIX promoter and the regulatory control of AE5' as compared to expression of hFIX in transgenic mice which harbor a transgenes (−416FIXm1 and −770FIXm1) (FIGS. 2A and E) in which hFIX is under the control of the hFIX promoter in the absence of AE5'. Transgenic mice harboring each of the −802FIXm1, −2231FIXm1, and −416FIXm1/AE5' constructs showed relatively unchanged hFIX activity levels over a period of time (e.g., from 1 to 7 months of age) while transgenic mice harboring either the −416FIXm1 or −770FIXm1 construct showed decreasing hFIX activity levels over the same time period.

In an additional embodiment, the invention shows that hFIX is expressed in an age-related manner in transgenic mice which harbor transgenes (−802FIXm1/1.4 and −2231FIXm1/1.4) (FIGS. 4B and D) each of which contains hFIX under the control of the hFIX promoter and the regulatory control of both AE3' and AE5' as compared to expression of hFIX in transgenic mice which harbor a transgene (−770FIXm1) (FIG. 2E) in which hFIX is under the control of the hFIX promoter in the absence of both AE3' and AE5'. Transgenic mice harboring either the −802FIXm1/1.4 or the −2231FIXm1/1.4 construct showed increasing levels of hFIX activity over a period of time (e.g., 1 to 3 months of age) as compared to decreasing hFIX activity levels over the same period of time in transgenic mice harboring the −770FIXm1 construct.

The present invention also provides transgenic non-human animals which express a nucleotide sequence of interest in a liver-specific manner. These animals are useful for targeting expression of a nucleotide sequence of interest to the liver. Examples of nucleotide sequences of interest are those which encode blood coagulation factors (e.g., factor VIII, factor VII, factor X and prothrombin) whose deficiency is known to play a role in abnormal bleeding disorders. Other examples of nucleotide sequences of interest include those which encode blood coagulation regulators and/or inhibitors (e.g., protein C, antithrombin III, and tissue factor pathway inhibitor [TFPI]) whose deficiency results in thrombosis, α1-antitrypsin whose deficiency results in emhysima, and LDL-receptor whose deficiency results in hypercholestrolemia.

Yet other examples of a nucleotide sequence of interest include those encoding enzymes involved in specific metabolic defects (e.g., urea cycle enzymes, especially ornithine transcarbamylase, argininosuccinate synthase, and carbamyl phosphate synthase); receptors (e.g., LDL receptor); toxins;

thymidine kinase to ablate specific cells or tissues; ion channels (e.g., chloride channel of cystic fibrosis); membrane transporters (e.g., glucose transporter); and cytoskeletal proteins (e.g., dystrophin). The nucleotide sequence of interest may be of synthetic, cDNA, or genomic origin, or a combination thereof. The nucleotide sequence of interest may be one which occurs in nature, a non-naturally occurring gene which nonetheless encodes a naturally occurring polypeptide, or a gene which encodes a recognizable mutant of such a polypeptide. It may also encode an mRNA which will be "antisense" to a DNA found or to an mRNA normally transcribed in the host cell, but which antisense RNA is not itself translatable into a protein. In one embodiment, the invention discloses transgenic mice which express in a liver-specific manner the exemplary hFIX coding sequence under the control of AE5' (Example 3).

The term "liver-specific manner" as used herein in reference to the expression of a nucleotide sequence of interest in a transgenic animal is a relative term which means that the quantity of mRNA and/or protein encoded in liver tissue by the nucleotide sequence of interest is greater than, preferably two times greater, more preferably five times greater, and most preferably ten times greater, than the quantity of mRNA and/or protein encoded by the nucleotide sequence of interest in tissues other than liver tissue of the same transgenic animal as detected by Northern blot hybridization and/or by the activity of the encoded protein as described herein. Thus, the term "liver-specific" when made in reference to expression of a nucleotide sequence of interest by a transgenic animal means that the transgenic animal expresses the nucleotide sequence of interest in an liver-specific manner.

A first step in the generation of the transgenic animals of the invention is the introduction of a construct containing nucleic acid sequences of interest under the expression regulatory control of sequences of the invention into target cells. Several methods are available for accomplishing this, including microinjection, retroviral infection, and implantation of embryonic stem cells. These methods are discussed as follows.

i. Microinjection Methods

Direct microinjection of expression vectors into pronuclei of fertilized eggs is the preferred, and most prevalent, technique for introducing heterologous nucleic acid sequences into the germ line. Technical aspects of the microinjection procedure and important parameters for optimizing integration of nucleic acid sequences have been previously described [Hogan et al., (1986) Manipulation of the Mouse Embryo: A Laboratory Manual. Cold Spring Harbor, N.Y.: Cold Spring Harbor Lab.].

Once the expression vector has been injected into the fertilized egg cell, the cell is implanted into the uterus of a pseudopregnant female and allowed to develop into an animal. Of the founder transgenic animals born, 70% carry the expression vector sequence in all of their cells, including the germ cells. The remaining 30% of the transgenic animals are chimeric in somatic and germ cells because integration of the expression vector sequence occurs after one or more rounds of replication. Heterozygous and homozygous animals can then be produced by interbreeding founder transgenics. This method has been successful in producing transgenic mice, sheep, pigs, rabbits and cattle [Hammer et al., (1986) J. Animal Sci.:63:269; Hammer et al., (1985) Nature 315:680-683].

ii. Retroviral Methods

Retroviral infection of pre-implantation embryos with genetically engineered retroviruses may also be used to introduce transgenes into an animal cell. For example, blastomeres have been used as targets for retroviral infection [Jaenisch, (1976) Proc. Natl. Acad. Sci USA 73:1260-1264]. Transfection is typically achieved using a replication-defective retrovirus carrying the transgene [Jahner et al., (1985) Proc. Natl. Acad. Sci. USA 82:6927-6931; Van der Putten et al., (1985) Proc. Natl. Acad Sci USA 82:6148-6152]. Transfection is obtained, for example, by culturing eight-cell embryos, from which the zona pellucida has been removed with fibroblasts which produce the virus [Van der Putten (1985), supra; Stewart et al., (1987) EMBO J. 6:383-388]. The transfected embryos are then transferred to foster mothers for continued development. Alternatively, infection can be performed at a later stage. Virus or virus-producing cells can be injected into the blastocoele [Jahner et al., (1982) Nature 298:623-628]. Yet another alternative method involves intrauterine retroviral infection of the midgestation embryos [Jahner et al. (1982), supra].

The advantages of retroviral infection methods include the ease of transfection and the insertion of a single copy of the transgene, which is flanked by the retroviral long terminal repeats (LTRs), into the chromosome. However, this method is not a preferred method because most of the founders will show mosaicism since infection occurs after cell division has begun. This necessitates outbreeding to establish homozygous and heterozygous lines suitable for analysis of gene expression. More importantly, the retroviral LTR sequences may interfere with the activity of the hINV upstream sequences in directing expression of the heterologous nucleic aid sequences.

iii. Embryonic Stem Cell Implantation

Another method of introducing transgenes into the germ line involves using embryonic stem (ES) cells as recipients of the expression vector. ES cells are pluripotent cells directly derived from the inner cell mass of blastocysts [Doetchman et al., (1988) Dev. Biol. 127:224-227], from inner cell masses [Tokunaga et al., (1989) Jpn. J. Anim. Reprod. 35:173-178], from disaggregated morulae [Eistetter, (1989) Dev. Gro. Differ. 31:275-282] or from primordial germ cells [Matsui et al., (1992) Cell 70:841-847]. Expression vectors can be introduced into ES cells using any method which is suitable for gene transfer into cells, e.g., by transfection, cell fusion, electroporation, microinjection, DNA viruses, and RNA viruses [Johnson et al., (1989) Fetal Ther. 4 (Suppl. 1):28-39].

The advantages of using ES cells include their ability to form permanent cell lines in vitro, thus providing an unlimited source of genetic material. Additionally ES cells are the most pluripotent cultured animal cells known. For example, when ES cells are injected into an intact blastocyst cavity or under the zona pellucida, at the morula stage embryo, ES cells are capable of contributing to all somatic tissues including the germ line in the resulting chimeras.

Once the expression vector has been introduced into an ES cell, the modified ES cell is then introduced back into the embryonic environment for expression and subsequent transmission to progeny animals. The most commonly used method is the injection of several ES cells into the blastocoel cavity of intact blastocysts [Bradley et al., (1984) Nature 309:225-256]. Alternatively, a clump of ES cells may be sandwiched between two eight-cell embryos [Bradley et al., (1987) in "Teratocarcinomas and Embryonic Stem Cells: A Practical Approach," Ed. Robertson E. J. (IRL, Oxford, U.K.), pp. 113-151; Nagy et al., (1990) Development 110: 815-821]. Both methods result in germ line transmission at high frequency.

Target cells which contain the heterologous nucleic acid sequences are recovered, and the presence of the heterologous nucleic acid sequence in the target cells as well as in the animal is accomplished as described supra.

E. Gene Therapy

The regulatory nucleic acid sequences provided herein may be used for gene therapy applications in both non-human animals as well as in humans. For example, the regulatory nucleic acid sequences of the invention may be introduced into cells using an expression vector which encodes a polypeptide sequence of interest using a variety of means known in the art to be useful both for delivery in vivo and ex vivo, including (1) recombinant retroviral transduction, (2) recombinant adenoviral vectors, (3) targeted cationic liposomes, and (4) gene transfer using biolistics, as described in the following sections.

1. Recombinant Retroviral Transduction

Retroviral vectors encoding polypeptides of interest may be used for the expression of the polypeptides in any desired cell, such as primary tumor cells. The transfer of polypeptides of interest using retroviruses may be made more efficient by increasing the titer of the virus encoding the polypeptides of interest and increasing the transduction efficiency. To increase the virus titer, the retroviral construct may be designed to include a selectable marker (e.g., neo gene), and cells harboring the retroviral construct are selected by growth in the presence of a suitable selective agent (e.g., G418) followed by expansion of clones producing the highest titers of virus. To improve the transduction efficiency, retrovirus are used in combination with liposomes or poly-L-ornithine or polylysine to enhance virus uptake.

Another way to improve gene transfer efficiency using retroviruses is to increase the targeting efficiency. Many tumor cells including glioblastomas and melanomas express excess levels of the transferrin receptor. Transferrin has been used to increase the transduction efficiency of adenovirus in combination with polylysine. Several recent reports demonstrated that replacing the SU (surface) domain of the env gene of a retrovirus can increase receptor-mediated transduction efficiency. The human transferrin gene is 2097 bp long and its insertion into the SU domain of the env gene of MLV vector may not produce a stable Env product. However, since earlier studies have suggested that the modified Env fusion protein requires the native Env for stable assembly and efficient entry, co-transfection of the transferrin-env fusion gene with the native env gene may be used to produce retrovirus particles bearing a mixture of wild type and recombinant Env. The gene transfer efficiency of the new vector may be examined by transducing tumor cells expressing high levels of transferrin receptor.

2. Recombinant Adenoviral Vectors

Recombinant adenoviruses can accommodate relatively large segments of foreign DNA (~7 kb), and have the advantage of a broad host cell range and high titer virus production. Adenoviruses have been used in vivo in rats to efficiently deliver genes to the liver and the pancreatic islets [reviewed in Becker et al. (1994) In *Protein Expression in Animal Cells*, Roth et al. eds.] and to the central nervous system [Davidson et al. (1993) Nature Genet. 3:219]. Rat livers have also been efficiently transduced ex vivo and then re-implanted [Shaked et al. (1994) Transplantation 57:1508]. Thus, the present invention contemplates ex vivo transfection followed by transplantation of the transfected cells or organ.

The replication defective recombinant adenoviruses are preferably employed; these viruses contain a deletion of the key immediate early genes E1a and E1b. To generate and propagate recombinant viruses, a packaging cell line such as 293 cells which supply the E1a and E2a proteins in trans is employed. Recombinant adenoviruses are created by making use of intracellular recombination between a much larger plasmid encoding most of the viral genome and a small plasmid containing the nucleotide sequence of interest flanked by regions of homology with the viral integration site. Standard methods may be used to construct the recombinant adenoviruses [Graham and Prevec (1991) Meth. Mol. Biol. 7:109-128; Becker et al. (1994) *In Protein Expression in Animal Cells*, Roth et al. eds.]. Briefly, each plasmid is co-transfected together with pJM17 (Microbix Systems, Toronto) into sub-confluent monolayers of 293 cells (ATCC CRL 1573) using calcium phosphate precipitation and a glycerol shock. Initial recombinant viral stocks are titered on monolayers of 293 cells, and isolated single plaques are obtained and tested for expression of the polypeptide of interest using ELISA. Viral stocks are amplified and titered on 293 cells, and stored in aliquots at −70° C.; if necessary, stocks are concentrated by centrifugation on density gradients. To infect tumor cells with recombinant adenoviruses, freshly isolated tumor cells are mixed with adenoviral stocks in a minimal volume. Titers of stocks are typically $10^5$-$10^8$/ml. Medium is replaced after several hours and the cells are followed for expression of the recombinant adenoviral-encoded polypeptide of interest (e.g., reporter genes).

A potential drawback of using an adenoviral delivery system is that the transduced cells may retain or express small quantities of adenoviral antigens on their surface. "Second generation" adenoviral vectors which contain deletions in the E2a gene are available and are associated with less inflammation in the recipient and a longer period of expression of the gene of interest [Engelhardt et al. (1994) Proc. Natl. Acad. Sci. USA 91:6196]. If necessary, nucleic acid sequences encoding polypeptides of interest are inserted into second generation adenoviral vectors.

Recently, adenoassociated virus (AAV) vectors and chimeric lentivirus vectors have also been shown promise in the expression of polypeptide sequences of interest.

3. Targeted Cationic Liposomes

Cationic liposomes have proven to be a safe and effective means for inducing the transient expression of DNA in target cells [Ledley (1995) Human Gene Ther. 6:1129]. Clinical trials are underway using cationic liposomes to introduce the CFTR gene into the lungs of cystic fibrosis patients [Caplen et al. (1994) Gene Ther. 1:139 and Alton et al. (1993) Nature Genet. 5:135] or to introduce, by direct intra-tumor injection, the T cell costimulator B7-1 into malignant melanoma lesions in order to induce a cell-mediated immune response [Nabel et al. (1993) Proc. Natl. Acad. Sci. USA 90:11307].

Cationic liposomes (e.g., DOTAP/DOPE) and ligand-targeted cationic liposomes may be employed for the delivery of polypeptides of interest to tumor cells. Recently, in addition to cationic liposomes, neutral liposomes have also been reproted to also be useful in targeing ligands to cells. Ligand-targeted liposomes are made by covalently attaching ligands or antibodies to the surface of the cationic liposome. For example, when glioblastoma cells are to be targeted, transferrin is used as the ligand as glioblastoma cells express high levels of the transferrin receptor on their surface. When melanoma cells are to be targeted, internalizing receptors, monoclonal antibodies directed against melanoma-specific surface antigens (e.g., mAb HMSA5) may be employed as the ligand.

Plasmid DNA encoding polypeptides of interest is formed into a complex with preformed cationic liposomes using standard methodology or alternatively the DNA is encapsulated into the liposome interior. The DNA-containing liposomes are then used to transfer the DNA to tumor cells in vivo by direct intra-tumor injection or in vitro (using freshly explanted tumor cells) followed by return of the transduced cells to the recipient (e.g., a human patient or non-human animal).

4. Gene Transfer Using Biolistics

Biolistics (microballistics) is a method of delivering DNA into cells by projection of DNA-coated particles into cells or tissues. DNA is coated onto the surface of gold or tungsten microparticles (~1-3 μm diameter) and these particles are accelerated to high velocity and are impacted onto the target cells. The particles burst through the cell membrane and lodge within the target cell. The cell membrane quickly reseals and the passenger DNA elutes off of the particle and is expressed. The biolistic method has been used to transfect mammalian cells [Sanford et al. (1993) Methods Enzymol. 217:483].

A hand-held biolistic apparatus (BioRad) is used to transfer DNA into tumor cells or isolated tumor fragments. This device uses compressed helium to drive a disc-shaped macroprojectile which carries on its surface microparticles (1-5 μm) of gold which have been coated with purified plasmid DNA (coprecipitated with spermine) (Williams et al., supra). This apparatus has been used to successfully transfect primary tissues.

Plasmid DNA encoding the polypeptides of interest may be coated onto the surface of gold microparticles according to the manufacturer's instructions (BioRad) and the biolistic apparatus is used to transfer the DNA into freshly explanted tumor cells or directly into exposed tumors (e.g., metastatic nodules on the surface of the liver, melanoma lesions on the skin).

Regardless of the method of delivery of the expression vector into a cell, it is preferred, though not required, that the expression vector contain a selection marker (e.g., neo gene) to facilitate selection of transfected cells. Transfected cells are selected by growth in the presence of G418 (e.g., 200 μg/ml), followed by culture in growth medium containing reduced concentrations of G418 (e.g., 100 μg/ml) and growth to confluence. Expression of the polypeptides of interest is evaluated using, for example, immunoblot analysis or flow cytometry using monoclonal antibodies which are specific for the polypeptides of interest. It is preferred, though not necessary, that expression of the polypeptides of interest in the transfected tumor cells is both constitutive and stable. Constitutive expression refers to expression in the absence of a triggering event or condition, and can be achieved by the selection of a promoter which drives expression of the nucleic acid sequence encoding the polypeptides of interest. Examples of promoters which drive constitutive expression of a structural nucleic acid sequence which is operably linked to the promoter include the SRα promoter, CMV promoter, and HIV promoter.

Regardless of the type of expression vector used for delivery of the nucleic acid sequences of interest into a cell, the expression vector may be introduced to the cell by direct injection into tumor and/or preneoplastic tissue, systemic (e.g., intravenous) administration, aerosol administration (e.g., for delivery to the bronchial tree and other lung tissues), injection into breast ducts (e.g., for delivery to breast tissue), and topical administration (e.g., for delivery to cervical tissue).

F. Reducing Expression of Factor IX in an Animal

The regulatory sequences of the invention may also be used to reduce expression of a polypeptide sequence of interest which is encoded by a nucleic acid sequence whose transcription is under the regulatory control of the regulatory sequences provided herein. For example, the regulatory sequences of the invention may be used to reduce the rate of age-related increase of FIX activity in an animal as a means of treating diseases (e.g., thrombosis, cardiovascular disease, etc.) which are associated with age-related increases in FIX activity. Since the inventors have discovered that the exemplary nucleic acid sequences AE5' and AE3' regulate stable and increased expression levels, respectively, of hFIX, the increase in the level of hFIX activity over time may be reduced by inhibiting the function of AE3' which regulates increased expression of hFIX. This approach has the advantage that expression of hFIX remains under the control of AE5' thus providing hFIX activities which are stable over time and which continue to play an important role in normal blood coagulation processes.

The function of AE3' in age-related expression of FIX may be inhibited by, for example, inhibiting the activity of the protein which specifically binds to AE3'. The protein(s) which bind to AE3' may be identified by using the AE3' (or the minimum portion of AE3' which has age-related regulatory activity) to screen protein libraries for specific binding to AE3' or its portion. Once the protein which binds to AE3' is identified, the function of this protein may be inhibited using antibodies which are specific for this protein. Antibodies which are specific for the protein which binds to AE3' are expected to disrupt the interaction between AE3' and this protein.

Antibodies (polyclonal and monoclonal) which are specific for the protein that binds to AE3' or portions thereof may be generated using methods known in the art. The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells. The terms "specific binding," "specifically binding" and grammatical equivalents thereof when used in reference to the interaction of an antibody and an immunogen mean that the interaction is dependent upon the presence of a particular structure (i.e., the antigenic determinant or epitope) on the immunogen; in other words the antibody is recognizing and binding to a specific immunogen structure rather than to immunogens in general. For example, if an antibody is specific for epitope "A", the presence of an immunogen containing epitope A (or free, unlabelled A) in a reaction containing labelled "A" and the antibody will reduce the amount of labelled A bound to the antibody.

Polyclonal and monoclonal antibodies which are specific to a desirable polypeptide, given the teachings herein, may readily be prepared by one of skill in the art. For example, monoclonal antibodies may be generated by immunizing an animal (e.g., mouse, rabbit, etc.) with a desired antigen and the spleen cells from the immunized animal are immortalized, commonly by fusion with a myeloma cell. Immunization with antigen may be accomplished in the presence or absence of an adjuvant, e.g., Freund's adjuvant. Typically, for a mouse, 10 μg antigen in 50-200 μL adjuvant or aqueous solution is administered per mouse by subcutaneous, intraperitoneal or intra-muscular routes. Booster immunization may be given at intervals, e.g., 2-8 weeks. The final boost is given approximately 2-4 days prior to fusion and is generally given in aqueous form rather than in adjuvant.

Spleen cells from the immunized animals may be prepared by teasing the spleen through a sterile sieve into culture medium at room temperature, or by gently releasing the spleen cells into medium by pressure between the frosted ends of two sterile glass microscope slides. The cells are harvested by centrifugation (400 ×g for 5 min.), washed and counted. Spleen cells are fused with myeloma cells to generate hybridoma cell lines. Several mouse myeloma cell lines which have been selected for sensitivity to hypoxanthine-aminopterin-thymidine (HAT) are commercially available and may be grown in, for example, Dulbecco's modified Eagle's medium (DMEM) (Gibco BRL) containing 10-15% fetal calf serum. Fusion of myeloma cells and spleen cells may be accomplished using polyethylene glycol (PEG) or by electrofusion using protocols which are routine in the art. Fused cells are distributed into 96-well plates followed by selection of fused cells by culture for 1-2 weeks in 0.1 ml DMEM containing 10-15% fetal calf serum and HAT. The supernatants are screened for antibody production using methods well known in the art. Hybridoma clones from wells containing cells which produce antibody are obtained, e.g., by limiting dilution. Cloned hybridoma cells (4-5×10$^{6}$) are implanted intraperitoneally in recipient mice, preferably of a BALB/c genetic background. Sera and ascites fluids are collected from mice after 10-14 days.

The invention also contemplates humanized antibodies which may be generated using methods known in the art, such as those described in U.S. Pat. Nos. 5,545,806; 5,569, 825 and 5,625,126, the entire contents os which are incorporated by reference. Such methods include, for example, generation of transgenic non-human animals which contain human immunoglobulin chain genes and which are capable of expressing these genes to produce a repertoire of antibodies of various isotypes encoded by the human immunoglobulin genes.

Alternatively, the function of AE3' in age-related expression of FIX may be inhibited by, for example, inhibiting the activity of AE3' using antisense sequences which are directed to AE3'. The term "antisense" as used herein refers to a deoxyribonucleotide sequence whose sequence of deoxyribonucleotide residues is in reverse 5' to 3' orientation in relation to the sequence of deoxyribonucleotide residues in a strand of a DNA duplex. AE3' antisense sequences may be used to turn off genes under the expression regulation of AE3' by transfecting a cell or tissue with expression vectors which express high levels of a desired AE3' antisense oligomer (e.g., 15-20 nucleotides) or larger fragment. Such constructs can flood cells with antisense sequences which inhibit expression of FIX. Antisense sequences can be designed from various locations along the AE3' sequence. Animals (e.g., mice) treated with vectors expressing AE3' antisense sequences are monitored for changes in the age-related symptoms associated with FIX expression. The alleviation or treatment of one or more of these symptoms in animal by an antisense sequence suggests that the antisense sequence may be useful in the treatment and/or prevention of age-related FIX expression in humans.

Experimental

The following examples serve to illustrate certain preferred embodiments and aspects of the present invention and are not to be construed as limiting the scope thereof. Unless otherwise mentioned, all reference to nucleotide numbers with respect to the factor IX nucleotide sequence, refers to the nucleotide numbers of the hFIX gene sequence shown in FIG. 8.

EXAMPLE 1

Construction of a Series of Twelve Exemplary Human Factor IX (hFIX) Minigene Expression Vectors To explore the molecular mechanisms underlying age-related regulation of Factor IX, a series of twelve hFIX minigene expression vectors were constructed. These vectors were first analyzed in vitro in HepG2 cells, a human hepatoma cell line (see Example 2, infra). Transgenic mice harboring the hFIX minigene vectors were generated and longitudinal analyses of hFIX expression for the entire life spans of founders and successive generations of transgenic mice were carried out (See Example 3, infra).

The twelve exemplary minigenes contained sequences derived entirely from the hFIX gene sequence, including (a) promoter sequences of various lengths spanning up to nucleotide (nt)-2231 in the 5' flanking region, (b) the coding region containing a first intron in which the first intron's middle portion is truncated. i.e., nt+1098 through nt+5882 of FIG. 8, and (c) either the complete 3' UTR sequence or the 3' UTR sequence in which the middle portion was deleted. FIG. 1 shows the structure of eleven out of the twelve human FIX minigene expression constructs. The name of each construct is shown at left. The structure is depicted with the promoter-containing regions (solid thick line on left) with the 5' terminal nucleotide number. Transcribed hFIX regions (open rectangles connected with thin lines representing the shortened first intron) are followed by 3' flanking sequence regions (solid thick line at right). Arrow: transcription start site; asterisk: translation stop codon; pA: polyadenylation; sl: potential stem-loop forming dinucleotide repeats.

Construction of hFIX minigene expression vectors was carried out using −416FIXm1 as the starting construct (Kurachi et al. (1995) J. Biol. Chem. 270:5276-5281). The nucleotide (nt) numbering system used in this study was based on the complete hFIX gene sequence previously reported (Yoshitake et al. (1985) Biochem. 24:3736-3750). Minigene −416FIXm1/1.4 was constructed from −416FIXm1 by inserting the middle portion of the 3' UTR (1.2 kb in size) which was generated by PCR using the following primer set with BamH I linkers: 5' primer, TAACAGGATCCGGCCTCTCACTAACTAATCAC (nt+31418 through +31438) (SEQ ID NO:14) and 3' primer, CAACTGGATCCAAGATTCAAGATAGAAGGAT (nt+32690 through +32671) (SEQ ID NO:15), and human genomic DNA as an amplification template. The PCR product was digested with BamH I, and the generated fragment was inserted into the 3' UTR BamH I site of −416FIXm1, thus producing −416FIXm1/1.4 which contained the entire 3' UTR. −416FIX ml/0.7 was constructed by inserting the PCR-amplified 700 bp fragment with BamH I linker, containing the 3' contiguous sequence to nt+32117. The primers used were, 5' primer: same as that for −416FIXm1/1.4, 3'primer: GGACAGGATCCCC CAAACTTTTCAGGCAC (nt+32117 through +32097) (SEQ ID NO:16). Minigenes −590FIXm1, −679FIXm1, −770FIXm1, −802FIXm1 and −2231FIXm1 were produced by replacing the 5' end 433 bp sequence of −416FIXm1 released by Sph I/Nhe I digestion with 607, 696, 787, 819 and 2248 bp fragments containing the 5' end hFIX region extended up to nt −590, −679, −770, −802 and −2231, respectively. These latter fragments were generated by Sph I/Nhe I digestion of the PCR product obtained with 5' primers: CAAGCATGCATCTAGTGTTAGTGGAAGAG (nt −590 through −571) (SEQ ID NO:17), CAAGCATGCAAATATTAACTCAAAATGGA (nt −679 through −660) (SEQ ID NO:18), CAAGCATGCTGTTGTTTTTTGTTTTAAC (nt −770 through −752) (SEQ ID NO:19), CAAGCATGCAGCCATTCAGTCGAGGAAGG (nt −802 through −783) (SEQ ID NO:20), CAAGCATGCGATCCCTTCCTTATACCT (nt −2231 through −2214) (SEQ ID NO:21) with Sph I linker and the common 3' primer TAAGCTTAACCTTTGCTAGCAGATTGT (nt+30 through +10) (SEQ ID NO:22) and human genomic DNA as the amplification template. Minigene −802FIXm1/0.7 (whose structure is not shown in FIG. 1) contains the 3' UTR region through nt 32,140, which is then connected to nt 32,690 through its downstream poly (A) signal sequence that is common to each of the other eleven constructs.

−416FIXm1/AE5' depicts a construct with the AE5' region moved to the 3'-end position and shown as an open box at right. −416FIX ml/AE5' was constructed by inserting the Kpn I fragment generated by PCR (nt −802 through nt −417) into the −416FIXm1 vector (the Kpn I site is outside of the FIX gene, FIG. 1). The 5' and 3' primers used for PCR were CTTGGTACCAGCCATTCAGTCGAGGAAGG (nt −802 through −783) (SEQ ID NO:23) and CTTGGTACCATATGAATCCTTTCATAGAT, (nt −417 through −436) (SEQ ID NO:24) respectively. All constructs were sequenced through PCR amplified regions as well as fragment ligation sites to confirm the correct sequences and orientations.

EXAMPLE 2

Transient Expression of Eleven hFIX Minigene Expression Vectors In Vitro In Human Hepatoma HepG2 Cell Line Transient in vitro expression activities of hFIX minigene constructs were assayed using HepG2 cells and hFIX specific enzyme linked immunosorbent assay (ELISA) as previously described (Kurachi et al. (1995) J. Biol. Chem. 270:5276-5281) with some modifications. Cell transfection was carried out by the calcium phosphate-DNA conjugate method or later, using FuGene 6 (Boehringer Manheim). The latter, improved transfection method consistently increased transfection efficiency to >20% (Kurachi et al. (1998) Biochemica 3:43-44), and all earlier assays were reexamined using FuGene 6. Four to five independent assays of factor IX activity were carried out and the averages were shown with standard errors. With FuGene 6 transfection, the control minigene −416FIXm1 typically produced hFIX at a level of ~50 ng/$10^6$ cells/48 hr.

FIG. 1 shows the relative in vitro transient expression activities of the human FIX minigene expression constructs (transient expression activity of minigene −802FIXm1/0.7 which is not shown in FIG. 1 was 81.5% of the acitity of minigene −416FIXm1). Transient expression activities relative to the activity of −416FIXm1 (~50 ng/$10^6$ cells/48 hour, and defined as 100% activity) are shown on the right side with standard deviations (from 4-5 independent assays). Activities were normalized to the size of minigenes used.

The relative transient expression activities shown in FIG. 1 show that all constructs showed comparable high transient hFIX expression in HepG2 cells (~50 ng/$10^6$ cells/48 hours). However, all the constructs containing the complete 3' UTR, including a 102 base pair (bp) stretch of inverted AT, GT and GC dinucleotide repeats [Yoshitake et al. (1985) Biochem. 24:3736-3750], reproducibly showed expression activity levels which were 25-30% lower than corresponding minigenes without the repeat sequences. Dinucleotide repeats similar to those seen in the hFIX 3' UTR, which can form stable stem-loop (sl) structures in mRNA, have been implicated in controlling mRNA stability in mammals as well as yeast and plants, thus providing an important layer of protein biosynthesis regulation [Ross (1995) Microbiol. Rev. 59:423-450]. Together, these results suggest a similar negative regulatory activity for this structure of the hFIX gene in the HepG2 assay system on expression of the hFIX gene. As described below (e.g., Example 3), however, the 3' UTR structure of the hFIX gene containing the dinucleotide repeat region showed unexpected functions in vivo which are critical for advancing age-related regulation of the hFIX gene.

Another important and surprising finding with the HepG2 cell assay system is that expression by these hFIX minigenes (which contained sequences which are positioned upstream and downstream of the hFIX gene, and which are derived from the homologous hFIX gene instead of from heterologous reporter genes) does not show any down-regulation in the presence of the 5' upstream region (nt −802 up through nt −1900) [Salier et al. (1990) J. Biol. Chem. 265:7062-7068] (FIG. 1). In contrast, when a CAT reporter gene was used, negative regulatory elements were identified in this region [Salier et al. (1990) J. Biol. Chem. 265:7062-7068].

EXAMPLE 3

Generation And Analysis Of Transgenic Mice Harboring hFIX Minigene Expression Vectors Transgenic animals were constructed using the expression plasmids described above in Example 2 according to standard methods [Hogan et al. (1994) in "Manipulating the Mouse Embryo, a Laboratory Manual" (Cold Spring Harbor Press, New York, 2nd Edition)]. All animal experiments were carried out in accordance with the institutional guidelines of the University of Michigan (OPRR No. A3114-01).

Briefly, Factor IX minigene expression plasmids were double-digested with Sph I/Kpn I and the factor IX minigene-containing fragments released were isolated by 0.8% agarose gel electrophoresis, followed by purification with SpinBind DNA extraction units (FMC). Fertilized eggs of C57B/6×SJL mice were microinjected with the DNA (1-2 ng/egg), and implanted into foster mother animals (CD-1).

A. Multiplex PCR Analysis

Offspring produced were screened for founder animals with high transgene copy numbers (5-10 copies per genome) using quantitative multiplex PCR analyses of tail tissue DNA samples. Two pairs of primers were used, one specific to the hFIX transgenes and the other specific to mouse β-globin gene (endogenous control); 5' primer: CTGTGGGAACACACAGATTTTGG (nt+6172 through +6195) (SEQ ID NO:25) and 3' primer: GGAATAATTCGAATCACAT (nt+30885 through +30867) (SEQ ID NO:26), and 5' primer: CCAATCTGCTCACACAGGAT (nt+2590 through +2609) (SEQ ID NO:27) and 3' primer: CCTTGAGGCTGTCCAAGTGA (nt+3083 through +3064) (SEQ ID NO:28), respectively. These primers were designed to amplify a unique 966 bp fragment from the hFIX transgenes and a 494 bp fragment from the mouse β-globin gene, respectively. PCR was initiated with 3 min incubation at 94° C., followed by 25 cycles of 94° C. for 30 sec, 65° C. annealing for 1 min and 72° C. extension for 2 min.

Founders were back-crossed with non-transgenic mice (C57B/6×SJL) to generate F1 progeny animals. Homozygous F2 animals were generated by crossing among heterozygous F1 littermates and the following generations were similarly generated. Zygosity status of animals was determined by quantitative multiplex PCR analysis as described above. Minimally, three founder lines for each minigene construct were subjected to longitudinal analysis for their entire life spans up to two years.

Figure 3A:
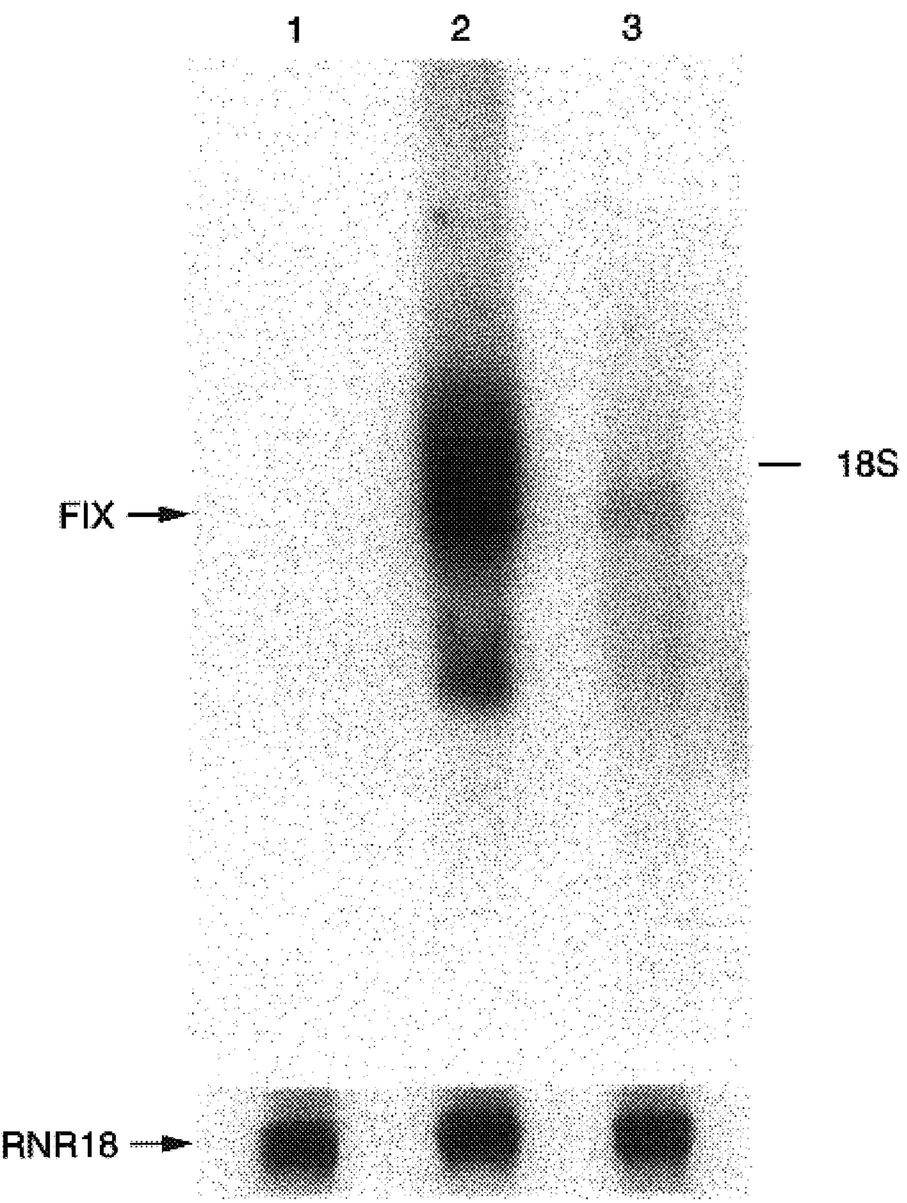
FIG. 3 shows a Northern blot of human FIX mRNA levels (A) and a gel showing hFIX transgene DNA levels as determined by multiplex PCR analysis (B) in the livers and tails of animals carrying −416FIXm1.
Figure 3B:
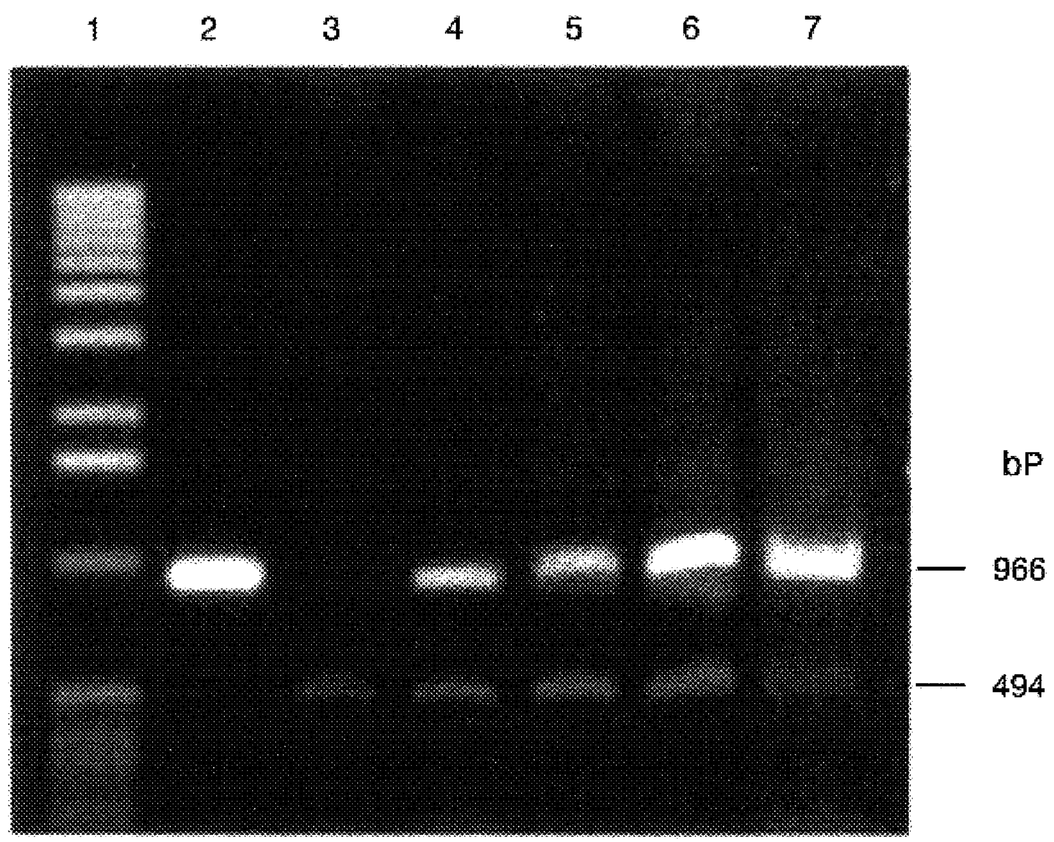

FIG. 3B shows the results of quantitative multiplex PCR analysis to determine the relative transgene levels in tail and liver tissues. Genomic DNA was extracted from snipped tail tissue of a transgenic −416FIXm1 animal (PA112) at 3 weeks and at 19 months of age. Liver DNA was extracted from the same animal (PA112) sacrificed at 19 months of age and a −416FIXm1 animal (PA412) sacrificed at 1 month of age. Positions of hFIX specific fragment (966 bp) and mouse β-globin specific fragment (494 bp, internal copy number control) are shown on the right. Lane 1: kb size ladder; lane 2: fragment size control amplified from −416FIXm1 plasmid; lane 3: non-transgenic mouse tail DNA as template; lane 4: tail DNA of PA112 at 3 weeks of age; lane 5: tail DNA of PA112 at 19 months of age; lane 6: liver DNA of PA412 at 1 month of age; lane 7: liver DNA of PA112 at 19 month of age. The relative transgene copy numbers for the 1 month-old versus the 19 month-old animals, normalized to the endogenous mouse β-globin gene, were 1.0-1.1 for both tail as well as liver genomic DNA preparations, showing no sign of loss of the hFIX transgene in the genome with age (Multi Analyst program from BioRad used for quantitation and calculation of ratios).

B. Immunoassay of hFIX Levels in Transgenic Mice

Circulatory hFIX levels were monitored during longitudinal analyses of transgenic mice from the representative founder lines carrying various hFIX minigene transgenes. At various ages, starting at one month of age, transgenic mice were individually subjected to blood sample collection (aliquot of ~100 μl) via tail-tip snipping, and the obtained serum was routinely used to quantify hFIX levels in the circulation using duplicated hFIX-specific ELISA for each age point. Pooled human plasma (George King Bio-Medical) was used to prepare a hFIX standard curve for each assay. In order to minimize experimental fluctuations from assay to assay in the longitudinal analysis, overlapped serum samples from the previous assay group were included in each assay. To ensure reproducibility, three to six independent founder lines were generated for each minigene construct, and animals from at least three representative lines were subjected to longitudinal analyses for their entire life spans. The duplicated ELISA values varied less than 11% from the averages. The results are shown in FIGS. 2 and 4.

In all panels in FIGS. 2 and 4, labeling of animals is based on the tag numbers plus additional information. The first letters of the label F or P represent founder or progeny, respectively. Information on progeny generation (F1 or F2) and sex are in parenthesis (m: male; f: female), followed by status (+: alive in good health; d: died; s: sacrificed for various examinations; mo: age of death or sacrifice). To avoid overcrowding of the panels, the results from representative animals are shown for each minigene construct. Importantly, age-regulation patterns were remarkably similar among all animals for each specific construct and different founder lines. Panels A-E of FIG. 2 show representative founder line animals with −416FIXm1 (A); −416FIXm1/1.4 (B), −590 FIXm1 (C), −679FIXm1 (D) and −770FIXm1 (E). Panels A-D of FIG. 4 show representative founder line animals with −802FIXm1, −802FIXm1/1.4, −2231 FIXm1 and −2231FIXm1/1.4, respectively. Panel E shows representative founder line animals with −416FIXm1/AE5'.

FIG. 2 shows that at one month of age, the mice carrying the −416FIXm1 minigene produced hFIX at varying levels, from as high as that of natural hFIX gene expression (4 μg/ml) to much lower levels (~50 ng/ml) (FIG. 2A). Such variations are primarily due to the transgene positional effects in the genome. Circulatory hFIX levels of animals from the representative founder lines carrying the minigene, however, declined drastically through puberty and during the subsequent two to three month period to much lower levels, which then remained stable for the remaining life span. This rapid age-dependent characteristic decline in the circulatory hFIX level was observed in all animals analyzed (n=69), regardless of founder line, differences in initial hFIX level at pre-pubertal age (one month) due to transgene positional effects, generation (founders and F1 or F2 progeny), sex, or zygosity status (homozygous/heterozygous) of the transgenes.

C. Northern Blot Analysis of hFIX mRNA in Transgenic Mice

Northern blot analyses of the liver RNA samples from animals (15 μg per lane) were carried out as previously described [Kurachi et al. (1995) supra] using the $^{32}$P_labeled Ssp I/BamH I fragment (the 3' half of the hFIX coding region of the cDNA) as a probe, and employing stringent washing conditions. Under these conditions, the probe preferentially hybridized strongly with hFIX minigene mRNA bands (~1.7 kb) with little cross-hybridization with the mouse FIX mRNA bands (3.2 kb and 2.2 kb) [Yao et al. (1994) Gene Therapy 1:99-107]. To confirm the presence of equivalent amounts of RNA in each lane, the filters previously hybridized with hFIX probe were stripped of probe and re-probed with the RNR18 cDNA (ribosomal RNA 18S). After completion of longitudinal analyses of animals from key founder lines for their entire life spans, the representative lines were subjected to embryo-freezing for preservation.

The results of Northern analysis of human FIX mRNA and transgene DNA levels in the livers of animals carrying −416FIXm1 are shown in FIG. 3A. hFIX mRNA levels in the liver of young (PA412: F1/f, 1 month of age) and old (PA112; F1/f, 19 months of age) transgenic animals were analyzed by Northern blot analysis of total liver RNA. PA412 and PA112 animals were from the same litter produced by the founder FA661, and expressed 1252 and 1675 ng/ml circulatory hFIX at one month of age, respectively. PA112 was expressing 63.8 ng/ml serum hFIX at the time of sacrifice. Lane 1: non-transgenic mouse liver RNA; lane 2: transgenic PA412 liver RNA; lane 3: transgenic PA112 liver RNA. FIX and 18S on the left or right sides indicate the band position of hFIXm1 mRNA (~1.7 kb) and RNR18 (1.9 kb, ribosomal RNA), respectively.

FIG. 3A shows that the decline in blood hFIX level observed in FIG. 2 was correlated with a similar decline in the steady-state liver hFIX mRNA, which was not due to a loss of the hFIX transgene with age (FIG. 3B). This was further supported by the fact that when 4-5 month old mice with much decreased hFIX levels had progeny, their pups depicted pre-pubertal high hFIX expression levels equivalent to those of their parents at the same time point (one-month of age).

Minigene vector −416FIXm1/1.4 is identical to −416FIXm1 except that −416FIXm1/1.4 contains the complete 3'UTR, including the dinucleotide repeat structure (102 bp in length) in its middle region [Yoshitake et al. (1985)

Biochem. 24:3736-3750] (FIG. 1). Transgenic mice with −416FIXm1/1.4 (n=48) (FIG. 2B) showed pre-pubertal high and subsequent age-dependent decline in hFIX levels similar to those of −416FIXm1 (FIG. 2A), although the decline was less steep and expression levels were stabilized at significantly higher levels than those observed for −416FIXm1 (FIG. 2B).

These results indicate that, while the 102-bp sequence containing the dinucleotide repeat structure of hFIX 3' UTR reduces the age-related decline in expression of hFIX, the presence of the complete 3' UTR containing the extensive dinucleotide repeat structure nonetheless does not completely rescue hFIX expression from the age-decline observed in all of these animals, regardless of founder line, initial pre-pubertal hFIX level, generation, sex, or zygosity status of the transgenes.

All animals carrying minigenes −590FIXm1 and −679FIXm1 (a total of 25 and 26 animals subjected to longitudinal analysis, respectively) also showed an age-associated rapid decline in hFIX expression similar to that seen in animals carrying −416FIXm1 (FIG. 2, C and D). Furthermore, hFIX expression levels in three independent founder animals generated to date carrying −770 FIXm1 also rapidly decreased over the puberty period in a similar pattern as the above minigenes (FIG. 2E). These observations indicated that minigenes with the promoter region up to nt −770 contain the basic structural elements necessary for hFIX expression, but lack a structural element(s) which functions in age-associated stability of hFIX gene expression.

In contrast, striking and unexpected differences in hFIX expression patterns were observed with animals carrying the minigene −802FIXm1 (FIG. 4A) as comp[ared to those carrying the minigene −416FIXm1 (FIG. 2A). −802FIXm1 is composed of a vector frame identical to −416FIXm1, except that the 5' end flanking sequence included was extended to nt −802 (FIG. 1).

All animals with −802FIXm1, −2231FIXm1 and −416FIXm1/AE5' (panels A, C, E) exhibited stable expression throughout their life spans. Animals with −802FIXm1/1.4 and −2231FIXm1/1.4 (FIG. 4 B, D) exhibited age-associated increases in hFIX expression levels. All animals maintained or increased stable circulatory hFIX levels regardless of founder line, initial expression levels at one month of age, sex, generation or zygosity status. Mice which died at much younger ages than their normal life expectancies are marked with d. The above results show that all animals from three independent founder lines obtained with −802FIXm1 (FIG. 4A) showed characteristic differences in hFIX expression pattern from animals with −416FIXm1 (FIG. 2A) and −416FIXm1/1.4 (FIG. 2B).

The −802FIXm1 transgenic animals (n=62) subjected to longitudinal analysis invariably showed age-stable plasma hFIX levels for their entire life spans, mostly up to 20-24 months of age. Age-stable circulatory hFIX levels were correlated with age-stable mRNA levels (FIG. 5). These observations with −802FIXm1 were further supported by age-stable hFIX expression by mice carrying −2231FIXm1 (FIG. 4C). Together, these results suggest that the structural element which is responsible for age-stable expression of the hFIX gene resides in the small region spanning nt −770 through −802. We designated this small region "age-regulatory element in the 5' end" (AE5'). This region contains a transcription factor PEA-3 nucleotide sequence (GAGGAAG: nt −784 through −790), which completely matches the consensus motif (C/G)AGGA(A/T)G [Martin et al. (1988) Proc. Natl. Acad. Sci. 85:5839-5843; Xin et al. (1992) Genes & Develop. 6:481-496; Chotteau-Lelievre et al. (1997) Oncogene 15:937-952; Gutman and Wasylyk (1990) EMBO J. 9:2241-2246]. The function of AE5' nucleotide sequence is position-independent as shown by age-stable hFIX expression by animals containing −416FIXm1/AE5', in which AE5' was moved to the 3' end outside of the hFIX minigene (FIG. 4E).

Since transgenes of −416FIXm1, −590FIXm1, −679FIXm1 and −770FIXm1 differ from the minigenes −802FIXm1 and −2231FIXm1 only by their promoters, the hFIX mRNA produced from all of these minigenes (an intron spliced form of FIXm1 RNA) was expected to produce identical hFIX protein. Thus, it was hypothesized that the age-dependent decline in the circulatory hFIX level observed in animals with −416FIXm1, −590FIXm1, −679FIXm1 and −770FIXm1, but not with −802FIXm1 and −2231 FIXm1, must be due to an age-dependent decline in the transcriptional activity of the transgenes. This agrees with the facts that no significant changes with age in hFIX mRNA levels in the liver were observed for animals carrying −802FIXm1 (FIG. 5, lanes 2 and 3), while advancing age-dependent declines in steady-state mRNA level were observed for −416FIXm1 (FIG. 3A, lanes 2 and 3).

To further determine whether the age-dependent decline in the circulatory hFIX levels was due to an age-dependent decline in transcriptional activity of the transgenes, the effects of age on hFIX clearance from the circulation were tested as follows. Aliquots of plasma-derived hFIX preparation (5 μg/0.1 ml of PBS) were injected via tail vein into normal animals at 2, 9-10 and 19-23 months of age (n=3 per age group), which have the same genetic background as the transgenic mice (C57B/6×SJL). The hFIX level in circulation was monitored by ELISA of collected blood samples (~50 μl aliquot) at 10 min, 2, 6, 12, 18, 24, 30, 36 and 48 hrs after protein injection. As expected, all animals of different age groups showed a typical bi-phasic clearance kinetics (two compartment distribution and clearance) with an initial rapid clearance phase α-phase), followed by a slower clearance phase (β-phase). The results are shown in Table 1.

TABLE 1

Clearance Time of Human Factor IX in Mice

| Age (months) | Clearance Time ($T_{1/2}$ of Human Factor IX) |
|---|---|
| 2 | 16.8 ± 0.21 |
| 9-10 | 17.4 ± 0.55 |
| 19-23 | 16.9 ± 0.35 |

As shown in Table 1, very similar half clearance times were observed for all age groups tested. This agreed with our previous results (17.8 hours) for hFIX clearance in a different strain, BALB/c mice (2 months of age) (Yao et al. (1994) supra].

Furthermore, the results in Table 1 demonstrate that the hFIX turnover time from the circulation does not change significantly in vivo with increasing age, from youth (2 months), to middle age (9-10 months) to old age (19-23 months). These results further confirm that the age-dependent decline in the circulatory hFIX levels was due to an age-dependent decline in transcriptional activity of the transgenes.

It is important to note that in the in vitro HepG2 cell assay system, the presence or absence of AE5' in the minigenes did not make any significant difference in hFIX expression from the hFIX minigenes (FIG. 1, and Example 2, supra). In contrast, as mentioned above in this Example, the presence or absence in vivo of AE5' makes a dramatic age-dependent difference in hFIX gene expression. This further demonstrates that in vivo longitudinal analysis is important for studying age-regulation of a gene.

Unlike the animals with −802FIXm1, mice with −802FIXm1/1.4 (which contains the complete 3'UTR) showed an advancing age-associated increase in the hFIX level in the circulation (n=48) (FIG. 4 A and B). Thus, to determine whether this unexpected age-dependent increase in the circulatory hFIX level was directly correlated with an increased level of liver hFIX mRNA, Northern blot analyses of transgenic mice carrying −802FIXm1 and −802FIXm1/1.4 were conducted. The hFIX mRNA levels in the liver of 1-month (young) or 15-month (aged) mice carrying −802FIXm1 (mouse P327 or P552, respectively) and −802FIXm1/1.4 (mouse P32 and P697, respectively) are shown in FIG. 5. These animals were from the same litter produced by the founder F17549 for −802FIX ml and F229 for −802FIXm1/1.4 (FIG. 4 A and B). At the time of sacrifice, P552 and P697 were expressing 2200 and 1658 ng/ml of hFIX, respectively. The total liver RNA (15 μg from each animal was used for the Northern blot analysis performed as described in FIG. 3A. Upper panel: probed with the Ssp I/BamH I fragment of hFIX cDNA; lower panel: rehybridized with RNR18 (ribosomal RNA) probe. Lane 1: non-transgenic mouse liver; lane 2: transgenic P327 liver RNA; lane 3: transgenic P552 liver RNA; lane 4: transgenic P32 liver RNA; lane 5: transgenic P697 liver RNA. PhosphorImager (Molecular Dynamics) was used for quantitation of mRNA levels (counts) and ratios of young versus old were calculated. Young and old animals carrying −802FIXm1 showed no significant differences in the mRNA level (the ratio of old over young: 0.92). In contrast, −802FIXm1/1.4 animals showed a substantial elevation in the mRNA level with older age (the ratio of old over young: 1.54).

These results (FIG. 5, lanes 4 and 5) indicated the presence of another important age-regulatory nucleotide sequence, designated AE3', which is located approximately in the middle of the 3' UTR where an extensive stretch of dinucleotide repeating structures were contained. In the presence of AE5', AE3' clearly confers a crucial age-associated increase in hFIX expression. This conclusion was further supported by results obtained with −2231FIXm1/1.4 (n=42) (FIG. 4D). The unique concerted function conferred by the combination of AE5' and AE3' was again independent of founder line, initial expression levels at one month of age, sex, generation, or zygosity status of animals.

Figure 4B:
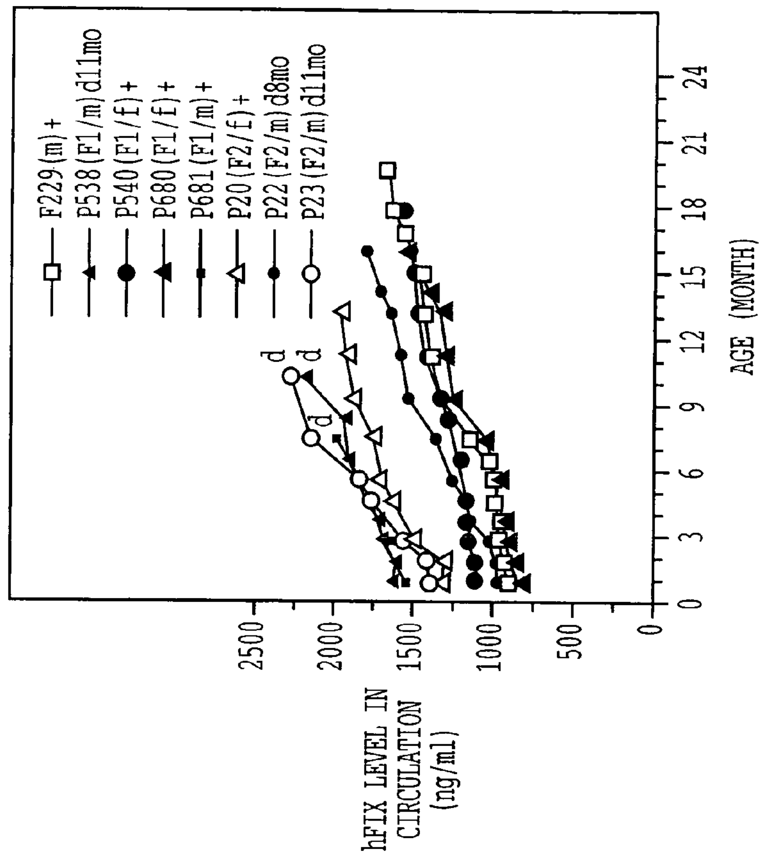
FIG. 4 shows graphs of longitudinal analysis of transgenic mice which carry −802FIXm1 (A), −802FIXm1/1.4 (B), −2231FIXm1 (C), −2231FIXm1/1.4 (D) and −416FIXm1/AE5' (E) expression vectors and which produce hFIX at stable and increasing levels with age.
Figure 4A:
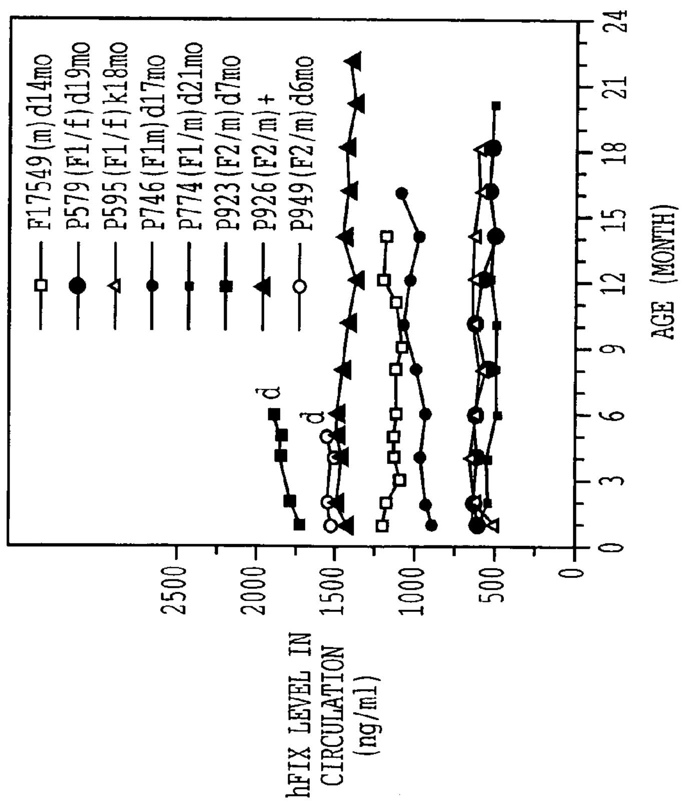
Figure 4D:
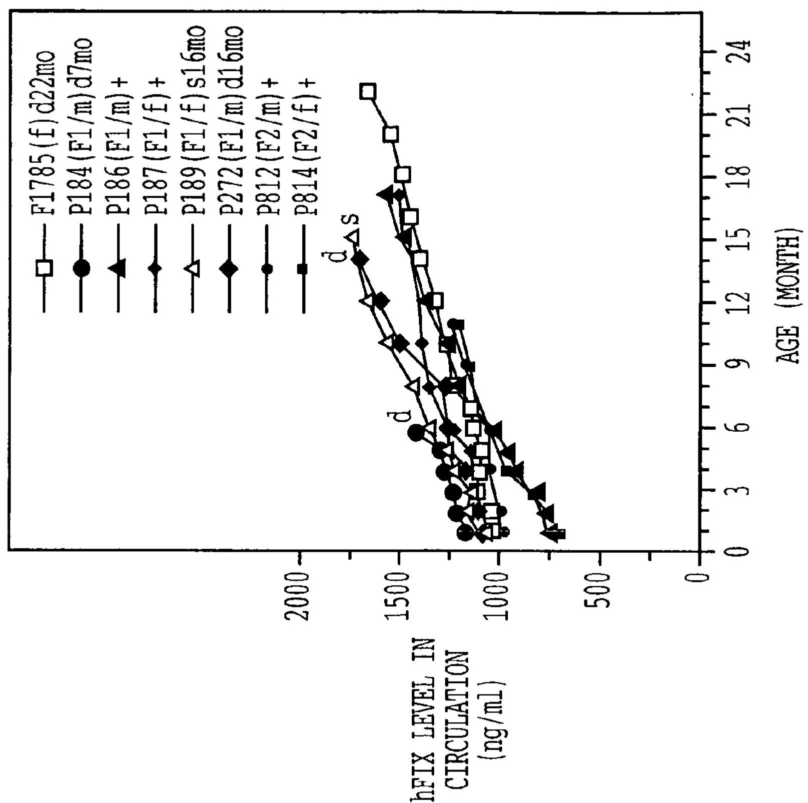
Figure 4C:
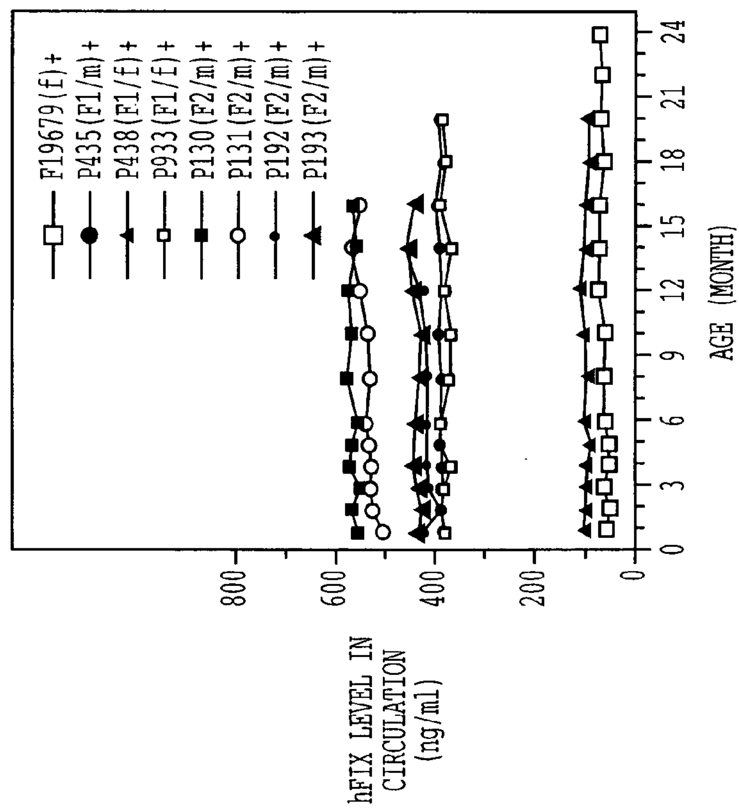
Figure 4E:
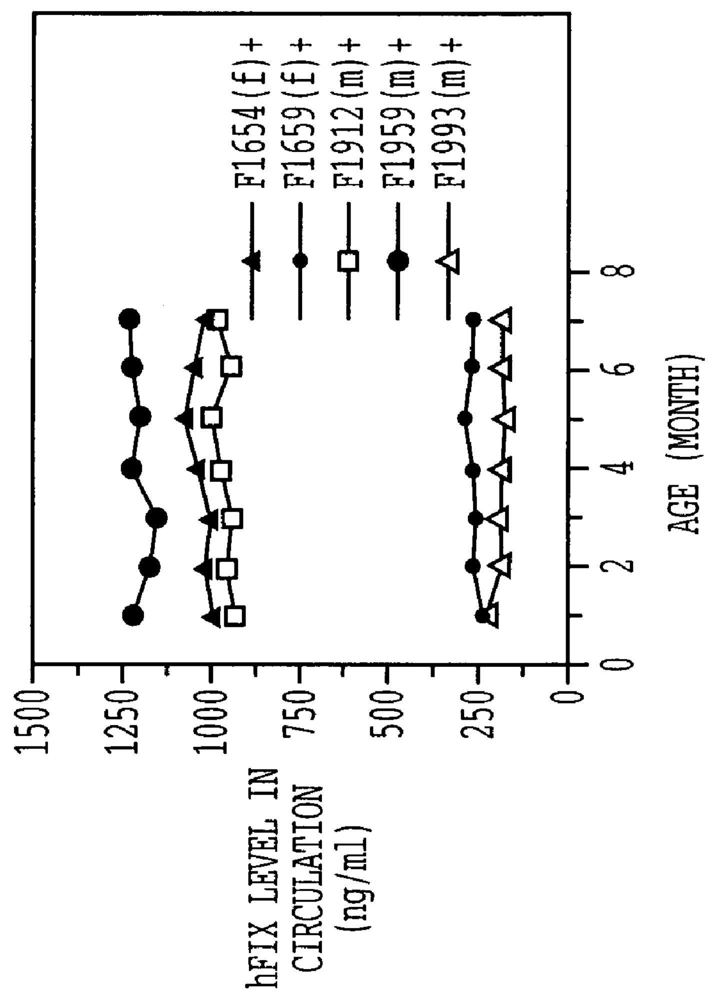

Interestingly, animals with sustained high hFIX levels in the circulation (approximately 1,500 ng/ml or higher) tended to die at a much earlier age than the expected life span (~2 years) (FIG. 4A, B, D). This happened to both males and females, but appears to be more frequent in males. Without limiting the invention to any particular mechanism, it is believed that since these transgenic mice have hFIX in addition to their own mFIX, they may be at an increased risk of lethal thrombosis compared to wild type mice which do not express the transgenes.

The above-described characterization of transgenic mice harboring hFIX transgenes demonstrates that (a) while the presence of AE5' in vitro in HepG2 cells did not affect hFIX gene expression, the presence of AE5' in vivo resulted in a dramatic age-dependent increased stability in hFIX gene expression, (b) the age-dependent decline in the circulatory hFIX level observed in animals with −416FIXm1, −590FIXm1, −679FIXm1 and −770FIXm1 is directly correlated with the decrease in the steady-state mRNA level, which the inventors believe to be due to an age-dependent decline in the transcriptional activity of the transgenes, and (c) animals carrying −802FIXm1/1.4 shwoed a substantial elevation in the liver mRNA levels of hFIX with older age.

EXAMPLE 4

Footprint and Gel Electrophoretic Mobility Shift Analysis of the Region from Nucleotides −665 to −805 of Human Factor IX In order to make a preliminary determination of the region within AE5' which is involved in the function of AE5', footprint analysis and gel electrophoretic mobility shift assays were performed as follows.

A. Footprint Analysis

For footprint analysis of the region spanning from nt −665 through nt −805, the fragments used were amplified by PCR with the $^{32}$P-labeled 5' primer ATGGTTAACTGACTTACGAA (nt −833 through −814) (SEQ ID NO:29) and 3' unlabeled primer GCTCCATTTGAGTTAATATTTGTGT (nt −657 through −682) (SEQ ID NO:30). The nuclear extracts (NEs) from HepG2 human hepatoma cells and livers of young (1 month of age) and old (19 months of age) mice were prepared as previously reported [Kurachi et al. (1986) Biochemistry 33:1580-1591]. Various amounts of NEs (0, 100 and 150 μg) were incubated with the labeled fragments (30,000 CPM) for 1 hour on ice and subjected to DNase 1 digestion (0.5 unit) for 2 min at room temperature. The samples tested included those without NEs, with 100 μg and 150 μg of HepG2 cell NEs, with 100 μg and 150 μg NEs from old mice, and with 100 μg and 150 μg NEs from young mice. Major and minor footprints and apparent DNase hypersensitivity sites were observed.

Footprint analysis of the region nt −665 through −805 with aged mouse liver nuclear extracts showed a major footprint (nt −784 through −802), a minor foot print (nt −721 through −728) and an interesting DNase hypersensitive region (nt −670 through −714). With nuclear extracts from one month-old animals or HepG2 cells, no such clear footprints were observed.

B. Gel Electrophoretic Mobility Shift Assay

Figure 6A:
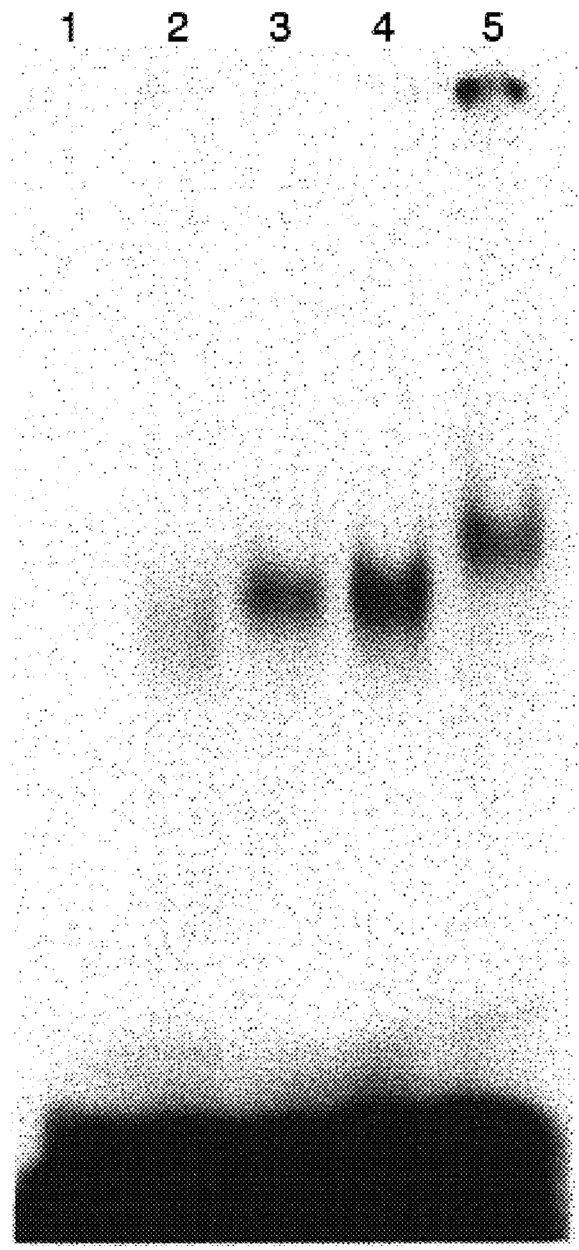
FIG. 6 is a gel of a gel electrophoretic mobility shift assay using mouse liver nuclear extract (NEs) from three different age groups, and using double-stranded oligonucleotides containing a PEA-3 nucleotide sequence spanning from nt −797 to −776 of the hFIX gene (A), and using a competition assay for $^{32}$P-labelled double stranded oligonucleotides containing the PEA-3 nucleotide sequence (B).

Gel electrophoretic mobility shift assay using mouse liver nuclear extracts from three different age groups was used. Nuclear extracts were prepared from 1, 5 or 19 month-old mouse livers (as described supra). Double stranded oligonucleotides containing a PEA-3 nucleotide sequence spanning from nt −797 to −776 of the hFIX gene (TTCAGTCGAGGAAGGATAGGGT) (SEQ ID NO:31) were $^{32}$P-labeled at the 5' end to a specific activity of $1.9\times10^9$ cpm. Aliquots of the radio-labeled oligonucleotide (20,000 cpm) were incubated with 10 μg of NEs in the presence of 1 μg of poly dI-dC in DNA binding buffer for 20 min at room temperature and subjected to polyacrylamide gel electrophoresis (Kurachi et al. (1986) supra). In FIG. 6A, Lane 1: without NEs; lane 2: with NEs of 1 month-old mice; lane 3: with NEs of 5 month-old mice; land 4: with NEs of 19 month-old mice; lane 5: with mouse brain NEs (positive control for PEA-3, showing a slightly higher size of shifted band).

Figure 6B:
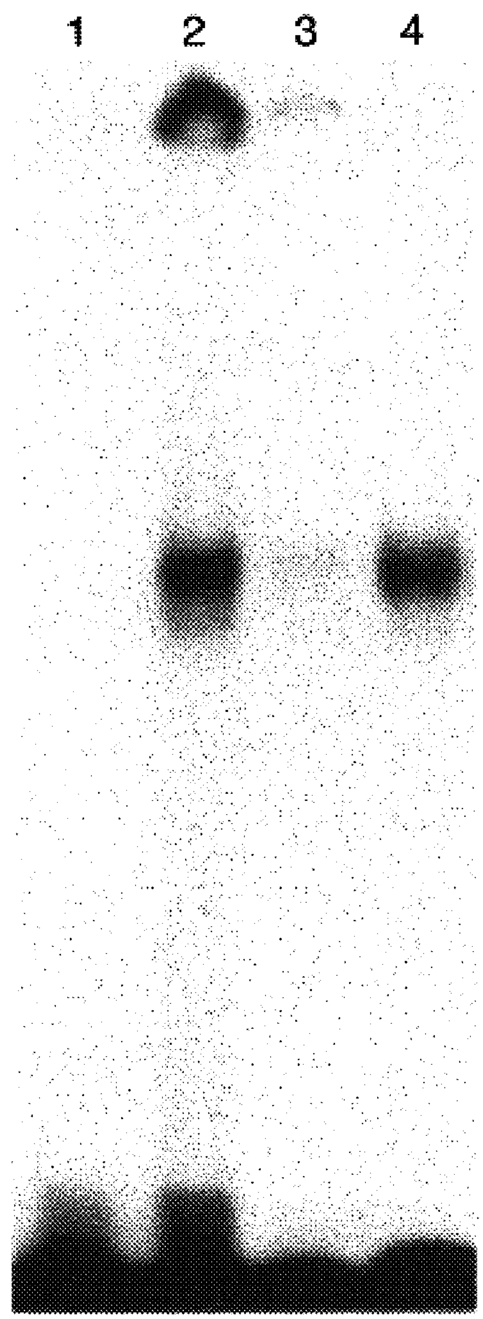

FIG. 6B shows the results of the competition assay for $^{32}$P-labeled double stranded oligonucleotides containing the PEA-3 nucleotide sequence. A 100-fold excess unlabeled oligonucleotide described in the preceding paragraph or mutant oligonucleotide [TTCAGTCGGTTGGTGATAGGGT (SEQ ID NO:32) with mutated sequences underlined] was incubated with 10 μg of 19 month-old mouse liver NEs for 5 min followed by addition of $^{32}$P-labeled oligonucleotides as described supra. Lane 1: without NEs; lane 2: with NEs; lane 3: with NEs and wildtype competitor; lane 4: with NEs and mutant competitor.

In agreement with the above results of footprinting, gel electrophoretic mobility-shift (bandshift) assays showed an increase in protein binding with the nuclear extracts of aged mice (19 months of age) (FIG. 6A). Bandshifts were competitively reduced with excess amounts of oligonucleotides harboring the PEA-3 motif, but not with oligonucleotides harboring a mutant PEA-3 motif sequence (FIG. 6B), thus confirming the presence of the PEA-3 motif in AE5'. This is the first time that the PEA-3 protein, which is a member of the Ets family of transcription factors and which has been shown to bind to nucleotide sequences [SEQ ID NO:40; SEQ ID NO:48; and SEQ ID NO:84] that are homologous to the PEA-3 nucleotide sequence within the AE5' region [Karim et al. (1990) Genes & Develop. 4:1451-1453; Nelsen et al. (1993) Science 261:82-86; Fisher et al. (1991) Oncogene 6:2249-2254], has been implicated in such a unique role in age-stable regulation of a gene.

Without limiting the invention to any particular mechanism, the PEA-3 nucleotide sequence in the hFIX gene appears to have been generated through evolutionary drift of a L1 sequence originally recruited presumably via its retrotransposition into the 5' specific location. Modern retrotransposable L1 [Kazazian et al. (1988) Nature 332:164-166; Dombroski et al. (1993) Proc. Natl. Acad. Sci. USA 90:6513-6517; Minakami et al. (1992) Nucl. Acids Res. 20:3139-3145; Dombroskiet et al. (1994) Mol. Cell. Biol. 14:4485-4492] does not have the corresponding PEA-3 nucleotide sequence. The PEA-3 nucleotide sequence of AE5' nucleotide sequence resides within the L1-derived sequence retaining a 63-70% similarity with the ORF2 corresponding region of the modern retrotransposable L1 in the 5' to 3' orientation. Interestingly, the murine FIX gene also has the L1-derived nucleotide sequence in its 5' end region in an almost identical position as in the hFIX gene, and has multiple PEA-3 consensus nucleotide elements [Kawarura et al. in *Organization of L1 Sequence in the 5'Flanking Region of Factor IX Gene* [in preparation]. Age-regulation of the murine FIX gene is indeed very similar to that of the hFIX gene [Sweeney and Hoernig (1993) Am. J. Clin. Pathol. 99:687-688; Kurachi et al. (1996) Thromb. Haemost. 76:965-969], thus providing further insights into the evolutionary origin of the molecular mechanisms underlying age-associated regulation of the FIX gene.

EXAMPLE 5

Liver-Specific Expression of the Exemplary hFIX Gene under Control of the hFIX Promoter Expression of the natural FIX gene is virtually restricted to the liver [Salier et al. (1990) J. Biol. Chem. 265:7062-7068]. In order to determine whether any of the upstream and/or downstream sequences in the hFIX minigenes directed liver-specific expression of the hFIX transgene, Northern blot analysis was carried out as described supra (Example 3) in transgenic mice carrying −416FIXm1 and −802 FIXm1 expression vectors. Animals expressing hFIX at high level (PA412 and P580 carrying −416FIXm1 and −802FIXm1, respectively) were sacrificed at one month of age and total RNA was extracted from liver, lung, intestine, muscle, kidney, brain and heart and from untransfected HepG2 cells (negative control). The results in transgenic mice carrying −416FIXm1 and −802 FIXm1 are shown in FIGS. 7A and B, respectively.

Figure 7:
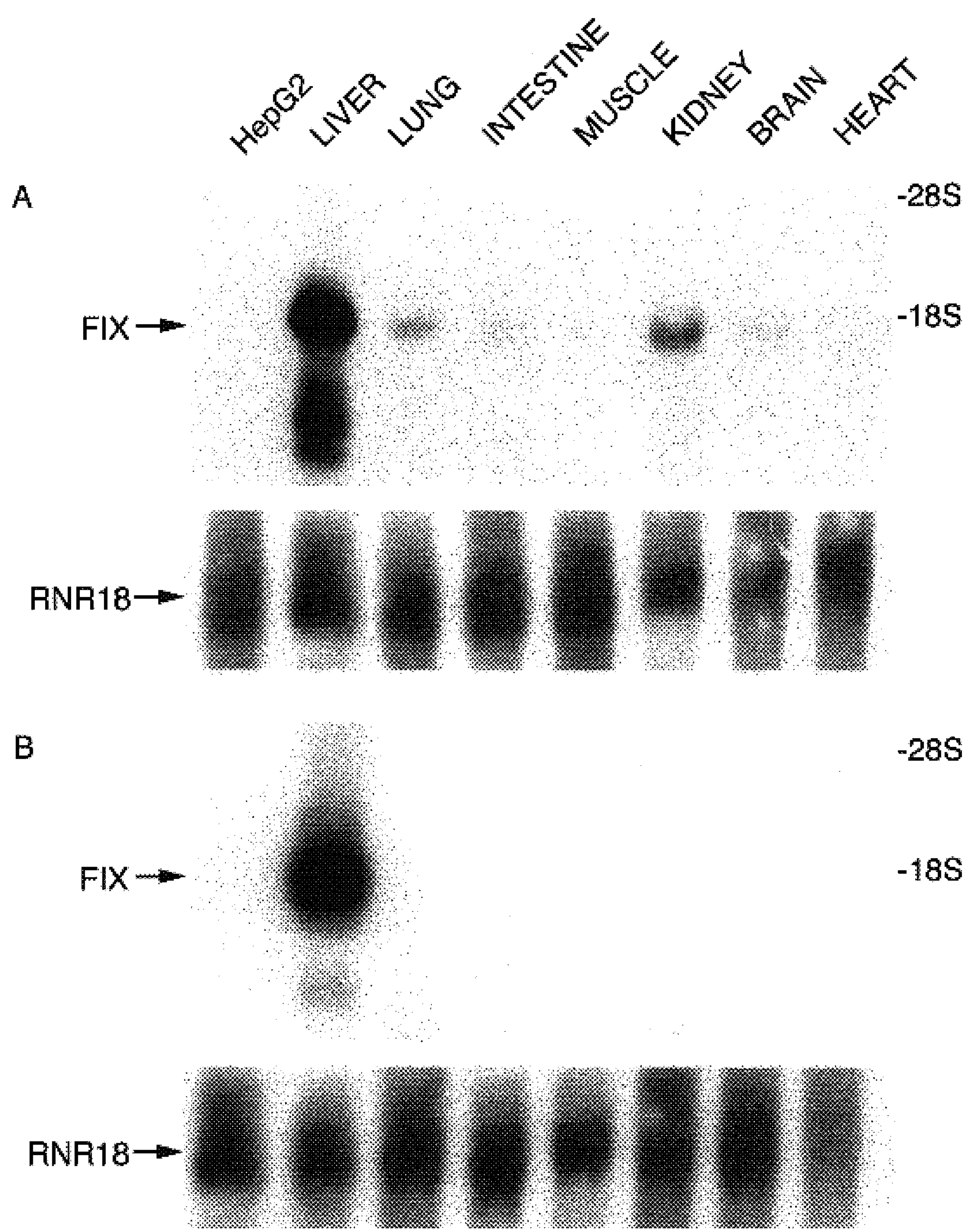
FIG. 7 is a Northern blot showing tissue specificity of hFIX expression in transgenic mice carrying −416FIXm1 (A) and −802 FIXm1 (B) expression vectors.

In FIG. 7, the positions of hFIX mRNA, RNR18 (control for RNA loading in wells), and ribosomal 28S and 18S RNA bands are shown on the left and right sides, respectively. Animals with −416FIXm/1.4 and −679FIXm1 showed tissue specific expression patterns similar to that of −416FIXm1 (A) (data not shown). Interestingly, liver expression of hFIX observed for minigenes lacking the region containing AE5' (except −770FIXm1, which remains to be tested as sufficient progeny animals become available) was high, but not as robust, as that seen with the natural gene. In addition, these minigenes expressed not only in the liver, but also in other tissues, such as kidney, lung and muscle, at various levels as high as ~20% of the liver level (FIG. 7A). In clear contrast, animals with −802FIXm1 showed substantially liver-specific hFIX expression similar to that for the natural FIX gene (FIG. 7B). These results suggest that the AE5' region controls liver specific expression of hFIX.

An apolipoprotein(a) transcription cotnrol region (ACR) whcih contains an ETS family target sequence 5'-CCCGGAAG-3' (SEQ ID NO:48) has been shown to exhibit enahncer activity in vitro in liver-derived HepG2 cells. However, the ACR does not appear to be liver-specific [Yang et al. (1998), supra].

EXAMPLE 6

Expression of PEA-3 Protein in HepG2 Liver Cells

Expression of the transgene FIX was observed in vivo, but not in vitro in HepG2 cells, when expression vectors containing AE5' were used (See, Examples 2 and 3, supra). This observation, together with the absence of a footprint in HepG2 cell NEs (See, Example 4, supra) suggested to the inventors that HepG2 cells' lack of expression of the FIX transgene may be a result of the cells' expression of low levels of the PEA-3 protein (and/or the PEA-3 related protein) which binds to homologs of the invention's PEA-3 nucleotide sequence. The complete human PEA-3 cDNA has not yet been cloned (the human PEA-3 cDNA sequence of GenBank accession number U18018 lacks 8 amino acids at the N-terminal region when compared to the mouse PEA-3 cDNA sequence). In order to determine the role of the PEA-3 nucleotide sequence in gene expression in vitro, HepG2 cells which overexpress mouse PEA-3 protein were constructed as follows.

Expression constructs containing the mouse PEA-3 cDNA sequence (GenBank Accession Number X63190; FIG. 9) were constructed as follows. Using the reported mouse PEA-3 cDNA sequence three sets of PCR primers were synthesized such that the entire coding region and parts of the flanking sequences would be amplified. Reverse transcription PCR (RT-PCR) was carried out, and the amplified mouse PEA-3 cDNA sequence was inserted into an expression vector under the control of the SV40 promoter, which does not interfere with the factor IX promoter (data not shown).

The PEA-3 expression vector is used to transfect HepG2 cells using the FuGene 6 (Boehringer Manheim) since this method was shown to improve transfection efficiency (See, Example 2, supra). Transfected HepG2 cells are screened for expression of PEA-3 by Northern blot analysis and/or Western blot analysis using commercially available antibody. Transfected HepG2 cell lines which stably express PEA-3 protein are selected for further use, e.g., to analyze the underlying mechanism of PEA-3 action.

EXAMPLE 7

In Vitro and In Vivo Expression of Exemplary Human Protein C Minigene Expression Vectors Containing AE5' and AE3'

Protein C is a factor which plays a critical role in the anti-blood coagulation mechanism. Unlike factor IX, whose level in the circulation substantially increases with advancing age, protein C levels in the circulation do not increase with advancing age, but rather show a slight decrease over time. This decrease in circulating protein C levels is believed by the inventors to be the result of regulation at the gene transcription level. For this reason, the protein C gene provides an interesting exemplary gene for demonstrating the universality of the AE5' and AE3' function in gene expression both in vitro and in vivo as follows.

A. Construction of Human Protein C Minigene Expression Vectors

The human protein C genomic sequence has been previously reported (GenBank accession number M11228; FIG. 12B]. Using this sequence, three protein C minigene expression vectors were prepared. The first human protein C minigene vector (−1424PCml) contained the human protein C promoter region of the protein C gene (GenBank accession number M11228; FIG. 12 B) ligated to the human protein C cDNA (GenBank accession number X02750; FIG. 12 A) which contains the first entire intron and poly-A sequence. The second human protein C minigene (AE5'/−1424PCml) was the same as the first vector vector except that it additionally contained the nucleotide sequence AE5' at the 5' end of the human protein C cDNA. The third human protein C minigene (AE5'/−1424PCml/AE3') was the same as the first vector vector except that it additionally contained the nucleotide sequences AE5' and AE3' at the 5' and 3' ends, respectively, of the human protein C cDNA.

B. Transient Expression of Human Protein C In Vitro in HepG2 Cells

Each of the protein C minigene expression vectors was transfected into HepG2 cells using the FuGene 6 (Boehringer Mannheim). Four to five independent assays of human protein C activity were carried out as previously described [Turkey et al (1999) Throm. Haemost. 81:727-732]. HepG2 cells transfected with the −1424PCml vector showed in vitro transient protein C activities which were comperable to the activities shown by HepG2 cells transfected with the AE5'/−1424PCml vector (i.e., (60-70 ng/10E6 cells/24 hrs).

C. Generation of Transgenic Mice Harboring the Protein C Minigene Expression Vectors In order to determine whether AE5' in combination with AE3' is capable of increasing human protein C expression with advancing age, as observed for factor IX expression (Example 3, supra), transgenic mice which harbor the protein C minigene expression vectors are generated according to standard methods [Hogan et al. (1994), supra]. Briefly, protein C minigene vector plasmids are injected into fertilized eggs of C57B/6×SJL mice and implanted into foster mother animals (CD-1). Offspring produced are screened for founder animals with high transgene copy numbers (5-10 copies per genome) using quantitative multiplex PCR analyses of tail tissue DNA samples using two pairs of primers which are designed to amplify a unique fragment from the protein C transgenes and a 494 bp fragment from the mouse β-globin gene, respectively.

Founders are back-crossed with non-transgenic mice (C57B/6×SJL) to generate F1 progeny animals. Homozygous F2 animals are generated by crossing among heterozygous F1 littermates and the following generations are similarly generated. Zygosity status of animals is determined by quantitative multiplex PCR analysis as described above. Founder lines for each minigene construct are subjected to longitudinal analysis for their entire life spans up to two years.

Circulatory human protein C levels are monitored during longitudinal analyses of transgenic mice from the representative founder lines carrying the protein C minigene transgenes. Age-regulation patterns of circulatory human protein C levels are compared among all animals for each specific construct, different founder lines, different initial human protein C level at pre-pubertal age (one month) due to transgene positional effects, generation (founders and F1 or F2 progeny), sex, and zygosity (homozygous/heterozygous) status of the transgenes.

Northern blot analyses of the liver RNA samples from animals is carried out using stringent washing conditions to determine whether any changes in circulatory human protein C levels are correlated with similar changes in the steady-state liver human protein C mRNA, rather than with loss of the human protein C transgene with age or with changes in human protein C turnover time. Observation of transgenic animals which contain the human protein C sequence as well as AE5' and AE3' and which increase stable circulatory human protein C levels with increasing animal age, as compared to the levels in transgenic animals which express the human protein C sequence in the absence of AE5' and AE3', demonstrates that the combination of AE5' and AE3' functions in age-stable expression of the exemplary human protein C gene. This observation will confirm that these results may ba achieved for genes other than the exempary hFIX and protein C genes.

EXAMPLE 8

In Vivo Expression of Exemplary Expression Vectors Containing the Cytomegalovirus (CMV) Promoter and the AE5' and AE3'

This Example is carried out to demonstrate the universality of the age-related gene expression regulatory function of AE5' and AE3' with viral promoters. The CMV promoter is currently used in several gene therapy constructs but its activity decreases with time in the Liver. Furthermore, the activity of the CMVpromoter in the liver of transgenic mice is known to be lower than the activity in other tissues, such as muscle. Thus, this Example investigates whether the combination of AE5' and AE3' halts or reverses the decline in the activity of the CMVpromoter in the liver.

The above-described −416FIXm1 expression vector (Example 1, and FIG. 1) is used to construct a control vector to determine the effect of AE5' and AE3' on liver and circulatory levels of expression of human factor IX in transgenic animals. The control vector in which expression of the hFIX gene is under the control of the CMV promoter in the absence of both AE5' and AE3' is constructed by replacing the human factor IX promoter sequence with the CMV promoter sequence (National Vector Core for Non-Viral Vectors at the University of Michigan) (the CMV promoter is also located between positions +1 to +596 in vector plasmid pCR3 from Invitrogen). The resultant expression vector in which the human factor IX gene is under the control of the CMV promoter is transfected into HepG2 cells. Transfected cells are expected to show human factor IX activity.

The −802FIXm1/1.4 vector of FIG. 1 is used to construct a test vector in which the human factor IX promoter sequence of −802FIXm1/1.4 vector (which contains both AE5' and AE3') is replaced with the CMV promoter sequence.

In order to determine whether the combination of AE5' and AE3' is capable of increasing human factor IX expression with advancing age under the control of the CMV promoter, as observed for factor IX expression under the control of the factor IX promoter (Example 3, supra), transgenic mice which harbor either the control vector or the test vector are generated according to standard methods as described supra (Examples 3 and 7). The mRNA levels of human factor IX in the blood, liver and other tissues are monitored during longitudinal analyses of the transgenic mice. Age-regulation patterns of human factor IX mRNA levels in the different tissues are compared among all animals as described supra for each specific construct, different founder lines, different initial human factor IX levels at pre-pubertal age due to transgene positional effects, generation, sex, and zygosity status of the transgenes.

The observation of transgenic animals which contain the test vector and which increase stable circulatory human factor IX mRNA levels, as compared to the circulatory mRNA levels in transgenic animals which contain the control vector, demonstrates that the combination of AE5' and AE3' functions in increasing the activity of the exemplary CMV promoter.

EXAMPLE 9

Liver-Specific Expression of the Exmplary Human Factor IX Gene under the Control of the CMV Promoter This Example investigates whether the presence of AE5' imparts liver specific activity to the CMV promoter, which otherwise drives gene expression in several tissues in addition to the liver.

The −802FIXm1 vector which contains AE5' and lacks AE3' (FIG. 1) is used to construct a test vector in which the human factor IX promoter sequence of the −802FIXm1 vector is replaced with the CMV promoter sequence. This test vector is used in parallel experiments with the control vector of Example 8 in which expression of the hFIX gene is under the control of the CMV promoter in the absence of both AE5' and AE3'. Northern blot analysis is carried out as described supra (Example 3) in transgenic mice carrying the control vector or test vector. Animals expressing hFIX at high level are sacrificed at one month of age and total RNA is extracted from liver, lung, intestine, muscle, kidney, brain and heart and from untransfected HepG2 cells (negative control). The levels of hFIX mRNA in the different tissues are compared. It is expected that transgenic animals harboring the control vector will express hFIX mRNA in liver as well as in at least one other tissue. In contrast, the observation that transgenic animals which harbor the test vector express hFIX mRNA in the liver and not in other tissues indicates that AE5' confers liver-specific activity to the exemplary CMV promoter.

From the above, it is clear that the invention provides methods for age-related and liver-specific gene expression and models for age-related and liver-specific diseases.

We claim:

1. A method of expressing a nucleic acid sequence of interest in a mammalian cell, comprising:

a) providing:

i) an isolated mammalian cell selected from the group consisting of (a) a liver cell, and (b) a mouse cell selected from the group consisting of an embryonic stem cell, an eight-cell embryo cell, a blastomere cell, a blastocoele cell, and a fertilized egg cell;

ii) a nucleic acid sequence of interest heterologous to SEQ ID NO:3;

iii) a promoter sequence, and iv) one or more age regulatory sequences selected from SEQ ID NO:3 and a functional portion of SEQ ID NO:3;

b) operably linking said nucleic acid sequence of interest, said promoter sequence, and said one or more age regulatory sequences to produce a transgene, wherein said age regulatory sequence comprised in said transgene is located at a position selected from the group consisting of the 3' end of said promoter sequence and the 3' end of said nucleic acid sequence of interest; and c) introducing said transgene into said mammalian cell under conditions such that said nucleic acid sequence of interest is expressed in said mammalian cell.

2. The method of claim 1, wherein said promoter sequence is a human factor IX promoter, said nucleic acid sequence of interest encodes a PEA-3 protein, and said mammalian cell is a liver cell.

3. The method of claim 1, wherein said promoter sequence is a human factor IX promoter, said nucleic acid sequence of interest encodes a PEA-3 protein, and said mammalian cell is mouse cell selected from the group consisting of an embryonic stem cell, an eight-cell embryo cell, a blastocoele cell, a blastomere cell, a fertilized egg cell, and a liver cell.

4. The method of claim 1, wherein said functional portion of SEQ ID NO:3 is selected from the group consisting of SEQ ID NO:51, SEQ ID NO:52, SEQ ID NO:53, SEQ ID NO:54, SEQ ID NO:55, and SEQ ID NO:56.

5. A method of expressing a protein in a mammalian cell, comprising:

a) providing:

i) an isolated mammalian cell selected from a liver cell and a mouse cell, said mouse cell selected from the group consisting of a fertilized egg cell, an embryonic stem cell, a blastomere cell, a blastocoele cell, and an eight-cell embryo cell;

ii) a nucleic acid sequence of interest heterologous to SEQ ID NO:3 encoding a protein;

iii) a human Factor IX promoter sequence; and iv) one or more age regulatory sequences selected from the group consisting of SEQ ID NO:3 and a functional portion of SEQ ID NO:3;

b) operably linking said nucleic acid sequence, said human Factor IX promoter sequence, and said one or more age regulatory sequences to produce a transgene, wherein said age regulatory sequence comprised in said transgene is located at a position selected from the group consisting of the 3' end of said promoter sequence and the 3' end of said nucleic acid sequence; and c) introducing said transgene into said mammalian cell under conditions such that said protein is expressed in said mammalian cell.

6. The method of claim 1, wherein said nucleic acid sequence of interest comprises a structural gene.

* * * * *